(12) United States Patent
Lee et al.

(10) Patent No.: US 8,835,436 B2
(45) Date of Patent: Sep. 16, 2014

(54) ARYLPIPERAZINE-CONTAINING IMIDAZOLE 4-CARBOXAMIDE DERIVATIVES AND PHARMACEUTICAL COMPOSITION COMPRISING SAME

(75) Inventors: Jinhwa Lee, Yongin-si (KR); Hee Jeong Seo, Yongin-si (KR); Suk Youn Kang, Yongin-si (KR); Eun-Jung Park, Yongin-si (KR); Min Ju Kim, Yongin-si (KR); Suk Ho Lee, Yongin-si (KR); Jong Yup Kim, Yongin-si (KR); Jeongmin Kim, Yongin-si (KR); Myung Eun Jung, Yongin-si (KR); Hyun Jung Kim, Yongin-si (KR); Mi-soon Kim, Yongin-si (KR); Ho Kyun Han, Yongin-si (KR); Kwang Woo Ahn, Yongin-si (KR); Min Woo Lee, Yongin-si (KR); Ki-Nam Lee, Yongin-si (KR); Ae Nim Pae, Seoul (KR); Woo-Kyu Park, Daejeon (KR)

(73) Assignee: Green Cross Corporation, Yongin-Si (KR)

( * ) Notice: Subject to any disclaimer, the term of this patent is extended or adjusted under 35 U.S.C. 154(b) by 174 days.

(21) Appl. No.: 13/383,143

(22) PCT Filed: Jul. 9, 2010

(86) PCT No.: PCT/KR2010/004479
§ 371 (c)(1),
(2), (4) Date: Jan. 9, 2012

(87) PCT Pub. No.: WO2011/005052
PCT Pub. Date: Jan. 13, 2011

(65) Prior Publication Data
US 2012/0115881 A1 May 10, 2012

Related U.S. Application Data

(60) Provisional application No. 61/224,673, filed on Jul. 10, 2009.

(51) Int. Cl.
| | | |
|---|---|---|
| A61K 31/496 | (2006.01) | |
| C07D 233/88 | (2006.01) | |
| C07D 401/12 | (2006.01) | |
| C07D 403/06 | (2006.01) | |
| C07D 405/04 | (2006.01) | |
| C07D 417/14 | (2006.01) | |

(52) U.S. Cl.
CPC ............ C07D 417/14 (2013.01); C07D 401/12 (2013.01); C07D 403/06 (2013.01); A61K 31/496 (2013.01); C07D 405/04 (2013.01); C07D 233/88 (2013.01)
USPC ............ 514/253.06; 514/253.09; 514/254.05; 514/254.07; 544/363; 544/364; 544/366; 544/370

(58) Field of Classification Search
None
See application file for complete search history.

(56) References Cited

U.S. PATENT DOCUMENTS

| | | | |
|---|---|---|---|
| 4,988,814 A | 1/1991 | Abou-Gharbia et al. | |
| 5,380,725 A | 1/1995 | Abou-Gharbia et al. | |

FOREIGN PATENT DOCUMENTS

| | | | |
|---|---|---|---|
| KR | 10-2008-0100765 A | | 11/2008 |
| WO | 2008/047883 | * | 4/2008 |

OTHER PUBLICATIONS

Seo et al. J.Med.Chem. vol. 54, pp. 6305-6318 (2011).*

* cited by examiner

*Primary Examiner* — Emily Bernhardt
(74) *Attorney, Agent, or Firm* — Sughrue Mion, PLLC

(57) ABSTRACT

A novel arylpiperazine-containing imidazole 4-carboxamide derivative or a pharmaceutically acceptable salt thereof, and a pharmaceutical composition comprising the same as an active ingredient for preventing or treating a depressive disorder are provided.

3 Claims, No Drawings

ARYLPIPERAZINE-CONTAINING IMIDAZOLE 4-CARBOXAMIDE DERIVATIVES AND PHARMACEUTICAL COMPOSITION COMPRISING SAME

FIELD OF THE INVENTION

The present invention relates to a novel arylpiperazine-containing imidazole 4-carboxamide derivative or a pharmaceutically acceptable salt thereof, and a pharmaceutical composition comprising the same as an active ingredient for preventing or treating depressive disorders.

BACKGROUND OF THE INVENTION

Depressive disorders involve all major bodily functions, mood, and thoughts, affecting the ways in which an individual eats and sleeps, feel about themselves, and think. Without treatment, depression symptoms can last for weeks, months or years. Expression is the leading cause of disability in the United States. An increasing number of treatment options have become more available over the past two decades for individuals with major depression disorder. The clinical description of depression is complex, covering a broad range of symptoms that lack a unifying biological hypothesis. Depression has both genetic and environmental components, with linkage studies suggesting it is a polygenic disorder. Modern treatment for depression, which focuses exclusively on agents that modulate monoamine neurotransmission, began with a monoamine oxidase inhibitor (MAOI). MAOIs increase serotonin and norepinephrine concentrations in the brain by inhibiting the MAO enzyme. They are highly effective in treating depression but are used only scarcely owing to potentially dangerous drug interaction effects.

A second breakthrough in depression treatment came from chlorpromazine derivatives. Imipramine, one such derivative, was exceptionally effective in patients who had severe depression. Imipramine is a tricyclic antidepressant (TCA) that acts by inhibiting cellular reuptake mechanisms for norepinephrine and serotonin to increase activity within these G protein-coupled receptor (GPCR) families. Imipramine retains activity at GPCRs, but this activity contributes to unattractive side effects. Subsequently, structural analogs of diphenhydramine were discovered as novel antidepressants. The phenoxyphenylpropylamine was used to identify fluoxetine, the first selective serotonin reuptake inhibitor (SSRI). The remarkable success of fluoxetine as an antidepressant extended to the identification of other SSRIs including paroxetine, citalopram, fluvoxamine, and sertraline. SSRIs became a family of antidepressants considered to be the current standard of drug treatment. It is thought that one cause of depression is an inadequate amount of serotonin SSRIs are said to work by preventing the reuptake of serotonin by the presynaptic neuron, thus maintaining higher levels of 5-HT in the synapse. These antidepressants typically have fewer adverse events and side effects than the tricyclics or the MAOIs, although such effects as drowsiness, dry mouth, nervousness, anxiety, insomnia, decreased appetite, and decreased ability to function sexually may occur.

Although there are a number of treatments currently available, there are still clear opportunities for improvement of existing therapies. Much research has been focused to address unmet medical needs of currently available drug therapies: slow onset of action, inability to achieve full remission, difficulty of targeting significant populations of nonresponding patients, and minimalization of residual side effects including sexual dysfunction. Recent developments include serotonin+norepinephrine reuptake inhibitors (SNRIs), and norepinephrine+dopamine reuptake inhibitors (NDRIs), implying multiple neurotransmitter pathways in the spectrum of disorders that incorporate major depression [Pacher, P. et al., *Curr. Med. Chem.* 2004, 11, 925-943]. It is the hope that drugs acting by newer mechanisms will meet some, if not all, of these unmet needs.

Along the line, SARI (serotonin antagonist/reuptake inhibitor) drugs that block both the serotonin 5-HT$_2$ receptors and the serotonin transporters have been developed. Typical examples are Bristol-Myers Squibb's nefazodone [DeBattista, C. et al., *Biol. Psychiatry,* 1998, 44, 341] and Yamanouchi's YM-992 [Hatanaka, K. et al., *Neuropharmacology,* 1997, 35(11), 1621] and Lilly's LY367265 [Pullar, I. A. et al., *Eur. J. Pharmacol.* 2000, 407(1-2), 39], the structures thereof being shown below:

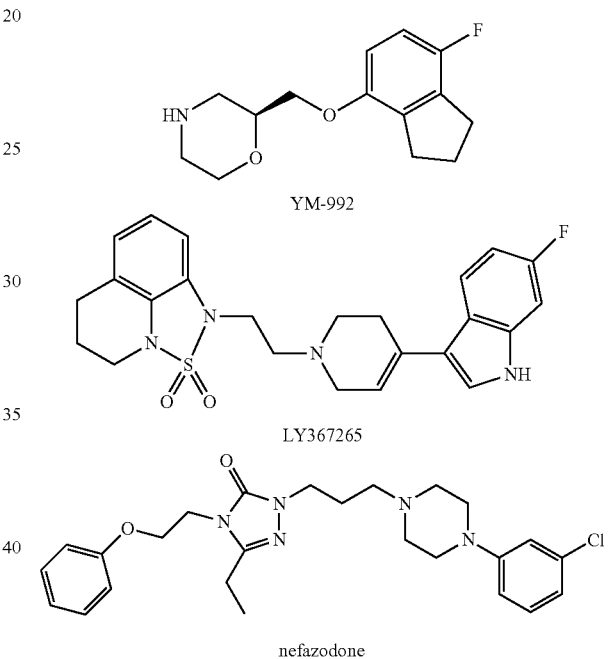

These compounds demonstrated improved results in the treatment of central nervous system disorders, compared with either the serotonin 5-HT$_2$ receptors or the selective serotonin reuptake inhibitors only, in clinical effects, side effects, reduction in drug action time, etc. [Avila, A. et al., *J. Clin. Psychopharmacol.,* 2003, 23(5), 509]. Nefazodone is most closely related to trazodone in terms of chemical structure [Temple, D. L, Jr. et al., U.S. Pat. No. 4,338,317]. Unlike most SSRIs, nefazodone is reported to have no negative effects on libido or sexual functioning Nefazodone's claimed advantages over other antidepressants include reduced possibility of disturbed sleep or sexual dysfunction, and ability to treat some patients who did not respond to other antidepressant drugs [Greene, D. S. et al., *Clin. Pharmacokinet.,* 1997, 33(4), 260]. However, nefazodone is a potent inhibitor of the CYP3A4 isoenzyme both in vitro and in vivo [Kent, J. M., *Lancet,* 2000, 355, 911-918]. In the end, its sale was discontinued in 2003 in some countries, due to the small possibility of hepatic injury, which could lead to the need for a liver transplant, or even death. At 2004, Bristol-Myers Squibb withdrew nefazodone in the United States.

In this regard, there is an urgent medical need on the discovery of new drugs that act as a mode of nefazodone, but have better developability characteristics. This new class of antidepressants would significantly broaden the physician's and patient's choice.

SUMMARY OF THE INVENTION

It is a primary object of the present invention to provide a novel compound of formula (I) or a pharmaceutically acceptable salt thereof, which is useful for preventing or treating depressive disorders.

It is another object of the present invention to provide a method for preparing said compound.

It is a further object of the present invention to provide a pharmaceutical composition for preventing or treating depressive disorders, comprising said compound as an active ingredient.

It is a still further object of the present invention to provide a method for preventing or treating depressive disorders in a mammal.

In accordance with one aspect of the present invention, there is provided an arylpiperazine-containing imidazole 4-carboxamide compound of formula (I) or a pharmaceutically acceptable salt thereof:

Wherein, $R_1$ is hydrogen, $C_{1-3}$ alkyl, or $C_{1-3}$ alkoxy;

$R_2$ is selected from the group consisting of hydrogen, carbocycle, substituted carbocycle, aryl, substituted aryl, heteroaryl, substituted heteroaryl, heterocycle, substituted heterocycle, $C_{1-8}$ alkyl optionally substituted with hydroxyl or acyloxy, $C_{1-6}$ alkoxy, substituted $C_{1-6}$ alkoxy, $C_{3-5}$ alkenyloxy, substituted $C_{3-5}$ alkenyloxy, $C_{3-5}$ alkynyloxy, substituted $C_{3-5}$ alkynyloxy, aryloxy, substituted aryloxy, heteroaryloxy, substituted heteroaryloxy or halogen, $C_{2-6}$ alkenyl optionally substituted with alkoxy or halogen, $C_{2-6}$ alkynyl optionally substituted with alkoxy or halogen, —$(CH_2)_n$—$C_{3-6}$ carbocycle optionally substituted with alkoxy or halogen, and —$(CH_2)_n$—$R_7$, n being 1 or 2;

$R_3$ is selected from the group consisting of hydrogen, $C_{1-4}$ alkyl, substituted $C_{1-4}$ alkyl, $C_{3-7}$ cycloalkyl, substituted $C_{3-7}$ cycloalkyl, aryl, substituted aryl, heteroaryl, substituted heteroaryl, heterocycloalkyl, and substituted heterocycloalkyl;

$R_4$ is hydrogen or $C_{1-3}$ alkyl;

$R_5$ and $R_6$ are each independently hydrogen, halogen, $C_{1-3}$ alkyl, $C_{1-3}$ alkoxy, cyano, monofluoromethyl, difluoromethyl or trifluoromethyl; or $R_5$ and $R_6$, together with the carbon atoms to which they are bonded, form a 5- to 7-membered saturated or unsaturated heterocyclic ring or aryl ring which is optionally substituted by one or more $C_{1-3}$ alkyl, $C_{1-3}$ alkoxy, halogen, trifluoromethyl, or cyano;

$R_7$ is phenyl, furanyl, benzofuranyl, thienyl, benzothienyl, pyridinyl, pyridiminyl, pyrazinyl, pyridizinyl, tetrahydrofuranyl, tetrahydropyranyl, dioxanyl, 1,4-benzodioxanyl, or benzo[1,3]dioxolyl, each of which is optionally substituted with one or more halogen, $C_{1-3}$ alkyl, or $C_{1-3}$ alkoxy, wherein $C_{1-3}$ alkyl and $C_{1-3}$ alkoxy optionally have one to three fluorine substituents;

m is an integer of 0 to 2;

X is —$CH_2$— when m is 0 or 2, and X is —CH(OH)—, —CHF—, or —$CF_2$— when m is 1; and Y is —N= or with the proviso that when Y is —N=, $R_5$ or $R_6$ are not bonded to Y.

In accordance with another aspect of the present invention, there is provided a method for preparing a compound of formula (I).

In accordance with a further aspect of the present invention, there is provided a pharmaceutical composition for preventing or treating a depressive disorder which comprises the compound of formula (I) or the pharmaceutically acceptable salt thereof as an active ingredient, and a pharmaceutically acceptable carrier.

In accordance with a still further aspect of the present invention, there is provided a method for preventing or treating a depressive disorder in a mammal, comprising administering the compound of formula (I) or a pharmaceutically acceptable salt thereof to the mammal in need thereof.

DETAILED DESCRIPTION OF THE INVENTION

Hereinafter, a detailed description of the present invention is given.

As used herein, the term "alkyl" refers to a straight or branched chain saturated hydrocarbon radical. Examples of "alkyl" as used herein include, but are not limited to, methyl, ethyl, n-propyl, isopropyl, n-butyl, isobutyl, t-butyl, n-pentyl, isopentyl and hexyl.

As used herein, the term "substituted alkyl" refers to a straight or branched chain saturated hydrocarbon radical, which is optionally substituted with one or more substituents selected from the group consisting of $C_{1-3}$ alkyl optionally having one to three fluorine substituents, $C_{2-3}$ alkenyl, $C_{2-3}$ alkynyl, $C_{1-2}$ alkoxy optionally having one to three fluorine substituents, sulfanyl, sulfinyl, sulfonyl, oxo, hydroxy, mercapto, amino, guanidino, carboxy, aminocarbonyl, aryl, aryloxy, heteroaryl, heteroaryloxy, heterocyclic, aminosulfonyl, sulfonylamino, carboxyamide, ureido, nitro, cyano and halogen.

As used herein, the term "alkenyl" refers to a straight or branched chain hydrocarbon radical having at least one carbon-carbon double bond. Examples of "alkenyl" as used herein include, but are not limited to, ethenyl and propenyl.

As used herein, the term "substituted alkenyl" refers to a straight or branched chain hydrocarbon radical having at least one carbon-carbon double bond, which has optional substituents selected from the group consisting of $C_{1-3}$ alkyl optionally having one to three fluorine substituents, amino, aryl, cyano and halogen.

As used herein, the term "alkynyl" refers to a straight or branched chain hydrocarbon radical having at least one carbon-carbon triple bond. Examples of "alkynyl" as used herein include, but are not limited to, acetylenyl and 1-propynyl.

As used herein, the term "substituted alkynyl" refers to a straight or branched chain hydrocarbon radical having at least one carbon-carbon triple bond, optionally having one or more substituents selected from the group consisting of $C_{1-3}$ alkyl optionally having one to three fluorine substituents, amino, aryl and halogen.

As used herein, the term "halogen" refers to fluorine (F), chlorine (Cl), bromine (Br), or iodine (I).

As used herein, the term "carbocycle" refers to a non-aromatic cyclic hydrocarbon radical composed of three to seven carbon atoms. Five- to seven-membered rings may contain a double bond in the ring structure. Exemplary "carbocycle" groups include, but are not limited to, cyclopropyl, cyclobutyl, cyclopentyl, cyclopentenyl, cyclohexyl, and cycloheptyl.

As used herein, the term "substituted carbocycle" refers to a non-aromatic cyclic hydrocarbon radical composed by three to seven carbon atoms, which is optionally substituted with one or more substituents selected from the group consisting of $C_{1-3}$ alkyl optionally having one to three fluorine substituents, $C_{2-3}$ alkenyl, $C_{2-3}$ alkynyl, $C_{1-2}$ alkoxy optionally having one to three fluorine substituents, sulfanyl, sulfinyl, sulfonyl, oxo, hydroxy, mercapto, amino, guanidino, carboxy, aminocarbonyl, aryl, aryloxy, heteroaryl, heterocyclic, aminosulfonyl, sulfonylamino, carboxyamide, nitro, ureido, cyano and halogen.

As used herein, the term "aryl" refers to an optionally substituted benzene ring or refers to a ring system which may result by fusing one or more optional substituents. Exemplary optional substituents include substituted $C_{1-3}$ alkyl, substituted $C_{2-3}$ alkenyl, substituted $C_{2-3}$ alkynyl, heteroaryl, heterocyclic, aryl, alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, or ureido. Such a ring or ring system may be optionally fused to aryl rings (including benzene rings) optionally having one or more substituents, carbocycle rings or heterocyclic rings. Examples of "aryl" groups include, but are not limited to, phenyl, naphthyl, tetrahydronaphthyl, biphenyl, indanyl, anthracyl or phenanthryl, as well as substituted derivatives thereof.

As used herein, the term "heteroaryl" refers to an optionally substituted monocyclic five to six-membered aromatic ring containing one or more heteroatomic substitutions selected from S, SO, $SO_2$, O, N, or N-oxide, or refers to such an aromatic ring fused to one or more rings such as heteroaryl rings, aryl rings, heterocyclic rings, or carbocycle rings (e.g., a bicyclic or tricyclic ring system), each having optional subsituents.

Examples of optional substituents are selected from the group consisting of substituted $C_{1-3}$ alkyl, substituted $C_{2-3}$ alkenyl, substituted $C_{2-3}$ alkynyl, heteroaryl, heterocyclic, aryl, $C_{1-3}$ alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen or ureido. Examples of "heteroaryl" groups used herein include, but are not limited to, benzoimidazolyl, benzothiazolyl, benzoisothiazolyl, benzothiophenyl, benzopyrazinyl, benzotriazolyl, benzo[1,4]dioxanyl, benzofuranyl, 9H-a-carbolinyl, cinnolinyl, furanyl, furo[2,3-b]pyridinyl, imidazolyl, imidazolidinyl, imidazopyridinyl, isoxazolyl, isothiazolyl, isoquinolinyl, indolyl, indazolyl, indolizinyl, naphthyridinyl, oxazolyl, oxothiadiazolyl, oxadiazolyl, phthalazinyl, pyridyl, pyrrolyl, purinyl, pteridinyl, phenazinyl, pyrazolyl, pyridyl, pyrazolopyrimidinyl, pyrrolizinyl, pyridazyl, pyrazinyl, pyrimidyl, 4-oxo-1,2-dihydro-4H-pyrrolo[3,2,1-ij]-quinolin-4-yl, quinoxalinyl, quinazolinyl, quinolinyl, quinolizinyl, thiophenyl, triazolyl, triazinyl, tetrazolopyrimidinyl, triazolopyrimidinyl, tetrazolyl, thiazolyl, thiazolidinyl, and substituted versions thereof.

As used herein, the term "heterocyclic" refers to a three to seven-membered ring containing one or more heteroatomic moieties selected from S, SO, $SO_2$, O, N, or N-oxide, optionally substituted with one or more substituents selected from the group which includes substituted $C_{1-3}$ alkyl, substituted $C_{2-3}$ alkenyl, substituted $C_{2-3}$ alkynyl, heteroaryl, heterocyclic, aryl, $C_{1-3}$ alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, and ureido. Such a ring can be saturated or have one or more degrees of unsaturation. Such a ring may be optionally fused to one or more "heterocyclic" ring(s), aryl ring(s), heteroaryl ring(s) or carbocycle ring(s), each having optional substituents.

Examples of "heterocyclic" moieties include, but are not limited to, 1,4-dioxanyl, 1,3-dioxanyl, pyrrolidinyl, pyrrolidin-2-onyl, piperidinyl, imidazolidine-2,4-dionepiperidinyl, piperazinyl, piperazine-2,5-dionyl, morpholinyl, dihydropyranyl, dihydrocinnolinyl, 2,3-dihydrobenzo[1,4]dioxinyl, 3,4-dihydro-2H-benzo[b][1,4]-dioxepinyl, tetrahydropyranyl, 2,3-dihydrofuranyl, 2,3-dihydrobenzofuranyl, dihydroisoxazolyl, tetrahydrobenzodiazepinyl, tetrahydroquinolinyl, tetrahydrofuranyl, tetrahydronaphthyridinyl, tetrahydropurinyl, tetrahydrothiopyranyl, tetrahydrothiophenyl, tetrahydroquinoxalinyl, tetrahydropyridinyl, tetrahydrocarbolinyl, 4H-benzo[1,3]-dioxinyl, benzo[1,3]dioxonyl, 2,2-difluorobenzo-[1,3]-dioxonyl, 2,3-dihydro-phthalazine-1,4-dionyl, and isoindole-1,3-dionyl.

As used herein, the term "alkoxy" refers to the group —$OR_a$, where $R_a$ is alkyl as defined above. Exemplary alkoxy groups useful in the present invention include, but are not limited to, methoxy, difluoromethoxy, trifluoromethoxy, ethoxy, n-propoxy, isopropoxy, n-butoxy and t-butoxy.

As used herein, the term "aralkoxy" refers to the group —$OR_aR_b$, wherein $R_a$ is alkyl and $R_b$ is aryl as defined above.

As used herein, the term "aryloxy" refers to the group —$OR_b$, wherein $R_b$ is aryl as defined above.

As used herein, the term "heteroaryloxy" refers to the group —$OC(O)R_f$, wherein $R_f$ is heteroaryl as defined above.

As used herein, the term "mercapto" refers to the group —SH.

As used herein, the term "sulfanyl" refers to the group —$SR_c$, wherein $R_c$ is substituted alkyl, substituted carbocycle, aryl, heteroaryl or heterocyclic, as defined above.

As used herein, the term "sulfinyl" refers to the group —S—(O)$R_c$, wherein $R_c$ is substituted alkyl, substituted carbocycle, aryl, heteroaryl or heterocyclic, as defined above.

As used herein, the term "sulfonyl" refers to the group —$S(O)_2R_c$, wherein $R_c$ is substituted alkyl, substituted carbocycle, aryl, heteroaryl or heterocyclic, as defined above.

As used herein, the term "oxo" refers to the group =O.

As used herein, the term "hydroxy" refers to the group —OH.

As used herein, the term "amino" refers to the group —NH$_2$. The amino group is optionally substituted with substituted alkyl, substituted carbocycle, aryl, heteroaryl or heterocyclic, as defined above.

As used herein, the term "cyano" refers to the group —CN.

As used herein, the term "aminosulfonyl" refers to the group —S(O)$_2$NH$_2$. The aminosulfonyl group is optionally substituted with substituted alkyl, substituted carbocycle, aryl, heteroaryl or heterocyclic, as defined above.

As used herein, the term "sulfonylamino" refers to the group —NHS(O)$_2$R$_c$ wherein R$_c$ is substituted alkyl, substituted carbocycle, aryl, heteroaryl or heterocyclic, as defined above.

As used herein, the term "carboxyamide" refers to the group —NHC(O)R$_c$ wherein R$_c$ is substituted alkyl, substituted carbocycle, aryl, heteroaryl or heterocyclic, as defined above.

As used herein, the term "carboxy" refers to the group —C(O)OH. The carboxy group is optionally substituted with substituted alkyl, substituted carbocycle, aryl, heteroaryl or heterocyclic, as defined above.

As used herein, the term "aminocarbonyl" refers to the group —C(O)NH$_2$. The aminocarbonyl group is optionally substituted with substituted alkyl, substituted carbocycle, aryl, heteroaryl or heterocyclic, as defined above.

As used herein, the term "ureido" refers to the group —NHC(O)NHR$_c$ wherein R$_c$ is hydrogen, alkyl, carbocycle or aryl as defined above.

As used herein, the term "guanidino" refers to the group —NHC(=NH)NH$_2$.

As used herein, the term "acyl" refers to the group —C(O)R$_c$, wherein R$_c$ is alkyl, carbocycle, or heterocyclic as defined above.

As used herein, the term "aroyl" refers to the group —C(O)R$_b$, wherein R$_b$ is aryl as defined above.

As used herein, the term "heteroaroyl" refers to the group —C(O)R$_d$, wherein R$_d$ is heteroaryl as defined above.

As used herein, the term "acyloxy" refers to the group —OC(O)R$_c$, wherein R$_c$ is alkyl, carbocycle, or heterocyclic as defined above.

As used herein, the term "aroyloxy" refers to the group —OC(O)R$_b$, wherein R$_b$ is aryl as defined above.

As used herein, the term "heteroaroyloxy" refers to the group —OC(O)R$_d$, wherein R$_d$ is heteroaryl as defined above.

In the present invention, representative examples of the arylpiperazine-containing imidazole 4-carboxamide derivative include:

1-(4-chlorophenyl)-N-(3-(4-(2,3-dichlorophenyl)piperazin-1-yl)-2-hydroxypropyl)-2-propyl-1H-imidazole-4-carboxamide;

1-(4-chlorophenyl)-N-(3-(4-(2,3-dichlorophenyl)piperazin-1-yl)propyl)-2-propyl-1H-imidazole-4-carboxamide dihydrochloride;

1-(4-chlorophenyl)-N-(3-(4-(2,3-dimethylphenyl)piperazin-1-yl)propyl)-2-propyl-1H-imidazole-4-carboxamide;

1-(4-chlorophenyl)-N-(2-(4-(2,3-dichlorophenyl)piperazin-1-yl)ethyl)-2-propyl-1H-imidazole-4-carboxamide;

N-(3-(4-(2,3-dichlorophenyl)piperazin-1-yl)-2-hydroxypropyl)-2,5-dimethyl-1-phenyl-1H-imidazole-4-carboxamide;

N-(3-(4-(2,3-dichlorophenyl)piperazin-1-yl)propyl)-2,5-dimethyl-1-phenyl-1H-imidazole-4-carboxamide;

N-(3-(4-(2,3-dichlorophenyl)piperazin-1-yl)propyl)-5-methyl-1-phenyl-2-propyl-1H-imidazole-4-carboxamide dihydrochloride;

N-(2-(4-(2,3-dichlorophenyl)piperazin-1-yl)ethyl)-2,5-dimethyl-1-phenyl-1H-imidazole-4-carboxamide;

N-(2-(4-(2,3-dichlorophenyl)piperazin-1-yl)ethyl)-5-methyl-1-phenyl-2-propyl-1H-imidazole-4-carboxamide;

N-(3-(4-(2,3-dichlorophenyl)piperazin-1-yl)propyl)-1-(4-methoxyphenyl)-2,5-dimethyl-1H-imidazole-4-carboxamide;

1-(4-chlorophenyl)-N-(3-(4-(2,3-dichlorophenyl)piperazin-1-yl)propyl)-2,5-dimethyl-1H-imidazole-4-carboxamide;

N-(3-(4-(2,3-dichlorophenyl)piperazin-1-yl)propyl)-2-ethyl-5-methyl-1-phenyl-1H-imidazole-4-carboxamide;

N-(2-(4-(2,3-dichlorophenyl)piperazin-1-yl)ethyl)-2-ethyl-5-methyl-1-phenyl-1H-imidazole-4-carboxamide;

N-(2-(4-(2,3-dimethylphenyl)piperazin-1-yl)ethyl)-2,5-dimethyl-1-phenyl-1H-imidazole-4-carboxamide;

N-(3-(4-(2,3-dimethylphenyl)piperazin-1-yl)propyl)-2,5-dimethyl-1-phenyl-1H-imidazole-4-carboxamide;

N-(3-(4-(2,3-dimethylphenyl)piperazin-1-yl)propyl)-2-ethyl-5-methyl-1-phenyl-1H-imidazole-4-carboxamide;

N-(3-(4-(2,3-dimethylphenyl)piperazin-1-yl)propyl)-5-methyl-1-phenyl-2-propyl-1H-imidazole-4-carboxamide dihydrochloride;

N-(2-(4-(2,3-dimethylphenyl)piperazin-1-yl)ethyl)-2-ethyl-5-methyl-1-phenyl-1H-imidazole-4-carboxamide;

N-(2-(4-(2,3-dimethylphenyl)piperazin-1-yl)ethyl)-5-methyl-1-phenyl-2-propyl-1H-imidazole-4-carboxamide dihydrochloride;

N-(3-(4-(2,3-dichlorophenyl)piperazin-1-yl)propyl)-1-(4-fluorophenyl)-2,5-dimethyl-1H-imidazole-4-carboxamide;

N-(2-(4-(2,3-dichlorophenyl)piperazin-1-yl)ethyl)-1-(4-fluorophenyl)-2,5-dimethyl-1H-imidazole-4-carboxamide;

1-(4-chlorophenyl)-N-(3-(4-(2,3-dimethylphenyl)piperazin-1-yl)propyl)-2,5-dimethyl-1H-imidazole-4-carboxamide;

N-(3-(4-(2,3-dichlorophenyl)piperazin-1-yl)-2-hydroxypropyl)-2-ethyl-5-methyl-1-phenyl-1H-imidazole-4-carboxamide;

N-(3-(4-(2,3-dichlorophenyl)piperazin-1-yl)-2-hydroxypropyl)-5-methyl-1-phenyl-2-propyl-1H-imidazole-4-carboxamide;

1-(4-chlorophenyl)-N-(3-(4-(2,3-dichlorophenyl)piperazin-1-yl)propyl)-2-ethyl-5-methyl-1H-imidazole-4-carboxamide;

N-(3-(4-(2,3-dichlorophenyl)piperazin-1-yl)-2-hydroxypropyl)-1-(4-fluorophenyl)-2,5-dimethyl-1H-imidazole-4-carboxamide;

1-(4-chlorophenyl)-N-(2-(4-(2,3-dichlorophenyl)piperazin-1-yl)ethyl)-2,5-dimethyl-1H-imidazole-4-carboxamide;

1-(4-chlorophenyl)-N-(2-(4-(2,3-dichlorophenyl)piperazin-1-yl)ethyl)-2-ethyl-5-methyl-1H-imidazole-4-carboxamide;

N-(3-(4-(2,3-dichlorophenyl)piperazin-1-yl)propyl)-2,5-dimethyl-1-p-tolyl-1H-imidazole-4-carboxamide;

N-(2-(4-(2,3-dichlorophenyl)piperazin-1-yl)ethyl)-2,5-dimethyl-1-p-tolyl-1H-imidazole-4-carboxamide;

N-(3-(4-(2,3-dichlorophenyl)piperazin-1-yl)-2-hydroxypropyl)-2,5-dimethyl-1-p-tolyl-1H-imidazole-4-carboxamide;

1-(4-chlorophenyl)-N-(3-(4-(2,3-dichlorophenyl)piperazin-1-yl)-2-hydroxypropyl)-2,5-dimethyl-1H-imidazole-4-carboxamide;

1-(4-chlorophenyl)-N-(3-(4-(2,3-dichlorophenyl)piperazin-1-yl)-2-hydroxypropyl)-2-ethyl-5-methyl-1H-imidazole-4-carboxamide;

N-(3-(4-(2,3-dimethylphenyl)piperazin-1-yl)propyl)-1-(4-fluorophenyl)-2,5-dimethyl-1H-imidazole-4-carboxamide;

N-(3-(4-(2,3-dimethylphenyl)piperazin-1-yl)-2-hydroxypropyl)-1-(4-fluorophenyl)-2,5-dimethyl-1H-imidazole-4-carboxamide;

N-(3-(4-(2,3-dimethylphenyl)piperazin-1-yl)-2-hydroxypropyl)-2,5-dimethyl-1-phenyl-1H-imidazole-4-carboxamide;

N-(3-(4-(2,3-dimethylphenyl)piperazin-1-yl)propyl)-2,5-dimethyl-1-(4-(trifluoromethyl)phenyl)-1H-imidazole-4-carboxamide;

1-(benzo[d][1,3]dioxol-5-yl)-N-(3-(4-(2,3-dimethylphenyl)piperazin-1-yl)propyl)-2,5-dimethyl-1H-imidazole-4-carboxamide;

1-(benzo[d][1,3]dioxol-5-yl)-N-(3-(4-(2,3-dimethylphenyl)piperazin-1-yl)-2-hydroxypropyl)-2,5-dimethyl-1H-imidazole-4-carboxamide;

1-(2,3-dihydrobenzo[b][1,4]dioxin-6-yl)-N-(3-(4-(2,3-dimethylphenyl)piperazin-1-yl)propyl)-2,5-dimethyl-1H-imidazole-4-carboxamide;

1-(2,3-dihydrobenzo[b][1,4]dioxin-6-yl)-N-(3-(4-(2,3-dimethylphenyl)piperazin-1-yl)-2-hydroxypropyl)-2,5-dimethyl-1H-imidazole-4-carboxamide;

N-(2-(4-(2,3-dichlorophenyl)piperazin-1-yl)ethyl)-1-(4-methoxyphenyl)-2,5-dimethyl-1H-imidazole-4-carboxamide;

N-(3-(4-(2,3-dichlorophenyl)piperazin-1-yl)-2-hydroxypropyl)-1-(4-methoxyphenyl)-2,5-dimethyl-1H-imidazole-4-carboxamide;

N-(3-(4-(2,3-dichlorophenyl)piperazin-1-yl)propyl)-2-ethyl-1-(4-methoxyphenyl)-5-methyl-1H-imidazole-4-carboxamide;

N-(3-(4-(2,3-dichlorophenyl)piperazin-1-yl)-2-hydroxypropyl)-2-ethyl-1-(4-methoxyphenyl)-5-methyl-1H-imidazole-4-carboxamide;

N-(2-(4-(2,3-dimethylphenyl)piperazin-1-yl)ethyl)-1-(4-methoxyphenyl)-2,5-dimethyl-1H-imidazole-4-carboxamide;

N-(3-(4-(2,3-dimethylphenyl)piperazin-1-yl)propyl)-1-(4-methoxyphenyl)-2,5-dimethyl-1H-imidazole-4-carboxamide;

1-(3-chlorophenyl)-N-(3-(4-(2,3-dimethylphenyl)piperazin-1-yl)propyl)-2,5-dimethyl-1H-imidazole-4-carboxamide;

1-(3-chlorophenyl)-N-(3-(4-(2,3-dimethylphenyl)piperazin-1-yl)-2-hydroxypropyl)-2,5-dimethyl-1H-imidazole-4-carboxamide;

N-(3-(4-(3-chloro-2-methylphenyl)piperazin-1-yl)propyl)-1-(3-chlorophenyl)-2,5-dimethyl-1H-imidazole-4-carboxamide;

N-(3-(4-(3-chloro-2-methylphenyl)piperazin-1-yl)-2-hydroxypropyl)-1-(3-chlorophenyl)-2,5-dimethyl-1H-imidazole-4-carboxamide;

N-(3-(4-(2,3-dimethylphenyl)piperazin-1-yl)propyl)-1-(3-fluorophenyl)-2,5-dimethyl-1H-imidazole-4-carboxamide;

N-(3-(4-(2,3-dimethylphenyl)piperazin-1-yl)-2-hydroxypropyl)-1-(3-fluorophenyl)-2,5-dimethyl-1H-imidazole-4-carboxamide;

1-(3,4-dimethoxyphenyl)-N-(3-(4-(2,3-dimethylphenyl)piperazin-1-yl)propyl)-2,5-dimethyl-1H-imidazole-4-carboxamide;

1-(3,4-dimethoxyphenyl)-N-(3-(4-(2,3-dimethylphenyl)piperazin-1-yl)-2-hydroxypropyl)-2,5-dimethyl-1H-imidazole-4-carboxamide;

N-(3-(4-(2,3-dimethylphenyl)piperazin-1-yl)-2-hydroxypropyl)-1-(4-methoxyphenyl)-2,5-dimethyl-1H-imidazole-4-carboxamide;

N-(3-(4-(2,3-dimethylphenyl)piperazin-1-yl)propyl)-2,5-dimethyl-1-(4-(methylthio)phenyl)-1H-imidazole-4-carboxamide;

N-(3-(4-(2,3-dimethylphenyl)piperazin-1-yl)-2-hydroxypropyl)-2,5-dimethyl-1-(4-(methylthio)phenyl)-1H-imidazole-4-carboxamide;

N-(3-(4-(2,3-dimethylphenyl)piperazin-1-yl)propyl)-1-(3-methoxyphenyl)-2,5-dimethyl-1H-imidazole-4-carboxamide;

N-(3-(4-(2,3-dimethylphenyl)piperazin-1-yl)-2-hydroxypropyl)-1-(3-methoxyphenyl)-2,5-dimethyl-1H-imidazole-4-carboxamide;

1-(2,4-dimethoxyphenyl)-N-(3-(4-(2,3-dimethylphenyl)piperazin-1-yl)propyl)-2,5-dimethyl-1H-imidazole-4-carboxamide;

1-(2,4-dimethoxyphenyl)-N-(3-(4-(2,3-dimethylphenyl)piperazin-1-yl)-2-hydroxypropyl)-2,5-dimethyl-1H-imidazole-4-carboxamide;

(S)—N-(3-(4-(2,3-dichlorophenyl)piperazin-1-yl)-2-hydroxypropyl)-2,5-dimethyl-1-phenyl-1H-imidazole-4-carboxamide;

(S)—N-(3-(4-(2,3-dichlorophenyl)piperazin-1-yl)-2-hydroxypropyl)-5-methyl-1-phenyl-2-propyl-1H-imidazole-4-carboxamide;

N-(3-(4-(2,3-dichlorophenyl)piperazin-1-yl)-2,2-difluoropropyl)-2,5-dimethyl-1-phenyl-1H-imidazole-4-carboxamide;

N-(3-(4-(2,3-dichlorophenyl)piperazin-1-yl)-2,2-difluoropropyl)-5-methyl-1-phenyl-2-propyl-1H-imidazole-4-carboxamide;

N-(3-(4-(2,3-dimethylphenyl)piperazin-1-yl)propyl)-1-(2-fluorophenyl)-2,5-dimethyl-1H-imidazole-4-carboxamide;

N-(3-(4-(2,3-dimethylphenyl)piperazin-1-yl)-2-hydroxypropyl)-1-(2-fluorophenyl)-2,5-dimethyl-1H-imidazole-4-carboxamide;

N-(2-(4-(3-chloro-2-fluorophenyl)piperazin-1-yl)ethyl)-2,5-dimethyl-1-phenyl-1H-imidazole-4-carboxamide;

N-(3-(4-(3-chloro-2-fluorophenyl)piperazin-1-yl)propyl)-2,5-dimethyl-1-phenyl-1H-imidazole-4-carboxamide;

N-(2-(4-(3-chloro-2-methylphenyl)piperazin-1-yl)ethyl)-2,5-dimethyl-1-phenyl-1H-imidazole-4-carboxamide;

N-(3-(4-(3-chloro-2-methylphenyl)piperazin-1-yl)propyl)-2,5-dimethyl-1-phenyl-1H-imidazole-4-carboxamide;

2,5-dimethyl-N-(2-(4-(2-methylquinolin-8-yl)piperazin-1-yl)ethyl)-1-phenyl-1H-imidazole-4-carboxamide;

2,5-dimethyl-1-phenyl-N-(2-(4-(quinolin-8-yl)piperazin-1-yl)ethyl)-1H-imidazole-4-carboxamide;

N-(3-(4-(3-chloro-2-methylphenyl)piperazin-1-yl)-2-hydroxypropyl)-2,5-dimethyl-1-phenyl-1H-imidazole-4-carboxamide;

1-cyclopentyl-N-(3-(4-(2,3-dimethylphenyl)piperazin-1-yl)propyl)-2,5-dimethyl-1H-imidazole-4-carboxamide;

1-cyclopentyl-N-(3-(4-(2,3-dimethylphenyl)piperazin-1-yl)-2-hydroxypropyl)-2,5-dimethyl-1H-imidazole-4-carboxamide;

N-(3-(4-(3-chloro-2-methylphenyl)piperazin-1-yl)propyl)-1-cyclopentyl-2,5-dimethyl-1H-imidazole-4-carboxamide;

N-(3-(4-(3-chloro-2-methylphenyl)piperazin-1-yl)-2-hydroxypropyl)-1-cyclopentyl-2,5-dimethyl-1H-imidazole-4-carboxamide;

1-cyclopentyl-N-(4-(4-(2,3-dimethylphenyl)piperazin-1-yl)butyl)-2,5-dimethyl-1H-imidazole-4-carboxamide;

1-cyclopentyl-N-(2-(4-(2,3-dichlorophenyl)piperazin-1-yl)ethyl)-2,5-dimethyl-1H-imidazole-4-carboxamide;

N-(3-(4-(2,3-dimethylphenyl)piperazin-1-yl)-2-hydroxypropyl)-1-(4-fluorophenyl)-5-methyl-2-phenyl-1H-imidazole-4-carboxamide;

N-(3-(4-(2,3-dimethylphenyl)piperazin-1-yl)propyl)-1-(4-fluorophenyl)-5-methyl-2-phenyl-1H-imidazole-4-carboxamide;

N-(3-(4-(3-chloro-2-methylphenyl)piperazin-1-yl)-2-hydroxypropyl)-1-(4-fluorophenyl)-5-methyl-2-phenyl-1H-imidazole-4-carboxamide;

N-(3-(4-(3-chloro-2-methylphenyl)piperazin-1-yl)propyl)-1-(4-fluorophenyl)-5-methyl-2-phenyl-1H-imidazole-4-carboxamide;

N-(3-(4-(2,3-dimethylphenyl)piperazin-1-yl)propyl)-5-methyl-1,2-diphenyl-1H-imidazole-4-carboxamide;

N-(3-(4-(3-chloro-2-methylphenyl)piperazin-1-yl)propyl)-5-methyl-1,2-diphenyl-1H-imidazole-4-carboxamide;

1-(4-bromophenyl)-N-(3-(4-(3-chlorophenyl)piperazin-1-yl)propyl)-2-(2,4-dichlorophenyl)-5-ethyl-1H-imidazole-4-carboxamide;

1-(4-bromophenyl)-2-(2,4-dichlorophenyl)-N-(3-(4-(2,3-dichlorophenyl)piperazin-1-yl)propyl)-5-ethyl-1H-imidazole-4-carboxamide;

1-(4-bromophenyl)-2-(2,4-dichlorophenyl)-N-(3-(4-(2,3-dimethylphenyl)piperazin-1-yl)propyl)-5-ethyl-1H-imidazole-4-carboxamide;

5-((1H-1,2,4-triazol-1-yl)methyl)-N-(3-(4-(3-chloro-2-methylphenyl)piperazin-1-yl)propyl)-1,2-diphenyl-1H-imidazole-4-carboxamide;

N-(3-(4-(2,3-dimethylphenyl)piperazin-1-yl)propyl)-1-isobutyl-2,5-dimethyl-1H-imidazole-4-carboxamide;

N-(3-(4-(3-chloro-2-methylphenyl)piperazin-1-yl)propyl)-1-isobutyl-2,5-dimethyl-1H-imidazole-4-carboxamide N-(3-(4-(2,3-dimethylphenyl)piperazin-1-yl)-2-hydroxypropyl)-1-isobutyl-2,5-dimethyl-1H-imidazole-4-carboxamide N-(3-(4-(2,3-dimethylphenyl)piperazin-1-yl)propyl)-2,5-dimethyl-1-propyl-1H-imidazole-4-carboxamide;

N-(3-(4-(2,3-dimethylphenyl)piperazin-1-yl)-2-hydroxypropyl)-2,5-dimethyl-1-propyl-1H-imidazole-4-carboxamide;

N-(3-(4-(3-chloro-2-methylphenyl)piperazin-1-yl)propyl)-2,5-dimethyl-1-propyl-1H-imidazole-4-carboxamide;

N-(3-(4-(3-chloro-2-methylphenyl)piperazin-1-yl)-2-hydroxypropyl)-2,5-dimethyl-1-propyl-1H-imidazole-4-carboxamide;

N-(3-(4-(2,3-dimethylphenyl)piperazin-1-yl)propyl)-1-(2-methoxyphenyl)-2,5-dimethyl-1H-imidazole-4-carboxamide;

N-(3-(4-(2,3-dimethylphenyl)piperazin-1-yl)-2-hydroxypropyl)-1-(2-methoxyphenyl)-2,5-dimethyl-1H-imidazole-4-carboxamide;

1-(2-chlorophenyl)-N-(3-(4-(2,3-dimethylphenyl)piperazin-1-yl)propyl)-2,5-dimethyl-1H-imidazole-4-carboxamide;

1-(2-chlorophenyl)-N-(3-(4-(2,3-dimethylphenyl)piperazin-1-yl)-2-hydroxypropyl)-2,5-dimethyl-1H-imidazole-4-carboxamide;

1-(2-chlorophenyl)-N-(4-(4-(2,3-dimethylphenyl)piperazin-1-yl)butyl)-2,5-dimethyl-1H-imidazole-4-carboxamide;

N-(3-(4-(2,3-dimethylphenyl)piperazin-1-yl)propyl)-2-isopropyl-5-methyl-1-phenyl-1H-imidazole-4-carboxamide;

1-(3,5-dimethoxyphenyl)-N-(3-(4-(2,3-dimethylphenyl)piperazin-1-yl)propyl)-2,5-dimethyl-1H-imidazole-4-carboxamide;

N-(3-(4-(2,3-dimethylphenyl)piperazin-1-yl)-2-hydroxypropyl)-2-isopropyl-5-methyl-1-phenyl-1H-imidazole-4-carboxamide;

1-(3,5-dimethoxyphenyl)-N-(3-(4-(2,3-dimethylphenyl)piperazin-1-yl)-2-hydroxypropyl)-2,5-dimethyl-1H-imidazole-4-carboxamide;

N-(3-(4-(2,3-dimethylphenyl)piperazin-1-yl)-2-hydroxypropyl)-2,5-dimethyl-1-(4-(trifluoromethyl)phenyl)-1H-imidazole-4-carboxamide;

N-(3-(4-(2,3-dimethylphenyl)piperazin-1-yl)-2-hydroxypropyl)-2-ethyl-5-methyl-1-phenyl-1H-imidazole-4-carboxamide;

N-(3-(4-(2,3-dimethylphenyl)piperazin-1-yl)-2-hydroxypropyl)-5-methyl-1-phenyl-2-propyl-1H-imidazole-4-carboxamide;

1-(4-chlorophenyl)-N-(3-(4-(2,3-dimethylphenyl)piperazin-1-yl)-2-hydroxypropyl)-2-propyl-1H-imidazole-4-carboxamide;

1-(3,5-dimethoxyphenyl)-N-(2-(4-(2,3-dimethylphenyl)piperazin-1-yl)ethyl)-2,5-dimethyl-1H-imidazole-4-carboxamide;

N-(2-(4-(2,3-dimethylphenyl)piperazin-1-yl)ethyl)-2-isopropyl-5-methyl-1-phenyl-1H-imidazole-4-carboxamide;

N-(2-(4-(2,3-dimethylphenyl)piperazin-1-yl)ethyl)-1-(4-fluorophenyl)-2,5-dimethyl-1H-imidazole-4-carboxamide;

1-(benzo[d][1,3]dioxol-5-yl)-N-(2-(4-(2,3-dimethylphenyl)piperazin-1-yl)ethyl)-2,5-dimethyl-1H-imidazole-4-carboxamide;

1-(2,3-dihydrobenzo[b][1,4]dioxin-6-yl)-N-(2-(4-(2,3-dimethylphenyl)piperazin-1-yl)ethyl)-2,5-dimethyl-1H-imidazole-4-carboxamide;

N-(3-(4-(2,3-dimethylphenyl)piperazin-1-yl)propyl)-1-phenyl-2-propyl-1H-imidazole-4-carboxamide;

N-(3-(4-(2,3-dichlorophenyl)piperazin-1-yl)propyl)-1-phenyl-2-propyl-1H-imidazole-4-carboxamide;

N-(2-(4-(2,3-dichlorophenyl)piperazin-1-yl)ethyl)-1-phenyl-2-propyl-1H-imidazole-4-carboxamide;

N-(2-(4-(2,3-dimethylphenyl)piperazin-1-yl)ethyl)-1-phenyl-2-propyl-1H-imidazole-4-carboxamide;

N-(3-(4-(2,3-dimethylphenyl)piperazin-1-yl)-2-hydroxypropyl)-1-phenyl-2-propyl-1H-imidazole-4-carboxamide;

N-(3-(4-(2,3-dimethylphenyl)piperazin-1-yl)propyl)-1-(4-methoxyphenyl)-5-methyl-2-propyl-1H-imidazole-4-carboxamide;

N-(2-(4-(2,3-dimethylphenyl)piperazin-1-yl)ethyl)-1-(4-methoxyphenyl)-5-methyl-2-propyl-1H-imidazole-4-carboxamide;

N-(3-(4-(2,3-dimethylphenyl)piperazin-1-yl)propyl)-2,5-dimethyl-1-(quinolin-6-yl)-1H-imidazole-4-carboxamide;

N-(3-(4-(2,3-dichlorophenyl)piperazin-1-yl)-2-hydroxypropyl)-2,5-dimethyl-1-(quinolin-6-yl)-1H-imidazole-4-carboxamide;

N-(3-(4-(2,3-dichlorophenyl)piperazin-1-yl)-2-hydroxypropyl)-1-phenyl-2-propyl-1H-imidazole-4-carboxamide;

N-(3-(4-(2,3-dichlorophenyl)piperazin-1-yl)-2-hydroxypropyl)-1-(4-fluorophenyl)-2-propyl-1H-imidazole-4-carboxamide;

N-(3-(4-(2,3-dimethylphenyl)piperazin-1-yl)-2-hydroxypropyl)-1-(4-fluorophenyl)-2-propyl-1H-imidazole-4-carboxamide;

N-(3-(4-(2,3-dimethylphenyl)piperazin-1-yl)propyl)-1-(4-fluorophenyl)-2-propyl-1H-imidazole-4-carboxamide;

N-(3-(4-(2,3-dichlorophenyl)piperazin-1-yl)-2-hydroxypropyl)-1,2-diphenyl-1H-imidazole-4-carboxamide;

N-(3-(4-(2,3-dimethylphenyl)piperazin-1-yl)propyl)-1,2-diphenyl-1H-imidazole-4-carboxamide;

N-(3-(4-(2,3-dimethylphenyl)piperazin-1-yl)propyl)-2,5-dimethyl-1-(pyridin-2-yl)-1H-imidazole-4-carboxamide trihydrochloride;

N-(3-(4-(2,3-dichlorophenyl)piperazin-1-yl)-2-hydroxypropyl)-1-(4-methoxyphenyl)-2-phenyl-1H-imidazole-4-carboxamide;

N-(3-(4-(2,3-dimethylphenyl)piperazin-1-yl)propyl)-1-(4-methoxyphenyl)-2-phenyl-1H-imidazole-4-carboxamide;

N-(3-(4-(3-chloro-2-methylphenyl)piperazin-1-yl)propyl)-1-(4-methoxyphenyl)-5-methyl-2-propyl-1H-imidazole-4-carboxamide;

N-(3-(4-(2,3-dichlorophenyl)piperazin-1-yl)-2-hydroxypropyl)-1-(4-methoxyphenyl)-5-methyl-2-propyl-1H-imidazole-4-carboxamide;

N-(3-(4-(2,3-dimethylphenyl)piperazin-1-yl)-2-hydroxypropyl)-1-(4-methoxyphenyl)-5-methyl-2-propyl-1H-imidazole-4-carboxamide;

N-(3-(4-(3-chloro-2-methylphenyl)piperazin-1-yl)propyl)-1-(4-methoxyphenyl)-2,5-dimethyl-1H-imidazole-4-carboxamide;

(S)—N-(3-(4-(2,3-dimethylphenyl)piperazin-1-yl)-2-hydroxypropyl)-2,5-dimethyl-1-phenyl-1H-imidazole-4-carboxamide;

N—((S)-3-(4-(2,3-dimethylphenyl)piperazin-1-yl)-2-hydroxypropyl)-1-(2-fluorophenyl)-2,5-dimethyl-1H-imidazole-4-carboxamide;

(S)-1-(4-chlorophenyl)-N-(3-(4-(2,3-dichlorophenyl)piperazin-1-yl)-2-hydroxypropyl)-2-propyl-1H-imidazole-4-carboxamide;

(S)—N-(3-(4-(3-chloro-2-methylphenyl)piperazin-1-yl)-2-hydroxypropyl)-1-(4-fluorophenyl)-5-methyl-2-phenyl-1H-imidazole-4-carboxamide;

N-(3-(4-(2,3-dichlorophenyl)piperazin-1-yl)propyl)-1-(4-methoxyphenyl)-5-methyl-2-propyl-1H-imidazole-4-carboxamide;

N-(3-(4-(3-chloro-2-methylphenyl)piperazin-1-yl)propyl)-1-(2-methoxyphenyl)-2,5-dimethyl-1H-imidazole-4-carboxamide;

N-(3-(4-(2,3-dichlorophenyl)piperazin-1-yl)propyl)-1-(2-methoxyphenyl)-2,5-dimethyl-1H-imidazole-4-carboxamide;

N-(3-(4-(2,3-dichlorophenyl)piperazin-1-yl)-2-hydroxypropyl)-1-(2-methoxyphenyl)-2,5-dimethyl-1H-imidazole-4-carboxamide;

N-(3-(4-(2,3-dimethylphenyl)piperazin-1-yl)propyl)-2,5-dimethyl-1-p-tolyl-1H-imidazole-4-carboxamide;

N-(3-(4-(2,3-dimethylphenyl)piperazin-1-yl)-2-hydroxypropyl)-2,5-dimethyl-1-p-tolyl-1H-imidazole-4-carboxamide;

N-(3-(4-(2,3-dichlorophenyl)piperazin-1-yl)-2-hydroxypropyl)-1-(2,3-dihydrobenzo[b][1,4]dioxin-6-yl)-2,5-dimethyl-1H-imidazole-4-carboxamide;

N-(3-(4-(2,3-dichlorophenyl)piperazin-1-yl)propyl)-1-(2,3-dihydrobenzo[b][1,4]dioxin-6-yl)-2,5-dimethyl-1H-imidazole-4-carboxamide;

(R)—N-(3-(4-(2,3-dimethyl-phenyl)piperazin-1-yl)-2-hydroxypropyl)-2,5-dimethyl-1-phenyl-1H-imidazole-4-carboxamide;

N—((R)-3-(4-(2,3-dimethyl-phenyl)piperazin-1-yl)-2-hydroxypropyl)-1-(2-fluorophenyl)-2,5-dimethyl-1H-imidazole-4-carboxamide;

N-(3-(4-(3-chloro-2-methylphenyl)piperazin-1-yl)propyl)-1-(2-fluorophenyl)-2,5-dimethyl-1H-imidazole-4-carboxamide;

N-(3-(4-(2,3-dichlorophenyl)piperazin-1-yl)propyl)-1-(2-fluorophenyl)-2,5-dimethyl-1H-imidazole-4-carboxamide;

N-(3-(4-(2,3-dimethylphenyl)piperazin-1-yl)-2-hydroxypropyl)-5-methyl-1,2-diphenyl-1H-imidazole-4-carboxamide;

N-(3-(4-(2,3-dichlorophenyl)piperazin-1-yl)-2-hydroxypropyl)-5-methyl-1,2-diphenyl-1H-imidazole-4-carboxamide;

N-(3-(4-(2,3-dichlorophenyl)piperazin-1-yl)-2-hydroxypropyl)-1-(4-fluorophenyl)-5-methyl-2-phenyl-1H-imidazole-4-carboxamide;

N-(3-(4-(2,3-dichlorophenyl)piperazin-1-yl)propyl)-5-methyl-1,2-diphenyl-1H-imidazole-4-carboxamide;

N-(3-(4-(2,3-dichlorophenyl)piperazin-1-yl)propyl)-1-(4-fluorophenyl)-5-methyl-2-phenyl-1H-imidazole-4-carboxamide;

N-(3-(4-(3-chloro-2-methylphenyl)piperazin-1-yl)-2-hydroxypropyl)-5-methyl-1,2-diphenyl-1H-imidazole-4-carboxamide;

N-(3-(4-(3-chloro-2-methylphenyl)piperazin-1-yl)-2-hydroxypropyl)-1-(4-fluorophenyl)-5-methyl-2-propyl-1H-imidazole-4-carboxamide;

N-(3-(4-(3-chloro-2-methylphenyl)piperazin-1-yl)-2-hydroxypropyl)-1-(4-fluorophenyl)-2,5-dimethyl-1H-imidazole-4-carboxamide;

1-cyclopentyl-N-(3-(4-(2,3-dichlorophenyl)piperazin-1-yl)propyl)-2,5-dimethyl-1H-imidazole-4-carboxamide;

1-cyclopentyl-N-(3-(4-(2,3-dichlorophenyl)piperazin-1-yl)-2-hydroxypropyl)-2,5-dimethyl-1H-imidazole-4-carboxamide;

N-(3-(4-(2,3-dichlorophenyl)piperazin-1-yl)propyl)-2,5-dimethyl-1-propyl-1H-imidazole-4-carboxamide;

N-(3-(4-(2,3-dichlorophenyl)piperazin-1-yl)-2-hydroxypropyl)-2,5-dimethyl-1-propyl-1H-imidazole-4-carboxamide;

N-(3-(4-(2,3-dimethylphenyl)piperazin-1-yl)propyl)-1-(2-methoxyphenyl)-5-methyl-2-propyl-1H-imidazole-4-carboxamide;

N-(3-(4-(3-chloro-2-methylphenyl)piperazin-1-yl)propyl)-1-(2-methoxyphenyl)-5-methyl-2-propyl-1H-imidazole-4-carboxamide;

N-(3-(4-(2,3-dichlorophenyl)piperazin-1-yl)propyl)-1-(2-methoxyphenyl)-5-methyl-2-propyl-1H-imidazole-4-carboxamide;

N-(3-(4-(2,3-dimethylphenyl)piperazin-1-yl)-2-hydroxypropyl)-1-(2-methoxyphenyl)-5-methyl-2-propyl-1H-imidazole-4-carboxamide;

N-(3-(4-(3-chloro-2-methylphenyl)piperazin-1-yl)-2-hydroxypropyl)-1-(2-methoxyphenyl)-5-methyl-2-propyl-1H-imidazole-4-carboxamide;

N-(3-(4-(2,3-dichlorophenyl)piperazin-1-yl)-2-hydroxypropyl)-1-(2-methoxyphenyl)-5-methyl-2-propyl-1H-imidazole-4-carboxamide;

N-(3-(4-(2,3-dimethylphenyl)piperazin-1-yl)propyl)-2,5-dimethyl-1-(2-(trifluoromethyl)phenyl)-1H-imidazole-4-carboxamide;

N-(3-(4-(3-chloro-2-methylphenyl)piperazin-1-yl)propyl)-2,5-dimethyl-1-(2-(trifluoromethyl)phenyl)-1H-imidazole-4-carboxamide;

N-(3-(4-(2,3-dichlorophenyl)piperazin-1-yl)propyl)-2,5-dimethyl-1-(2-(trifluoromethyl)phenyl)-1H-imidazole-4-carboxamide;

N-(3-(4-(3-chloro-2-methylphenyl)piperazin-1-yl)-2-hydroxypropyl)-2,5-dimethyl-1-(2-(trifluoromethyl)phenyl)-1H-imidazole-4-carboxamide;

N-(3-(4-(2,3-dichlorophenyl)piperazin-1-yl)-2-hydroxypropyl)-2,5-dimethyl-1-(2-(trifluoromethyl)phenyl)-1H-imidazole-4-carboxamide;

N-(3-(4-(3-chloro-2-methylphenyl)piperazin-1-yl)-2-hydroxypropyl)-1-(4-methoxyphenyl)-5-methyl-2-propyl-1H-imidazole-4-carboxamide;

N-(3-(4-(3-chloro-2-methylphenyl)piperazin-1-yl)-2-hydroxypropyl)-1-(2-methoxyphenyl)-2,5-dimethyl-1H-imidazole-4-carboxamide;

N-(3-(4-(3-chloro-2-methylphenyl)piperazin-1-yl)-2-hydroxypropyl)-1-(4-chlorophenyl)-2-propyl-1H-imidazole-4-carb oxamide;

N-(3-(4-(3-chloro-2-methylphenyl)piperazin-1-yl)propyl)-1-(4-chlorophenyl)-2-propyl-1H-imidazole-4-carboxamide;

N-(3-(4-(3-chloro-2-methylphenyl)piperazin-1-yl)-2-hydroxypropyl)-1-(2,3-dihydrobenzo[b][1,4]dioxin-6-yl)-2,5-dimethyl-1H-imidazole-4-carboxamide;

N-(3-(4-(3-chloro-2-methylphenyl)piperazin-1-yl)propyl)-1-(2,3-dihydrobenzo[b][1,4]dioxin-6-yl)-2,5-dimethyl-1H-imidazole-4-carboxamide;

1-(2,3-dihydrobenzo[b][1,4]dioxin-6-yl)-N-(3-(4-(2,3-dimethylphenyl)piperazin-1-yl)propyl)-5-methyl-2-propyl-1H-imidazole-4-carboxamide;

N-(3-(4-(2,3-dichlorophenyl)piperazin-1-yl)propyl)-1-(2,3-dihydrobenzo[b][1,4]dioxin-6-yl)-5-methyl-2-propyl-1H-imidazole-4-carboxamide;

N-(3-(4-(3-chloro-2-methylphenyl)piperazin-1-yl)propyl)-5-methyl-1-phenyl-2-propyl-1H-imidazole-4-carboxamide;

N-(3-(4-(3-chloro-2-methylphenyl)piperazin-1-yl)-2-hydroxypropyl)-5-methyl-1-phenyl-2-propyl-1H-imidazole-4-carb oxamide;

N-(3-(4-(3-chloro-2-methylphenyl)piperazin-1-yl)propyl)-1-(2,3-dihydrobenzo[b][1,4]dioxin-6-yl)-5-methyl-2-propyl-1H-imidazole-4-carboxamide;

N-(3-(4-(3-chloro-2-methylphenyl)piperazin-1-yl)-2-hydroxypropyl)-1-(2,3-dihydrobenzo[b][1,4]dioxin-6-yl)-5-methyl-2-propyl-1H-imidazole-4-carboxamide;

1-(2,3-dihydrobenzo[b][1,4]dioxin-6-yl)-N-(3-(4-(2,3-dimethylphenyl)piperazin-1-yl)-2-hydroxypropyl)-5-methyl-2-propyl-1H-imidazole-4-carboxamide;

N-(3-(4-(2,3-dichlorophenyl)piperazin-1-yl)-2-hydroxypropyl)-1-(2,3-dihydrobenzo[b][1,4]dioxin-6-yl)-5-methyl-2-propyl-1H-imidazole-4-carboxamide;

N-(3-(4-(2,3-dimethylphenyl)piperazin-1-yl)propyl)-1-(4-fluorophenyl)-5-methyl-2-propyl-1H-imidazole-4-carboxamide;

N-(3-(4-(2,3-dichlorophenyl)piperazin-1-yl)propyl)-1-(4-fluorophenyl)-5-methyl-2-propyl-1H-imidazole-4-carboxamide;

N-(3-(4-(2,3-dimethylphenyl)piperazin-1-yl)-2-hydroxypropyl)-1-(4-fluorophenyl)-5-methyl-2-propyl-1H-imidazole-4-carboxamide;

N-(3-(4-(2,3-dichlorophenyl)piperazin-1-yl)-2-hydroxypropyl)-1-(4-fluorophenyl)-5-methyl-2-propyl-1H-imidazole-4-carboxamide;

N-(3-(4-(3-chloro-2-methylphenyl)piperazin-1-yl)propyl)-1-(4-fluorophenyl)-2,5-dimethyl-1H-imidazole-4-carboxamide;

N-(3-(4-(3-chloro-2-methylphenyl)piperazin-1-yl)propyl)-1-(4-fluorophenyl)-5-methyl-2-propyl-1H-imidazole-4-carboxamide;

N-(3-(4-(2,3-dichlorophenyl)piperazin-1-yl)-2-hydroxypropyl)-1-(2-fluorophenyl)-2,5-dimethyl-1H-imidazole-4-carboxamide;

1-(2-chlorophenyl)-N-(3-(4-(2,3-dimethylphenyl)piperazin-1-yl)-2-hydroxypropyl)-5-methyl-2-propyl-1H-imidazole-4-carboxamide;

1-(2-chlorophenyl)-N-(3-(4-(2,3-dimethylphenyl)piperazin-1-yl)propyl)-5-methyl-2-propyl-1H-imidazole-4-carboxamide;

(R)—N-(3-(4-(3-chloro-2-methyl-phenyl)piperazin-1-yl)-2-hydroxypropyl)-1-(4-fluorophenyl)-5-methyl-2-phenyl-1H-imidazole-4-carboxamide;

(R)-1-(4-chlorophenyl)-N-(3-(4-(2,3-dichlorophenyl)piperazin-1-yl)-2-hydroxypropyl)-2-propyl-1H-imidazole-4-carboxamide;

N-(3-(4-(3-chloro-2-methylphenyl)piperazin-1-yl)propyl)-1-(2-chlorophenyl)-2,5-dimethyl-1H-imidazole-4-carboxamide;

N-(3-(4-(3-chloro-2-methylphenyl)piperazin-1-yl)-2-hydroxypropyl)-1-(2-fluorophenyl)-2,5-dimethyl-1H-imidazole-4-carboxamide;

N-(3-(4-(3-chloro-2-methylphenyl)piperazin-1-yl)-2-hydroxypropyl)-1-(4-methoxyphenyl)-2,5-dimethyl-1H-imidazole-4-carboxamide;

N-(3-(4-(2,3-dimethylphenyl)piperazin-1-yl)propyl)-1-(4-methoxyphenyl)-5-methyl-2-phenyl-1H-imidazole-4-carboxamide;

N-(3-(4-(3-chloro-2-methylphenyl)piperazin-1-yl)propyl)-1-(4-methoxyphenyl)-5-methyl-2-phenyl-1H-imidazole-4-carboxamide;

N-(3-(4-(2,3-dichlorophenyl)piperazin-1-yl)propyl)-1-(4-methoxyphenyl)-5-methyl-2-phenyl-1H-imidazole-4-carboxamide;

N-(3-(4-(2,3-dimethylphenyl)piperazin-1-yl)-2-hydroxypropyl)-1-(4-methoxyphenyl)-5-methyl-2-phenyl-1H-imidazole-4-carboxamide;

N-(3-(4-(3-chloro-2-methylphenyl)piperazin-1-yl)-2-hydroxypropyl)-1-(4-methoxyphenyl)-5-methyl-2-phenyl-1H-imidazole-4-carboxamide;

N-(3-(4-(2,3-dichlorophenyl)piperazin-1-yl)-2-hydroxypropyl)-1-(4-methoxyphenyl)-5-methyl-2-phenyl-1H-imidazole-4-carboxamide;

1-(2,3-dihydrobenzo[b][1,4]dioxin-6-yl)-N-(3-(4-(2,3-dimethylphenyl)piperazin-1-yl)propyl)-5-methyl-2-phenyl-1H-imidazole-4-carboxamide;

N-(3-(4-(3-chloro-2-methylphenyl)piperazin-1-yl)propyl)-1-(2,3-dihydrobenzo[b][1,4]dioxin-6-yl)-5-methyl-2-phenyl-1H-imidazole-4-carboxamide;

N-(3-(4-(2,3-dichlorophenyl)piperazin-1-yl)propyl)-1-(2,3-dihydrobenzo[b][1,4]dioxin-6-yl)-5-methyl-2-phenyl-1H-imidazole-4-carboxamide;

1-(2,3-dihydrobenzo[b][1,4]dioxin-6-yl)-N-(3-(4-(2,3-dimethylphenyl)piperazin-1-yl)-2-hydroxypropyl)-5-methyl-2-phenyl-1H-imidazole-4-carboxamide;

N-(3-(4-(3-chloro-2-methylphenyl)piperazin-1-yl)-2-hydroxypropyl)-1-(2,3-dihydrobenzo[b][1,4]dioxin-6-yl)-5-methyl-2-phenyl-1H-imidazole-4-carboxamide;

N-(3-(4-(2,3-dichlorophenyl)piperazin-1-yl)-2-hydroxypropyl)-1-(2,3-dihydrobenzo[b][1,4]dioxin-6-yl)-5-methyl-2-phenyl-1H-imidazole-4-carboxamide;

1-(benzo[d][1,3]dioxol-5-yl)-N-(3-(4-(3-chloro-2-methylphenyl)piperazin-1-yl)propyl)-2,5-dimethyl-1H-imidazole-4-carboxamide;

1-(benzo[d][1,3]dioxol-5-yl)-N-(3-(4-(3-chloro-2-methylphenyl)piperazin-1-yl)propyl)-5-methyl-2-propyl-1H-imidazole-4-carboxamide;

N-(3-(4-(2,3-dimethylphenyl)piperazin-1-yl)propyl)-2,5-dimethyl-1-o-tolyl-1H-imidazole-4-carboxamide;

N-(3-(4-(3-chloro-2-methylphenyl)piperazin-1-yl)propyl)-2,5-dimethyl-1-o-tolyl-1H-imidazole-4-carboxamide;

N-(3-(4-(2,3-dichlorophenyl)piperazin-1-yl)propyl)-2,5-dimethyl-1-O— tolyl-1H-imidazole-4-carboxamide;

N-(3-(4-(2,3-dimethylphenyl)piperazin-1-yl)-2-hydroxypropyl)-2,5-dimethyl-1-o-tolyl-1H-imidazole-4-carboxamide;

N-(3-(4-(3-chloro-2-methylphenyl)piperazin-1-yl)-2-hydroxypropyl)-2,5-dimethyl-1-o-tolyl-1H-imidazole-4-carboxamide;

N-(3-(4-(2,3-dichlorophenyl)piperazin-1-yl)-2-hydroxypropyl)-2,5-dimethyl-1-o-tolyl-1H-imidazole-4-carboxamide;

N-(3-(4-(3-chloro-2-methylphenyl)piperazin-1-yl)propyl)-1-(4-chlorophenyl)-2,5-dimethyl-1H-imidazole-4-carboxamide;

1-(4-chlorophenyl)-N-(3-(4-(2,3-dimethylphenyl)piperazin-1-yl)-2-hydroxypropyl)-2,5-dimethyl-1H-imidazole-4-carboxamide;

N-(3-(4-(3-chloro-2-methylphenyl)piperazin-1-yl)-2-hydroxypropyl)-1-(4-chlorophenyl)-2,5-dimethyl-1H-imidazole-4-carboxamide;

1-(4-chlorophenyl)-N-(3-(4-(2,3-dichlorophenyl)piperazin-1-yl)-2-hydroxypropyl)-2,5-dimethyl-1H-imidazole-4-carboxamide;

1-(4-chlorophenyl)-N-(3-(4-(2,3-dimethylphenyl)piperazin-1-yl)propyl)-5-methyl-2-propyl-1H-imidazole-4-carboxamide;

N-(3-(4-(3-chloro-2-methylphenyl)piperazin-1-yl)propyl)-1-(4-chlorophenyl)-5-methyl-2-propyl-1H-imidazole-4-carboxamide;

1-(4-chlorophenyl)-N-(3-(4-(2,3-dichlorophenyl)piperazin-1-yl)propyl)-5-methyl-2-propyl-1H-imidazole-4-carboxamide;

1-(4-chlorophenyl)-N-(3-(4-(2,3-dimethylphenyl)piperazin-1-yl)-2-hydroxypropyl)-5-methyl-2-propyl-1H-imidazole-4-carboxamide;

N-(3-(4-(3-chloro-2-methylphenyl)piperazin-1-yl)-2-hydroxypropyl)-1-(4-chlorophenyl)-5-methyl-2-propyl-1H-imidazole-4-carboxamide;

1-(4-chlorophenyl)-N-(3-(4-(2,3-dichlorophenyl)piperazin-1-yl)-2-hydroxypropyl)-5-methyl-2-propyl-1H-imidazole-4-carboxamide;

1-(2-chlorophenyl)-N-(3-(4-(2,3-dichlorophenyl)piperazin-1-yl)-2-hydroxypropyl)-5-methyl-2-propyl-1H-imidazole-4-carboxamide;

1-(2-chlorophenyl)-N-(3-(4-(2,3-dichlorophenyl)piperazin-1-yl)propyl)-2,5-dimethyl-1H-imidazole-4-carboxamide;

1-(2-chlorophenyl)-N-(3-(4-(2,3-dichlorophenyl)piperazin-1-yl)-2-hydroxypropyl)-2,5-dimethyl-1H-imidazole-4-carboxamide;

N-(3-(4-(3-chloro-2-methylphenyl)piperazin-1-yl)propyl)-1-(2-fluorophenyl)-5-methyl-2-propyl-1H-imidazole-4-carboxamide;

N-(3-(4-(2,3-dimethylphenyl)piperazin-1-yl)propyl)-1-(2-methoxyphenyl)-5-methyl-2-phenyl-1H-imidazole-4-carboxamide;

N-(3-(4-(3-chloro-2-methylphenyl)piperazin-1-yl)propyl)-1-(2-methoxyphenyl)-5-methyl-2-phenyl-1H-imidazole-4-carboxamide;

N-(3-(4-(2,3-dichlorophenyl)piperazin-1-yl)propyl)-1-(2-methoxyphenyl)-5-methyl-2-phenyl-1H-imidazole-4-carboxamide;

N-(3-(4-(2,3-dimethylphenyl)piperazin-1-yl)propyl)-1-(2-fluorophenyl)-5-methyl-2-propyl-1H-imidazole-4-carboxamide;

N-(3-(4-(2,3-dimethylphenyl)piperazin-1-yl)-2-hydroxypropyl)-1-(2-fluorophenyl)-5-methyl-2-propyl-1H-imidazole-4-carboxamide;

N-(3-(4-(2,3-dichlorophenyl)piperazin-1-yl)-2-hydroxypropyl)-1-(2-fluorophenyl)-5-methyl-2-propyl-1H-imidazole-4-carboxamide;

N-(3-(4-(2,3-dimethylphenyl)piperazin-1-yl)propyl)-5-methyl-2-propyl-1-o-tolyl-1H-imidazole-4-carboxamide;

N-(3-(4-(3-chloro-2-methylphenyl)piperazin-1-yl)propyl)-5-methyl-2-propyl-1-o-tolyl-1H-imidazole-4-carboxamide;

N-(3-(4-(2,3-dichlorophenyl)piperazin-1-yl)propyl)-5-methyl-2-propyl-1-o-tolyl-1H-imidazole-4-carboxamide;

1-(4-chlorophenyl)-N-(3-(4-(2,3-dimethylphenyl)piperazin-1-yl)propyl)-5-methyl-2-phenyl-1H-imidazole-4-carboxamide;

N-(3-(4-(3-chloro-2-methylphenyl)piperazin-1-yl)propyl)-1-(4-chlorophenyl)-5-methyl-2-phenyl-1H-imidazole-4-carboxamide;

1-(4-chlorophenyl)-N-(3-(4-(2,3-dichlorophenyl)piperazin-1-yl)propyl)-5-methyl-2-phenyl-1H-imidazole-4-carboxamide;

1-(4-chlorophenyl)-N-(3-(4-(2,3-dimethylphenyl)piperazin-1-yl)-2-hydroxypropyl)-5-methyl-2-phenyl-1H-imidazole-4-carboxamide;

N-(3-(4-(3-chloro-2-methylphenyl)piperazin-1-yl)-2-hydroxypropyl)-1-(4-chlorophenyl)-5-methyl-2-phenyl-1H-imidazole-4-carboxamide;

1-(4-chlorophenyl)-N-(3-(4-(2,3-dichlorophenyl)piperazin-1-yl)-2-hydroxypropyl)-5-methyl-2-phenyl-1H-imidazole-4-carboxamide;

1-(benzo[d][1,3]dioxol-5-yl)-N-(3-(4-(2,3-dichlorophenyl)piperazin-1-yl)propyl)-2,5-dimethyl-1H-imidazole-4-carboxamide;

1-(benzo[d][1,3]dioxol-5-yl)-N-(3-(4-(2,3-dichlorophenyl)piperazin-1-yl)-2-hydroxypropyl)-2,5-dimethyl-1H-imidazole-4-carboxamide;

1-(benzo[d][1,3]dioxol-5-yl)-N-(3-(4-(2,3-dimethylphenyl)piperazin-1-yl)propyl)-5-methyl-2-propyl-1H-imidazole-4-carboxamide;

1-(benzo[d][1,3]dioxol-5-yl)-N-(3-(4-(2,3-dichlorophenyl)piperazin-1-yl)propyl)-5-methyl-2-propyl-1H-imidazole-4-carboxamide;

1-(benzo[d][1,3]dioxol-5-yl)-N-(3-(4-(2,3-dimethylphenyl)piperazin-1-yl)-2-hydroxypropyl)-5-methyl-2-propyl-1H-imidazole-4-carboxamide;

1-(benzo[d][1,3]dioxol-5-yl)-N-(3-(4-(2,3-dichlorophenyl)piperazin-1-yl)-2-hydroxypropyl)-5-methyl-2-propyl-1H-imidazole-4-carboxamide;

N-(3-(4-(3-chloro-2-methylphenyl)piperazin-1-yl)propyl)-2,5-dimethyl-1-p-tolyl-1H-imidazole-4-carboxamide;

N-(3-(4-(2,3-dimethylphenyl)piperazin-1-yl)propyl)-5-methyl-2-propyl-1-p-tolyl-1H-imidazole-4-carboxamide;

N-(3-(4-(3-chloro-2-methylphenyl)piperazin-1-yl)propyl)-5-methyl-2-propyl-1-p-tolyl-1H-imidazole-4-carboxamide;

N-(3-(4-(2,3-dimethylphenyl)piperazin-1-yl)-2-hydroxypropyl)-1-(2-methoxyphenyl)-5-methyl-2-phenyl-1H-imidazole-4-carboxamide;

N-(3-(4-(3-chloro-2-methylphenyl)piperazin-1-yl)-2-hydroxypropyl)-1-(2-methoxyphenyl)-5-methyl-2-phenyl-1H-imidazole-4-carboxamide;

N-(3-(4-(2,3-dichlorophenyl)piperazin-1-yl)-2-hydroxypropyl)-1-(2-methoxyphenyl)-5-methyl-2-phenyl-1H-imidazole-4-carboxamide;

1-(benzo[d][1,3]dioxol-5-yl)-N-(3-(4-(2,3-dimethylphenyl)piperazin-1-yl)propyl)-5-methyl-2-phenyl-1H-imidazole-4-carboxamide;

1-(benzo[d][1,3]dioxol-5-yl)-N-(3-(4-(3-chloro-2-methylphenyl)piperazin-1-yl)propyl)-5-methyl-2-phenyl-1H-imidazole-4-carboxamide;

1-(benzo[d][1,3]dioxol-5-yl)-N-(3-(4-(2,3-dichlorophenyl)piperazin-1-yl)propyl)-5-methyl-2-phenyl-1H-imidazole-4-carboxamide;

1-(benzo[d][1,3]dioxol-5-yl)-N-(3-(4-(2,3-dimethylphenyl)piperazin-1-yl)-2-hydroxypropyl)-5-methyl-2-phenyl-1H-imidazole-4-carboxamide;

1-(benzo[d][1,3]dioxol-5-yl)-N-(3-(4(3-chloro-2-methylphenyl)piperazin-1-yl)-2-hydroxypropyl)-5-methyl-2-phenyl-1H-imidazole-4-carboxamide;

1-(benzo[d][1,3]dioxol-5-yl)-N-(3-(4-(2,3-dichlorophenyl)piperazin-1-yl)-2-hydroxypropyl)-5-methyl-2-phenyl-1H-imidazole-4-carboxamide;

N-(3-(4-(2,3-dimethylphenyl)piperazin-1-yl)propyl)-1-(2-fluorophenyl)-5-methyl-2-phenyl-1H-imidazole-4-carboxamide;

N-(3-(4-(3-chloro-2-methylphenyl)piperazin-1-yl)propyl)-1-(2-fluorophenyl)-5-methyl-2-phenyl-1H-imidazole-4-carboxamide;

N-(3-(4-(2,3-dichlorophenyl)piperazin-1-yl)propyl)-1-(2-fluorophenyl)-5-methyl-2-phenyl-1H-imidazole-4-carboxamide;

N-(3-(4-(2,3-dimethylphenyl)piperazin-1-yl)-2-hydroxypropyl)-1-(2-fluorophenyl)-5-methyl-2-phenyl-1H-imidazole-4-carboxamide;

N-(3-(4-(3-chloro-2-methylphenyl)piperazin-1-yl)-2-hydroxypropyl)-1-(2-fluorophenyl)-5-methyl-2-phenyl-1H-imidazole-4-carboxamide;

N-(3-(4-(2,3-dichlorophenyl)piperazin-1-yl)-2-hydroxypropyl)-1-(2-fluorophenyl)-5-methyl-2-phenyl-1H-imidazole-4-carboxamide;

N-(3-(4-(2,3-dichlorophenyl)piperazin-1-yl)propyl)-5-methyl-2-propyl-1-p-tolyl-1H-imidazole-4-carboxamide;

1-(benzo[d][1,3]dioxol-5-yl)-N-(3-(4(3-chloro-2-methylphenyl)piperazin-1-yl)-2-hydroxypropyl)-2,5-dimethyl-1H-imidazole-4-carboxamide;

1-(benzo[d][1,3]dioxol-5-yl)-N-(3-(4(3-chloro-2-methylphenyl)piperazin-1-yl)-2-hydroxypropyl)-5-methyl-2-propyl-1H-imidazole-4-carboxamide;

N-(3-(4-(3-chloro-2-methylphenyl)piperazin-1-yl)-2-hydroxypropyl)-2,5-dimethyl-1-p-tolyl-1H-imidazole-4-carboxamide;

N-(3-(4-(2,3-dimethylphenyl)piperazin-1-yl)-2-hydroxypropyl)-5-methyl-2-propyl-1-p-tolyl-1H-imidazole-4-carboxamide;

N-(3-(4-(3-chloro-2-methylphenyl)piperazin-1-yl)-2-hydroxypropyl)-5-methyl-2-propyl-1-p-tolyl-1H-imidazole-4-carboxamide;

N-(3-(4-(2,3-dichlorophenyl)piperazin-1-yl)-2-hydroxypropyl)-5-methyl-2-propyl-1-p-tolyl-1H-imidazole-4-carboxamide;

N-(3-(4-(2,3-dimethylphenyl)piperazin-1-yl)propyl)-5-methyl-2-phenyl-1-p-tolyl-1H-imidazole-4-carboxamide;

N-(3-(4-(3-chloro-2-methylphenyl)piperazin-1-yl)-2-hydroxypropyl)-5-methyl-2-phenyl-1-p-tolyl-1H-imidazole-4-carboxamide;

N-(3-(4-(2,3-dichlorophenyl)piperazin-1-yl)propyl)-5-methyl-2-phenyl-1-p-tolyl-1H-imidazole-4-carboxamide;

N-(3-(4-(2,3-dimethylphenyl)piperazin-1-yl)-2-hydroxypropyl)-5-methyl-2-phenyl-1-p-tolyl-1H-imidazole-4-carboxamide;

N-(3-(4-(2,3-dichlorophenyl)piperazin-1-yl)-2-hydroxypropyl)-5-methyl-2-phenyl-1-p-tolyl-1H-imidazole-4-carboxamide;

N-(3-(4-(3-chloro-2-methylphenyl)piperazin-1-yl)-2-hydroxypropyl)-1-(2-chlorophenyl)-2,5-dimethyl-1H-imidazole-4-carboxamide;

1-(2-chlorophenyl)-N-(3-(4-(2,3-dimethylphenyl)piperazin-1-yl)propyl)-5-methyl-2-phenyl-1H-imidazole-4-carboxamide;

N-(3-(4-(3-chloro-2-methylphenyl)piperazin-1-yl)propyl)-1-(2-chlorophenyl)-5-methyl-2-phenyl-1H-imidazole-4-carboxamide;

1-(2-chlorophenyl)-N-(3-(4-(2,3-dichlorophenyl)piperazin-1-yl)propyl)-5-methyl-2-phenyl-1H-imidazole-4-carboxamide;

1-(2-chlorophenyl)-N-(3-(4-(2,3-dimethylphenyl)piperazin-1-yl)-2-hydroxypropyl)-5-methyl-2-phenyl-1H-imidazole-4-carboxamide;

N-(3-(4-(3-chloro-2-methylphenyl)piperazin-1-yl)-2-hydroxypropyl)-1-(2-chlorophenyl)-5-methyl-2-phenyl-1H-imidazole-4-carboxamide;

1-(2-chlorophenyl)-N-(3-(4-(2,3-dichlorophenyl)piperazin-1-yl)-2-hydroxypropyl)-5-methyl-2-phenyl-1H-imidazole-4-carboxamide;

N-(3-(4-(2,3-dimethylphenyl)piperazin-1-yl)propyl)-5-methyl-2-phenyl-1-o-tolyl-1H-imidazole-4-carboxamide;

N-(3-(4-(3-chloro-2-methylphenyl)piperazin-1-yl)propyl)-5-methyl-2-phenyl-1-o-tolyl-1H-imidazole-4-carboxamide;

N-(3-(4-(2,3-dichlorophenyl)piperazin-1-yl)propyl)-5-methyl-2-phenyl-1-o-tolyl-1H-imidazole-4-carboxamide;

N-(3-(4-(2,3-dimethylphenyl)piperazin-1-yl)-2-hydroxypropyl)-5-methyl-2-phenyl-1-o-tolyl-1H-imidazole-4-carboxamide;

N-(3-(4-(3-chloro-2-methylphenyl)piperazin-1-yl)-2-hydroxypropyl)-5-methyl-2-phenyl-1-o-tolyl-1H-imidazole-4-carboxamide;

N-(3-(4-(2,3-dichlorophenyl)piperazin-1-yl)-2-hydroxypropyl)-5-methyl-2-phenyl-1-o-tolyl-1H-imidazole-4-carboxamide;

N-(3-(4-(3-chloro-2-methylphenyl)piperazin-1-yl)-2-hydroxypropyl)-2,5-dimethyl-1-(4-(trifluoromethyl)phenyl)-1H-imidazole-4-carboxamide;

N-(3-(4-(3-chloro-2-methylphenyl)piperazin-1-yl)propyl)-2,5-dimethyl-1-(4-(trifluoromethyl)phenyl)-1H-imidazole-4-carboxamide;

N-(3-(4-(3-chloro-2-methylphenyl)piperazin-1-yl)propyl)-5-methyl-2-phenyl-1-p-tolyl-1H-imidazole-4-carboxamide;

N-(3-(4-(3-chloro-2-methylphenyl)piperazin-1-yl)propyl)-N, 5-dimethyl-1,2-diphenyl-1H-imidazole-4-carboxamide;

N-(3-(4-(2,3-dichlorophenyl)piperazin-1-yl)propyl)-N,5-dimethyl-1,2-diphenyl-1H-imidazole-4-carboxamide;

N-(3-(4-(2,3-dimethylphenyl)piperazin-1-yl)propyl)-N,5-dimethyl-1,2-diphenyl-1H-imidazole-4-carboxamide;

N-(3-(4-(3-chloro-2-methylphenyl)piperazin-1-yl)propyl)-1-cyclopentyl-N,2,5-trimethyl-1H-imidazole-4-carboxamide;

1-cyclopentyl-N-(3-(4-(2,3-dichlorophenyl)piperazin-1-yl)propyl)-N,2,5-trimethyl-1H-imidazole-4-carboxamide;

1-cyclopentyl-N-(3-(4-(2,3-dimethylphenyl)piperazin-1-yl)propyl)-N,2,5-trimethyl-1H-imidazole-4-carboxamide;

N-(3-(4-(2,3-dimethylphenyl)piperazin-1-yl)propyl)-1-(4-methoxyphenyl)-N, 5-dimethyl-2-phenyl-1H-imidazole-4-carboxamide;

1-(3-chlorophenyl)-N-(3-(4-(2,3-dimethylphenyl)piperazin-1-yl)propyl)-N,2,5-trimethyl-1H-imidazole-4-carboxamide;

N-(3-(4-(3-chloro-2-methylphenyl)piperazin-1-yl)propyl)-1-(4-methoxyphenyl)-N, 5-dimethyl-2-phenyl-1H-imidazole-4-carboxamide;
N-(3-(4-(3-chloro-2-methylphenyl)piperazin-1-yl)propyl)-1-(3-chlorophenyl)-N,2,5-trimethyl-1H-imidazole-4-carboxamide;
1-(2-chlorophenyl)-N-(3-(4-(2,3-dimethylphenyl)piperazin-1-yl)propyl)-N,2,5-trimethyl-1H-imidazole-4-carboxamide;
N-(3-(4-(3-chloro-2-methylphenyl)piperazin-1-yl)propyl)-1-(2-chlorophenyl)-N,2,5-trimethyl-1H-imidazole-4-carboxamide;
1-(2-chlorophenyl)-N-(3-(4-(2,3-dichlorophenyl)piperazin-1-yl)propyl)-N,2,5-trimethyl-1H-imidazole-4-carboxamide;
N-(3-(4-(2,3-dimethylphenyl)piperazin-1-yl)propyl)-N,2,5-trimethyl-1-phenyl-1H-imidazole-4-carboxamide;
N-(3-(4-(3-chloro-2-methylphenyl)piperazin-1-yl)propyl)-N,2,5-trimethyl-1-phenyl-1H-imidazole-4-carboxamide;
N-(3-(4-(2,3-dichlorophenyl)piperazin-1-yl)propyl)-N,2,5-trimethyl-1-phenyl-1H-imidazole-4-carboxamide;
N-(3-(4-(2,3-dimethylphenyl)piperazin-1-yl)propyl)-1-(4-fluorophenyl)-N,5-dimethyl-2-phenyl-1H-imidazole-4-carboxamide;
N-(3-(4-(3-chloro-2-methylphenyl)piperazin-1-yl)propyl)-1-(4-fluorophenyl)-N,5-dimethyl-2-phenyl-1H-imidazole-4-carboxamide;
N-(3-(4-(2,3-dichlorophenyl)piperazin-1-yl)propyl)-1-(4-fluorophenyl)-N,5-dimethyl-2-phenyl-1H-imidazole-4-carboxamide;
1-(2,3-dihydrobenzo[b][1,4]dioxin-6-yl)-N-(3-(4-(2,3-dimethylphenyl)piperazin-1-yl)propyl)-N,5-dimethyl-2-phenyl-1H-imidazole-4-carboxamide;
N-(3-(4-(3-chloro-2-methylphenyl)piperazin-1-yl)propyl)-1-(2,3-dihydrobenzo[b][1,4]dioxin-6-yl)-N,5-dimethyl-2-phenyl-1H-imidazole-4-carboxamide
N-(3-(4-(2,3-dichlorophenyl)piperazin-1-yl)propyl)-1-(2,3-dihydrobenzo[b][1,4]dioxin-6-yl)-N,5-dimethyl-2-phenyl-1H-imidazole-4-carboxamide;
(R)-1-(2,3-dihydrobenzo[b][1,4]dioxin-6-yl)-N-(3-(4-(2,3-dimethylphenyl)piperazin-1-yl)-2-hydroxypropyl)-2,5-dimethyl-1H-imidazole-4-carboxamide;
(R)—N-(3-(4-(3-chloro-2-methylphenyl)piperazin-1-yl)-2-hydroxypropyl)-1-(2,3-dihydrobenzo[b][1,4]dioxin-6-yl)-2,5-dimethyl-1H-imidazole-4-carboxamide; and
(R)—N-(3-(4-(2,3-dichlorophenyl)piperazin-1-yl)-2-hydroxypropyl)-1-(2,3-dihydrobenzo[b][1,4]dioxin-6-yl)-2,5-dimethyl-1H-imidazole-4-carboxamide.

General Synthetic Sequence

The following synthetic schemes are merely illustrative of the methods by which the compounds of the invention may be prepared and are not intended to limit the scope of the invention as defined in the appended claims.

The imidazole derivative (6) is prepared by a conventional method [Bayer Pharmaceuticals, WO 03/040107, 2003], for example, by subjecting a nitrile (2) to a reaction with an aniline derivative (1) using aluminum chloride to produce N-(4-chloro phenyl)-butyrimidamide (3). Subsequent reaction of the resulting compound (3) with ethyl 3-bromo-2-oxopropanoate (4) provides an intermediate ethyl 1-(4-chlorophenyl)-2-propyl-1H-imidazole-4-carboxylate (5). An acid form (6) is prepared from the ester (5) using lithium hydroxide, followed by acidification, as shown in Reaction Scheme 1.

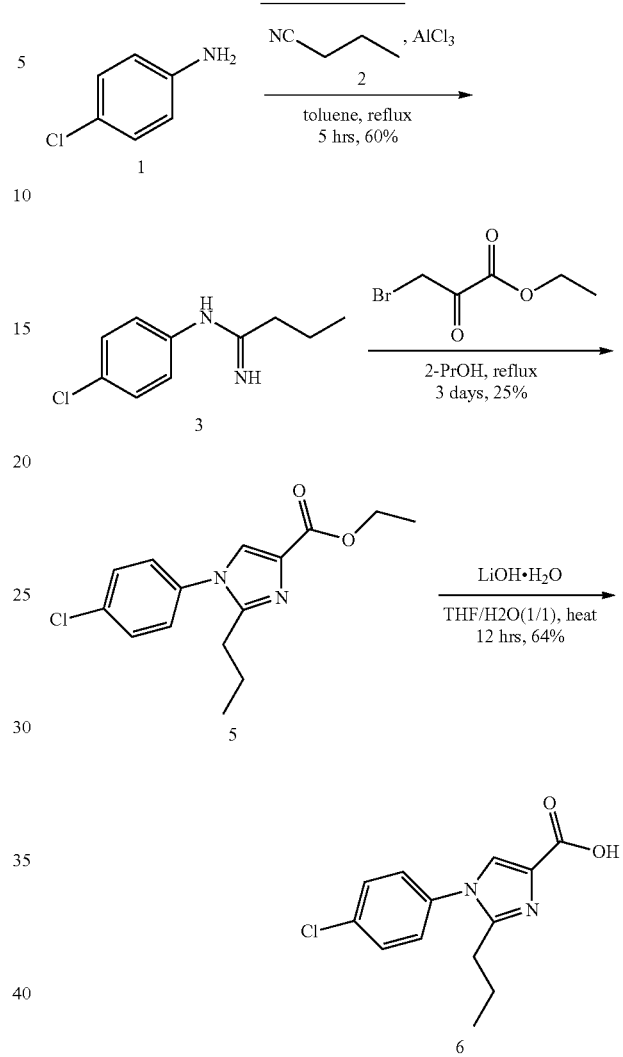

A compound (7) is subjected to a reaction with sodium nitrite in acetic acid to give ethyl 2-(hydroxyimino)-3-oxobutanoate (8) in 70% yield. The compound (8) is subjected to a reaction with an anhydride such as acetic anhydride (9) in the presence of a reducing agent such as hydrogen and a catalyst such as Pd on carbon (Pd/C) in EtOH to give an amide (10) [Lange, J. H. M. et al. US 2006/0194779, 2006]. The amide (10) is subjected to a reaction with an amine such as aniline (11a or 11b) in an inert solvent such as acetonitrile under microwave irradiation to obtain an imidazole derivative (12a or 12b). Hydrolysis of the imidazole derivative (12a or 12b) with lithium hydroxide produces a compound (13a or 13b) as shown in Reaction Scheme 2.

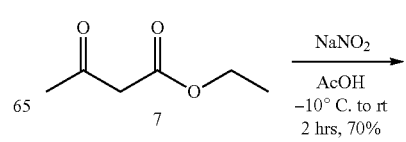

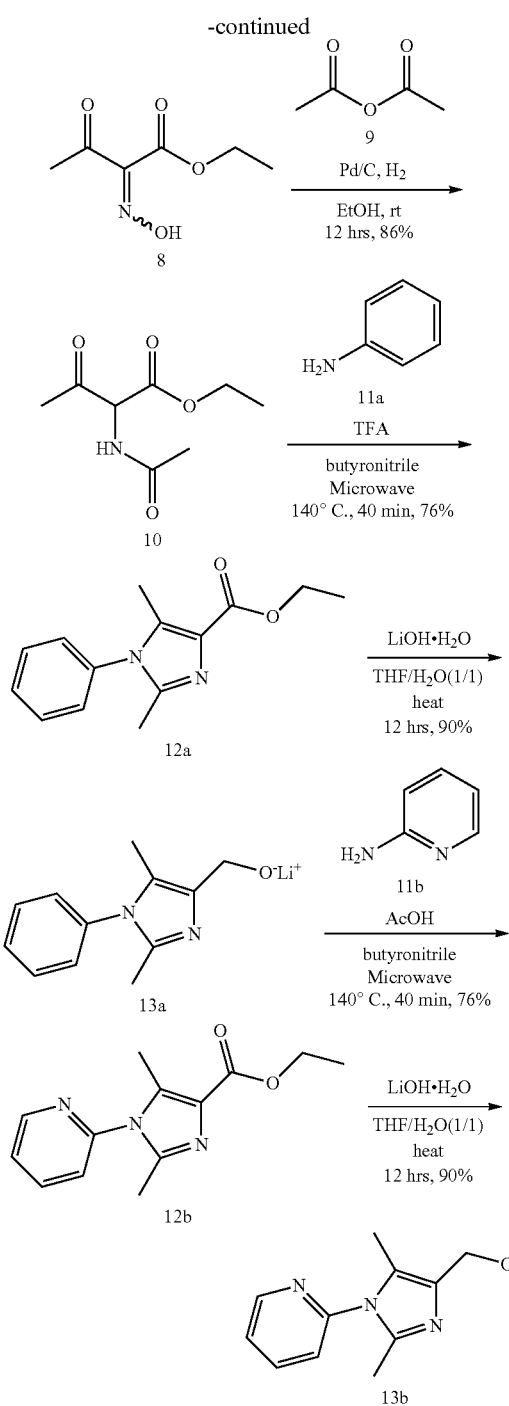

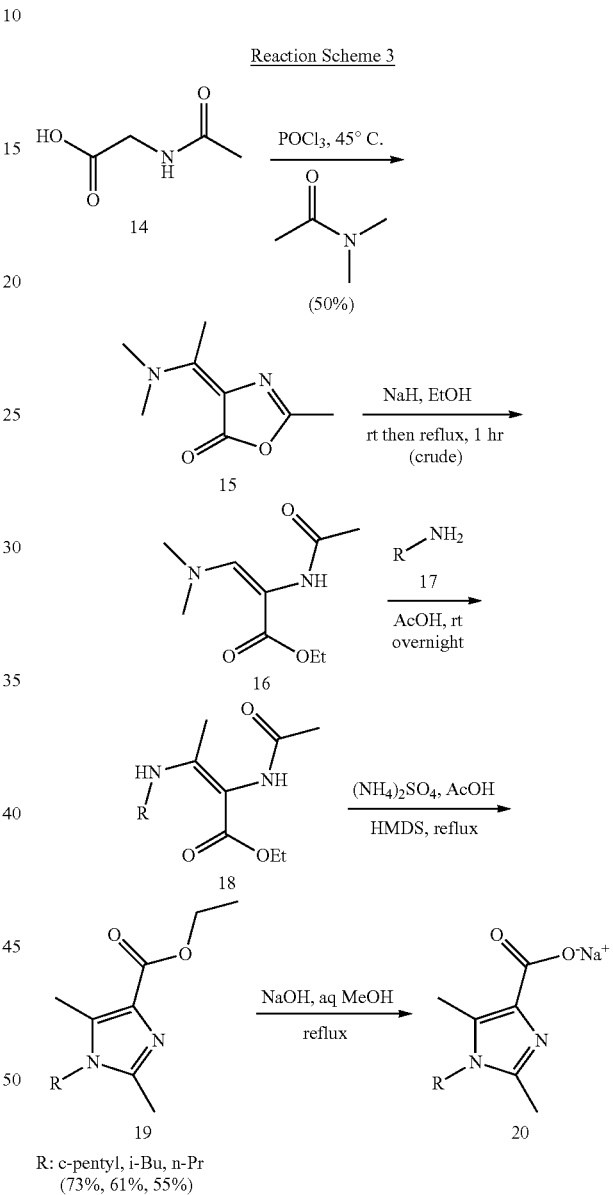

Reaction Scheme 3

R: c-pentyl, i-Bu, n-Pr
(73%, 61%, 55%)

Another approach toward imidazole intermediate is described in Reaction Scheme 3. The original reaction sequence was published by F. Hoffmann-La Roche A G [F. Hoffmann-La Roche A G, WO 2005/003117, 2005]. N-acetylglycine (14) and phosphorous oxychloride are mixed and dimethylacetamide is added thereto dropwise slowly at low temperature (exothermic). The reaction mixture is then stirred and warmed at 45° C. In this way, (E)-4-(1-(dimethylamino)ethylidene)-2-methyloxazol-5(4H)-one (15) is generated in 50% yield. The oxazolone (15) is cleaved with in situ generated ethoxide to produce (E)-ethyl 2-acetamido-3-(dimethylamino)but-2-enoate (16). Next, an amine (17) is subjected to a reaction with the compound (16) in acetic acid at rt overnight to give a Michael adduct (18). The crude intermediate (18) is then refluxed together with fine powdered ammonium sulfate in hexamethyldisilazane at 145° C. to provide the corresponding imidazole ester (19) in 55~73% yield for the three steps from the oxazolone (15). The imidazole ester (19) is hydrolyzed with sodium hydroxide to produce the corresponding sodium carboxylate (20) uneventfully.

An imidazole acid derivative (25) is synthesized by adopting a known method [Lange, J. H. M., et al. *J. Med. Chem.* 2005, 48, 1823-1838; and Kim, J. Y., et al. *Bioorg. Med. Chem. Lett.* 2009, 19, 142-145]. Thus, benzonitrile (21) is subjected to a reaction with aniline (11a) in the presence of sodium bis(trimethylsilyl)amide (NaHMDS) to produce a corresponding arylbenzamidine (22). Subsequent reaction of the resulting arylbenzamidine (22) with α-bromoketone (23) generates an intermediate ethyl 5-methyl-1,2-diphenyl-1H-imidazole-4-carboxylate (24) in 55% yield. Hydrolysis of the ester (24) with lithium hydroxide produces the corresponding lithium carboxylate (25) as shown in Reaction Scheme 4.

Reaction Scheme 4

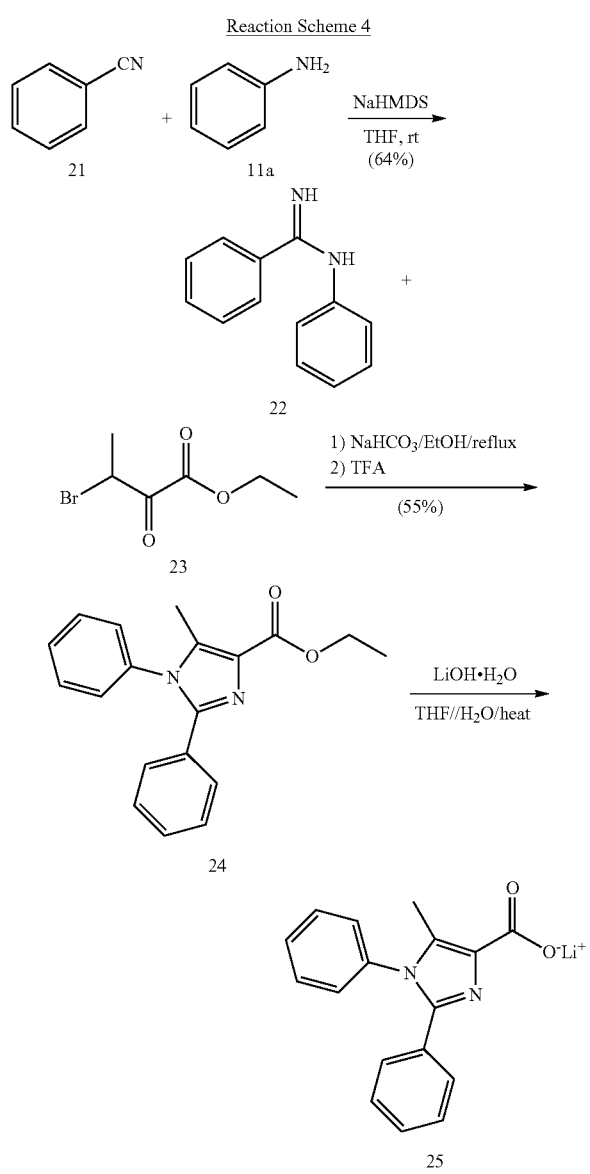

*Chem.* 2008, 16, 6707-6723]. Reaction of commercially available 8-hydroxyquinoline (29) with trifluoromethanesulfonic anhydride (triflic anhydride) in the presence of a base produces the corresponding triflate (30). Buchwald coupling [Buchwald, S. L., et al. *J. Am. Chem. Soc.* 1998, 120, 4960] between quinolin-8-yl trifluoromethanesulfonate (30) and 1-tert-butyl-4-piperazine carboxylate (31) affords compound (32) in 72% yield for the two steps. Deprotection of Boc group of the compound (32) using HCl in refluxed methanol produces quinolinyl piperazine (33).

Reaction Scheme 6

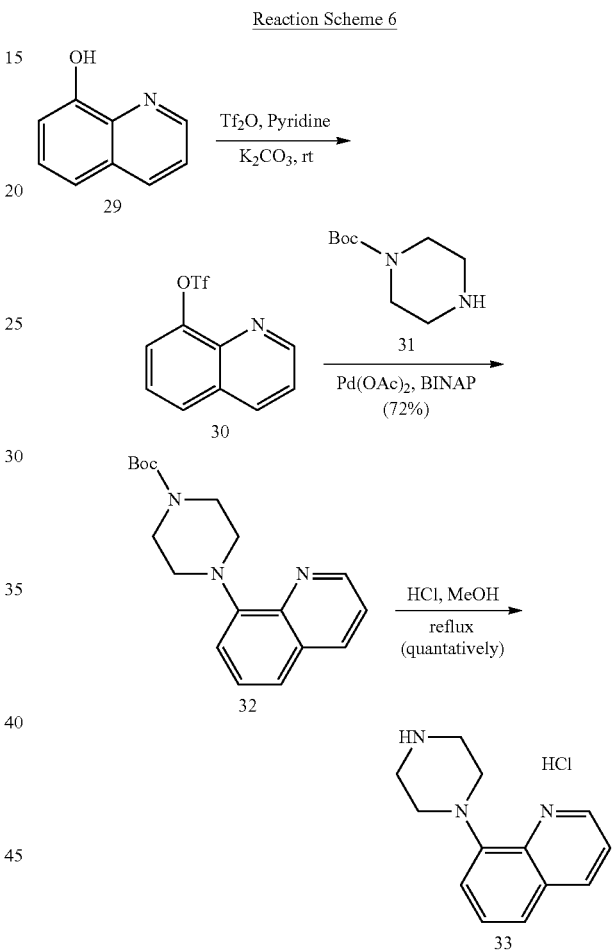

N-arylpiperazine (28) is prepared via condensation of the requisite aniline such as 3-chloro-2-methylaniline (26) with bis(2-chloroethyl)amine (27), following a reported procedure [Martin, G. E., et al. *J. Med. Chem.* 1989, 32, 1052-1056] as shown in Reaction Scheme 5.

Reaction Scheme 5

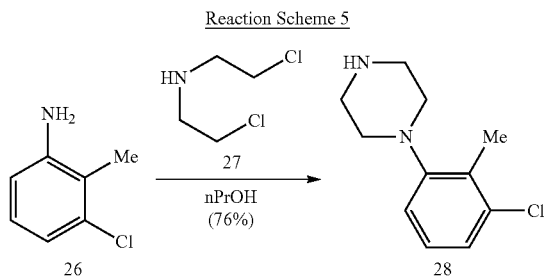 [SMILES: Cc1c(N)cccc1Cl ; ClCCNCCCl ; Cc1c(Cl)cccc1N1CCNCC1]

Next, 8-(piperazin-1-yl)quinoline (33) is prepared as depicted in Reaction Scheme 6 [Zhou, D., et al., *Bioorg. Med.*

As shown in Reaction Scheme 7, the synthesis of 3-(4-(2,3-dichlorophenyl)piperazin-1-yl)propan-1-amine (37), and the like, wherein the alkyl chain between the piperazine and the terminal amine corresponds to two carbons through four carbons, commences with N-(2-bromoethyl)phthalimide, N-(3-bromopropyl)phthalimide (34), and N-(4-bromobutyl)phthalimide by adopting a reported procedure [Robarge, M. J., et al. *J. Med. Chem.* 2001, 44, 3175-3186]. For example, N-(3-bromopropyl)phthalimide (34) is subjected to a reaction with 1-(2,3-dichlorophenyl)piperazine (35) in the presence of potassium carbonate in a suitable solvent such as dimethylformamide (DMF) at room temperature affords the corresponding alkylated compound (36) in 80% yield. Hydazinolysis of the compound (36), followed by treatment of HCl solution generates 3-(4-(2,3-dichlorophenyl)piperazin-1-yl)propan-1-amine as a HCl salt form (37) in 76% yield.

Reaction Scheme 7

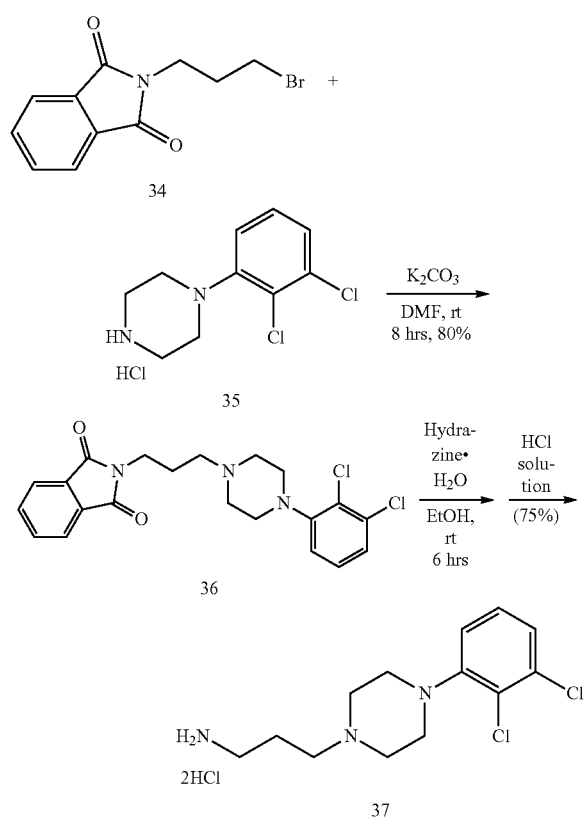

In order to increase hydrophilicity for compounds such as 3-(4-(2,3-dichlorophenyl)piperazin-1-yl)propan-1-amine (37), a compound such as 1-amino-3-(4-(2,3-dichlorophenyl)piperazin-1-yl)propan-2-ol (40) is prepared as shown in Reaction Scheme 8. Thus, commercially available N-(2,3-epoxypropyl)phthalimide (38) is treated with 1-(2,3-dichlorophenyl)piperazine (35) in the presence of a base such as triethylamine in a suitable solvent such as tetrahydrofuran (THF) at 80° C. to produce the alcohol (39) in about 91% yield. Subsequently, hydrazinolysis of the alcohol (39) generates 1-amino-3-(4-(2,3-dichlorophenyl)piperazin-1-yl)propan-2-ol (40) as a white solid in 95% yield.

Reaction Scheme 8

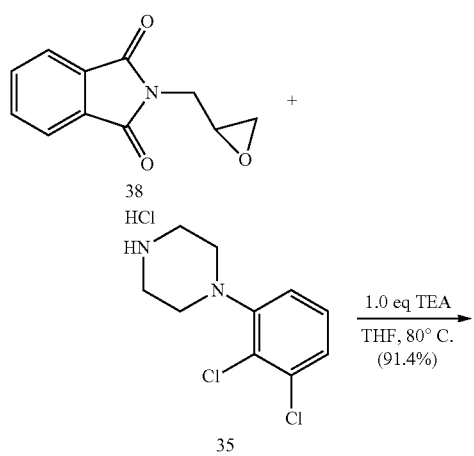

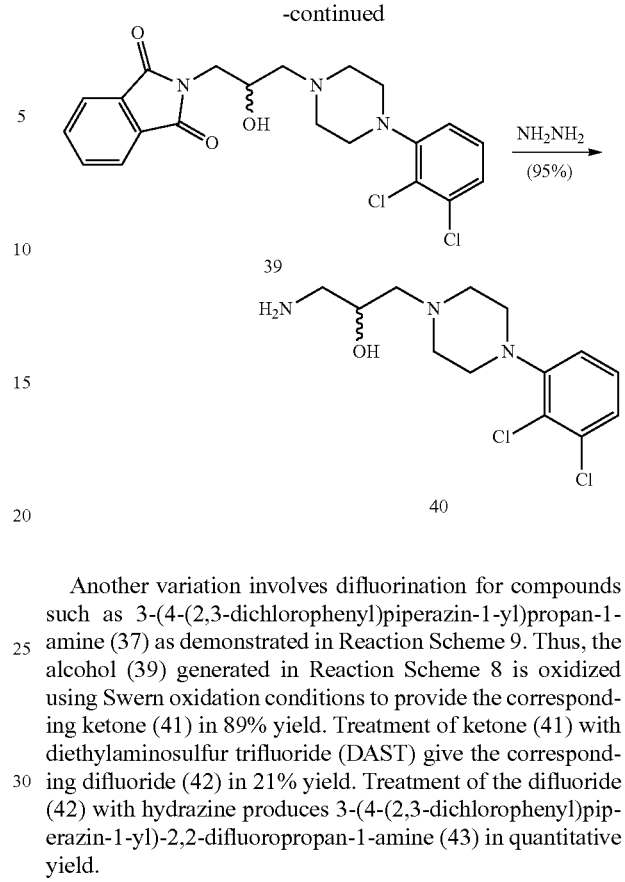

Another variation involves difluorination for compounds such as 3-(4-(2,3-dichlorophenyl)piperazin-1-yl)propan-1-amine (37) as demonstrated in Reaction Scheme 9. Thus, the alcohol (39) generated in Reaction Scheme 8 is oxidized using Swern oxidation conditions to provide the corresponding ketone (41) in 89% yield. Treatment of ketone (41) with diethylaminosulfur trifluoride (DAST) give the corresponding difluoride (42) in 21% yield. Treatment of the difluoride (42) with hydrazine produces 3-(4-(2,3-dichlorophenyl)piperazin-1-yl)-2,2-difluoropropan-1-amine (43) in quantitative yield.

Reaction Scheme 9

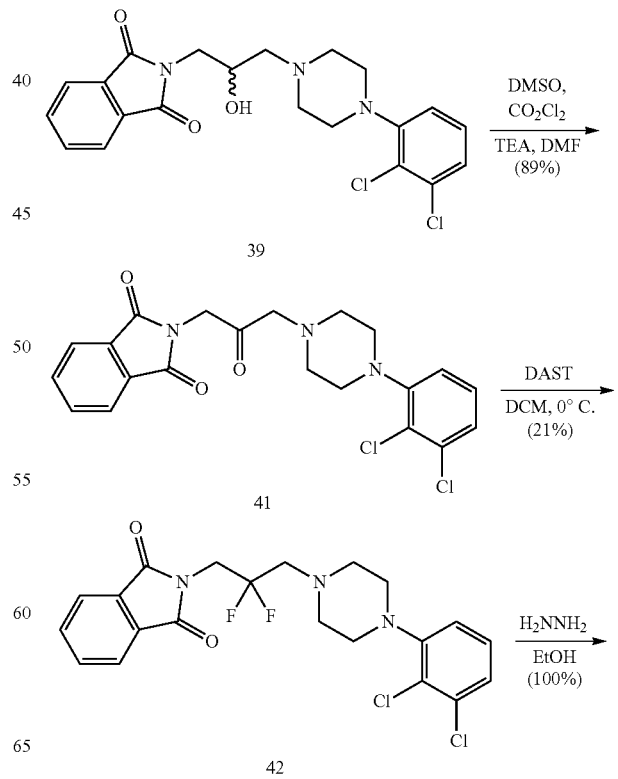

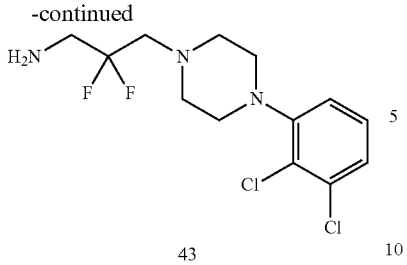

The target compound is prepared by amide bond formation of acid (44) and amine (37) by use of 1-ethyl-3-(3'-dimethylaminopropyl)carbedoomide hydrochloride (EDCI), 1-hydroxybenzotriazole (HOBt), N-methylmorphofine (NMM) in a suitable solvent such as DMF to generate a compound (45) in 31% yield as shown in Reaction Scheme 10. Generally, an acid (46) and an amine (47) produce the inventive compound (Ia) in an analogous manner.

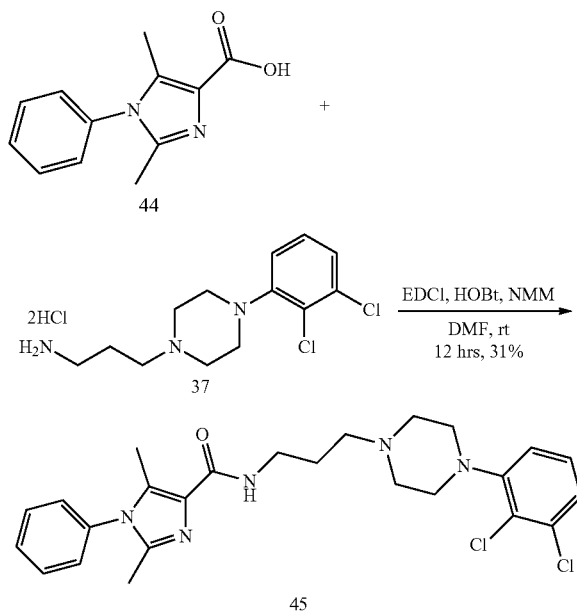

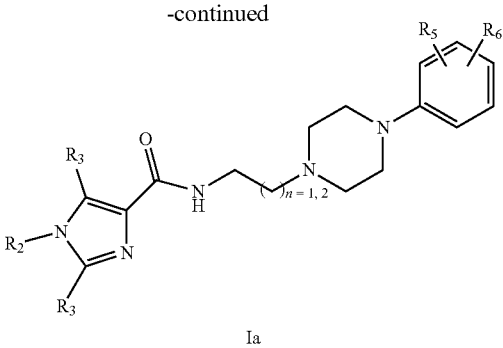

Wherein, $R_1$, $R_2$, $R_3$, $R_5$ and $R_6$ have the same meanings as defined above.

As shown in Reaction Scheme 11, the target compound is prepared by amide bond formation of acid (44) and amine (40) by use of EDCI, HOBt and NMM in a suitable solvent such as DMF to generate an alcohol (49) in 40% yield. Generally, an acid (46) and an amine (50) produce the inventive compound (Ib) in an analogous manner.

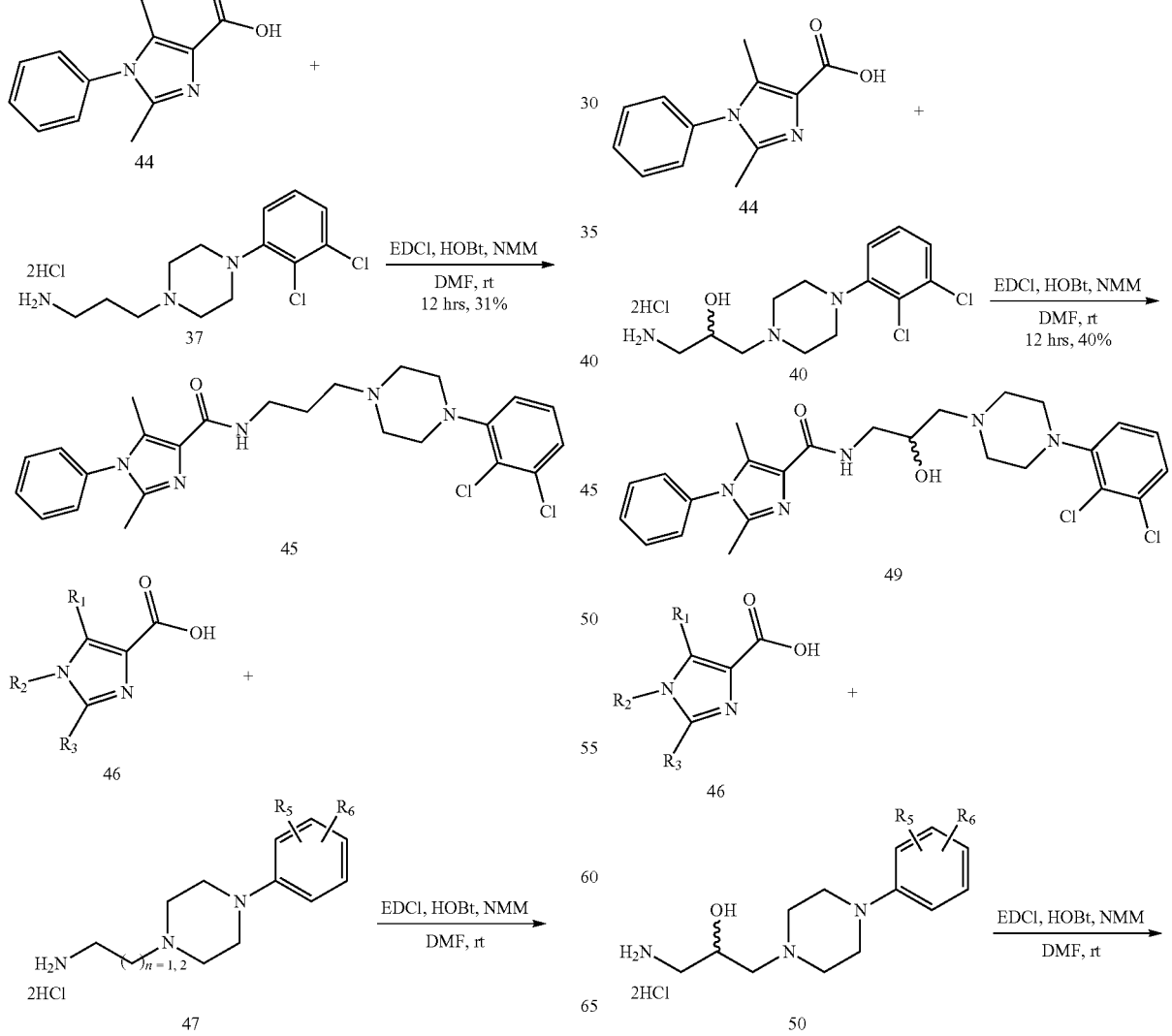

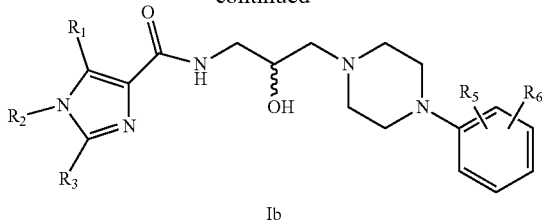

Ib

Wherein, $R_1$, $R_2$, $R_3$, $R_5$ and $R_6$ have the same meanings as defined above.

Further, the present invention provides a method for preventing or treating a depressive disorder in a mammal, comprising administering the compound of formula (I) or a pharmaceutically acceptable salt thereof to the mammal in need thereof.

Also, the present invention provides a pharmaceutical composition for preventing or treating a depressive disorder, which comprises the compound of formula (I) or a pharmaceutically acceptable salt thereof as an active ingredient, and a pharmaceutically acceptable carrier.

As used herein, the term "depressive disorders" refers to mental illnesses characterized by a profound and persistent feeling of sadness or despair and/or a loss of interest in things that once were pleasurable. Disturbance in sleep, appetite, and mental processes are common accompaniments.

The pharmaceutical composition may be administered orally, intramuscularly or subcutaneously. The formulation for oral administration may take various forms such as a syrup, tablet, capsule, cream and lozenge. A syrup formulation will generally contain a suspension or solution of the compound or its salt in a liquid carrier, e.g., ethanol, peanut oil, olive oil, glycerine or water, optionally with a flavoring or coloring agent. When the composition is in the form of a tablet, any one of pharmaceutical carriers routinely used for preparing solid formulations may be used. Examples of such carriers include magnesium stearate, terra alba, talc, gelatin, acacia, stearic acid, starch, lactose and sucrose. When the composition is in the form of a capsule, any of the routine encapsulation procedures may be employed, e.g., using the aforementioned carriers in a hard gelatin capsule shell. When the composition is formulated in the form of a soft gelatin shell capsule, any of the pharmaceutical carrier routinely used for preparing dispersions or suspensions may be prepared using an aqueous gum, cellulose, silicate or oil. The formulation for intramuscular or subcutaneous administration may take a liquid form such as a solution, suspension and emulsion which includes aqueous solvents such as water, physiological saline and Ringer's solution; or lipophilic solvents such as fatty oil, sesame oil, corn oil and synthetic fatty acid ester.

Preferably the composition is formulated in a specific dosage form for a particular patient. Each dosage unit for oral administration contains suitably from 0.1 mg to 500 mg/kg, and preferably from 1 mg to 100 mg/kg of the compound of formula (I) or a pharmaceutically acceptable salt thereof.

The suitable daily dosage for oral administration is about 0.01 mg/kg to 40 mg/kg of the compound of formula (I) or a pharmaceutically acceptable salt thereof, which may be administered 1 to 6 times a day, depending on the patient's condition.

The present invention further described and illustrated in Examples provided below, which are, however, not intended to limit the scope of the present invention.

SYNTHETIC EXAMPLES

As used herein the symbols and conventions used describing the processes, schemes and examples of the present invention are consistent with those used in the contemporary scientific literature, for example, the *Journal of the American Chemical Society or the Journal of Biological Chemistry*. Unless otherwise noted, all starting materials were obtained from commercial suppliers and used without further purification.

| | |
|---|---|
| Hz (Hertz) | TLC (thin layer chromatography) |
| $T_r$ (retention time) | |
| i-PrOH (isopropanol) | |
| MeOH (methanol) | |
| TFA (trifluoroacetic acid) | TEA (triethylamine) |
| EtOH (ethanol) | THF (tetrahydrofuran) |
| DMSO (dimethylsulfoxide) | EtOAc (ethyl acetate) |
| DCM (dichlromethane) | HOAc (acetic acid) |
| DMF (N,N-dimethylformamide) | Ac (acetyl) |
| Bn (benzyl) | |
| HOBt (1-hydroxybenzotriazole) | |
| Boc (tert-butyloxycarbonyl) | |
| mCPBA (meta-chloroperbenzoic acid) | |
| Cbz (benzyloxycarbonyl) | |
| NMM (N-methyl morpholine) | |
| EDCI (1-ethyl-3-[3-dimethylaminopropyl]-carbodiimide hydrochloride); | |
| HPLC (high pressure liquid chromatography) | |
| R.T. (room temperature) | |

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted, and all solvents are of the highest available purity unless otherwise indicated.

Microwave reaction was conducted with a Biotage Initiator™ microwave synthesizer.

$^1$H NMR spectra were recorded on either a Jeol ECX-400, or a Jeol JNM-LA300 spectrometer. Chemical shifts were expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

Mass spectra were obtained with either a Micromass, Quattro LC Triple Quadruple Tandem Mass Spectometer, ESI or Agilent, 1100LC/MSD, ESI.

For preparative HPLC, ca 100 mg of a product was injected in 1 mL of DMSO onto a SunFire™ Prep C18 OBD 5 μm 19×100 mm Column with a 10 min gradient from 10% $CH_3CN$ to 90% $CH_3CN$ in $H_2O$ (purification systems from Gilson, Inc). Flash chromatography was carried using Merck silica gel 60 (230-400 mesh). Biotage SP1™ FLASH Purification System and Biotage Isolera™ FLASH Purification System were used for normal phase column chromatography with ethyl acetate and hexane. Most of the reactions were monitored by thin-layer chromatography on 0.25 mm E. Merck silica gel plates (60E-254), visualized with UV light using a 5% ethanolic phosphomolybdic acid or p-anisaldehyde solution.

The following synthetic schemes are merely illustrative of the methods by which the compounds of the invention may be prepared and are not intended to limit the scope of the invention as defined in the appended claims.

Preparation of N-arylpiperazines

Preparation Example 1

1-(3-chloro-2-methylphenyl)piperazine (Compound 28)

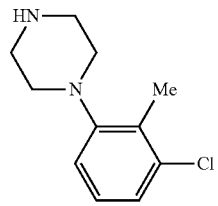 [SMILES: Cc1c(Cl)cccc1N1CCNCC1]

To a stirred solution of 3-chloro-2-methylaniline (compound 26, 21.6 g, 0.15 mol) in n-butanol (200 ml) was added bis(2-chloroethyl)amine hydrochloride (compound 27, 30 g, 0.17 mol) at room temperature and allowed to refluxed temperature for 2 days. After cooled to room temperature $Na_2CO_3$ (9 g, 0.08 mol) was added and then reaction mixture was refluxed 30 min. The resulting mixture was filtered with n-butanol (100 ml) and collected solid was dried under reduced pressure to be obtained title compound (24.8 g, 81%) as a white solid.

MH+211.

Preparation Example 2

8-(piperazin-1-yl)quinoline hydrochloride (Compound 33)

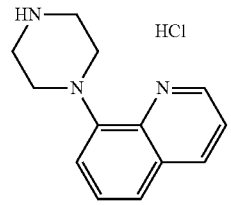 [SMILES: c1cnc2c(N3CCNCC3)cccc2c1 ; Cl]

Step 1: Quinolin-8-yl trifluoromethanesulfonate (Compound 31)

To a solution of quinolin-8-ol (compound 29, 8 g, 0.055 mol) and $K_2CO_3$ (15.2 g, 0.110 mol) in pyridine (60 ml) at −20° C. were added with trifluoromethanesulfonic anhydride (14 ml, 0.083 mol) dropwise. After stirring for 1 hour at −20° C., the reaction mixture was stirred at room temperature for 2 days. The resulting solution was quenched with water, and normal work-up was preceded. The residue was purified with normal preparative column to provide title compound (13 g, 85%) as white solid.

MH+278.

Step 2: tert-butyl 4-(quinolin-8-yl)piperazine-1-carboxylate (Compound 32)

t-butyl piperazine-1-carboxylate (compound 31, 8.6 g, 46 mmol) and quinolin-8-yl trifluoromethanesulfonate (compound 30, 11 g, 39.6 mmol) were added to a solution of $Cs_2CO_3$ (18 g, 55 mmol), BINAP (1.07 g) and $Pd(OAc)_2$ (367 mg) in THF (100 ml). The reaction mixture was refluxed for 1 day and then cooled down to room temperature. The resulting solution was diluted with $Et_2O$ (100 ml) and then filtered with Celite. The organic solution was evaporated under reduced pressure, the residue was purified with normal preparative column to give rise to desired compound (9.3 g, 74% yield) as a light yellow solid.

MH+314.

Step 3: 8-(piperazin-1-yl)quinoline hydrochloride (Compound 33)

t-butyl 4-(quinolin-8-yl)piperazine-1-carboxylate (compound 32, 2.4 g, 7.66 mmol) was dissolved in methanol (50 ml) and $SOCl_2$ was added to the solution dropwise at 0° C. The resulting solution was refluxed for 1 day and evaporated under reduced pressure. EtOAc (50 ml) was added to the residue and stirred for 2 hours to produce light yellow solid. The title compound was collected by filteration (1.7 g, 89%) as light yellow solid.

MH+214.

Preparation of Amines Containing N-arylpiperazines

Preparation Example 3

3-(4-(2,3-dichlorophenyl)piperazin-1-yl)propan-1-amine dihydrochloride (Compound 37)

Step 1: 2-(3-(4-(2,3-dichlorophenyl)piperazin-1-yl)propyl)isoindoline-1,3-dione (Compound 36)

The mixture of 1-(2,3-dichlorophenyl)piperazine hydrochloride (compound 35, 10.0 g, 37.4 mmol), N-(3-bromopropyl)phthalimide (compound 34, 9.09 g, 33.9 mmol) and potassium carbonate (11.7 g, 84.8 mmol) in DMF was stirred at room temperature. The mixture was concentrated under reduced pressure. The residue was diluted with $CH_2Cl_2$, and washed with water. The organic layer was dried over anhydrous $MgSO_4$, filtered, and concentrated in vacuo. The obtained product was washed with EtOH to provide the title compound (11.2 g, 80%) as a white solid.

$^1$H NMR (400 MHz, $CDCl_3$) δ 7.88-7.83 (m, 2H), 7.74-7.69 (m, 2H), 7.15-7.09 (m, 2H), 6.82 (dd, J=7.6, 2.4, 1H), 3.80 (t, J=7.2 Hz, 2H), 2.93-2.87 (m, 4H), 2.62-2.56 (m, 4H), 2.51 (t, J=5.6 Hz, 2H), 1.94-1.87 (m, 2H).

MH+418.

Step 2: 3-(4-(2,3-dichlorophenyl)piperazin-1-yl)propan-1-amine dihydrochloride (Compound 37)

To a suspension of 2-(3-(4-(2,3-dichlorophenyl)piperazin-1-yl)propyl)isoindoline-1,3-dione (compound 36, 11.1 g, 26.5 mmol) in EtOH was added hydrazine monohydrate. The reaction mixture was stirred at room temperature for 6 hrs, then the white solid filtered off. The filtrate was concentrated under reduced pressure. The residue was diluted with $CH_2Cl_2$, and washed with water. The organic layer was dried over anhydrous $MgSO_4$, filtered, and concentrated in vacuo.

To the crude product in diethyl ether was added 2M HCl solution in diethyl ether (10 mL). The obtained product was washed with diethyl ether to provide the title compound (6.98 g, 73%) as a white solid.

$^1$H NMR (400 MHz, CD$_3$OD) δ 7.22-7.18 (m, 2H), 7.08 (dd, J=7.2, 2.4, 1H), 3.06-3.02 (m, 6H), 2.72-2.64 (m, 4H), 2.60 (t, J=6.8 Hz, 2H), 1.90-1.84 (m, 2H).

MH+288.

Preparation of Amines Containing
β-hydroxy-N-arylpiperazines

Preparation Example 4

1-amino-3-(4-(2,3-dichlorophenyl)piperazin-1-yl) propan-2-ol (Compound 40)

To a stirred solution of N-(2,3-epoxypropyl)phthalimide (compound 38, 10 g, 0.049 mol) in THF (100 mL) was added 1-(2,3-dichlorophenyl)piperazine HCl (compound 35, 8.7 g, 0.033 mol) and triethylamine (4.6 mL, 0.033 mol) at R.T., and then the resultant solution was heated at 80° C. overnight. The reaction was quenched with H$_2$O and extracted with DCM. The organic layer was washed with brine, dried over MgSO$_4$, filtered, and evaporated. The solid residue was solidified with DCM (20 mL)/diethyl ether (200 mL), filtered and dried in vacuo, which was used for the following synthesis without further purification. To the prepared white solid piperazine (compound 39, 13 g, 0.030 mol) in EtOH was added hydrazine monohydrate (20 mL) and the reaction solution was refluxed at 80° C. for 2 hrs. The reaction solution was cooled to R.T. and evaporated. The oily crude compound was extracted with EtOAc/H$_2$O and organic layer was combined and evaporated. The pale yellow solid was tritylated with ether to afford pure targeted amine (8.7 g, 95%) as a white solid.

MH+304.

Preparation of Amines Containing
β-difluoride-N-arylpiperazines

Preparation Example 5

3-(4-(2,3-dichlorophenyl)piperazin-1-yl)-2,2-difluoropropan-1-amine (Compound 43)

Step 1: 2-(3-(4-(2,3-dichlorophenyl)piperazin-1-yl)-2-oxopropyl)isoindoline-1,3-dione (Compound 41)

To a stirred solution of oxalyl chloride (2.2 mL, 0.025 mol) in DCM (20 mL) was added dropwise a solution of DMSO (4 mL) in DCM (15 mL) at −60° C. The reaction mixture was warmed to −20° C. before a solution of (+/−)-hydroxy piperazine (compound 39, 5 g, 0.012 mol) in DCM (15 mL) was added. After the reaction mixture was stirred and allowed to warm to −10° C., triethylamine (8 mL, 0.058 mol) was added. The resultant mixture was warmed to R.T. and stirred for an additional 2 h, and then water was added. The aqueous layer was extracted with DCM, and the organic layers were combined, washed with brine, dried over MgSO$_4$, filtered, and evaporated. The oily residue was purified by flash column chromatography (Biotage SP1™) to obtain 4.4 g of the title compound (0.010 mol; 89%).

MH+432.

Step 2: 2-(3-(4-(2,3-dichlorophenyl)piperazin-1-yl)-2,2-difluoropropyl) isoindoline-1,3-dione (Compound 42)

To a stirred solution of ketone (compound 41, 4.4 g, 0.010 mol) in DCM (90 mL) was added dropwise (diethylamino)sulfur trifluoride (DAST, 3.8 mL, 0.029 mol) at −78° C. The reaction mixture was stirred at room temperature for 3 hrs. The reaction was quenched with aqueous NaHCO$_3$ and extracted with DCM/H$_2$O, and then the organic layers were combined, washed with brine, dried over MgSO$_4$, filtered, and evaporated. The oily residue was purified by flash column chromatography (Biotage SP1™) to obtain 990 mg of the title compound (2.2 mmol; 21%).

MH+454.

Step 3: 3-(4-(2,3-dichlorophenyl)piperazin-1-yl)-2,2-difluoropropan-1-amine (Compound 43)

To the difluoro-piperazine (compound 42, 1.2 g, 2.53 mmol) in EtOH (15 mL) was added hydrazine monohydrate (1.8 mL) and the reaction solution was refluxed at 80° C. for 1 hr. The reaction solution was cooled to R.T. and evaporated. The oily crude compound was extracted with EtOAc/H$_2$O and the organic layer was combined and evaporated. The crude compound was diluted with MeOH (5 mL) and added 2N HCl in ether solution to afford targeted amine HCl salts (1.0 g, 100%) as white solid.

MH+360.

Example 1

1-(4-chlorophenyl)-N-(3-(4-(2,3-dichlorophenyl) piperazin-1-yl)-2-hydroxy propyl)-2-propyl-1H-imidazole-4-carboxamide Step 1: N-(4-chlorophenyl)butyrimidamide (Compound 3)

To a solution of butyronitrile (compound 2, 7.5 mL, 86.2 mmol), AlCl$_3$ in toluene was added 4-chloroaniline (compound 1, 10.0 g, 78.4 mmol). The reaction mixture was stirred at 115° C. for 5 hrs. The mixture was diluted with water (200 mL) and extracted with EtOAc (200 mL) The aqueous layer was neutralized with saturated NaHCO$_3$ (500 mL) and extracted with EtOAc (300 mL×2). The organic layer was dried over anhydrous MgSO$_4$, filtered and concentrated in vacuo. The obtained product (9.2 g, pale brown solid) was used for the next step without purification.

Step 2: Ethyl 1-(4-chlorophenyl)-2-propyl-1H-imidazole-4-carboxylate (Compound 5)

To a solution of N-(4-chlorophenyl)butyrimidamide (compound 3, 3.5 g, 17.80 mmol), NaHCO$_3$ (3.14 g, 37.38 mmol) in i-PrOH was added ethyl bromopyruvate (compound 4, 4.7 mL, 37.38 mmol) under N$_2$. The reaction mixture was stirred at 85° C. for 72 hrs, then added AcOH (15 mL). After 4 hrs, the mixture was concentrated under reduced pressure. The residue was diluted with H$_2$O, and extracted with CH$_2$Cl$_2$. The organic layer was washed with saturated NaHCO$_3$ and 1N-HCl solution, then dried over anhydrous MgSO$_4$, filtered and concentrated in vacuo. The crude product was purified by flash column chromatography (Biotage Isolera™ FLASH Purification System was used for normal phase column chromatography with EtOAc and hexane) to provide the title compound (1.28 g, 25%) as a brown oil.

$^1$H NMR (400 MHz, CDCl$_3$) δ 7.62 (s, 1H), 7.51-7.47 (m, 2H), 7.26-7.23 (m, 2H), 4.39 (q, J=7.2 Hz, 2H), 2.62 (t, J=7.6 Hz, 2H), 1.71-1.61 (m, 2H), 1.39 (t, J=6.8 Hz, 3H), 0.86 (t, J=7.2 Hz, 3H).

MH+293.

Step 3: 1-(4-chlorophenyl)-2-propyl-1H-imidazole-4-carboxylic acid (Compound 6)

To a solution of ethyl 1-(4-chlorophenyl)-2-propyl-1H-imidazole-4-carboxylate (compound 5, 1.28 g, 4.37 mmol) in THF/water (20/20 mL) was added lithium hydroxide monohydrate at room temperature. The reaction mixture was stirred at 55° C. for 12 hrs. The mixture was washed with CH$_2$Cl$_2$, the aqueous layer was acidified with 1N-HCl solution (pH≈6), extracted with CH$_2$Cl$_2$. The organic layer was dried over anhydrous MgSO$_4$, filtered and concentrated in vacuo. The obtained product was washed with hexane to provide the title compound (740 mg, 64%) as a pale brown solid.

$^1$H NMR (400 MHz, CDCl$_3$) δ 7.71 (s, 1H), 7.53-7.50 (m, 2H), 7.31-7.29 (m, 2H), 7.71 (t, J=7.2 Hz, 2H), 1.73-1.63 (m, 2H), 0.88 (t, J=7.6 Hz, 3H).

MH+265.

Step 4: 1-(4-chlorophenyl)-N-(3-(4-(2,3-dichlorophenyl)piperazin-1-yl)-2-hydroxy propyl)-2-propyl-1H-imidazole-4-carboxamide To a mixture of lithium 1-(4-chlorophenyl)-2-propyl-1H-imidazole-4-carboxylic acid (compound 6, 150 mg, 0.57 mmol), 1-amino-3-(4-(2,3-dichlorophenyl)piperazin-1-yl)propan-2-ol dihydrochloride (compound 41, 260 mg, 0.68 mmol), EDCI (165 mg, 0.85 mmol) and HOBt (154 mg, 1.14 mmol) in anhydrous DMF (7 mL) was added NMM (190 μl, 1.71 mmol). The reaction mixture was stirred at room temperature for 15 hrs. The mixture was concentrated under reduced pressure. The residue was diluted with CH$_2$Cl$_2$, and washed with water. The organic layer was dried over anhydrous MgSO$_4$, filtered, and concentrated in vacuo. The crude product was purified by preparative HPLC (purification system, Gilson) to provide the title compound (74 mg, 24%) as a white solid.

$^1$H NMR (400 MHz, DMSO-d$_6$) δ 8.00 (t, J=5.6 Hz, 1H), 7.69 (s, 1H), 7.59-7.56 (m, 2H), 7.49-7.45 (m, 2H), 7.29-7.23 (m, 2H), 7.10 (dd, J=7.2, 2.8 Hz, 1H), 4.88 (br s, 1H), 3.81-3.75 (m, 1H), 3.38-2.29 (m, 2H), 3.06-2.98 (m, 4H), 2.62-2.55 (m, 4H), 2.52-2.48 (m, 2H), 2.45-2.37 (m, 2H), 1.53-1.43 (m, 2H), 0.70 (t, J=7.2 Hz, 3H).

MH+550.

The following compounds of Examples 2 to 4 were obtained by using corresponding starting materials and repeating the procedure of Example 1.

Example 2

1-(4-chlorophenyl)-N-(3-(4-(2,3-dichlorophenyl)piperazin-1-yl)propyl)-2-propyl-1H-imidazole-4-carboxamide dihydrochloride $^1$H NMR (400 MHz, CD$_3$OD) δ 8.17 (s, 1H), 7.71-7.67 (m, 2H), 7.63-7.60 (m, 2H), 7.31-7.25 (m, 2H), 7.15 (dd, J=6.8, 2.8 Hz, 1H), 3.72-3.69 (m, 2H), 3.55-3.37 (m, 4H), 3.35-3.33 (m, 4H), 3.21-3.15 (m, 2H), 2.88 (d, J=7.2 Hz, 2H), 2.18-2.11 (m, 2H), 1.68-1.62 (m, 2H), 0.89 (t, J=7.2 Hz, 3H).

MH+534.

Example 3

1-(4-chlorophenyl)-N-(3-(4-(2,3-dimethylphenyl)piperazin-1-yl)propyl)-2-propyl-1H-imidazole-4-carboxamide $^1$H NMR (400 MHz, CDCl$_3$) δ 7.60 (br s, 1H), 7.55 (s, 1H), 7.50-7.46 (m, 2H), 7.25-7.20 (m, 2H), 7.08 (d, J=8.0 Hz, 1H), 6.98-6.93 (m, 2H), 3.61-3.55 (m, 2H), 3.38-3.13 (m, 6H), 3.05-2.95 (m, 6H), 2.56 (t, J=7.6 Hz, 2H), 2.26 (s, 3H), 2.19 (s, 3H), 1.70-1.62 (m, 2H), 0.88 (t, J=7.2 Hz, 2H).

MH+494.

Example 4

1-(4-chlorophenyl)-N-(2-(4-(2,3-dichlorophenyl)piperazin-1-yl)ethyl)-2-propyl-1H-imidazole-4-carboxamide $^1$H NMR (400 MHz, DMSO-d$_6$) δ 7.87 (br s, 1H), 7.73 (s, 1H), 7.61-7.58 (m, 2H), 7.51-7.48 (m, 2H), 7.35-7.26 (m, 2H), 7.19-7.10 (m, 1H), 3.57-3.45 (m, 6H), 3.08-2.96 (m, 4H), 2.55 (t, J=7.2 Hz, 2H), 1.59-1.50 (m, 2H), 0.79 (t, J=7.6 Hz, 3H).

MH+520.

Preparation of Imidazoles Containing Substituted Phenyl Ring

Preparation Example 6

Lithium 2,5-dimethyl-1-phenyl-1H-imidazole-4-carboxylate (Compound 13a)

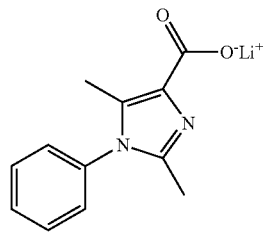

Step 1: Ethyl 2-(hydroxyimino)-3-oxobutanoate (Compound 8)

To a solution of ethyl acetoacetate (compound 7, 30 g, 0.23 mol) in acetic acid (35 mL) was added slowly sodium nitrite (18.0 g, 0.25 mol) in cold water (40 mL) at −10° C. The reaction mixture was stirred for 1 hr, then added cold water (120 mL) and stirred for 3 hrs. The mixture was extracted with diethyl ether (300 mL). The organic layer was washed with saturated NaHCO$_3$ (400 mL×2), then dried over anhydrous MgSO$_4$, filtered and concentrated in vacuo. The obtained product (21.46 g, white solid) was used for the next step without purification.

$^1$H NMR (400 MHz, DMSO-d$_6$) δ 13.20 (s, 1H), 4.21 (q, J=7.2 Hz, 2H), 2.32 (s, 3H), 1.92 (t, J=6.8 Hz, 3H).

Step 2: Ethyl 2-acetamido-3-oxobutanoate (Compound 10)

To a mixture of ethyl 2-(hydroxyimino)-3-oxobutanoate (compound 8, 9.32 g, 58.5 mmol), Pd/C (400 mg, palladium on carbon, 10 wt %, support activated carbon, wet, Degussa type E101 NE/W) in EtOH was added acetic anhydride (compound 9, 11.0 mL, 117.0 mmol) at room temperature. The reaction mixture was stirred at room temperature under $H_2$ for 15 hrs. The palladium was filtered off (filter aid, Celite 521 AW), then the filtrate was concentrated in vacuo. The crude product was purified by flash column chromatography (Biotage SP1™ FLASH Purification System was used for normal phase column chromatography with tetrahydrofuran and hexane) to provide the title compound (9.48 g, 86%) as a white solid.

$^1$H NMR (400 MHz, CDCl$_3$) δ 6.62 (br s, 1H), 5.25 (d, J=6.4 Hz, 1H), 4.28 (q, J=7.2 Hz, 2H), 2.39 (s, 3H), 2.07 (s, 3H), 1.32 (t, J=7.2 Hz, 3H).

Step 3: Ethyl 2,5-dimethyl-1-phenyl-1H-imidazole-4-carboxylate (Compound 12a)

To a solution of ethyl 2-acetamido-3-oxobutanoate (compound 10, 5.0 g, 26.7 mmol), aniline (compound 11a, 7.3 mL, 80.1 mmol) in butyronitrile (10 mL) was added trifluoroacetic acid (6.2 mL, 80.1 mmol) at room temperature. The reaction mixture was irradiated in a microwave reactor (Biotage Initiator™) for 40 minutes at 140° C. The mixture was concentrated under reduced pressure. The residue was diluted with CH$_2$Cl$_2$, and washed with aqueous K$_2$CO$_3$. The organic layer was dried over anhydrous MgSO$_4$, filtered, and concentrated in vacuo. The crude product was purified by flash column chromatography (Biotage SP1™ FLASH Purification System was used for normal phase column chromatography with tetrahydrofuran and hexane) to provide the title compound (4.97 g, 76%) as a yellow solid.

$^1$H NMR (400 MHz, CDCl$_3$) δ 7.57-7.51 (m, 3H), 7.20-7.18 (m, 2H), 4.41 (q, J=6.8 Hz, 2H), 2.31 (s, 3H), 2.22 (s, 3H), 1.42 (t, J=7.2 Hz, 3H).

MH+245.

Step 4: Lithium 2,5-dimethyl-1-phenyl-1H-imidazole-4-carboxylate (Compound 13a)

To a solution of ethyl 2,5-dimethyl-1-phenyl-1H-imidazole-4-carboxylate (compound 12a, 4.97 g, 20.3 mmol) in THF/water (15/15 mL) was added lithium hydroxide monohydrate at room temperature. The reaction mixture was stirred at 55° C. for 12 hrs, then the mixture was concentrated in vacuo. The crude solid was washed with diethyl ether to provide the title compound (4.06 g, 90%) as a white solid. The obtained product was used for the next step without purification.

Free form (non-Li$^+$ salt): $^1$H NMR (400 MHz, CDCl$_3$) δ 7.60-7.53 (m, 3H), 7.23-7.19 (m, 2H), 2.32 (s, 3H), 2.25 (s, 3H).

MH+217.

Preparation Example 7

Lithium 2,5-dimethyl-1-(pyridin-2-yl)-1H-imidazole-4-carboxylic acid (Compound 13b)

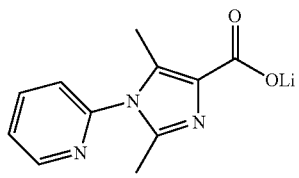

Step 1: Ethyl 2,5-dimethyl-1-(pyridin-2-yl)-1H-imidazole-4-carboxylate (Compound 12b)

To a solution of ethyl 2-acetamido-3-oxobutanoate (compound 10, 2.0 g, 10.6 mmol), aniline (compound 11b, 2.0 g, 21.3 mmol) in butyronitrile (15 mL) was added acetic acid (1.2 mL, 21.3 mmol) at room temperature. The reaction mixture was irradiated in a microwave reactor (Biotage Initiator™) for 40 minutes at 160° C. The mixture was concentrated under reduced pressure. The crude product was purified by preparative HPLC (purification system, Gilson) to provide the title compound (340 mg, 14%) as a brown oil.

MH+246.

Step 2: Lithium 2,5-dimethyl-1-(pyridin-2-yl)-1H-imidazole-4-carboxylic acid (Compound 13b)

To a solution of ethyl 2,5-dimethyl-1-(pyridin-2-yl)-1H-imidazole-4-carboxylate (compound 12b, 340 mg, 1.4 mmol) in THF/water (10/10 mL) was added lithium hydroxide monohydrate at room temperature. The reaction mixture was stirred at 60° C. for 12 hrs, then the mixture was concentrated in vacuo. The crude solid was washed with diethyl ether to provide the title compound as a pale yellow solid. The obtained product was used for the next step without purification.

Free form (non-Li$^+$ salt): $^1$H NMR (400 MHz, CD$_3$OD) δ 8.97-8.95 (m, 1H), 7.93-7.88 (m, 1H), 7.63-7.61 (m, 1H), 7.32-7.28 (m, 1H), 2.40 (s, 3H), 2.18 (s, 3H).

MH+218.

Example 5

N-(3-(4-(2,3-dichlorophenyl)piperazin-1-yl)-2-hydroxypropyl)-2,5-dimethyl-1-phenyl-1H-imidazole-4-carboxamide To a mixture of lithium 2,5-dimethyl-1-phenyl-1H-imidazole-4-carboxylate (compound 13a, 150 mg, 0.67 mmol), 1-amino-3-(4-(2,3-dichlorophenyl)piperazin-1-yl)propan-2-ol dihydrochloride (compound 41, 300 mg, 0.80 mmol), EDCI (260 mg, 1.34 mmol) and HOBt (180 mg, 1.34 mmol) in anhydrous DMF (7 mL) was added NMM (370 µl, 3.35 mmol). The reaction mixture was stirred at room temperature for 15 hrs. The reaction mixture was concentrated under reduced pressure. The residue was diluted with CH$_2$Cl$_2$, and washed with water. The organic layer was dried over anhydrous MgSO$_4$, filtered, and concentrated in vacuo. The crude product was purified by preparative HPLC (purification system, Gilson) to provide the title compound (134 mg, 40%) as a white solid.

$^1$H NMR (400 MHz, DMSO-$d_6$) δ 7.98 (t, J=5.6 Hz, 1H), 7.57-7.48 (m, 3H), 7.36-7.33 (m, 2H), 7.28-7.23 (m, 2H), 7.11 (dd, J=7.2, 3.2 Hz, 1H), 4.85 (d, J=4.8 Hz, 1H), 3.76-3.74 (m, 1H), 3.32-3.27 (m, 2H), 3.03-2.98 (m, 4H), 2.61-2.56 (m, 4H), 2.40-2.38 (m, 2H), 2.20 (s, 3H), 2.05 (s, 3H).

MH+502.

The following compounds of Examples 6 to 331 were obtained by using corresponding starting materials and repeating the procedure of Example 5.

Example 6

N-(3-(4-(2,3-dichlorophenyl)piperazin-1-yl)propyl)-2,5-dimethyl-1-phenyl-1H-imidazole-4-carboxamide $^1$H NMR (400 MHz, DMSO-$d_6$) δ 8.21 (t, J=5.6 Hz, 1H), 7.57-7.51 (m, 3H), 7.37-7.34 (m, 2H), 7.27-7.23 (m, 2H), 7.11 (dd, J=6.4, 2.8 Hz, 1H), 3.27-3.25 (m, 2H), 3.07-3.01 (m, 4H), 2.57-2.50 (m, 4H), 2.42-2.39 (m, 2H), 2.20 (s, 3H), 2.04 (s, 3H), 1.69-1.62 (m, 2H).

MH+486.

Example 7

N-(3-(4-(2,3-dichlorophenyl)piperazin-1-yl)propyl)-5-methyl-1-phenyl-2-propyl-1H-imidazole-4-carboxamide dihydrochloride $^1$H NMR (400 MHz, DMSO-$d_6$) δ 11.03 (s, 1H), 8.85 (br s, 1H), 7.65-7.62 (m, 3H), 7.53-7.51 (m, 2H), 7.36-7.30 (m, 2H), 7.18 (dd, J=6.8, 2.0 Hz, 1H), 3.57-3.54 (m, 2H), 3.42-3.33 (m, 4H), 3.23-3.12 (m, 6H), 2.57 (t, J=7.6 Hz, 2H), 2.23 (s, 3H), 2.05-1.99 (m, 2H), 1.61-1.51 (m, 2H), 0.76 (t, J=7.2 Hz, 3H).

MH+514.

Example 8

N-(2-(4-(2,3-dichlorophenyl)piperazin-1-yDethyl)-2,5-dimethyl-1-phenyl-1H-imidazole-4-carboxamide $^1$H NMR (400 MHz, DMSO-$d_6$) δ 7.78 (t, J=5.6 Hz, 1H), 7.58-7.49 (m, 3H), 7.38-7.35 (m, 2H), 7.28-7.25 (m, 2H), 7.13 (dd, J=6.4, 3.2 Hz, 1H), 3.37-3.32 (m, 2H), 2.99-2.94 (m, 4H), 2.59-2.54 (m, 4H), 2.50-2.48 (m, 2H), 2.20 (s, 3H), 2.08 (s, 3H).

MH+472.

Example 9

N-(2-(4-(2,3-dichlorophenyl)piperazin-1-yl)ethyl)-5-methyl-1-phenyl-2-propyl-1H-imidazole-4-carboxamide $^1$H NMR (400 MHz, DMSO-$d_6$) δ 7.78 (br s, 1H), 7.59-7.50 (m, 3H), 7.37-7.34 (m, 2H), 7.29-7.25 (m, 2H), 7.18-7.11 (m, 1H), 3.37-3.32 (m, 2H), 3.01-2.92 (m, 4H), 2.61-2.49 (m, 6H), 2.36 (t, J=7.6 Hz, 2H), 2.19 (s, 3H), 1.52-1.42 (m, 2H), 0.76 (t, J=7.2 Hz, 3H).

MH+500.

Example 10

N-(3-(4-(2,3-dichlorophenyl)piperazin-1-yl)propyl)-1-(4-methoxyphenyl)-2,5-dimethyl-1H-imidazole-4-carboxamide $^1$H NMR (400 MHz, DMSO-$d_6$) δ 8.14 (t, J=6.0 Hz, 1H), 7.29-7.23 (m, 2H), 7.11 (dd, J=6.4, 2.4 Hz, 1H), 7.08-7.04 (m, 2H), 3.80 (s, 3H), 3.27-3.24 (m, 2H), 3.07-3.01 (m, 4H), 2.55-2.50 (m, 4H), 2.41 (t, J=6.8 Hz, 2H), 2.19 (s, 3H), 2.03 (s, 3H), 1.69-1.62 (m, 2H).

MH+516.

Example 11

1-(4-chlorophenyl)-N-(3-(4-(2,3-dichlorophenyl)piperazin-1-yl)propyl)-2,5-dimethyl-1H-imidazole-4-carboxamide $^1$H NMR (400 MHz, DMSO-$d_6$) δ 8.18 (t, J=5.6 Hz, 1H), 7.63-7.59 (m, 2H), 7.44-7.40 (m, 2H), 7.29-7.23 (m, 2H), 7.11 (dd, J=6.8, 2.8 Hz, 1H), 3.27-3.24 (m, 2H), 3.07-3.01 (m, 4H), 2.55-2.50 (m, 4H), 2.42 (t, J=6.4 Hz, 2H), 2.21 (s, 3H), 2.05 (s, 3H), 1.69-1.62 (m, 2H).

MH+520.

Example 12

N-(3-(4-(2,3-dichlorophenyl)piperazin-1-yl)propyl)-2-ethyl-5-methyl-1-phenyl-1H-imidazole-4-carboxamide $^1$H NMR (400 MHz, DMSO-$d_6$) δ 8.10 (t, J=5.6 Hz, 1H), 7.58-7.49 (m, 3H), 7.36-7.33 (m, 2H), 7.29-7.22 (m, 2H), 7.10 (dd, J=6.8, 2.4 Hz, 1H), 3.32-3.28 (m, 2H), 3.05-3.01 (m, 4H), 2.55-2.52 (m, 4H), 2.42 (t, J=6.4 Hz, 2H), 2.36 (q, J=7.6 Hz, 2H), 2.19 (s, 3H), 1.70-1.63 (m, 2H), 0.96 (t, J=7.6 Hz, 3H).

MH+500.

Example 13

N-(2-(4-(2,3-dichlorophenyl)piperazin-1-yl)ethyl)-2-ethyl-5-methyl-1-phenyl-1H-imidazole-4-carboxamide $^1$H NMR (400 MHz, DMSO-$d_6$) δ 7.77 (t, J=5.6 Hz, 1H), 7.58-7.50 (m, 3H), 7.37-7.35 (m, 2H), 7.30-7.25 (m, 2H), 7.13-7.11 (m, 1H), 3.39-3.34 (m, 2H), 3.00-2.96 (m, 4H), 2.64-2.56 (m, 4H), 2.51 (t, J=6.4 Hz, 2H), 2.40 (q, J=7.6 Hz, 2H), 2.19 (s, 3H), 1.03 (t, J=7.2 Hz, 3H).

MH+486.

Example 14

N-(2-(4-(2,3-dimethylphenyl)piperazin-1-yl)ethyl)-2,5-dimethyl-1-phenyl-1H-imidazole-4-carboxamide $^1$H NMR (400 MHz, DMSO-$d_6$) δ 7.78 (t, J=5.6 Hz, 1H), 7.58-7.50 (m, 3H), 7.38-7.35 (m, 2H), 7.00 (t, J=7.6 Hz, 1H), 6.86 (d, J=7.6 Hz, 1H), 6.83 (d, J=7.6 Hz, 1H), 3.35-3.33 (m, 2H), 2.79-2.74 (m, 4H), 2.58-2.52 (m, 4H), 2.50-2.48 (m, 2H), 2.20 (s, 3H), 2.17 (s, 3H), 2.12 (s, 3H), 2.08 (s, 3H).

MH+432.

Example 15

N-(3-(4-(2,3-dimethylphenyl)piperazin-1-yl)propyl)-2,5-dimethyl-1-phenyl-1H-imidazole-4-carboxamide $^1$H NMR (400 MHz, DMSO-d$_6$) δ 8.16 (t, J=6.0 Hz, 1H), 7.58-7.48 (m, 3H), 7.37-7.34 (m, 2H), 6.98 (t, J=8.0 Hz, 1H), 6.86 (d, J=7.6 Hz, 1H), 6.81 (d, J=7.6 Hz, 1H), 3.27-3.25 (m, 2H), 2.85-2.82 (m, 4H), 2.59-2.52 (m, 4H), 2.40 (t, J=6.8 Hz, 2H), 2.20 (s, 3H), 2.16 (s, 3H), 2.11 (s, 3H), 2.05 (s, 3H), 1.69-1.62 (m, 2H).
MH+446.

Example 16

N-(3-(4-(2,3-dimethylphenyl)piperazin-1-yl)propyl)-2-ethyl-5-methyl-1-phenyl-1H-imidazole-4-carboxamide $^1$H NMR (400 MHz, DMSO-d$_6$) δ 8.08 (t, J=6.0 Hz, 1H), 7.58-7.51 (m, 3H), 7.36-7.33 (m, 2H), 6.98 (t, J=7.6 Hz, 1H), 6.85 (d, J=7.6 Hz, 1H), 6.82 (d, J=7.2 Hz, 1H), 3.27-3.25 (m, 2H), 2.85-2.82 (m, 4H), 2.59-2.52 (m, 4H), 2.42-2.35 (m, 4H), 2.19 (s, 3H), 2.16 (s, 3H), 2.11 (s, 3H), 1.69-1.65 (m, 2H), 0.98 (t, J=7.2 Hz, 3H).
MH+460.

Example 17

N-(3-(4-(2,3-dimethylphenyl)piperazin-1-yl)propyl)-5-methyl-1-phenyl-2-propyl-1H-imidazole-4-carboxamide dihydrochloride $^1$H NMR (400 MHz, DMSO-d$_6$) δ 10.63 (s, 1H), 8.31 (br s, 1H), 7.61-7.53 (m, 3H), 7.40-7.38 (m, 2H), 7.04 (t, J=7.6 Hz, 1H), 6.91-6.86 (m, 2H), 3.52-3.48 (m, 2H), 3.32 (q, J=6.4 Hz, 2H), 3.19-3.13 (m, 4H), 3.09-3.04 (m, 4H), 2.43-2.41 (m, 2H), 2.20 (s, 3H), 2.18 (s, 3H), 2.13 (s, 3H), 1.99-1.95 (m, 2H), 1.52-1.46 (m, 2H), 0.75 (t, J=7.6 Hz, 3H).
MH+474.

Example 18

N-(2-(4-(2,3-dimethylphenyl)piperazin-1-yl)ethyl)-2-ethyl-5-methyl-1-phenyl-1H-imidazole-4-carboxamide $^1$H NMR (400 MHz, DMSO-d$_6$) δ 7.78 (t, J=6.0 Hz, 1H), 7.58-7.50 (m, 3H), 7.37-7.35 (m, 2H), 7.01 (d, J=7.6 Hz, 1H), 6.86-6.82 (m, 2H), 3.37-3.33 (m, 2H), 2.78-2.76 (m, 4H), 2.58-2.52 (m, 4H), 2.51-2.48 (m, 2H), 2.40 (q, J=7.6 Hz, 2H), 2.19 (s, 3H), 2.17 (s, 3H), 2.12 (s, 3H), 1.04 (t, J=7.6 Hz, 3H).
MH+446.

Example 19

N-(2-(4-(2,3-dimethylphenyl)piperazin-1-yl)ethyl)-5-methyl-1-phenyl-2-propyl-1H-imidazole-4-carboxamide dihydrochloride $^1$H NMR (400 MHz, DMSO-d$_6$) δ 10.46 (s, 1H), 8.41 (br s, 1H), 7.61-7.53 (m, 3H), 7.39-7.37 (m, 2H), 7.04 (t, J=7.6 Hz, 1H), 6.91-6.86 (m, 2H), 3.69-3.61 (m, 4H), 3.33-3.30 (m, 2H), 3.29-3.24 (m, 2H), 3.13-3.04 (m, 4H), 2.43-2.41 (m, 2H), 2.21 (s, 3H), 2.18 (s, 3H), 2.14 (s, 3H), 1.52-1.46 (m, 2H), 0.76 (t, J=7.2 Hz, 3H).
MH+460.

Example 20

N-(3-(4-(2,3-dichlorophenyl)piperazin-1-yl)propyl)-1-(4-fluorophenyl)-2,5-dimethyl-1H-imidazole-4-carboxamide $^1$H NMR (400 MHz, DMSO-d$_6$) δ 8.17 (t, J=5.6 Hz, 1H), 7.46-7.36 (m, 4H), 7.29-7.23 (m, 2H), 7.14-7.11 (m, 1H), 3.29-3.25 (m, 2H), 3.06-3.01 (m, 4H), 2.54-2.51 (m, 4H), 2.41 (t, J=6.8 Hz, 2H), 2.20 (s, 3H), 2.04 (s, 3H), 1.69-1.62 (m, 2H).
MH+504.

Example 21

N-(2-(4-(2,3-dichlorophenyl)piperazin-1-yl)ethyl)-1-(4-fluorophenyl)-2,5-dimethyl-1H-imidazole-4-carboxamide $^1$H NMR (400 MHz, DMSO-d$_6$) δ 7.76 (t, J=6.0 Hz, 1H), 7.47-7.37 (m, 4H), 7.30-7.25 (m, 2H), 7.13 (dd, J=6.8, 2.8 Hz, 1H), 3.37-3.32 (m, 2H), 2.98-2.92 (m, 4H), 2.58-2.53 (m, 4H), 2.50-2.48 (m, 2H), 2.20 (s, 3H), 2.08 (s, 3H).
MH+490.

Example 22

1-(4-chlorophenyl)-N-(3-(4-(2,3-dimethylphenyl)piperazin-1-yl)propyl)-2,5-dimethyl-1H-imidazole-4-carboxamide $^1$H NMR (400 MHz, DMSO-d$_6$) δ 8.15 (t, J=6.0 Hz, 1H), 7.62-7.59 (m, 2H), 7.44-7.40 (m, 2H), 6.98 (t, J=7.6 Hz, 1H), 6.86 (d, J=7.6 Hz, 1H), 6.81 (d, J=7.6H, 1H), 3.29-3.24 (m, 2H), 2.84-2.81 (m, 4H), 2.53-2.51 (m, 4H), 2.41 (t, J=6.8 Hz, 2H), 2.21 (s, 3H), 2.16 (s, 3H), 2.12 (s, 3H), 2.06 (s, 3H), 1.69-1.62 (m, 2H).
MH+480.

Example 23

N-(3-(4-(2,3-dichlorophenyl)piperazin-1-yl)-2-hydroxypropyl)-2-ethyl-5-methyl-1-phenyl-1H-imidazole-4-carboxamide $^1$H NMR (400 MHz, DMSO-d$_6$) δ 7.92 (t, J=6.0 Hz, 1H), 7.57-7.49 (m, 3H), 7.35-7.32 (m, 2H), 7.28-7.23 (m, 2H), 7.10 (dd, J=7.2, 2.8 Hz, 1H), 4.86 (d, J=4.4 Hz, 1H), 3.77-3.74 (m, 1H), 3.32-3.30 (m, 2H), 3.03-2.98 (m, 4H), 2.62-2.56 (m, 4H), 2.40-2.34 (m, 4H), 2.18 (s, 3H), 0.98 (t, J=7.2 Hz, 3H).
MH+516.

Example 24

N-(3-(4-(2,3-dichlorophenyl)piperazin-1-yl)-2-hydroxypropyl)-5-methyl-1-phenyl-2-propyl-1H-imidazole-4-carboxamide $^1$H NMR (400 MHz, DMSO-d$_6$) δ 7.94 (t, J=6.0 Hz, 1H), 7.57-7.50 (m, 3H), 7.34-7.32 (m, 2H), 7.28-7.22 (m, 2H), 7.10 (dd, J=7.2, 2.4 Hz, 1H), 4.87 (d, J=4.4 Hz, 1H), 3.77-3.72 (m, 1H), 3.30 (t, J=6.0 Hz, 2H), 3.03-2.98 (m, 4H), 2.61-2.56 (m, 4H), 2.40 (d, J=6.4 Hz, 2H), 2.32 (t, J=7.6 Hz, 2H), 2.18 (s, 3H), 1.43-1.37 (m, 2H), 0.67 (t, J=7.2 Hz, 3H).
MH+530.

Example 25

1-(4-chlorophenyl)-N-(3-(4-(2,3-dichlorophenyl) piperazin-1-yl)propyl)-2-ethyl-5-methyl-1H-imidazole-4-carboxamide $^1$H NMR (400 MHz, DMSO-d$_6$) δ 8.09 (t, J=5.2 Hz, 1H), 7.61 (d, J=8.4 Hz, 2H), 7.41 (d, J=8.4 Hz, 2H), 7.28-7.24 (m, 2H), 7.10-7.08 (m, 1H), 3.28-3.24 (m, 2H), 3.06-3.01 (m, 4H), 2.57-2.52 (m, 4H), 2.41-2.33 (m, 4H), 2.19 (s, 3H), 1.67-1.63 (m, 2H), 0.96 (t, J=7.6 Hz, 3H).
MH+534.

Example 26

N-(3-(4-(2,3-dichlorophenyl)piperazin-1-yl)-2-hydroxypropyl)-1-(4-fluorophenyl)-2,5-dimethyl-1H-imidazole-4-carboxamide $^1$H NMR (400 MHz, DMSO-d$_6$) δ 7.98 (t, J=5.6 Hz, 1H), 7.46-7.35 (m, 4H), 7.28-7.23 (m, 2H), 7.10 (dd, J=6.4, 2.4 Hz, 1H), 4.85 (d, J=4.4 Hz, 1H), 3.77-3.72 (m, 1H), 3.35-3.22 (m, 2H), 3.03-2.97 (m, 4H), 2.61-2.45 (m, 4H), 2.40-2.38 (m, 2H), 2.19 (s, 3H), 2.04 (s, 3H).
MH+520.

Example 27

1-(4-chlorophenyl)-N-(2-(4-(2,3-dichlorophenyl) piperazin-1-yl)ethyl)-2,5-dimethyl-1H-imidazole-4-carboxamide $^1$H NMR (400 MHz, DMSO-d$_6$) δ 7.77 (t, J=5.6 Hz, 1H), 7.63-7.60 (m, 2H), 7.44-7.41 (m, 2H), 7.29-7.24 (m, 2H), 7.12 (dd, J=6.8, 3.2 Hz, 1H), 3.36-3.27 (m, 2H), 2.98-2.92 (m, 4H), 2.58-2.53 (m, 4H), 2.50-2.48 (m, 2H), 2.20 (s, 3H), 2.08 (s, 3H).
MH+506.

Example 28

1-(4-chlorophenyl)-N-(2-(4-(2,3-dichlorophenyl) piperazin-1-yl)ethyl)-2-ethyl-5-methyl-1H-imidazole-4-carboxamide $^1$H NMR (400 MHz, DMSO-d$_6$) δ 7.76 (t, J=5.6 Hz, 1H), 7.63-7.59 (m, 2H), 7.44-7.40 (m, 2H), 7.29-7.24 (m, 2H), 7.11 (dd, J=6.4, 2.8 Hz, 1H), 3.37-3.33 (m, 2H), 2.98-2.92 (m, 4H), 2.58-2.53 (m, 4H), 2.51-2.49 (m, 2H), 2.39 (q, J=7.6 Hz, 2H), 2.19 (s, 3H), 1.03 (t, J=7.2 Hz, 3H).
MH+520.

Example 29

N-(3-(4-(2,3-dichlorophenyl)piperazin-1-yl)propyl)-2,5-dimethyl-1-p-tolyl-1H-imidazole-4-carboxamide $^1$H NMR (400 MHz, DMSO-d$_6$) δ 8.14 (t, J=5.6 Hz, 1H), 7.34 (d, J=8.4 Hz, 2H), 7.28-7.20 (m, 4H), 7.11 (dd, J=6.8, 2.8 Hz, 1H), 3.28-2.24 (m, 2H), 3.04-3.01 (m, 4H), 2.57-2.52 (m, 4H), 2.40 (t, J=6.4 Hz, 2H), 2.36 (s, 3H), 2.18 (s, 3H), 2.03 (s, 3H), 1.67-1.63 (m, 2H).
MH+500.

Example 30

N-(2-(4-(2,3-dichlorophenyl)piperazin-1-yl)ethyl)-2,5-dimethyl-1-p-tolyl-1H-imidazole-4-carboxamide $^1$H NMR (400 MHz, DMSO-d$_6$) δ 7.74 (t, J=6.0 Hz, 1H), 7.34 (d, J=8.4 Hz, 2H), 7.29-7.21 (m, 4H), 7.12 (dd, J=6.8, 3.2 Hz, 1H), 3.36-3.33 (m, 2H), 2.98-2.92 (m, 4H), 2.58-2.52 (m, 4H), 2.49-2.45 (m, 2H), 2.36 (s, 3H), 2.18 (s, 3H), 2.06 (s, 3H).
MH+486.

Example 31

N-(3-(4-(2,3-dichlorophenyl)piperazin-1-yl)-2-hydroxypropyl)-2,5-dimethyl-1-p-tolyl-1H-imidazole-4-carboxamide $^1$H NMR (400 MHz, DMSO-d$_6$) δ 7.95 (t, J=5.6 Hz, 1H), 7.34 (d, J=8.0 Hz, 2H), 7.28-7.20 (m, 4H), 7.10 (dd, J=6.8, 2.4 Hz, 1H), 4.84 (br s, 1H), 3.76-3.73 (m, 1H), 3.35-3.22 (m, 2H), 3.03-2.97 (m, 4H), 2.61-2.55 (m, 4H), 2.40-2.37 (m, 2H), 2.36 (s, 3H), 2.18 (s, 3H), 2.03 (s, 3H).
MH+516.

Example 32

1-(4-chlorophenyl)-N-(3-(4-(2,3-dichlorophenyl) piperazin-1-yl)-2-hydroxypropyl)-2,5-dimethyl-1H-imidazole-4-carboxamide $^1$H NMR (400 MHz, DMSO-d$_6$) δ 7.97 (t, J=5.6 Hz, 1H), 7.62-7.59 (m, 2H), 7.44-7.40 (m, 2H), 7.28-7.23 (m, 2H), 7.10 (dd, J=6.8, 2.8 Hz, 1H), 4.84 (br s, 1H), 3.76-3.73 (m, 1H), 3.34-3.23 (m, 2H), 3.03-2.97 (m, 4H), 2.61-2.56 (m, 4H), 3.40-2.38 (m, 2H), 2.20 (s, 3H), 2.05 (s, 3H).
MH+536.

Example 33

1-(4-chlorophenyl)-N-(3-(4-(2,3-dichlorophenyl) piperazin-1-yl)-2-hydroxypropyl)-2-ethyl-5-methyl-1H-imidazole-4-carboxamide $^1$H NMR (400 MHz, DMSO-d$_6$) δ 7.92 (t, J=6.0 Hz, 1H), 7.62-7.59 (m, 2H), 7.43-7.40 (m, 2H), 7.28-7.23 (m, 2H), 7.10 (dd, J=7.2, 2.8 Hz, 1H), 4.85 (br s, 1H), 3.75-3.73 (m, 1H), 3.35-3.28 (m, 2H), 3.03-2.97 (m, 4H), 2.61-2.56 (m, 4H), 2.40-2.34 (m, 4H), 2.19 (s, 3H), 0.98 (t, J=7.6 Hz, 3H).
MH+550.

Example 34

N-(3-(4-(2,3-dimethylphenyl)piperazin-1-yl)propyl)-1-(4-fluorophenyl)-2,5-dimethyl-1H-imidazole-4-carboxamide $^1$H NMR (400 MHz, DMSO-d$_6$) δ 8.15 (t, J=5.6 Hz, 1H), 7.45-7.35 (m, 4H), 6.97 (t, J=7.6 Hz, 1H), 6.85 (d, J=7.6 Hz, 1H), 6.81 (d, J=7.6 Hz, 1H), 3.29-3.24 (m, 2H), 2.84-2.81 (m, 4H), 2.58-2.49 (m, 4H), 2.19 (s, 3H), 2.15 (s, 3H), 2.11 (s, 3H), 2.04 (s, 3H), 1.68-1.61 (m, 2H).
MH+464.

Example 35

N-(3-(4-(2,3-dimethylphenyl)piperazin-1-yl)-2-hydroxypropyl)-1-(4-fluorophenyl)-2,5-dimethyl-1H-imidazole-4-carboxamide $^1$H NMR (400 MHz, DMSO-$d_6$) δ 7.98 (t, J=5.6 Hz, 1H), 7.47-7.36 (m, 4H), 6.99 (t, J=7.6 Hz, 1H), 6.86 (d, J=7.6 Hz, 1H), 6.82 (d, J=7.2 Hz, 1H), 4.84 (br s, 1H), 3.77-3.75 (m, 1H), 3.36-3.24 (m, 2H), 2.88-2.82 (m, 4H), 2.45-2.35 (m, 4H), 2.21 (s, 3H), 2.17 (s, 3H), 2.12 (s, 3H), 2.06 (s, 3H).
MH+480.

Example 36

N-(3-(4-(2,3-dimethylphenyl)piperazin-1-yl)-2-hydroxypropyl)-2,5-dimethyl-1-phenyl-1H-imidazole-4-carboxamide $^1$H NMR (400 MHz, DMSO-$d_6$) δ 7.96 (t, J=5.6 Hz, 1H), 7.57-7.48 (m, 3H), 7.36-7.32 (m, 2H), 6.97 (t, J=7.6 Hz, 1H), 6.85 (d, J=7.6 Hz, 1H), 6.81 (d, J=7.6 Hz, 1H), 4.83 (br s, 1H), 3.77-3.74 (m, 1H), 3.35-3.23 (m, 2H), 2.76-2.66 (m, 4H), 2.59-2.55 (m, 4H), 2.39-2.38 (m, 2H), 2.19 (s, 3H), 2.15 (s, 3H), 2.10 (s, 3H), 2.05 (s, 3H).
MH+462.

Example 37

N-(3-(4-(2,3-dimethylphenyl)piperazin-1-yl)propyl)-2,5-dimethyl-1-(4-(trifluoromethyl)phenyl)-1H-imidazole-4-carboxamide $^1$H NMR (400 MHz, DMSO-$d_6$) δ 8.21 (t, J=5.6 Hz, 1H), 7.94 (d, J=8.4 Hz, 2H), 7.65 (d, J=8.0 Hz, 2H), 6.99 (t, J=8.0 Hz, 1H), 6.86 (d, J=7.6 Hz, 1H), 6.82 (d, J=7.2 Hz, 1H), 3.29-3.25 (m, 2H), 2.88-2.83 (m, 4H), 2.61-2.52 (m, 4H), 2.43-2.39 (m, 2H), 2.24 (s, 3H), 2.17 (s, 3H), 2.12 (s, 3H), 2.06 (s, 3H), 1.70-1.66 (m, 2H).
MH+514.

Example 38

1-(benzo[d][1,3]dioxol-5-yl)-N-(3-(4-(2,3-dimethylphenyl)piperazin-1-yl)propyl)-2,5-dimethyl-1H-imidazole-4-carboxamide $^1$H NMR (400 MHz, DMSO-$d_6$) δ 8.12 (t, J=6.0 Hz, 1H), 7.05-6.97 (m, 3H), 6.87-6.77 (m, 3H), 6.12 (s, 2H), 3.28-3.24 (m, 2H), 2.84-2.81 (m, 4H), 2.59-2.51 (m, 4H), 2.41-2.36 (m, 2H), 2.21 (s, 3H), 2.17 (s, 3H), 2.12 (s, 3H), 2.06 (s, 3H), 1.68-1.64 (m, 2H).
MH+490.

Example 39

1-(benzo[d][1,3]dioxol-5-yl)-N-(3-(4-(2,3-dimethylphenyl)piperazin-1-yl)-2-hydroxypropyl)-2,5-dimethyl-1H-imidazole-4-carboxamide $^1$H NMR (400 MHz, DMSO-$d_6$) δ 7.93 (t, J=5.6 Hz, 1H), 7.05-6.96 (m, 3H), 6.86-6.78 (m, 3H), 4.83 (br s, 1H), 3.76-3.72 (m, 1H), 3.32-3.25 (m, 2H), 2.85-2.77 (m, 4H), 2.59-2.55 (m, 4H), 2.38 (d, J=5.6 Hz, 2H), 2.21 (s, 3H), 2.16 (s, 3H), 2.11 (s, 3H), 2.06 (s, 3H).
MH+506.

Example 40

1-(2,3-dihydrobenzo[b][1,4]dioxin-6-yl)-N-(3-(4-(2,3-dimethylphenyl)piperazin-1-yl)propyl)-2,5-dimethyl-1H-imidazole-4-carboxamide $^1$H NMR (400 MHz, DMSO-$d_6$) δ 8.11 (t, J=5.6 Hz, 1H), 7.00-6.96 (m, 2H), 6.92 (d, J=2.8 Hz, 1H), 6.85 (d, J=7.6 Hz, 1H), 6.81 (d, J=7.2 Hz, 1H), 6.78 (dd, J=8.8, 2.8 Hz, 1H), 4.28 (s, 4H), 3.28-3.23 (m, 2H), 2.83-2.81 (m, 4H), 2.56-2.49 (m, 4H), 2.39 (t, J=6.8 Hz, 2H), 2.19 (s, 3H), 2.16 (s, 3H), 2.11 (s, 3H), 2.05 (s, 3H), 1.68-1.61 (m, 2H).
MH+504.

Example 41

1-(2,3-dihydrobenzo[b][1,4]dioxin-6-yl)-N-(3-(4-(2,3-dimethylphenyl)piperazin-1-yl)-2-hydroxypropyl)-2,5-dimethyl-1H-imidazole-4-carboxamide $^1$H NMR (400 MHz, DMSO-$d_6$) δ 7.93 (t, J=5.6 Hz, 1H), 7.00-6.96 (m, 2H), 6.92 (d, J=2.0 Hz, 1H), 6.85 (d, J=7.6 Hz, 1H), 6.81 (d, J=7.2 Hz, 1H), 6.78 (dd, J=8.4, 2.4 Hz, 1H), 4.84 (br s, 1H), 4.28 (s, 4H), 3.76-3.72 (m, 1H), 3.35-3.22 (m, 2H), 2.87-2.76 (m, 4H), 2.59-2.55 (m, 4H), 2.39-2.37 (m, 2H), 2.19 (s, 3H), 2.16 (s, 3H), 2.11 (s, 3H), 2.05 (s, 3H).
MH+520.

Example 42

N-(2-(4-(2,3-dichlorophenyl)piperazin-1-yl)ethyl)-1-(4-methoxyphenyl)-2,5-dimethyl-1H-imidazole-4-carboxamide $^1$H NMR (400 MHz, CDCl$_3$) δ 7.40 (t, J=6.0 Hz, 1H), 7.15-7.13 (m, 2H), 7.12-7.07 (m, 2H), 7.03-6.99 (m, 2H), 6.98-6.96 (m, 1H), 3.88 (s, 3H), 3.58 (q, J=6.0 Hz, 2H), 3.11 (br s, 4H), 2.73 (br s, 4H), 2.70 (q, J=6.4 Hz, 2H), 2.34 (s, 3H), 2.17 (s, 3H).
MH+502.

Example 43

N-(3-(4-(2,3-dichlorophenyl)piperazin-1-yl)-2-hydroxypropyl)-1-(4-methoxyphenyl)-2,5-dimethyl-1H-imidazole-4-carboxamide $^1$H NMR (400 MHz, CDCl$_3$) δ 7.55 (t, J=6.0 Hz, 1H), 7.18-7.14 (m, 2H), 7.12-7.08 (m, 2H), 7.03-7.00 (m, 2H), 6.97-6.95 (m, 1H), 4.03 (br s, 1H), 3.87 (s, 3H), 3.68-3.62 (m, 2H), 3.49-3.43 (m, 2H), 3.13 (br s, 4H), 2.91-2.62 (m, 4H), 2.32 (s, 3H), 2.16 (s, 3H).
MH+532.

Example 44

N-(3-(4-(2,3-dichlorophenyl)piperazin-1-yl)propyl)-2-ethyl-1-(4-methoxyphenyl)-5-methyl-1H-imidazole-4-carboxamide $^1$H NMR (400 MHz, CDCl$_3$) δ 7.77 (t, J=5.6 Hz, 1H), 7.15-7.08 (m, 4H), 7.01-6.95 (m, 3H), 3.87 (s, 3H), 3.52 (q, J=6.4 Hz, 2H), 3.15 (br s, 4H), 2.68 (br s, 4H), 2.70 (t, J=7.2 Hz, 2H), 2.43 (q, J=7.6 Hz, 2H), 2.32 (s, 3H), 1.87-1.80 (m, 2H), 1.10 (t, J=7.2 Hz, 3H).
MH+530.

Example 45

N-(3-(4-(2,3-dichlorophenyl)piperazin-1-yl)-2-hydroxypropyl)-2-ethyl-1-(4-methoxyphenyl)-5-methyl-1H-imidazole-4-carboxamide $^1$H NMR (400 MHz, CDCl$_3$) δ 7.59 (t, J=6.4 Hz, 1H), 7.17-7.08 (m, 4H), 7.02-6.94 (m, 3H), 3.97 (br s, 1H), 3.87 (s, 3H), 3.69-3.63 (m, 2H), 3.49-3.37 (m, 2H), 3.07 (br s, 4H), 2.84 (br s, 2H), 2.65 (br s, 2H), 2.48 (q, J=7.2 Hz, 2H), 2.31 (s, 3H), 1.15 (t, J=7.2 Hz, 3H).
MH+546.

Example 46

N-(2-(4-(2,3-dimethylphenyl)piperazin-1-yDethyl)-1-(4-methoxyphenyl)-2,5-dimethyl-1H-imidazole-4-carboxamide $^1$H NMR (400 MHz, CDCl$_3$) δ 7.40 (t, J=5.6 Hz, 1H), 7.10-7.00 (m, 4H), 6.94-6.88 (m, 3H), 3.78 (s, 3H), 3.58 (q, J=6.4 Hz, 2H), 2.94 (t, J=4.4 Hz, 4H), 2.69-2.66 (m, 6H), 2.33 (s, 3H), 2.26 (s, 3H), 2.22 (s, 3H), 2.17 (s, 3H).
MH+462.

Example 47

N-(3-(4-(2,3-dimethylphenyl)piperazin-1-yl)propyl)-1-(4-methoxyphenyl)-2,5-dimethyl-1H-imidazole-4-carboxamide $^1$H NMR (400 MHz, CDCl$_3$) δ 7.79 (t, J=5.6 Hz, 1H), 7.10-6.99 (m, 5H), 6.94-6.87 (m, 3H), 3.78 (s, 3H), 3.51 (q, J=6.4 Hz, 2H), 2.97 (t, J=4.4 Hz, 4H), 2.65 (br s, 4H), 2.65 (t, J=7.2 Hz, 2H), 2.33 (s, 3H), 2.26 (s, 3H), 2.22 (s, 3H), 2.14 (s, 3H), 1.87-1.80 (m, 2H).
MH+476.

Example 48

1-(3-chlorophenyl)-N-(3-(4-(2,3-dimethylphenyl)piperazin-1-yl)propyl)-2,5-dimethyl-1H-imidazole-4-carboxamide $^1$H NMR (400 MHz, CDCl$_3$) δ 7.87 (t, J=6.0 Hz, 1H), 7.51-7.45 (m, 2H), 7.20-7.10 (m, 1H), 7.10-7.03 (m, 2H), 6.93 (d, J=8.0 Hz, 1H), 6.87 (d, J=7.6 Hz, 1H), 3.54 (q, J=6.4 Hz, 2H), 2.98 (t, J=4.4 Hz, 4H), 2.65 (br s, 4H), 2.57 (t, J=6.4 Hz, 2H), 2.36 (s, 3H), 2.26 (s, 3H), 2.22 (s, 3H), 2.17 (s, 3H).
MH+480.

Example 49

1-(3-chlorophenyl)-N-(3-(4-(2,3-dimethylphenyl)piperazin-1-yl)-2-hydroxypropyl)-2,5-dimethyl-1H-imidazole-4-carboxamide $^1$H NMR (400 MHz, CDCl$_3$) δ 7.64 (t, J=6.0 Hz, 1H), 7.52-7.46 (m, 2H), 7.22-7.21 (m, 1H), 7.15-7.05 (m, 2H), 6.92 (d, J=2.8 Hz, 1H), 6.90 (d, J=2.0 Hz, 1H), 4.08-4.00 (m, 1H), 3.70-3.62 (m, 1H), 3.48-3.39 (m, 1H), 2.95-2.92 (m, 4H), 2.90 (br s, 2H), 2.72 (br s, 2H), 2.60-2.58 (m, 2H), 2.35 (s, 3H), 2.26 (s, 3H), 2.20 (s, 3H), 2.19 (s, 3H).
MH+496.

Example 50

N-(3-(4-(3-chloro-2-methylphenyl)piperazin-1-yl)propyl)-1-(3-chlorophenyl)-2,5-dimethyl-1H-imidazole-4-carboxamide $^1$H NMR (400 MHz, CDCl$_3$) δ 7.87 (t, J=6.0 Hz, 1H), 7.51-7.45 (m, 2H), 7.21 (br s, 1H), 7.10-7.03 (m, 3H), 6.94 (dd, J=2.8, 3.2 Hz, 1H), 3.52 (q, J=6.0 Hz, 2H), 2.98 (t, J=4.8 Hz, 4H), 2.65 (br s, 2H), 2.57 (t, J=6.4 Hz, 2H), 2.36 (s, 3H), 2.34 (s, 3H), 2.15 (s, 3H), 1.86-1.80 (m, 2H).
MH+500.

Example 51

N-(3-(4-(3-chloro-2-methylphenyl)piperazin-1-yl)-2-hydroxypropyl)-1-(3-chlorophenyl)-2,5-dimethyl-1H-imidazole-4-carboxamide $^1$H NMR (400 MHz, CDCl$_3$) δ 7.55 (t, J=5.6 Hz, 1H), 7.52-7.46 (m, 2H), 7.22 (br s, 1H), 7.11-7.05 (m, 3H), 6.94-6.91 (m, 1H), 3.98-3.93 (m, 1H), 3.65-3.62 (m, 1H), 3.45-3.42 (m, 1H), 2.94-2.89 (m, 4H), 2.80 (br s, 2H), 2.60 (br s, 2H), 2.52-2.50 (m, 2H), 2.39 (s, 3H), 2.36 (s, 3H), 2.19 (s, 3H).
MH+516.

Example 52

N-(3-(4-(2,3-dimethylphenyl)piperazin-1-yl)propyl)-1-(3-fluorophenyl)-2,5-dimethyl-1H-imidazole-4-carboxamide $^1$H NMR (400 MHz, CDCl$_3$) δ 7.86 (t, J=6.4 Hz, 1H), 7.53-7.48 (m, 1H), 7.25-7.20 (m, 2H), 7.06-6.98 (m, 2H), 6.93 (d, J=8.4 Hz, 1H), 6.88 (d, J=7.2 Hz, 1H), 3.52 (q, J=6.4 Hz, 2H), 2.98 (t, J=4.8 Hz, 4H), 2.65 (br s, 4H), 2.57 (t, J=6.8 Hz, 2H), 2.36 (s, 3H), 2.26 (s, 3H), 2.17s, 3H), 1.87-1.80 (m, 2H).
MH+464.

Example 53

N-(3-(4-(2,3-dimethylphenyl)piperazin-1-yl)-2-hydroxypropyl)-1-(3-fluorophenyl)-2,5-dimethyl-1H-imidazole-4-carboxamide $^1$H NMR (400 MHz, CDCl$_3$) δ 7.57-7.49 (m, 3H), 7.23-7.21 (m, 1H), 7.07 (t, J=7.6 Hz, 1H), 7.00 (d, J=7.6 Hz, 1H), 6.95-6.89 (m, 2H), 3.98-3.92 (m, 1H), 3.69-3.63 (m, 1H), 3.49-3.40 (m, 1H), 2.94-2.86 (m, 4H), 2.81 (br s, 2H), 2.60 (br s, 2H), 2.52-2.50 (m, 2H), 2.36 (s, 3H), 2.26 (s, 3H), 2.21 (s, 3H), 2.19 (s, 3H).
MH+480.

Example 54

1-(3,4-dimethoxyphenyl)-N-(3-(4-(2,3-dimethyl phenyl)piperazin-1-yl)propyl)-2,5-dimethyl-1H-imidazole-4-carboxamide $^1$H NMR (400 MHz, CDCl$_3$) δ 7.79 (t, J=6.4 Hz, 1H), 7.07-7.03 (m, 1H), 6.96-6.92 (m, 2H), 6.88 (d, J=7.2 Hz, 1H), 6.75 (dd, J=8.4, 2.0 Hz, 1H), 6.64 (d, J=2.4 Hz, 1H), 3.95 (s, 3H), 3.87 (s, 3H), 3.51 (q, J=6.4 Hz, 2H), 2.98 (br s, 4H), 2.65

(br s, 4H), 2.57 (br s, 2H), 2.35 (s, 3H), 2.26 (s, 3H), 2.22 (s, 3H), 2.16 (s, 3H), 1.84 (t, J=6.0 Hz, 2H).
MH+506.

Example 55

1-(3,4-dimethoxyphenyl)-N-(3-(4-(2,3-dimethyl phenyl)piperazin-1-yl)-2-hydroxypropyl)-2,5-dimethyl-1H-imidazole-4-carboxamide $^1$H NMR (400 MHz, CDCl$_3$) δ 7.54 (t, J=6.4 Hz, 1H), 7.09-7.05 (m, 1H), 6.97-6.89 (m, 2H), 6.75 (dd, J=8.4, 2.4 Hz, 1H), 6.65 (d, J=2.4 Hz, 1H), 3.95 (s, 3H), 3.88 (s, 3H), 3.69-3.63 (m, 1H), 3.49-3.40 (m, 1H), 2.86 (br s, 4H), 2.80 (br s, 2H), 2.60 (br s, 2H), 2.52 (d, J=7.2 Hz, 2H), 2.35 (s, 3H), 2.26 (s, 3H), 2.21 (s, 3H), 2.18 (s, 3H).
MH+522.

Example 56

N-(3-(4-(2,3-dimethylphenyl)piperazin-1-yl)-2-hydroxypropyl)-1-(4-methoxyphenyl)-2,5-dimethyl-1H-imidazole-4-carboxamide $^1$H NMR (400 MHz, CDCl$_3$) δ 7.55 (t, J=5.6 Hz, 1H), 7.10-7.00 (m, 4H), 6.92-6.89 (m, 3H), 3.98-3.94 (m, 1H), 3.87 (s, 3H), 3.68-3.62 (m, 1H), 3.47-3.40 (m, 1H), 2.95-2.92 (m, 4H), 2.81 (br s, 2H), 2.61 (br s, 2H), 2.52 (d, J=6.8 Hz, 2H), 2.33 (s, 3H), 2.26 (s, 3H), 2.21 (s, 3H), 2.16 (s, 3H).
MH+492.

Example 57

N-(3-(4-(2,3-dimethylphenyl)piperazin-1-yl)propyl)-2,5-dimethyl-1-(4-(methylthio)phenyl)-1H-imidazole-4-carboxamide $^1$H NMR (400 MHz, DMSO-d$_6$) δ 8.90 (br s, 1H), 7.48 (s, 4H), 7.06-7.01 (m, 1H), 6.91-6.84 (m, 2H), 3.50 (d, J=11.2 Hz, 2H), 3.38 (q, J=6.0 Hz, 2H), 3.23-3.02 (m, 8H), 2.52 (s, 3H), 2.34 (s, 3H), 2.26 (s, 3H), 2.19 (s, 3H), 2.14 (s, 3H), 2.05-1.98 (m, 2H).
MH+492.

Example 58

N-(3-(4-(2,3-dimethylphenyl)piperazin-1-yl)-2-hydroxypropyl)-2,5-dimethyl-1-(4-(methylthio)phenyl)-1H-imidazole-4-carboxamide $^1$H NMR (400 MHz, DMSO-d$_6$) δ 10.15 (br s, 1H), 8.54 (br s, 1H), 7.45 (dd, J=16.4, 8.8 Hz, 4H), 7.04 (t, J=8.0 Hz, 1H), 6.89 (dd, J=10.4, 8.0 Hz, 2H), 4.19-3.98 (m, 3H), 3.60 (d, J=11.6 Hz, 1H), 3.53 (d, J=11.6 Hz, 1H), 3.38-3.27 (m, 4H), 3.17-3.01 (m, 4H), 2.52 (s, 3H), 2.28 (s, 3H), 2.25 (s, 3H), 2.18 (s, 3H), 2.13 (s, 3H).
MH+508.

Example 59

N-(3-(4-(2,3-dimethylphenyl)piperazin-1-yl)propyl)-1-(3-methoxyphenyl)-2,5-dimethyl-1H-imidazole-4-carboxamide $^1$H NMR (400 MHz, DMSO-d$_6$) δ 8.79 (br s, 1H), 7.54 (t, J=8.0 Hz, 1H), 7.21-7.16 (m, 2H), 7.05 (dd, J=16.4, 8.8 Hz, 2H), 6.89 (t, J=8.8 Hz, 2H), 3.79 (s, 3H), 3.50 (d, J=10.8 Hz, 2H), 3.37 (q, J=6.0 Hz, 2H), 3.28-3.07 (m, 8H), 2.33 (s, 3H), 2.27 (s, 3H), 2.19 (s, 3H), 2.14 (s, 3H), 2.08-2.00 (m, 2H).
MH+476.

Example 60

N-(3-(4-(2,3-dimethylphenyl)piperazin-1-yl)-2-hydroxypropyl)-1-(3-methoxyphenyl)-2,5-dimethyl-1H-imidazole-4-carboxamide $^1$H NMR (400 MHz, DMSO-d$_6$) δ 10.01 (br s, 1H), 8.41 (br s, 1H), 7.52 (t, J=8.0 Hz, 1H), 7.16 (dd, J=8.0, 2.4 Hz, 1H), 7.07-7.00 (m, 3H), 6.89 (dd, J=10.4, 8.0 Hz, 2H), 3.79 (s, 3H), 3.78-3.51 (m, 3H), 3.37-3.28 (m, 4H), 3.18-2.99 (m, 6H), 2.26 (s, 3H), 2.25 (s, 3H), 2.18 (s, 3H), 2.13 (s, 3H).
MH+492.

Example 61

1-(2,4-dimethoxyphenyl)-N-(3-(4-(2,3-dimethylphenyl)piperazin-1-yl)propyl)-2,5-dimethyl-1H-imidazole-4-carboxamide $^1$H NMR (400 MHz, DMSO-d$_6$) δ 8.85 (br s, 1H), 7.21-7.17 (m, 1H), 7.10-7.02 (m, 2H), 6.91-6.85 (m, 3H), 3.84 (s, 3H), 3.78 (s, 3H), 3.50 (d, J=11.2 Hz, 2H), 3.38 (d, J=5.6 Hz, 2H), 3.23-3.08 (m, 8H), 2.34 (s, 3H), 2.27 (s, 3H), 2.19 (s, 3H), 2.14 (s, 3H), 2.04-2.01 (m, 2H).
MH+506.

Example 62

1-(2,4-dimethoxyphenyl)-N-(3-(4-(2,3-dimethylphenyl)piperazin-1-yl)-2-hydroxypropyl)-2,5-dimethyl-1H-imidazole-4-carboxamide $^1$H NMR (400 MHz, DMSO-d$_6$) δ 7.95 (t, J=5.6 Hz, 1H), 7.90 (br s, 1H), 7.19 (dd, J=8.8, 3.2 Hz, 1H), 7.00-6.94 (m, 2H), 6.86-6.81 (m, 3H), 3.81 (s, 3H), 3.77 (s, 3H), 3.75-3.72 (m, 1H), 2.81 (br s, 4H), 2.74 (br s, 2H), 2.55 (br s, 4H), 2.39 (d, J=6.0 Hz, 2H), 2.22 (s, 3H), 2.16 (s, 3H), 2.11 (s, 3H), 2.08 (s, 3H).
MH+522.

Example 63

(S)—N-(3-(4-(2,3-dichlorophenyl)piperazin-1-yl)-2-hydroxy propyl)-2,5-dimethyl-1-phenyl-1H-imidazole-4-carboxamide $^1$H NMR (400 MHz, DMSO-d$_6$) δ 7.99-7.97 (m, 1H), 7.58-7.51 (m, 3H), 7.36-7.34 (m, 2H), 7.27-7.17 (m, 2H), 7.12-7.10 (m, 1H), 4.85 (bs, 1H), 3.76 (bs, 1H), 3.34-3.24 (m, 4H), 3.02 (bs, 4H), 2.59 (m, 4H), 2.20 (s, 3H), 2.05 (s, 3H).
MH+501.

Example 64

(S)—N-(3-(4-(2,3-dichlorophenyl)piperazin-1-yl)-2-hydroxy propyl)-5-methyl-1-phenyl-2-propyl-1H-imidazole-4-carboxamide $^1$H NMR (400 MHz, DMSO-d$_6$) δ 7.95-7.92 (m, 1H), 7.57-7.49 (m, 3H), 7.34-7.32 (m, 2H), 7.28-7.22 (m, 2H), 7.11-7.08 (m, 1H), 4.84 (d, J=4.4 Hz, 1H), 3.76-3.74 (m, 1H), 3.32-3.30 (m, 2H), 3.02 (m, 4H), 2.61-2.57 (m, 4H), 2.40 (d, J=6.0 Hz, 2H), 2.32 (t, J=7.6 Hz, 2H), 2.18 (s, 3H), 1.43-1.38 (m, 2H), 0.66 (t, J=7.2 Hz, 3H).
MH+529.

Example 65

N-(3-(4-(2,3-dichlorophenyl)piperazin-1-yl)-2,2-difluoro propyl)-2,5-dimethyl-1-phenyl-1H-imidazole-4-carboxamide $^1$H NMR (400 MHz, DMSO-d$_6$) δ 8.10-8.07 (m, 1H), 7.58-7.49 (m, 3H), 7.38-7.35 (m, 2H), 7.29-7.24 (m, 2H), 7.13-7.11 (m, 1H), 3.81 (td, J=14.4, 6.4 Hz, 2H), 3.04-3.02 (m, 4H), 2.92-2.85 (m, 2H), 2.73-2.69 (m, 4H), 2.20 (s, 3H), 2.05 (s, 3H).
MH+523.

Example 66

N-(3-(4-(2,3-dichlorophenyl)piperazin-1-yl)-2,2-difluoro propyl)-5-methyl-1-phenyl-2-propyl-1H-imidazole-4-carboxamide $^1$H NMR (400 MHz, DMSO-d$_6$) δ 8.04 (bs, 1H), 7.58-7.52 (m, 3H), 7.36-7.34 (m, 2H), 7.30-7.25 (m, 2H), 7.12-7.10 (m, 1H), 3.84-3.82 (m, 2H), 3.50-3.20 (m, 2H), 3.06 (m, 4H), 2.74 (m, 4H), 2.33 (t, J=7.6 Hz, 2H), 2.19 (s, 3H), 1.45-1.39 (m, 2H), 0.66 (t, J=7.2 Hz, 3H).
MH+551.

Example 67

N-(3-(4-(2,3-dimethylphenyl)piperazin-1-yl)propyl)-1-(2-fluoro phenyl)-2,5-dimethyl-1H-imidazole-4-carboxamide $^1$H NMR (400 MHz, CDCl$_3$) δ 7.59 (bs, 1H), 7.56-7.50 (m, 1H), 7.35-7.30 (m, 2H), 7.27-7.22 (m, 1H), 7.10-7.06 (m, 1H), 6.98-6.93 (m, 2H), 3.61-3.50 (m, 3H), 3.37-2.99 (m, 11H), 2.35 (s, 3H), 2.27 (s, 3H), 2.21 (s, 3H), 2.18 (s, 3H), 2.19-2.10 (m, 2H).
MH+464.

Example 68

N-(3-(4-(2,3-dimethylphenyl)piperazin-1-yl)-2-hydroxypropyl)-1-(2-fluorophenyl)-2,5-dimethyl-1H-imidazole-4-carboxamide $^1$H NMR (400 MHz, CDCl$_3$) δ 8.05 (m, 1H), 7.62-7.57 (m, 1H), 7.40-7.25 (m, 3H), 7.11-7.07 (m, 1H), 6.99-6.95 (m, 2H), 4.56-4.54 (m, 1H), 3.81-3.74 (m, 2H), 3.66-3.63 (m, 2H), 3.61-3.49 (m, 2H), 3.40-3.18 (m, 4H), 3.11 (m, 2H), 2.37 (s, 3H), 2.31 (s, 3H), 2.27 (s, 3H), 2.19 (s, 3H).
MH+480.

Example 69

N-(2-(4-(3-chloro-2-fluorophenyl)piperazin-1-yl)ethyl)-2,5-dimethyl-1-phenyl-1H-imidazole-4-carboxamide $^1$H NMR (400 MHz, CDCl$_3$) δ 7.56-7.50 (m, 3H), 7.42 (t, J=5.2 Hz), 7.20-7.16 (m, 2H), 7.01-6.95 (m, 2H), 6.87-6.82 (m, 1H), 3.57 (q, dd=12.4, 6.4 Hz, 2H), 3.52 (t, J=4.8 Hz, 1H), 2.72-2.66 (m, 6H), 2.35 (s, 3H), 2.18 (s, 3H).
MH+456.

Example 70

N-(3-(4-(3-chloro-2-fluorophenyl)piperazin-1-yl)propyl)-2,5-dimethyl-1-phenyl-1H-imidazole-4-carboxamide $^1$H NMR (400 MHz, CDCl$_3$) δ 7.90 (brs, 1H), 7.55-7.47 (m, 3H), 7.17 (dd, J=7.6, 1.6 Hz, 2H), 6.99-6.93 (m, 2H), 6.87-6.82 (m, 1H), 3.52 (q, J=6.4 Hz, 2H), 3.21 (t, J=4.8 Hz, 2H), 2.67 (brs, 4H), 2.57 (t, J=6.8 Hz, 2H), 2.35 (s, 3H), 2.11 (s, 3H), 1.86-1.80 (m, 1H).
MH+470.

Example 71

N-(2-(4-(3-chloro-2-methylphenyl)piperazin-1-yl)ethyl)-2,5-dimethyl-1-phenyl-1H-imidazole-4-carboxamide $^1$H NMR (400 MHz, CDCl$_3$) δ 7.56-7.49 (m, 3H), 7.42 (m, 1H), 7.18 (dd, J=8.0, 1.6 Hz, 2H), 7.08 (dd, J=4.8, 0.8 Hz, 2H), 6.97-6.93 (m, 1H), 3.59 (q, J=6.4 Hz, 2H), 2.95 (t, J=4.8 Hz, 4H), 2.68 (t, J=6.4 Hz, 6H), 2.38 (s, 3H), 2.34 (s, 3H), 2.19 (s, 3H).
MH+452.

Example 72

N-(3-(4-(3-chloro-2-methylphenyl)piperazin-1-yl)propyl)-2,5-dimethyl-1-phenyl-1H-imidazole-4-carboxamide $^1$H NMR (400 MHz, CDCl$_3$) δ 7.84 (brs, 1H), 7.55-7.50 (m, 3H), 7.17 (dd, J=8.4, 2.0 Hz, 2H), 7.08-7.03 (m, 2H), 6.97-6.94 (m, 1H), 3.53 (q, J=6.4 Hz, 2H), 3.00 (t, J=4.8 Hz, 4H), 2.66 (brs, 3H), 2.58 (t, J=6.8 Hz, 3H), 2.35 (s, 3H), 2.34 (s, 3H), 2.15 (s, 3H).
MH+466.

Example 73

2,5-dimethyl-N-(2-(4-(2-methylquinolin-8-yl)piperazin-1-yl)ethyl)-1-phenyl-1H-imidazole-4-carboxamide $^1$H NMR (400 MHz, CDCl$_3$) δ 7.98 (d, J=8.4 Hz, 1H), 7.54-7.51 (m, 3H), 7.38-7.36 (m, 2H), 7.23-7.12 (m, 3H), 3.64 (dd, J=5.8, 6.0 Hz, 2H), 3.51 (brs, 3H), 2.90 (brs, 3H), 2.76-2.73 (m, 1H), 2.74 (s, 3H), 2.3.6 (s, 3H), 2.19 (s, 3H).
MH+469.

Example 74

2,5-dimethyl-1-phenyl-N-(2-(4-(quinolin-8-yOpiperazin-1-yl)ethyl)-1H-imidazole-4-carboxamide $^1$H NMR (400 MHz, CDCl$_3$) δ 8.89 (dd, J=2.4, 4.4 Hz, 1H), 8.11 (dd, J=1.6, 8.0 Hz, 1H), 7.56-7.44 (m, H), 7.38 (dd, J=4.4, 8.4 Hz, 1H), 7.21-7.16 (m, 3H), 3.65 (dd, J=5.4, 6.0 Hz, 2H), 3.50 (brs, 4H), 2.91 (brs, 4H), 2.77 (brs, 2H), 2.37 (s, 3H), 2.20 (s, 3H).
MH+455.

Example 75

N-(3-(4-(3-chloro-2-methylphenyl)piperazin-1-yl)-2-hydroxypropyl)-2,5-dimethyl-1-phenyl-1H-imidazole-4-carboxamide $^1$H NMR (400 MHz, CDCl$_3$) δ 7.58-7.47 (m, 3H), 7.18 (dd, J=2.0, 8.4 Hz, 2H), 7.11-7.06 (m, 2H), 6.95-6.91 (m, 1H), 3.99-3.93 (m, 1H), 3.69-3.63 (m, 1H), 3.48-3.41 (m, 1H), 2.95-2.88 (m, 4H), 2.80 (brs, 2H), 2.60 (brs, 2H), 2.52 (d, J=6.8 Hz, 2H), 2.35 (s, 3H), 2.33 (s, 3H), 2.18 (s, 3H).
MH+482.

Preparation of Imidazoles Containing Carbocyclic Ring

Preparation Example 8

Ethyl 1-cyclopentyl-2,5-dimethyl-1H-imidazole-4-carboxylate (Compound 19)

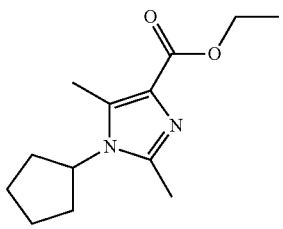 [SMILES: CCOC(=O)c1nc(C)n(C2CCCC2)c1C]

Step 1: 4-[1-dimethylamino-ethyl-(Z)-ylidene]-2-methyl-4H-oxazole-5-one (Compound 15)

N-Acetylglycine (10 g, 85.5 mmol) was dissolved in N,N'-dimethylacetamide (20 mL, 21.4 mmol) and POCl$_3$ (19.6 ml, 21.4 mmol) was added dropwise slowly at 0° C. The reaction mixture was stirred at 50° C. for 3 hrs and then cooled to room temperature. CH$_2$Cl$_2$ (50 mL) was added and the mixture poured into ice-water. The resulting solution was basified with ammonium hydroxide to over than pH 8. The organic extracts were washed with 50 ml water, dried over MgSO$_4$, filtered and evaporated under reduced pressure. The residue was purified by normal phase preparative column and the desired compound was obtained as an orange solid (6.7 g, 47%).
MH+169.

Step 2: (E)-ethyl 2-acetamido-3-(dimethylamino)but-2-enoate (Compound 16)

4-[1-dimethylamino-eth-(Z)-ylidene]-2-methyl-4H-oxazole-5-one (compound 15, 7.54 g, 44.8 mmol) was dissolved in ethanol (50 mL) and sodium hydride (179 mg, 4.5 mmol, 60% dispersion in mineral oil) wad added at room temperature. The solution was refluxed for 1 hr. The solvent was evaporated and the crude product was used without any further purification for the next step.
MH+215.

Step 3: (E)-Ethyl 2-acetamido-3-(cyclopentylamino)but-2-enoate (Compound 18)

(E)-ethyl 2-acetamido-3-(dimethylamino)but-2-enoate (compound 16, 1 g, 4.67 mmol) and cyclopentylamine (0.5 mL) were stirred at room temperature in AcOH (10 mL) for overnight. The reaction mixture was diluted slowly with water (10 mL) and evaporated under reduced pressure to obtain the desired product as a dark brown oil, which could be used without any further purification for the next step.
MH+256.

Step 4: Ethyl 1-cyclopentyl-2,5-dimethyl-1H-imidazole-4-carboxylate (Compound 19)

Ammonium sulfate (100 mg) was added to a solution of (E)-ethyl 2-acetamido-3-(cyclopentylamino)but-2-enoate (compound 18, 1.5 g, 5.9 mmol) and hexamethyldisilazane (15 mL) and refluxed overnight at 150° C. The reaction mixture was evaporated and extracted with EA and water. The organic layer was evaporated and the residue was purified with 20% methanol in CH$_2$Cl$_2$ to produce as a light brown solid (1.0 g, 71.4% yield).
$^1$H NMR (400 MHz, CDCl$_3$) δ 4.31 (q, J=6.5, 2H), 3.77 (m, 1H), 2.59 (s, 3H), 2.33 (s, 3H), 2.15-2.06 (m, 2H), 1.83-1.80 (m, 2H), 1.72-1.54 (m, 2H), 1.32 (t, J=6.5 3H).
MH+237.

Example 76

1-cyclopentyl-N-(3-(4-(2,3-dimethylphenyl)piperazin-1-yl)propyl)-2,5-dimethyl-1H-imidazole-4-carboxamide $^1$H NMR (400 MHz, CDCl$_3$) δ 8.03 (brs, 1H), 7.20-7.18 (m, 1H), 7.11-7.06 (m, 2H), 3.79-3.75 (m, 1H), 3.65 (t, J=6.9 Hz, 2H), 2.91 (brs, 3H), 2.86 (brs, 4H), 2.74-2.70 (m, 2H), 2.52 (s, 3H), 2.33 (s, 3H), 2.25 (s, 3H), 2.11-1.95 (m, 4H), 1.73-1.36 (m, 6H).
MH+438.

Example 77

1-cyclopentyl-N-(3-(4-(2,3-dimethylphenyl)piperazin-1-yl)-2-hydroxypropyl)-2,5-dimethyl-1H-imidazole-4-carboxamide $^1$H NMR (400 MHz, CDCl$_3$) δ 7.21-7.18 (m, 1H), 7.12-7.07 (m, 2H), 3.80-3.75 (m, 1H), 3.66 (d, J=6.9 Hz, 2H), 3.49-3.47 (m, 1H), 3.11 (brs, 2H), 2.94 (brs, 4H), 2.79-2.77 (m, 2H), 2.53 (s, 3H), 2.34 (s, 3H), 2.25 (s, 3H), 2.11-1.95 (m, 4H), 1.77-1.44 (m, 4H).
MH+454.

Example 78

N-(3-(4-(3-chloro-2-methylphenyl)piperazin-1-yl)propyl)-1-cyclopentyl-2,5-dimethyl-1H-imidazole-4-carboxamide $^1$H NMR (400 MHz, CDCl$_3$) δ 7.24-7.19 (m, 1H), 7.11-7.07 (m, 2H), 6.94 (brs, 1H), 3.82-3.79 (m, 1H), 3.71 (t, J=6.6 Hz, 2H), 3.21 (brs, 3H), 2.89 (brs, 4H), 2.79-2.77 (m, 2H), 2.59 (s, 3H), 2.20 (s, 3H), 2.11-1.95 (m, 4H), 1.77-1.44 (m, 4H).
MH+458.

Example 79

N-(3-(4-(3-chloro-2-methylphenyl)piperazin-1-yl)-2-hydroxypropyl)-1-cyclopentyl-2,5-dimethyl-1H-imidazole-4-carboxamide $^1$H NMR (400 MHz, CDCl$_3$) δ 7.24-7.19 (m, 1H), 7.11-7.07 (m, 2H), 6.94 (brs, 1H), 3.84-3.80 (m, 1H), 3.69-3.65 (m, 2H), 3.44-3.40 (m, 1H), 3.20 (brs, 3H), 2.81 (brs, 4H), 2.79-2.77 (m, 2H), 2.59 (s, 3H), 2.20 (s, 3H), 2.11-1.95 (m, 4H), 1.77-1.44 (m, 4H).
MH+474.

Example 80

1-cyclopentyl-N-(4-(4-(2,3-dimethylphenyl)piperazin-1-yl)butyl)-2,5-dimethyl-1H-imidazole-4-carboxamide $^1$H NMR (400 MHz, CDCl$_3$) δ 8.20 (brs, 1H), 7.24 (d, J=7.2 Hz, 1H), 7.11-7.07 (m, 2H), 3.82 (t, J=6.4 Hz, 2H), 3.54 (m, 1H), 3.30 (brs, 3H), 2.81 (brs, 4H), 2.79-2.77 (m, 2H), 2.59 (s, 3H), 2.20 (s, 3H), 2.11-1.85 (m, 5H), 1.77-1.44 (m, 5H).
MH+452.

Example 81

1-cyclopentyl-N-(2-(4-(2,3-dichlorophenyl)piperazin-1-yl)ethyl)-2,5-dimethyl-1H-imidazole-4-carboxamide $^1$H NMR (400 MHz, CDCl$_3$) δ 7.90 (brs, 1H), 7.26 (d, J=7.1 Hz, 1H), 7.14-7.07 (m, 2H), 3.88 (t, J=7.2 Hz, 2H), 3.64 (m, 1H), 3.21 (brs, 3H), 2.98 (brs, 5H), 2.74-2.60 (m, 2H), 2.54 (s, 3H), 2.44 (s, 3H), 2.11-1.85 (m, 4H), 1.77-1.44 (m, 4H).
MH+464.

Preparation of Diarylimidazoles

Preparaion Example 9

Ethyl 5-methyl-1,2-diphenyl-1H-imidazole-4-carboxylate (Compound 24)

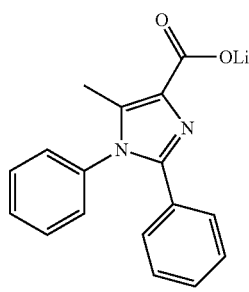

Step 1: N-Phenylbenzimidamide (Compound 23)

To NaHMDS (49 mL, 48.5 mmol, 1.0 M solution in THF) was added dropwise a solution of aniline (compound 11a, 4.5 mL, 48.5 mmol) in anhydrous THF (10 mL) under N$_2$. After 20 min, a solution of benzonitrile (compound 21, 5.0 mL, 48.5 mmol) in anhydrous THF (10 mL) was slowly added. The reaction mixture was stirred for 12 hrs, poured into cold water and extracted with EtOAc. The organic layer was dried over anhydrous MgSO$_4$, filtered, and concentrated in vacuo.

Step 2: Ethyl 5-methyl-1,2-diphenyl-1H-imidazole-4-carboxylate (compound 24)

A mixture of N-phenylbenzimidamide (compound 22, 1.0 g, 5.10 mmol), 3-bromo-2-oxovalerate (compound 23, 1.3 g, 6.12 mmol) and NaHCO$_3$ in i-PrOH was stirred at 90° C. for 12 hrs. The reaction mixture was concentrated under reduced pressure, then the residue was diluted with EtOAc and washed with H$_2$O. The organic layer was dried over anhydrous MgSO$_4$, filtered, and concentrated in vacuo. The crude product was purified by flash column chromatography (Biotage Isolera™ FLASH Purification System was used for normal phase column chromatography with EtOAc and hexane) to provide the title compound (0.86 g, 55%) as a yellow solid.

Example 82

N-(3-(4-(2,3-dimethylphenyl)piperazin-1-yl)-2-hydroxypropyl)-1-(4-fluorophenyl)-5-methyl-2-phenyl-1H-imidazole-4-carboxamide $^1$H NMR (400 MHz, CDCl$_3$) δ 7.92-7.79 (m, 1H), 7.38-7.31 (m, 2H), 7.28-7.16 (m, 7H), 7.07 (t, J=9.6 Hz, 1H), 6.89 (d, J=8.0 Hz, 2H), 4.05-3.95 (m, 1H), 3.87 (br s, 1H), 3.76-3.68 (m, 1H), 3.53-3.42 (m, 1H), 2.99-2.74 (m, 6H), 2.68-2.51 (m, 4H), 2.44 (s, 3H), 2.26 (s, 3H), 2.21 (s, 3H).
MH+542.

Example 83

N-(3-(4-(2,3-dimethylphenyl)piperazin-1-yl)propyl)-1-(4-fluorophenyl)-5-methyl-2-phenyl-1H-imidazole-4-carboxamide $^1$H NMR (400 MHz, CDCl$_3$) δ 7.89-7.82 (m, 1H), 7.34-7.12 (m, 9H), 6.97 (t, J=8.0 Hz, 1H), 6.86 (d, J=8.0 Hz, 1H), 6.74 (d, J=8.0 Hz, 1H), 3.55 (q, J=6.0 Hz, 2H), 2.93 (t, J=4.8 Hz, 4H), 2.75-2.52 (m, 6H), 2.45 (s, 3H), 2.25 (s, 3H), 2.20 (s, 3H), 1.87 (quint, J=6.8 Hz, 2H).
MH+526.

Example 84

N-(3-(4-(3-chloro-2-methylphenyl)piperazin-1-yl)-2-hydroxypropyl)-1-(4-fluorophenyl)-5-methyl-2-phenyl-1H-imidazole-4-carboxamide $^1$H NMR (400 MHz, CDCl$_3$) δ 7.73 (t, J=6.0 Hz, 1H), 7.37-7.13 (m, 9H), 7.12-7.05 (m, 2H), 6.93-6.89 (m, 1H), 4.04-3.95 (m, 1H), 3.80 (br s, 1H), 3.75-3.66 (m, 1H), 3.53-3.44 (m, 1H), 2.99-2.76 (m, 6H), 2.67-2.52 (m, 4H), 2.44 (s, 3H), 2.33 (s, 3H).
MH+562.

Example 85

N-(3-(4-(3-chloro-2-methylphenyl)piperazin-1-yl)propyl)-1-(4-fluorophenyl)-5-methyl-2-phenyl-1H-imidazole-4-carboxamide $^1$H NMR (400 MHz, CDCl$_3$) δ 7.97-7.89 (m, 1H), 7.34-7.11 (m, 9H), 7.04 (d, J=7.2 Hz, 1H), 6.95 (t, J=8.0 Hz, 1H), 6.70 (d, J=7.2 Hz, 1H), 3.55 (q, J=6.4 Hz, 2H), 2.94 (t, J=4.8 Hz, 4H), 2.67-2.54 (m, 6H), 2.45 (s, 3H), 2.32 (s, 3H), 1.86 (quint, J=6.4 Hz, 2H).
MH+546.

Example 86

N-(3-(4-(2,3-dimethylphenyl)piperazin-1-yl)propyl)-5-methyl-1,2-diphenyl-1H-imidazole-4-carboxamide $^1$H NMR (400 MHz, CDCl$_3$) δ 9.34 (br s, 1H), 7.69-7.43 (m, 5H), 7.41-7.24 (m, 5H), 7.09 (t, J=7.6 Hz, 1H), 7.01-6.92 (m, 2H), 3.71-3.61 (m, 4H), 3.59-3.48 (m, 2H), 3.47-3.37 (m, 2H), 3.23-3.04 (m, 4H), 2.52 (s, 3H), 2.47-2.36 (m, 2H), 2.27 (s, 3H), 2.19 (s, 3H).
MH+508.

Example 87

N-(3-(4-(3-chloro-2-methylphenyl)piperazin-1-yl)propyl)-5-methyl-1,2-diphenyl-1H-imidazole-4-carboxamide $^1$H NMR (400 MHz, CDCl$_3$) δ 7.99 (br s, 1H), 7.56-7.463 (m, 3H), 7.40-7.35 (m, 2H), 7.33-7.14 (m, 6H), 7.11 (t, J=8.0 Hz, 1H), 7.01 (dd, J=8.0, 0.8 Hz, 1H), 3.73-3.54 (m, 6H), 3.31-3.22 (m, 2H), 3.17-3.01 (m, 4H), 2.45 (s, 3H), 2.41-2.33 (m, 2H), 2.31 (s, 3H).
MH+528.

Example 88

1-(4-bromophenyl)-N-(3-(4-(3-chlorophenyl)piperazin-1-yOpropyl)-2-(2,4-dichlorophenyl)-5-ethyl-1H-imidazole-4-carboxamide $^1$H NMR (400 MHz, CDCl$_3$) δ 8.52 (br s, 1H), 7.47 (d, J=8.0 Hz, 2H), 7.11-7.07 (m, 3H), 6.98-6.94 (m, 3H), 6.78 (d, J=8.0 Hz, 1H), 6.72 (s, 1H), 6.59 (d, J=8.4 Hz, 1H), 3.57 (q, J=5.6 Hz, 2H), 3.21-3.18 (m, 4H), 2.96 (q, J=7.2 Hz, 2H), 2.62-2.55 (m, 6H), 1.85-1.79 (m, 2H), 1.05 (t, J=7.2 Hz, 3H).
MH+674.

Example 89

1-(4-bromophenyl)-2-(2,4-dichlorophenyl)-N-(3-(4-(2,3-dichlorophenyl)piperazin-1-yl)propyl)-5-ethyl-1H-imidazole-4-carboxamide $^1$H NMR (400 MHz, CDCl$_3$) δ 8.27 (br s, 1H), 7.49 (d, J=8.4 Hz, 2H), 7.21 (d, J=8.4 Hz, 2H), 7.14-7.09 (m, 2H), 7.04-6.98 (m, 3H), 6.59 (dd, J=8.4, 1.6 Hz, 1H), 3.56 (q, J=6.0 Hz, 2H), 3.11-3.06 (m, 4H), 3.00-2.92 (m, 2H), 2.67-2.62 (m, 4H), 2.60-2.57 (m, 2H), 1.86-1.79 (m, 2H), 1.06 (t, J=7.2 Hz, 3H).
MH+708.

Example 90

1-(4-bromophenyl)-2-(2,4-dichlorophenyl)-N-(3-(4-(2,3-dimethylphenyl)piperazin-1-yl)propyl)-5-ethyl-1H-imidazole-4-carboxamide $^1$H NMR (400 MHz, CDCl$_3$) δ 7.49-7.46 (m, 2H), 7.26 (d, J=2.0 Hz, 1H), 7.22 (d, J=8.4 Hz, 1H), 7.13 (dd, J=8.0, 2.0 Hz, 1H), 7.00-6.96 (m, 3H), 6.87 (d, J=7.2 Hz, 1H), 6.67 (d, J=8.0 Hz, 1H), 3.53 (q, J=6.4 Hz, 2H), 2.96-2.90 (m, 6H), 2.78-2.57 (m, 6H), 2.23 (s, 3H), 2.16 (s, 3H), 1.93-1.85 (m, 2H), 1.04 (t, J=7.2 Hz, 3H).
MH+668.

Example 91

5-((1H-1,2,4-triazol-1-yl)methyl)-N-(3-(4-(3-chloro-2-methylphenyl)piperazin-1-yl)propyl)-1,2-diphenyl-1H-imidazole-4-carboxamide $^1$H NMR (400 MHz, CDCl$_3$) δ 8.27 (s, 1H), 8.22 (t, J=5.2 Hz, 1H), 7.80 (s, 1H), 7.54-7.42 (m, 3H), 7.30 (d, J=8.4 Hz, 2H), 7.28-7.18 (m, 3H), 7.17-7.09 (m, 2H), 7.03 (d, J=7.6 Hz, 1H), 6.90 (t, J=8.0 Hz, 1H), 6.63 (d, J=8.0 Hz, 1H), 5.65 (s, 2H), 3.60 (q, J=6.0 Hz, 2H), 2.95 (t, J=4.8 Hz, 4H), 2.81-2.56 (m, 6H), 2.32 (s, 3H), 1.87 (q, J=6.4 Hz, 2H).
MH+595.

Example 92

N-(3-(4-(2,3-dimethylphenyl)piperazin-1-yl)propyl)-1-isobutyl-2,5-dimethyl-1H-imidazole-4-carboxamide dihydrochloride $^1$H NMR (400 MHz, MeOH-d$_4$) δ 7.09-7.06 (m, 1H), 7.01-6.96 (m, 2H), 3.99 (d, J=8.0 Hz, 2H), 3.71-3.68 (m, 2H), 3.63 (s, 3H), 3.56 (t, J=6.4 Hz, 2H), 3.42-3.38 (m 2H), 3.36-3.34 (m, 4H), 3.33-3.5 (m, 4H), 2.68 (s, 3H), 2.58 (s, 3H), 2.25 (s, 6H), 2.20-2.12 (m, 2H), 0.99 (s, 3H), 0.98 (s, 3H).
MH+426 (−2HCl).

Example 93

N-(3-(4-(3-chloro-2-methylphenyl)piperazin-1-yl)propyl)-1-isobutyl-2,5-dimethyl-1H-imidazole-4-carboxamide dihydrochloride $^1$H NMR (400 MHz, MeOH-d$_4$) δ 8.21 (brs, 1H), 7.22 (d, J=7.0 Hz, 1H), 7.15-7.12 (m, 2H), 3.88 (t, J=6.3 Hz, 2H), 3.53 (m, 2H), 3.30 (brs, 3H), 2.80-2.77 (m, 1H), 2.64 (s, 3H), 2.58 (s, 3H), 2.54-2.49 (m, 2H), 2.22 (s, 3H), 2.09 (s, 3H), 1.14 (s, 3H), 0.88 (s, 3H).
MH+447 (−2HCl).

Example 94

N-(3-(4-(2,3-dimethylphenyl)piperazin-1-yl)-2-hydroxypropyl)-1-isobutyl-2,5-dimethyl-1H-imidazole-4-carboxamide dihydrochloride $^1$H NMR (400 MHz, MeOH-d$_4$) δ 8.11 (brs, 1H), 7.24 (d, J=6.9 Hz, 1H), 7.17-7.14 (m, 2H), 3.94 (t, J=6.3 Hz, 2H), 3.47 (m, 1H), 3.53 (m, 2H), 3.29 (brs, 3H), 2.82-2.79 (m, 1H), 2.64 (s, 3H), 2.58 (s, 3H), 2.22 (s, 3H), 2.01 (s, 3H), 1.13 (s, 3H), 0.94 (s, 3H).
MH+442 (−2HCl).

Example 95

N-(3-(4-(2,3-dimethylphenyl)piperazin-1-yl)propyl)-2,5-dimethyl-1-propyl-1H-imidazole-4-carboxamide dihydrochloride $^1$H NMR (400 MHz, MeOH-d$_4$) δ 7.92 (brs, 1H), 7.18 (d, J=7.2 Hz, 1H), 7.15-7.10 (m, 2H), 3.94 (t, J=6.2 Hz, 2H), 3.53 (m, 2H), 3.29-3.25 (m, 5H), 2.82-2.79 (m, 1H), 2.64 (s, 3H), 2.58 (s, 3H), 2.42-2.40 (m, 2H), 2.22 (s, 3H), 2.01 (s, 3H), 1.70 (m, 2H), 0.93 (t, J=3.4 Hz, 3H).
MH+412 (−2HCl).

Example 96

N-(3-(4-(2,3-dimethylphenyl)piperazin-1-yl)-2-hydroxypropyl)-2,5-dimethyl-1-propyl-1H-imidazole-4-carboxamide dihydrochloride $^1$H NMR (400 MHz, MeOH-$d_4$) δ 8.04 (brs, 1H), 7.22 (m, 1H), 7.17-7.15 (m, 2H), 3.89 (t, J=5.4 Hz, 2H), 3.71-3.69 (m, 1H), 3.53-3.51 (m, 2H), 3.29-3.25 (m, 5H), 2.83-2.80 (m, 1H), 2.63 (s, 3H), 2.57 (s, 3H), 2.42-2.40 (m, 1H), 2.27 (s, 3H), 2.03 (s, 3H), 1.79 (m, 2H), 0.97 (t, J=3.8 Hz, 3H).
MH+428 (−2HCl).

Example 97

N-(3-(4-(3-chloro-2-methylphenyl)piperazin-1-yl)propyl)-2,5-dimethyl-1-propyl-1H-imidazole-4-carboxamide dihydrochloride $^1$H NMR (400 MHz, MeOH-$d_4$) δ 8.05 (brs, 1H), 7.23 (m, 1H), 7.18-7.15 (m, 2H), 3.88 (t, J=6.4 Hz, 2H), 3.55-3.53 (m, 2H), 3.29-3.25 (m, 5H), 2.83-2.80 (m, 1H), 2.63 (s, 3H), 2.57 (s, 3H), 2.42-2.40 (m, 1H), 2.23-2.21 (m, 2H), 2.03 (s, 3H), 1.79 (m, 2H), 0.97 (t, J=3.8 Hz, 3H).
MH+432 (−2HCl).

Example 98

N-(3-(4-(3-chloro-2-methylphenyl)piperazin-1-yl)-2-hydroxypropyl)-2,5-dimethyl-1-propyl-1H-imidazole-4-carboxamide dihydrochloride $^1$H NMR (400 MHz, MeOH-$d_4$) δ 8.07 (brs, 1H), 7.20 (m, 1H), 7.19-7.15 (m, 2H), 3.88 (t, J=6.4 Hz, 2H), 3.73-3.70 (m, 1H), 3.55-3.53 (m, 2H), 3.29-3.25 (m, 5H), 2.83-2.80 (m, 1H), 2.63 (s, 3H), 2.57 (s, 3H), 2.42-2.40 (m, 1H), 2.03 (s, 3H), 1.80 (m, 2H), 0.97 (t, J=3.9 Hz, 3H).
MH+448 (−2HCl).

Example 99

N-(3-(4-(2,3-dimethylphenyl)piperazin-1-yl)propyl)-1-(2-methoxyphenyl)-2,5-dimethyl-1H-imidazole-4-carboxamide dihydrochloride $^1$H NMR (400 MHz, CDCl$_3$) δ 7.76 (t, J=5.6 Hz, 1H), 7.45 (td, J=8.8, 1.6 Hz 1H), 7.13-7.02 (m, 4H), 6.94-6.86 (m, 2H), 3.77 (s, 3H), 3.51 (q, J=6.4 Hz, 2H), 2.97 (t, J=4.8 Hz, 4H), 2.90 (br s, 2H), 2.65 (t, J=5.6 Hz, 4H), 2.56 (t, J=6.8 Hz, 2H), 2.29 (s, 3H), 2.26 (s, 3H), 2.22 (s, 3H), 2.09 (s, 3H).
MH+476.

Example 100

N-(3-(4-(2,3-dimethylphenyl)piperazin-1-yl)-2-hydroxypropyl)-1-(2-methoxyphenyl)-2,5-dimethyl-1H-imidazole-4-carboxamide dihydrochloride $^1$H NMR (400 MHz, CDCl$_3$) δ 7.55 (t, J=5.6 Hz, 1H), 7.45 (td, J=8.4, 2.0 Hz 1H), 7.13-7.05 (m, 4H), 6.90 (t, J=6.8 Hz, 2H), 3.99-3.93 (m, 1H), 3.78 (s, 3H), 3.69-3.62 (m, 1H), 3.47-3.40 (m, 1H), 2.94-2.86 (m, 4H), 2.80 (br s, 2H), 2.60 (br.s, 2H), 2.52 (d, J=6.4 Hz, 4H), 2.29 (s, 3H), 2.26 (s, 3H), 2.21 (s, 3H), 2.11 (s, 3H).
MH+492.

Example 101

1-(2-chlorophenyl)-N-(3-(4-(2,3-dimethylphenyl)piperazin-1-yl)propyl)-2,5-dimethyl-1H-imidazole-4-carboxamide dihydrochloride $^1$H NMR (400 MHz, DMSO-$d_6$) δ 10.97 (s, 1H), 8.66 (s, 1H), 7.85 (m, 1H), 7.71-7.61 (m, 3H), 7.04 (t, J=7.6 Hz, 1H), 6.91-6.86 (m, 2H), 3.52-3.49 (m, 2H), 3.38-3.34 (m, 2H), 3.23-3.15 (m, 4H), 3.10-3.06 (m, 4H), 2.23 (s, 3H), 2.20 (s, 3H), 2.19 (s, 3H), 2.14 (s, 3H), 2.06-1.98 (m, 2H).
MH+480.

Example 102

1-(2-chlorophenyl)-N-(3-(4-(2,3-dimethylphenyl)piperazin-1-yl)-2-hydroxypropyl)-2,5-dimethyl-1H-imidazole-4-carboxamide dihydrochloride $^1$H NMR (400 MHz, DMSO-$d_6$) δ 10.30 (s, 1H), 8.48 (s, 1H), 7.82 (m, 1H), 7.70-7.61 (m, 3H), 7.04 (t, J=7.6 Hz, 1H), 6.91-6.86 (m, 2H), 4.23-4.22 (m, 1H), 3.62-3.52 (m, 2H), 3.36-3.28 (m, 5H), 3.17-3.08 (m, 5H), 2.21 (s, 3H), 2.19 (s, 3H), 2.18 (s, 3H), 2.13 (s, 3H).
MH+496.

Example 103

1-(2-chlorophenyl)-N-(4-(4-(2,3-dimethylphenyl)piperazin-1-yl)butyl)-2,5-dimethyl-1H-imidazole-4-carboxamide dihydrochloride $^1$H NMR (400 MHz, DMSO-$d_6$) δ 10.74 (s, 1H), 8.51 (s, 1H), 7.82 (dd, J=8.0, 1.6 Hz, 1H), 7.70-7.60 (m, 3H), 7.04 (t, J=7.6 Hz, 1H), 6.91-6.86 (m, 2H), 3.51-3.48 (m, 2H), 3.28 (q, J=6.8 Hz, 2H), 3.16-3.12 (m, 4H), 3.08-3.03 (m, 4H), 2.20 (s, 3H), 2.18 (s, 6H), 2.14 (s, 3H), 1.83-1.75 (m, 2H), 1.60-1.53 (m, 2H).
MH+494.

Example 104

N-(3-(4-(2,3-dimethylphenyl)piperazin-1-yl)propyl)-2-isopropyl-5-methyl-1-phenyl-1H-imidazole-4-carboxamide dihydrochloride $^1$H NMR (400 MHz, DMSO-$d_6$) δ 10.9 (br s, 1H), 9.19 (br s, 1H), 7.66-7.63 (m, 3H), 7.59-7.49 (m, 2H), 7.05 (t, J=7.6 Hz, 1H), 6.92-6.87 (m, 2H), 3.52-3.50 (m, 2H), 3.41-3.36 (m, 2H), 3.27-3.13 (m, 4H), 3.10-3.08 (m, 4H), 2.80-2.74 (m, 1H), 2.22 (s, 3H), 2.19 (s, 3H), 2.15 (s, 3H), 2.06-2.02 (m, 2H), 1.27 (d, J=7.2 Hz, 6H).
MH+474.

Example 105

1-(3,5-dimethoxyphenyl)-N-(3-(4-(2,3-dimethylphenyl)piperazin-1-yl)propyl)-2,5-dimethyl-1H-imidazole-4-carboxamide dihydrochloride $^1$H NMR (400 MHz, DMSO-$d_6$) δ 11.24 (brs, 1H), 8.95 (br s, 1H), 7.05 (t, J=7.6 Hz, 1H), 6.91-6.87 (m, 2H), 6.78-6.74

(m, 3H), 3.78 (s, 6H), 3.51-3.48 (m, 2H), 3.41-3.36 (m, 2H), 3.26-3.13 (m, 4H), 3.10-3.06 (m, 4H), 2.39 (s, 3H), 2.31 (s, 3H), 2.19 (s, 3H), 2.14 (s, 3H), 2.08-2.02 (m, 2H).
MH+506.

Example 106

N-(3-(4-(2,3-dimethylphenyl)piperazin-1-yl)-2-hydroxypropyl)-2-isopropyl-5-methyl-1-phenyl-1H-imidazole-4-carboxamide dihydrochloride $^1$H NMR (400 MHz, DMSO-d$_6$) δ 10.23 (br s, 1H), 8.90 (br s, 1H), 7.66-7.63 (m, 3H), 7.56-7.54 (m, 2H), 7.04 (t, J=7.6 Hz, 1H), 6.91-6.86 (m, 2H), 4.25-4.23 (m, 1H), 3.62-3.60 (m, 1H), 3.55-3.52 (m, 1H), 3.43-3.39 (m, 2H), 3.35-3.28 (m, 2H), 3.20-3.09 (m, 6H), 2.79-2.74 (m, 1H), 2.22 (s, 3H), 2.18 (s, 3H), 2.14 (s, 3H), 1.25 (d, J=6.8 Hz, 6H).
MH+490.

Example 107

1-(3,5-dimethoxyphenyl)-N-(3-(4-(2,3-dimethylphenyl)piperazin-1-yl)-2-hydroxypropyl)-2,5-dimethyl-1H-imidazole-4-carboxamide dihydrochloride $^1$H NMR (400 MHz, DMSO-d$_6$) δ 10.49 (br s, 1H), 8.65 (br s, 1H), 7.06-7.02 (m, 1H), 6.91-6.86 (m, 2H), 6.74-6.71 (m, 3H), 4.24-4.22 (m, 1H), 3.77 (s, 6H), 3.62-3.60 (m, 1H), 3.54-3.51 (m, 1H), 3.38-3.35 (m, 2H), 3.29-3.27 (m, 2H), 3.16-3.08 (m, 6H), 2.35 (s, 3H), 2.29 (s, 3H), 2.18 (s, 3H), 2.13 (s, 3H).
MH+522.

Example 108

N-(3-(4-(2,3-dimethylphenyl)piperazin-1-yl)-2-hydroxypropyl)-2,5-dimethyl-1-(4-(trifluoromethyl)phenyl)-1H-imidazole-4-carboxamide dihydrochloride $^1$H NMR (400 MHz, DMSO-d$_6$) δ 10.29 (br s, 1H), 8.50 (br s, 1H), 8.02 (d, J=8.4 Hz, 2H), 7.78 (d, J=8.4 Hz, 2H), 7.06-7.02 (m, 1H), 6.90-6.86 (m, 2H), 4.23-4.20 (m, 1H), 3.61-3.59 (m, 1H), 3.54-3.51 (m, 1H), 3.38-3.35 (m, 2H), 3.33-3.27 (m, 2H), 3.17-3.08 (m, 6H), 2.28 (s, 3H), 2.27 (s, 3H), 2.18 (s, 3H), 2.13 (s, 3H).
MH+530.

Example 109

N-(3-(4-(2,3-dimethylphenyl)piperazin-1-yl)-2-hydroxypropyl)-2-ethyl-5-methyl-1-phenyl-1H-imidazole-4-carboxamide dihydrochloride $^1$H NMR (400 MHz, DMSO-d$_6$) δ 10.47 (br s, 1H), 8.92 (br s, 1H), 7.66-7.63 (m, 3H), 7.56-7.54 (m, 2H), 7.06-7.02 (m, 1H), 6.91-6.86 (m, 2H), 4.27-4.24 (m, 1H), 3.62-3.61 (m, 1H), 3.53-3.51 (m, 1H), 3.44-3.41 (m, 2H), 3.32-3.27 (m, 2H), 3.17-3.08 (m, 6H), 2.64 (q, J=7.6 Hz, 2H), 2.25 (s, 3H), 2.18 (s, 3H), 2.13 (s, 3H), 1.16 (t, J=7.6 Hz, 3H).
MH+476.

Example 110

N-(3-(4-(2,3-dimethylphenyl)piperazin-1-yl)-2-hydroxypropyl)-5-methyl-1-phenyl-2-propyl-1H-imidazole-4-carboxamide dihydrochloride $^1$H NMR (400 MHz, DMSO-d$_6$) δ 10.34 (br s, 1H), 8.67 (br s, 1H), 7.65-7.62 (m, 3H), 7.52-7.50 (m, 2H), 7.06-7.02 (m, 1H), 6.90-6.86 (m, 2H), 4.24-4.22 (m, 1H), 3.62-3.60 (m, 1H), 3.55-3.52 (m, 1H), 3.39-3.37 (m, 2H), 3.30-3.27 (m, 2H), 3.15-3.08 (m, 6H), 2.57 (t, J=7.6 Hz, 2H), 2.24 (s, 3H), 2.19 (s, 3H), 2.14 (s, 3H), 1.59-1.53 (m, 2H), 0.77 (t, J=7.6 Hz, 3H).
MH+490.

Example 111

1-(4-chlorophenyl)-N-(3-(4-(2,3-dimethylphenyl)piperazin-1-yl)-2-hydroxypropyl)-2-propyl-1H-imidazole-4-carboxamide dihydrochloride $^1$H NMR (400 MHz, DMSO-d$_6$) δ 10.44 (br s, 1H), 9.01 (br s, 1H), 8.40 (s, 1H), 7.70 (d, J=8.8 Hz, 2H), 7.63 (d, J=8.8 Hz, 2H), 7.06-7.02 (m, 1H), 6.91-6.85 (m, 2H), 4.26-4.24 (m, 1H), 3.63-3.60 (m, 1H), 3.53-3.50 (m, 1H), 3.38-3.35 (m, 2H), 3.31-3.23 (m, 2H), 3.17-3.03 (m, 6H), 2.72 (t, J=7.6 Hz, 2H), 2.18 (s, 3H), 2.13 (s, 3H), 1.58-1.52 (m, 2H), 0.77 (t, J=6.8 Hz, 3H).
MH+510.

Example 112

1-(3,5-dimethoxyphenyl)-N-(2-(4-(2,3-dimethylphenyl)piperazin-1-yl)ethyl)-2,5-dimethyl-1H-imidazole-4-carboxamide dihydrochloride $^1$H NMR (400 MHz, DMSO-d$_6$) δ 11.07 (br s, 1H), 8.90 (br s, 1H), 7.05 (t, J=7.6 Hz, 1H), 6.91-6.86 (m, 2H), 6.75-6.73 (m, 3H), 3.78 (s, 6H), 3.76-3.73 (m, 2H), 3.64-3.61 (m, 2H), 3.36-3.28 (m, 4H), 3.13-3.10 (m, 4H), 2.36 (s, 3H), 2.30 (s, 3H), 2.19 (s, 3H), 2.14 (s, 3H).
MH+492.

Example 113

N-(2-(4-(2,3-dimethylphenyl)piperazin-1-yl)ethyl)-2-isopropyl-5-methyl-1-phenyl-1H-imidazole-4-carboxamide dihydrochloride $^1$H NMR (400 MHz, DMSO-d$_6$) δ 10.77 (br s, 1H), 9.11 (br s, 1H), 7.65-7.62 (m, 3H), 7.55-7.53 (m, 2H), 7.05 (t, J=7.6 Hz, 1H), 6.91-6.87 (m, 2H), 3.76-3.71 (m, 2H), 3.65-3.62 (m, 2H), 3.38-3.27 (m, 4H), 3.11-3.09 (m, 4H), 2.79-2.76 (m, 1H), 2.22 (s, 3H), 2.19 (s, 3H), 2.15 (s, 3H), 1.24 (d, J=7.2 Hz, 6H).
MH+460.

Example 114

N-(2-(4-(2,3-dimethylphenyl)piperazin-1-yl)ethyl)-1-(4-fluorophenyl)-2,5-dimethyl-1H-imidazole-4-carboxamide dihydrochloride $^1$H NMR (400 MHz, DMSO-d$_6$) δ 11.23 (br s, 1H), 9.08 (br s, 1H), 7.67-7.63 (m, 2H), 7.53-7.49 (m, 2H), 7.04 (t, J=7.6 Hz, 1H), 6.91-6.86 (m, 2H), 7.53 (q, J=6.0 Hz, 2H), 3.63-3.59 (m, 2H), 3.37-3.28 (m, 4H), 3.18-3.06 (m, 4H), 2.34 (s, 3H), 2.27 (s, 3H), 2.19 (s, 3H), 2.14 (s, 3H).
MH+450.

Example 115

1-(benzo[d][1,3]dioxol-5-yl)-N-(2-(4-(2,3-dimethylphenyl)piperazin-1-yl)ethyl)-2,5-dimethyl-1H-imidazole-4-carboxamide dihydrochloride $^1$H NMR (400 MHz, DMSO-d$_6$) δ 11.22 (br s, 1H), 9.09 (br s, 1H), 7.20-7.19 (m, 1H), 7.15 (d, J=8.4 Hz, 1H), 7.06-7.02

(m, 2H), 6.90-6.86 (m, 2H), 6.17 (s, 2H), 3.76 (q, J=6.0 Hz, 2H), 3.63-3.59 (m, 2H), 3.37-3.28 (m, 4H), 3.17-3.06 (m, 4H), 2.36 (s, 3H), 2.29 (s, 3H), 2.19 (s, 3H), 2.14 (s, 3H).
MH+476.

Example 116

1-(2,3-dihydrobenzo[b][1,4]dioxin-6-yl)-N-(2-(4-(2, 3-dimethylphenyl)piperazin-1-yl)ethyl)-2,5-dimethyl-1H-imidazole-4-carboxamide dihydrochloride $^{1}$H NMR (400 MHz, DMSO-d$_{6}$) δ 11.17 (br s, 1H), 9.08 (br s, 1H), 7.16 (d, J=2.4 Hz, 1H), 7.09 (d, J=8.4 Hz, 1H), 7.04 (t, J=7.6 Hz, 1H), 6.99 (dd, J=6.0 Hz, 2.4 Hz, 1H), 6.90-6.86 (m, 2H), 4.30 (s, 4H), 3.77-3.73 (m, 2H), 3.63-3.59 (m, 2H), 3.37-3.28 (m, 4H), 3.17-3.06 (m, 4H), 2.34 (s, 3H), 2.27 (s, 3H), 2.18 (s, 3H), 2.14 (s, 3H).
MH+490.

Example 117

N-(3-(4-(2,3-dimethylphenyl)piperazin-1-yl)propyl)-1-phenyl-2-propyl-1H-imidazole-4-carboxamide dihydrochloride $^{1}$H NMR (400 MHz, CD$_{3}$OD) δ 8.24 (s, 1H), 7.69-7.64 (m, 3H), 7.62-7.59 (m, 2H), 7.05 (t, J=7.6 Hz, 1H), 6.96-6.92 (m, 2H), 3.68-3.65 (m, 2H), 3.54 (t, J=6.4 Hz, 2H), 3.36-3.34 (m, 4H), 3.22-3.08 (m, 4H), 2.89 (t, J=7.6 Hz, 2H), 2.25 (s, 3H), 2.23 (s, 3H), 2.19-2.12 (m, 2H), 1.69-1.59 (m, 2H), 0.88 (t, J=7.2 Hz, 1H).
MH+460.

Example 118

N-(3-(4-(2,3-dichlorophenyl)piperazin-1-yl)propyl)-1-phenyl-2-propyl-1H-imidazole-4-carboxamide dihydrochloride $^{1}$H NMR (400 MHz, CD$_{3}$OD) δ 8.27 (s, 1H), 7.69-7.67 (m, 3H), 7.65-7.62 (m, 2H), 7.30-7.25 (m, 2H), 7.17-7.14 (m, 1H), 3.73-3.69 (m, 2H), 3.56-3.50 (m, 4H), 3.29-3.28 (m, 4H), 3.25-3.18 (m, 2H), 2.91 (t, J=7.6 Hz, 2H), 2.19-2.14 (m, 2H), 1.70-1.59 (m, 2H), 0.88 (t, J=7.6 Hz, 3H).
MH+500.

Example 119

N-(2-(4-(2,3-dichlorophenyl)piperazin-1-yl)ethyl)-1-phenyl-2-propyl-1H-imidazole-4-carboxamide dihydrochloride $^{1}$H NMR (400 MHz, CD$_{3}$OD) δ 8.28 (s, 1H), 7.71-7.67 (m, 3H), 7.63-7.61 (m, 2H), 7.29-7.27 (m, 2H), 7.17-7.14 (m, 1H), 3.89-3.84 (m, 4H), 3.53-3.50 (m, 4H), 3.47-3.31 (m, 4H), 2.91 (t, J=7.6 Hz, 2H), 1.69-1.59 (m, 2H), 0.88 (t, J=7.6 Hz, 3H).
MH+486.

Example 120

N-(2-(4-(2,3-dimethylphenyl)piperazin-1-yl)ethyl)-1-phenyl-2-propyl-1H-imidazole-4-carboxamide dihydrochloride $^{1}$H NMR (400 MHz, CD$_{3}$OD) δ 8.30 (s, 1H), 7.69-7.67 (m, 3H), 7.64-7.61 (m, 2H), 7.09-7.04 (m, 1H), 6.99-6.94 (m, 2H), 3.89-3.82 (m, 4H), 3.53-3.50 (m, 2H), 3.47-3.42 (m, 2H), 3.28-3.26 (m, 4H), 2.92 (t, J=7.6 Hz, 2H), 2.25 (s, 6H), 1.69-1.59 (m, 2H), 0.88 (t, J=7.2 Hz, 3H).
MH+446.

Example 121

N-(3-(4-(2,3-dimethylphenyl)piperazin-1-yl)-2-hydroxypropyl)-1-phenyl-2-propyl-1H-imidazole-4-carboxamide dihydrochloride $^{1}$H NMR (400 MHz, CD$_{3}$OD) δ 8.27 (s, 1H), 7.69-7.67 (m, 3H), 7.63-6.61 (m, 2H), 7.07-7.03 (m, 1H), 6.97-6.92 (m, 2H), 4.34 (br s, 1H), 3.73-3.70 (m, 2H), 3.55-3.51 (m, 2H), 3.47-3.41 (m, 4H), 3.24-3.11 (m, 4H), 2.91 (t, J=7.6 Hz, 2H), 2.24 (s, 6H), 1.68-1.61 (m, 2H), 0.88 (t, J=7.2 Hz, 3H).
MH+476.

Example 122

N-(3-(4-(2,3-dimethylphenyl)piperazin-1-yl)propyl)-1-(4-methoxyphenyl)-5-methyl-2-propyl-1H-imidazole-4-carboxamide dihydrochloride $^{1}$H NMR (400 MHz, CD$_{3}$OD) δ 7.43 (d, J=8.4 Hz, 2H), 7.19 (d, J=7.6 Hz, 2H), 7.08-7.03 (m, 1H), 6.98-6.92 (m, 2H), 3.90 (s, 3H), 3.70-3.67 (m, 2H), 3.58-3.54 (m, 2H), 3.37-3.31 (m, 4H), 3.23-3.13 (m, 4H), 2.76 (t, J=7.2 Hz, 2H), 2.32 (s, 3H), 2.17 (s, 6H), 1.69-1.63 (m, 2H), 0.90 (t, J=7.2 Hz, 3H).
MH+504.

Example 123

N-(2-(4-(2,3-dimethylphenyl)piperazin-1-yl)ethyl)-1-(4-methoxyphenyl)-5-methyl-2-propyl-1H-imidazole-4-carboxamide dihydrochloride $^{1}$H NMR (400 MHz, CD$_{3}$OD) δ 7.44 (d, J=8.8 Hz, 2H), 7.20 (d, J=9.2 Hz, 2H), 7.08-7.04 (m, 1H), 6.98-6.93 (m, 2H), 3.93-3.87 (m, 2H), 3.89 (s, 3H), 3.86-3.82 (m, 2H), 3.53-3.50 (m, 2H), 3.47-3.37 (m, 2H), 3.29-3.22 (m, 4H), 2.76 (t, J=7.2 Hz, 2H), 2.33 (s, 3H), 2.25 (s, 6H), 1.70-1.62 (m, 2H), 0.92-0.88 (t, J=7.6 Hz, 3H).
MH+490.

Example 124

N-(3-(4-(2,3-dimethylphenyl)piperazin-1-yl)propyl)-2,5-dimethyl-1-(quinolin-6-yl)-1H-imidazole-4-carboxamide dihydrochloride $^{1}$H NMR (400 MHz, CD$_{3}$OD) δ 9.47 (d, J=5.2 Hz, 1H), 9.41 (d, J=8.4 Hz, 1H), 8.77 (s, 1H), 8.60 (d, J=9.2 Hz, 1H), 8.34 (d, J=9.2 Hz, 1H), 8.32-8.29 (m, 1H), 7.09-7.05 (m, 1H), 6.99-6.94 (m, 2H), 3.72-3.69 (m, 2H), 3.60-3.57 (m, 2H), 3.49-3.41 (m, 4H), 3.29-3.15 (m, 4H), 2.56 (s, 3H), 2.42 (s, 3H), 2.25 (s, 6H), 2.22-2.16 (m, 2H).
MH+497.

Example 125

N-(3-(4-(2,3-dichlorophenyl)piperazin-1-yl)-2-hydroxypropyl)-2,5-dimethyl-1-(quinolin-6-yl)-1H-imidazole-4-carboxamide dihydrochloride $^{1}$H NMR (400 MHz, CD$_{3}$OD) δ 9.43 (d, J=4.8 Hz, 1H), 9.33 (d, J=8.0 Hz, 1H), 8.73 (s, 1H), 8.57 (d, J=9.2 Hz, 1H), 8.31 (d, J=8.8 Hz, 1H), 8.27-8.24 (m, 1H), 7.30-7.28 (m, 2H), 7.18-7.15 (m, 1H), 4.40-4.37 (m, 1H), 3.79-3.76 (m, 2H), 3.62-3.55 (m, 2H), 3.54-3.39 (m, 4H), 3.35-3.17 (m, 4H), 2.55 (s, 3H), 2.42 (s, 3H).
MH+553.

Example 126

N-(3-(4-(2,3-dichlorophenyl)piperazin-1-yl)-2-hydroxypropyl)-1-phenyl-2-propyl-1H-imidazole-4-carboxamide dihydrochloride $^1$H NMR (400 MHz, CD$_3$OD) δ 8.25 (s, 1H), 7.69-7.65 (m, 3H), 7.63-7.60 (m, 2H), 7.30-7.25 (m, 2H), 7.18-7.14 (m, 1H), 4.35-4.33 (m, 1H), 3.77-3.73 (m, 2H), 3.54-3.38 (m, 6H), 3.32-3.19 (m, 4H), 2.91 (t, J=7.6 Hz, 2H), 1.67-1.61 (m, 2H), 0.88 (t, J=7.2 Hz, 3H).
MH+516.

Example 127

N-(3-(4-(2,3-dichlorophenyl)piperazin-1-yl)-2-hydroxypropyl)-1-(4-fluorophenyl)-2-propyl-1H-imidazole-4-carboxamide dihydrochloride $^1$H NMR (400 MHz, CD$_3$OD) δ 8.21 (s, 1H), 7.69-7.65 (m, 2H), 7.44-7.39 (m, 2H), 7.29-7.27 (m, 2H), 7.17-7.15 (m, 1H), 4.35-4.33 (m, 1H), 3.77-3.73 (m, 2H), 3.54-3.35 (m, 6H), 3.32-3.19 (m, 4H), 2.87 (t, J=7.6 Hz, 2H), 1.67-1.62 (m, 2H), 0.89 (t, J=7.2 Hz, 3H).
MH+534.

Example 128

N-(3-(4-(2,3-dimethylphenyl)piperazin-1-yl)-2-hydroxypropyl)-1-(4-fluorophenyl)-2-propyl-1H-imidazole-4-carboxamide dihydrochloride $^1$H NMR (400 MHz, CD$_3$OD) δ 8.18 (s, 1H), 7.68-7.64 (m, 2H), 7.43-7.39 (m, 2H), 7.07-7.03 (m, 1H), 6.96-6.92 (m, 2H), 4.34-4.32 (m, 1H), 3.72-3.69 (m, 2H), 3.57-3.47 (m, 2H), 3.44-3.32 (m, 4H), 3.24-3.06 (m, 4H), 2.86 (t, J=7.2 Hz, 2H), 2.24 (s, 3H), 2.23 (s, 3H), 1.69-1.60 (m, 2H), 0.89 (t, J=7.6 Hz, 3H).
MH+494.

Example 129

N-(3-(4-(2,3-dimethylphenyl)piperazin-1-yl)propyl)-1-(4-fluorophenyl)-2-propyl-1H-imidazole-4-carboxamide dihydrochloride $^1$H NMR (400 MHz, CD$_3$OD) δ 8.14 (s, 1H), 7.65-7.59 (m, 2H), 7.49-7.46 (m, 2H), 7.10-6.93 (m, 3H), 3.69-3.62 (m, 2H), 3.59-3.52 (m, 2H), 3.20-3.09 (m, 4H), 3.87-3.83 (m, 4H), 2.23 (s, 6H), 2.15-2.13 (m, 2H), 1.69-1.61 (m, 2H), 0.92-0.86 (m, 3H).
MH+478.

Example 130

N-(3-(4-(2,3-dichlorophenyl)piperazin-1-yl)-2-hydroxypropyl)-1,2-diphenyl-1H-imidazole-4-carboxamide dihydrochloride $^1$H NMR (400 MHz, CD$_3$OD) δ 8.37 (s, 1H), 7.59-7.51 (m, 4H), 7.49-7.43 (m, 6H), 7.30-7.28 (m, 2H), 7.17-7.14 (m, 1H), 4.36-4.34 (m, 1H), 3.77-3.74 (m, 2H), 3.61-3.50 (m, 4H), 3.47-3.32 (m, 4H), 3.23-3.15 (m, 2H).
MH+550.

Example 131

N-(3-(4-(2,3-dimethylphenyl)piperazin-1-yl)propyl)-1,2-diphenyl-1H-imidazole-4-carboxamide dihydrochloride $^1$H NMR (400 MHz, CD$_3$OD) δ 8.41 (s, 1H), 7.58-7.53 (m, 4H), 7.52-7.46 (m, 6H), 7.08-7.04 (m, 1H), 6.97-6.93 (m, 2H), 3.69-3.67 (m, 2H), 3.60-3.56 (m, 2H), 3.36-3.20 (m, 6H), 3.14-3.11 (m, 2H), 2.25 (s, 6H), 2.18-2.16 (m, 2H).
MH+494.

Example 132

N-(3-(4-(2,3-dimethylphenyl)piperazin-1-yl)propyl)-2,5-dimethyl-1-(pyridin-2-yl)-1H-imidazole-4-carboxamide trihydrochloride $^1$H NMR (400 MHz, CD$_3$OD) δ 8.76 (d, J=4.4 Hz, 1H), 8.21 (t, J=6.8 Hz, 1H), 7.78-7.72 (m, 2H), 7.09-7.04 (m, 1H), 7.00-6.94 (m, 2H), 3.71-3.68 (m, 2H), 3.65-3.61 (m, 2H), 3.49-3.32 (m, 4H), 3.30-3.14 (m, 4H), 2.55 (s, 3H), 2.42 (s, 3H), 2.25 (s, 6H), 2.22-2.13 (m, 2H).
MH+447.

Example 133

N-(3-(4-(2,3-dichlorophenyl)piperazin-1-yl)-2-hydroxypropyl)-1-(4-methoxyphenyl)-2-phenyl-1H-imidazole-4-carboxamide dihydrochloride $^1$H NMR (400 MHz, CD$_3$OD) δ 8.34 (s, 1H), 7.58-7.56 (m, 1H), 7.50-7.46 (m, 4H), 7.37 (d, J=8.4 Hz, 2H), 7.30-7.28 (m, 2H), 7.17-7.15 (m, 1H), 7.04 (d, J=8.4 Hz, 2H), 4.36-4.35 (m, 1H), 3.83 (s, 3H), 3.77-3.74 (m, 2H), 3.59-3.53 (m, 2H), 3.52-3.32 (m, 6H), 3.24-3.16 (m, 2H).
MH+580.

Example 134

N-(3-(4-(2,3-dimethylphenyl)piperazin-1-yl)propyl)-1-(4-methoxyphenyl)-2-phenyl-1H-imidazole-4-carboxamide dihydrochloride $^1$H NMR (400 MHz, DMSO-d$_6$) δ 8.35 (s, 1H), 7.61-7.57 (m, 1H), 7.50-7.45 (m, 4H), 7.37 (d, J=9.2 Hz, 2H), 7.08-7.03 (m, 3H), 6.95 (t, J=6.8 Hz, 2H), 3.83 (s, 3H), 3.69-3.66 (m, 2H), 3.59-3.55 (m, 2H), 3.38-3.32 (m, 4H), 3.23-3.20 (m, 2H), 3.14-3.08 (m, 2H), 2.25 (s, 3H), 2.24 (s, 3H), 2.20-2.13 (m, 2H).
MH+524.

Example 135

N-(3-(4-(3-chloro-2-methylphenyl)piperazin-1-yl)propyl)-1-(4-methoxyphenyl)-5-methyl-2-propyl-1H-imidazole-4-carboxamide dihydrochloride $^1$H NMR (400 MHz, DMSO-d$_6$) δ 11.01 (br s, 1H), 9.01 (br s, 1H), 7.47 (d, J=8.8 Hz, 2H), 7.18-7.14 (m, 4H), 7.02 (dd, J=6.8, 2.0 Hz, 1H), 3.82 (s, 3H), 3.52-3.49 (m, 2H), 3.36 (q, J=6.4 Hz, 2H), 3.23-3.11 (m, 6H), 2.59 (t, J=7.6 Hz, 2H), 2.26 (s, 3H), 2.22 (s, 3H), 2.04-2.00 (m, 2H), 1.63-1.54 (m, 2H), 0.77 (t, J=7.6 Hz, 3H).
MH+523.

Example 136

N-(3-(4-(2,3-dichlorophenyl)piperazin-1-yl)-2-hydroxypropyl)-1-(4-methoxyphenyl)-5-methyl-2-propyl-1H-imidazole-4-carboxamide dihydrochloride $^1$H NMR (400 MHz, DMSO-d$_6$) δ 10.41 (br s, 1H), 8.68 (br s, 1H), 7.43 (d, J=8.8 Hz, 2H), 7.36-7.30 (m, 2H), 7.18-7.13 (m, 3H), 4.22-4.20 (m, 1H), 3.82 (s, 3H), 3.66-3.55 (m, 2H), 3.42-3.34 (m, 5H), 3.30-3.13 (m, 5H), 2.55 (t, J=7.6 Hz, 2H), 2.22 (s, 3H), 1.60-1.51 (m, 2H), 0.77 (t, J=7.6 Hz, 3H).
MH+560.

Example 137

N-(3-(4-(2,3-dimethylphenyl)piperazin-1-yl)-2-hydroxypropyl)-1-(4-methoxyphenyl)-5-methyl-2-propyl-1H-imidazole-4-carboxamide dihydrochloride $^1$H NMR (400 MHz, DMSO-d$_6$) δ 10.40 (br s, 1H), 8.93 (br s, 1H), 7.48 (d, J=8.8 Hz, 2H), 7.16 (d, J=8.8 Hz, 2H), 7.03 (t, J=7.6 Hz, 1H), 6.90-6.86 (m, 2H), 4.25-4.23 (m, 1H), 3.82 (s, 3H), 3.63-3.51 (m, 2H), 3.44-3.24 (m, 5H), 3.20-3.08 (m, 5H), 2.61 (t, J=7.6 Hz, 2H), 2.23 (s, 3H), 2.18 (s, 3H), 2.13 (s, 3H), 1.63-1.54 (m, 2H), 0.77 (t, J=7.6 Hz, 3H).
MH+520.

Example 138

N-(3-(4-(3-chloro-2-methylphenyl)piperazin-1-yl)propyl)-1-(4-methoxyphenyl)-2,5-dimethyl-1H-imidazole-4-carboxamide dihydrochloride $^1$H NMR (400 MHz, DMSO-d$_6$) δ 11.22 (br s, 1H), 8.92 (br s, 1H), 7.48 (d, J=7.2 Hz, 2H), 7.20-7.15 (m, 4H), (dd, J=6.8, 2.4 Hz, 1H), 3.82 (s, 3H), 3.51-3.48 (m, 2H), 3.37 (q, J=6.4 Hz, 2H), 3.22-3.12 (m, 8H), 2.32 (s, 3H), 2.26 (s, 3H), 2.24 (s, 3H), 2.06-1.99 (m, 2H).
MH+496.

Example 139

(S)—N-(3-(4-(2,3-dimethylphenyl)piperazin-1-yl)-2-hydroxypropyl)-2,5-dimethyl-1-phenyl-1H-imidazole-4-carboxamide dihydrochloride $^1$H NMR (400 MHz, DMSO-d$_6$) δ 10.15 (br s, 1H), 8.54 (br s, 1H), 7.66-7.59 (m, 3H), 7.50-7.48 (m, 2H), 7.04 (t, J=7.2 Hz, 1H), 6.88 (dd, J=7.6, 8.0 Hz, 2H), 4.21-4.19 (m, 1H), 3.61-3.51 (m, 2H), 3.38-3.24 (m, 5H), 3.17-3.01 (m, 5H), 2.27 (s, 3H), 2.25 (s, 3H), 2.18 (s, 3H), 2.13 (s, 3H).
MH+462.

Example 140

N—((S)-3-(4-(2,3-dimethylphenyl)piperazin-1-yl)-2-hydroxypropyl)-1-(2-fluorophenyl)-2,5-dimethyl-1H-imidazole-4-carboxamide dihydrochloride $^1$H NMR (400 MHz, DMSO-d$_6$) δ 10.06 (br s, 1H), 8.30 (br s, 1H), 7.69-7.54 (m, 3H), 7.44 (t, J=7.6 Hz, 1H), 7.03 (t, J=7.6 Hz, 1H), 6.87 (dd, J=7.6, 8.0 Hz, 2H), 4.19-4.17 (m, 1H), 3.59-3.51 (m, 2H), 3.40-3.28 (m, 5H), 3.14-3.00 (m, 5H), 2.23 (s, 3H), 2.19 (s, 3H), 2.18 (s, 3H), 2.13 (s, 3H).
MH+480.

Example 141

(S)-1-(4-chlorophenyl)-N-(3-(4-(2,3-dichlorophenyl)piperazin-1-yl)-2-hydroxypropyl)-2-propyl-1H-imidazole-4-carboxamide dihydrochloride $^1$H NMR (400 MHz, DMSO-d$_6$) δ 10.73 (br s, 1H), 9.16 (br s, 1H), 8.50 (br s, 1H), 7.72-7.64 (m, 4H), 7.34-7.29 (m, 2H), 7.16 (dd, J=2.4, 2.8 Hz, 1H), 4.27-4.25 (m, 1H), 3.67-3.53 (m, 2H), 3.41-3.30 (m, 5H), 3.27-3.12 (m, 5H), 2.72 (t, J=7.2 Hz, 2H), 1.56-1.49 (m, 2H), 0.75 (t, J=7.6 Hz, 3H).
MH+550.

Example 142

(S)—N-(3-(4-(3-chloro-2-methylphenyl)piperazin-1-yl)-2-hydroxypropyl)-1-(4-fluorophenyl)-5-methyl-2-phenyl-1H-imidazole-4-carboxamide dihydrochloride $^1$H NMR (400 MHz, DMSO-d$_6$) δ 10.42 (br s, 1H), 8.40 (t, J=5.6 Hz, 1H), 7.48-7.44 (m, 2H), 7.38 (d, J=8.8 Hz, 1H), 7.35-7.27 (m, 6H), 7.19-7.14 (m, 2H), 7.00 (dd, J=2.4, 2.0 Hz, 1H), 4.25-4.23 (m, 1H), 3.63-3.51 (m, 2H), 3.38 (t, J=5.6 Hz, 2H), 3.32-3.29 (m, 3H), 3.13-3.07 (m, 5H), 2.31 (s, 3H), 2.25 (s, 3H).
MH+562.

Example 143

N-(3-(4-(2,3-dichlorophenyl)piperazin-1-yl)propyl)-1-(4-methoxyphenyl)-5-methyl-2-propyl-1H-imidazole-4-carboxamide dihydrochloride $^1$H NMR (400 MHz, DMSO-d$_6$) δ 10.87 (br s, 1H), 8.80 (br s, 1H), 7.43 (d, J=8.8 Hz, 2H), 7.36-7.32 (m, 2H), 7.19-7.13 (m, 3H), 3.81 (s, 3H), 3.56-3.54 (m, 2H), 3.41-3.34 (m, 4H), 3.21-3.16 (m, 6H), 2.55 (t, J=7.6 Hz, 2H), 2.21 (s, 3H), 2.02-1.98 (m, 2H), 1.58-1.53 (m, 2H), 0.77 (t, J=7.2 Hz, 3H).
MH+544.

Example 144

N-(3-(4-(3-chloro-2-methylphenyl)piperazin-1-yl)propyl)-1-(2-methoxyphenyl)-2,5-dimethyl-1H-imidazole-4-carboxamide dihydrochloride $^1$H NMR (400 MHz, DMSO-d$_6$) δ 10.77 (br s, 1H), 8.64 (br s, 1H), 7.63-7.58 (m, 1H), 7.45 (d, J=8.0 Hz, 1H), 7.33 (d, J=8.4 Hz, 1H), 7.20-7.14 (m, 3H), (dd, J=2.0, 2.4 Hz, 1H), 3.78 (s, 3H), 3.53-3.50 (m, 2H), 3.35 (q, J=6.4 Hz, 2H), 3.21-3.06 (m, 8H), 2.26 (s, 3H), 2.22 (s, 3H), 2.17 (s, 3H), 2.02-1.98 (m, 2H).
MH+496.

Example 145

N-(3-(4-(2,3-dichlorophenyl)piperazin-1-yl)propyl)-1-(2-methoxyphenyl)-2,5-dimethyl-1H-imidazole-4-carboxamide dihydrochloride $^1$H NMR (400 MHz, DMSO-d$_6$) δ 11.03 (br s, 1H), 8.67 (br s, 1H), 7.60 (t, J=7.6 Hz, 1H), 7.46 (d, J=7.2 Hz, 1H), 7.34-

7.30 (m, 3H), 7.18-7.14 (m, 2H), 3.78 (s, 3H), 3.56-3.54 (m, 2H), 3.41-3.34 (m, 4H), 3.24-3.14 (m, 6H), 2.23 (s, 3H), 2.17 (s, 3H), 2.00-1.96 (m, 2H).
MH+516.

Example 146

N-(3-(4-(2,3-dichlorophenyl)piperazin-1-yl)-2-hydroxypropyl)-1-(2-methoxyphenyl)-2,5-dimethyl-1H-imidazole-4-carboxamide dihydrochloride $^1$H NMR (400 MHz, DMSO-d$_6$) δ 10.44 (br s, 1H), 8.55 (br s, 1H), 7.60 (t, J=7.6 Hz, 1H), 7.46 (d, J=7.6 Hz 1H), 7.36-7.30 (m, 3H), 7.18-7.14 (m, 2H), 4.22-4.20 (m, 1H), 3.78 (s, 3H), 3.67-3.55 (m, 2H), 3.42-3.31 (m, 4H), 3.28-3.12 (m, 6H), 2.23 (s, 3H), 2.18 (s, 3H).
MH+532.

Example 147

N-(3-(4-(2,3-dimethylphenyl)piperazin-1-yl)propyl)-2,5-dimethyl-1-p-tolyl-1H-imidazole-4-carboxamide dihydrochloride $^1$H NMR (400 MHz, DMSO-d$_6$) δ 11.19 (br s, 1H), 8.97 (br s, 1H), 7.46-7.41 (m, 4H), 7.04 (t, J=7.6 Hz, 1H), 6.90-6.85 (m, 2H), 3.51-3.48 (m, 2H), 3.40-3.35 (m, 2H), 3.26-3.17 (m, 4H), 3.14-3.05 (m, 4H), 2.39 (s, 3H), 2.34 (s, 3H), 2.25 (s, 3H), 2.18 (s, 3H), 2.13 (s, 3H), 2.08-2.00 (m, 2H).
MH+460.

Example 148

N-(3-(4-(2,3-dimethylphenyl)piperazin-1-yl)-2-hydroxypropyl)-2,5-dimethyl-1-p-tolyl-1H-imidazole-4-carboxamide dihydrochloride $^1$H NMR (400 MHz, DMSO-d$_6$) δ 10.56 (br s, 1H), 8.82 (br s, 1H), 7.46-7.41 (m, 4H), 7.04 (t, J=8.0 Hz, 1H), 6.90-6.85 (m, 2H), 4.26-2.24 (m, 1H), 3.64-3.61 (m, 1H), 3.54-3.51 (m, 1H), 3.43-3.38 (m, 2H), 3.36-3.27 (m, 4H), 3.18-3.08 (m, 4H), 2.39 (s, 3H), 2.34 (s, 3H), 2.25 (s, 3H), 2.18 (s, 3H), 2.13 (s, 3H).
MH+476.

Example 149

N-(3-(4-(2,3-dichlorophenyl)piperazin-1-yl)-2-hydroxypropyl)-1-(2,3-dihydrobenzo[b][1,4]dioxin-6-yl)-2,5-dimethyl-1H-imidazole-4-carboxamide dihydrochloride $^1$H NMR (400 MHz, DMSO-d$_6$) δ 10.65 (br s, 1H), 8.69 (br s, 1H), 7.36-7.30 (m, 2H), 7.18-7.07 (m, 2H), 6.98 (d, J=2.4 Hz, 1H), 6.96 (d, J=2.4 Hz, 1H), 4.30 (s, 4H), 4.27-4.23 (m, 1H), 3.67-3.63 (m, 2H), 3.56-3.54 (m, 2H), 3.42-3.33 (m, 4H), 3.25-3.17 (m, 4H), 2.32 (s, 3H), 2.26 (s, 3H).
MH+560.

Example 150

N-(3-(4-(2,3-dichlorophenyl)piperazin-1-yl)propyl)-1-(2,3-dihydrobenzo[b][1,4]dioxin-6-yl)-2,5-dimethyl-1H-imidazole-4-carboxamide dihydrochloride $^1$H NMR (400 MHz, DMSO-d$_6$) δ 11.32 (br s, 1H), 8.87 (br s, 1H), 7.36-7.30 (m, 2H), 7.20-7.07 (m, 2H), 7.00 (d, J=2.4 Hz, 1H), 6.97 (d, J=2.4 Hz, 1H), 4.30 (s, 4H), 3.56-3.53 (m, 2H), 3.41-3.34 (m, 4H), 3.25-3.11 (m, 6H), 2.32 (s, 3H), 2.52 (s, 3H), 2.05-1.98 (m, 2H).
MH+544.

Example 151

(R)—N-(3-(4-(2,3-dimethylphenyl)piperazin-1-yl)-2-hydroxypropyl)-2,5-dimethyl-1-phenyl-1H-imidazole-4-carboxamide dihydrochloride $^1$H NMR (400 MHz, DMSO-d$_6$) δ 10.51 (s, 1H), 8.75 (s, 1H), 7.68-7.50 (m, 5H), 7.04 (t, J=7.6 Hz, 1H), 6.90-6.86 (m, 2H), 4.26-4.24 (m, 1H), 3.64-3.51 (m, 2H), 3.43-3.33 (m, 3H), 3.32-3.27 (m, 2H), 3.20-3.08 (m, 5H), 2.33 (s, 3H), 2.26 (s, 3H), 2.18 (s, 3H), 2.13 (s, 3H).
MH+462.

Example 152

N—((R)-3-(4-(2,3-dimethylphenyl)piperazin-1-yl)-2-hydroxypropyl)-1-(2-fluorophenyl)-2,5-dimethyl-1H-imidazole-4-carboxamide dihydrochloride $^1$H NMR (400 MHz, DMSO-d$_6$) δ 10.33 (s, 1H), 8.45 (s, 1H), 7.72-7.51 (m, 3H), 7.46 (t, J=7.6 Hz, 1H), 7.04 (t, J=7.6 Hz, 1H), 6.90-6.86 (m, 2H), 4.23-4.21 (m, 1H), 3.62-3.51 (m, 2H), 3.41-3.27 (m, 5H), 3.13-3.02 (m, 5H), 2.24 (s, 6H), 2.18 (s, 3H), 2.13 (s, 3H).
MH+480.

Example 153

N-(3-(4-(3-chloro-2-methylphenyl)piperazin-1-yl)propyl)-1-(2-fluorophenyl)-2,5-dimethyl-1H-imidazole-4-carboxamide dihydrochloride $^1$H NMR (400 MHz, DMSO-d$_6$) δ 11.15 (s, 1H), 8.70 (s, 1H), 7.74-7.67 (m, 2H), 7.60 (t, J=8.8 Hz, 1H), 7.48 (t, J=7.6 Hz, 1H), 7.20-7.14 (m, 2H), 7.01 (dd, J=6.8, 2.0 Hz, 1H), 3.52-3.49 (m, 2H), 3.36-3.35 (m, 2H), 3.22-3.13 (m, 8H), 2.30 (s, 3H), 2.26 (s, 3H), 2.25 (s, 3H), 2.03-2.00 (m, 2H).
MH+484.

Example 154

N-(3-(4-(2,3-dichlorophenyl)piperazin-1-yl)propyl)-1-(2-fluorophenyl)-2,5-dimethyl-1H-imidazole-4-carboxamide dihydrochloride $^1$H NMR (400 MHz, DMSO-d$_6$) δ 11.17 (s, 1H), 8.60 (s, 1H), 7.72-7.64 (m, 2H), 7.59 (t, J=9.2 Hz, 1H), 7.47 (t, J=7.6 Hz, 1H), 7.35-7.30 (m, 2H), 7.01 (dd, J=7.2, 2.4 Hz, 1H), 3.56-3.53 (m, 2H), 3.41-3.33 (m, 4H), 3.24-3.13 (m, 6H), 2.26 (s, 3H), 2.24 (s, 3H), 2.02-1.98 (m, 2H).
MH+504.

Example 155

N-(3-(4-(2,3-dimethylphenyl)piperazin-1-yl)-2-hydroxypropyl)-5-methyl-1,2-diphenyl-1H-imidazole-4-carboxamide dihydrochloride $^1$H NMR (400 MHz, DMSO-d$_6$) δ 10.28 (s, 1H), 8.41 (s, 1H), 7.58-7.23 (m, 11H), 7.07 (t, J=8.0 Hz, 1H), 6.90 (d, J=8.4 Hz, 2H), 4.33-4.19 (m, 1H), 3.67-3.54 (m, 2H), 3.49-3.23 (m, 6H), 3.20-3.03 (m, 6H), 2.45 (s, 3H), 2.26 (s, 3H), 2.21 (s, 3H).
MH+524.

Example 156

N-(3-(4-(2,3-dichlorophenyl)piperazin-1-yl)-2-hydroxypropyl)-5-methyl-1,2-diphenyl-1H-imidazole-4-carboxamide dihydrochloride $^1$H NMR (400 MHz, DMSO-d$_6$) δ 10.35 (s, 1H), 8.39 (s, 1H), 7.55-7.21 (m, 13H), 6.93 (dd, J=7.2, 2.4 Hz, 1H), 4.35-4.21 (m, 1H), 3.71-3.55 (m, 2H), 3.50-3.23 (m, 6H), 3.21-3.01 (m, 6H), 2.45 (s, 3H).
MH+564.

Example 157

N-(3-(4-(2,3-dichlorophenyl)piperazin-1-yl)-2-hydroxypropyl)-1-(4-fluorophenyl)-5-methyl-2-phenyl-1H-imidazole-4-carboxamide dihydrochloride $^1$H NMR (400 MHz, DMSO-d$_6$) δ 10.30 (s, 1H), 8.39 (s, 1H), 7.55-7.21 (m, 12H), 6.93 (dd, J=7.2, 2.4 Hz, 1H), 4.33-4.19 (m, 1H), 3.69-3.53 (m, 2H), 3.48-3.20 (m, 6H), 3.19-3.02 (m, 6H), 2.44 (s, 3H), 2.33 (s, 3H).
MH+562.

Example 158

N-(3-(4-(2,3-dichlorophenyl)piperazin-1-yl)propyl)-5-methyl-1,2-diphenyl-1H-imidazole-4-carboxamide dihydrochloride $^1$H NMR (400 MHz, DMSO-d$_6$) δ 10.52 (s, 1H), 8.45 (s, 1H), 7.59-7.20 (m, 13H), 6.97 (dd, J=7.2, 2.4 Hz, 1H), 3.81-3.68 (m, 2H), 3.65-3.51 (m, 2H), 3.50-3.31 (m, 4H), 2.77-2.60 (m, 4H), 2.45 (s, 3H), 2.09-1.95 (m, 2H).
MH+548.

Example 159

N-(3-(4-(2,3-dichlorophenyl)piperazin-1-yl)propyl)-1-(4-fluorophenyl)-5-methyl-2-phenyl-1H-imidazole-4-carboxamide dihydrochloride $^1$H NMR (400 MHz, DMSO-d$_6$) δ 10.35 (s, 1H), 8.45 (s, 1H), 7.55-7.21 (m, 12H), 6.97 (dd, J=7.2, 2.4 Hz, 1H), 3.77-3.65 (m, 2H), 3.63-3.51 (m, 2H), 3.49-3.28 (m, 4H), 2.79-2.59 (m, 4H), 2.44 (s, 3H), 2.09-1.94 (m, 2H).
MH+566.

Example 160

N-(3-(4-(3-chloro-2-methylphenyl)piperazin-1-yl)-2-hydroxypropyl)-5-methyl-1,2-diphenyl-1H-imidazole-4-carboxamide dihydrochloride $^1$H NMR (400 MHz, DMSO-d$_6$) δ 10.33 (s, 1H), 8.36 (s, 1H), 7.55-7.46 (m, 3H), 7.44-6.97 (m, 10H), 4.33-4.18 (m, 1H), 3.68-3.52 (m, 2H), 3.46-3.22 (m, 6H), 3.20-3.05 (m, 6H), 2.35 (s, 3H), 2.29 (s, 3H).
MH+544.

Example 161

N-(3-(4-(3-chloro-2-methylphenyl)piperazin-1-yl)-2-hydroxypropyl)-1-(4-fluorophenyl)-5-methyl-2-propyl-1H-imidazole-4-carboxamide dihydrochloride $^1$H NMR (400 MHz, DMSO-d$_6$) δ 10.53 (s, 1H), 8.83 (s, 2H), 7.71-7.62 (m, 2H), 7.59-7.47 (m, 2H), 7.27-7.16 (m, 2H), 7.09-7.01 (m, 1H), 4.34-4.25 (m, 1H), 3.71-3.55 (m, 3H), 3.48-3.27 (m, 6H), 3.25-3.11 (m, 6H), 2.62 (t, J=7.2 Hz, 2H), 2.31 (s, 3H), 2.27 (s, 3H), 1.66-1.54 (m, 2H), 0.87 (t, J=3.2 Hz, 3H).
MH+528.

Example 162

N-(3-(4-(3-chloro-2-methylphenyl)piperazin-1-yl)-2-hydroxypropyl)-1-(4-fluorophenyl)-2,5-dimethyl-1H-imidazole-4-carboxamide dihydrochloride $^1$H NMR (400 MHz, DMSO-d$_6$) δ 10.51 (s, 1H), 8.90 (s, 2H), 7.75-7.63 (m, 2H), 7.60-7.49 (m, 2H), 7.27-7.15 (m, 2H), 7.09-6.99 (m, 1H), 4.40-4.31 (m, 1H), 3.71-3.49 (m, 3H), 3.44-3.23 (m, 6H), 3.21-3.07 (m, 6H), 2.34 (s, 3H), 2.33 (s, 3H), 2.18 (s, 3H).
MH+500.

Example 163

1-cyclopentyl-N-(3-(4-(2,3-dichlorophenyl)piperazin-1-yl)propyl)-2,5-dimethyl-1H-imidazole-4-carboxamide dihydrochloride $^1$H NMR (400 MHz, MeOH-d$_4$) δ 7.30-7.26 (m, 2H), 7.18-7.15 (m, 1H), 3.71 (d, J=8.0 Hz, 2H), 3.64 (s, 3H), 3.58 (s, 3H), 3.53-3.50 (m, 4H), 3.37-3.34 (m, 3H), 3.30-3.28 (m, 2H), 3.22-3.18 (m, 2H), 2.72 (s, 3H), 2.64 (s, 3H), 2.31-2.25 (m, 2H), 2.18-2.13 (m, 2H), 2.04-1.95 (m, 4H), 1.79-1.78 (m, 2H).
MH+478 (−2HCl).

Example 164

1-cyclopentyl-N-(3-(4-(2,3-dichlorophenyl)piperazin-1-yl)-2-hydroxypropyl)-2,5-dimethyl-1H-imidazole-4-carboxamide dihydrochloride $^1$H NMR (400 MHz, MeOH-d$_4$) δ 7.31-7.26 (m, 2H), 7.17-7.15 (m, 2H), 4.34-4.31 (m, 1H), 3.74 (d, J=12.0 Hz, 2H), 3.57-3.35 (m, 8H), 3.20-3.15 (m, 3H), 2.72 (s, 3H), 2.61 (s, 3H), 2.28-2.25 (m, 2H), 2.05-1.96 (m, 4H), 1.79-1.82 (m, 2H).
MH+494 (−2HCl).

Example 165

N-(3-(4-(2,3-dichlorophenyl)piperazin-1-yl)propyl)-2,5-dimethyl-1-propyl-1H-imidazole-4-carboxamide dihydrochloride $^1$H NMR (400 MHz, MeOH-d$_4$) δ 7.31-7.23 (m, 2H), 7.18-7.16 (m, 1H), 4.09 (t, J=8.0 Hz, 2H), 3.71 (d, J=9.2 Hz, 2H), 3.53 (t, J=6.4 Hz, 2H), 3.37-3.31 (m, 3H), 3.30-3.28 (m, 4H), 3.22-3.21 (m, 2H), 2.67 (s, 3H), 2.58 (s, 3H), 2.18-2.11 (m, 2H), 1.82-1.77 (m, 2H), 1.01 (t, J=6.4 Hz, 3H).
MH+452 (−2HCl).

Example 166

N-(3-(4-(2,3-dichlorophenyl)piperazin-1-yl)-2-hydroxypropyl)-2,5-dimethyl-1-propyl-1H-imidazole-4-carboxamide dihydrochloride $^1$H NMR (400 MHz, MeOH-d$_4$) δ 7.28-7.27 (m, 2H), 7.19-7.17 (m, 1H), 4.36-4.34 (m, 1H), 4.10 (t, J=8.0 Hz, 2H), 3.78-3.7 (m, 2H), 3.53-3.42 (m, 7H), 3.21-2.60 (m, 3H), 2.69 (s, 3H), 2.60 (s, 3H), 1.83-1.77 (m, 2H), 1.01 (t, J=7.2 Hz, 3H).
MH+468 (−2HCl).

Example 167

N-(3-(4-(2,3-dimethylphenyl)piperazin-1-yl)propyl)-1-(2-methoxyphenyl)-5-methyl-2-propyl-1H-imidazole-4-carboxamide dihydrochloride $^1$H NMR (400 MHz, DMSO-d$_6$) δ 10.95 (br s, 1H), 9.06 (br s, 1H), 7.64 (t, J=7.6 Hz, 1H), 7.54 (dd, J=8.6, 1.2 Hz, 1H), 7.03 (d, J=8.0 Hz, 1H), 7.18 (td, J=7.6, 0.8 Hz, 1H), 7.03 (t, J=7.6 Hz, 1H), 6.90-6.86 (m, 2H), 3.78 (s, 3H), 3.52-3.49 (m, 2H), 3.38-3.36 (m, 2H), 3.26-3.07 (m, 8H), 2.60-2.56 (m, 2H), 2.18 (s, 6H), 2.13 (s, 3H), 2.06-1.99 (m, 2H), 1.59-1.51 (m, 2H), 0.75 (t, J=7.6 Hz, 3H).
MH+504.

Example 168

N-(3-(4-(3-chloro-2-methylphenyl)piperazin-1-yl)propyl)-1-(2-methoxyphenyl)-5-methyl-2-propyl-1H-imidazole-4-carboxamide dihydrochloride $^1$H NMR (400 MHz, DMSO-d$_6$) δ 10.81 (br s, 1H), 8.86 (br s, 1H), 7.62 (t, J=8.0 Hz, 1H), 7.49 (d, J=7.6 Hz, 1H), 7.34 (d, J=8.0 Hz, 1H), 7.20-7.15 (m, 3H), 7.05-7.01 (m, 1H), 3.78 (s, 3H), 3.53-3.50 (m, 2H), 3.37-3.35 (m, 2H), 3.23-3.06 (m, 8H), 2.53 (t, J=7.6 Hz, 2H), 2.27 (s, 6H), 2.17 (s, 3H), 2.04-1.99 (m, 2H), 1.58-1.49 (m, 2H), 0.75 (t, J=7.6 Hz, 3H).
MH+524.

Example 169

N-(3-(4-(2,3-dichlorophenyl)piperazin-1-yl)propyl)-1-(2-methoxyphenyl)-5-methyl-2-propyl-1H-imidazole-4-carboxamide dihydrochloride $^1$H NMR (400 MHz, DMSO-d$_6$) δ 11.06 (br s, 1H), 8.91 (br s, 1H), 7.62 (t, J=8.0 Hz, 1H), 7.51 (d, J=7.6 Hz, 1H), 7.51 (d, J=6.8 Hz, 1H), 7.35-7.32 (m, 3H), 7.20-7.15 (m, 2H), 3.78 (s, 3H), 3.59-3.54 (m, 2H), 3.41-3.35 (m, 4H), 3.26-3.17 (m, 6H), 2.54 (t, J=7.2 Hz, 2H), 2.17 (s, 6H), 2.04-1.99 (m, 2H), 1.59-1.50 (m, 2H), 0.73 (t, J=7.2 Hz, 3H).
MH+544.

Example 170

N-(3-(4-(2,3-dimethylphenyl)piperazin-1-yl)-2-hydroxypropyl)-1-(2-methoxyphenyl)-5-methyl-2-propyl-1H-imidazole-4-carboxamide dihydrochloride $^1$H NMR (400 MHz, DMSO-d$_6$) δ 10.26 (br s, 1H), 8.79 (br s, 1H), 7.64 (t, J=7.6 Hz, 1H), 7.50 (d, J=8.0 Hz, 1H), 7.35 (d, J=7.6 Hz, 1H), 7.17 (td, J=7.6, 0.8 Hz, 1H), 7.03 (t, J=7.6 Hz, 1H), 6.90-6.86 (m, 2H), 4.24-4.22 (m, 1H), 3.78 (s, 3H), 3.52-3.40 (m, 2H), 3.38-3.27 (m, 5H), 3.16-3.05 (m, 5H), 2.56-2.53 (m, 2H), 2.18 (s, 6H), 2.13 (s, 3H), 1.57-1.51 (m, 2H), 0.76 (t, J=7.6 Hz, 3H).
MH+520.

Example 171

N-(3-(4-(3-chloro-2-methylphenyl)piperazin-1-yl)-2-hydroxypropyl)-1-(2-methoxyphenyl)-5-methyl-2-propyl-1H-imidazole-4-carboxamide dihydrochloride $^1$H NMR (400 MHz, DMSO-d$_6$) δ 10.68 (br s, 1H), 8.54 (br s, 1H), 7.59 (t, J=8.0 Hz, 1H), 7.43 (d, J=7.6 Hz, 1H), 7.32 (d, J=8.0 Hz, 1H), 7.18-7.13 (m, 3H), 7.03-7.01 (m, 1H), 4.21-4.19 (m, 1H), 3.76 (s, 3H), 3.62-3.52 (m, 2H), 3.37-3.25 (m, 5H), 3.18-3.04 (m, 7H), 2.26 (s, 3H), 2.16 (s, 3H), 1.54-1.48 (m, 2H), 0.75 (t, J=7.6 Hz, 3H).
MH+540.

Example 172

N-(3-(4-(2,3-dichlorophenyl)piperazin-1-yl)-2-hydroxypropyl)-1-(2-methoxyphenyl)-5-methyl-2-propyl-1H-imidazole-4-carboxamide dihydrochloride $^1$H NMR (400 MHz, DMSO-d$_6$) δ 10.41 (br s, 1H), 8.66 (br s, 1H), 7.61 (t, J=8.0 Hz, 1H), 7.60 (d, J=7.6 Hz, 1H), 7.35-7.32 (m, 3H), 7.18-7.15 (m, 2H), 4.23-4.21 (m, 1H), 3.77 (s, 3H), 3.64-3.56 (m, 2H), 3.42-3.32 (m, 5H), 3.28-3.12 (m, 7H), 2.51 (t, J=7.6 Hz, 2H), 2.17 (s, 3H), 1.56-1.50 (m, 2H), 0.75 (t, J=7.6 Hz, 3H).
MH+560.

Example 173

N-(3-(4-(2,3-dimethylphenyl)piperazin-1-yl)propyl)-2,5-dimethyl-1-(2-(trifluoromethyl)phenyl)-1H-imidazole-4-carboxamide dihydrochloride $^1$H NMR (400 MHz, MeOH-d$_4$) δ 8.11 (d, J=7.6 Hz, 1H), 8.04-7.95 (m, 2H), 7.78 (d, J=3.6 Hz, 1H), 7.06 (t, J=7.2 Hz, 1H), 6.95 (t, J=7.2 Hz, 2H), 3.70-3.60 (m, 3H), 3.58-3.52 (m, 4H), 3.40-3.21 (m, 4H), 3.16-3.09 (m, 6H), 2.43 (s, 3H), 2.29 (s, 3H), 2.25 (s, 3H), 2.24 (s, 3H), 2.20-2.13 (m, 2H).
MH+514 (−2HCl).

Example 174

N-(3-(4-(3-chloro-2-methylphenyl)piperazin-1-yl)propyl)-2,5-dimethyl-1-(2-(trifluoromethyl)phenyl)-1H-imidazole-4-carboxamide dihydrochloride $^1$H NMR (400 MHz, MeOH-d$_4$) δ 8.11 (d, J=3.2 Hz, 1H), 8.01-7.97 (m, 2H), 7.76 (d, J=4.0 Hz, 1H), 7.17 (d, J=4.4 Hz, 2H), 7.09-7.06 (m, 1H), 3.72-3.65 (m, 3H), 3.64 (s, 3H), 3.61-3.54 (m, 3H), 3.40-3.26 (m, 4H), 3.17-3.09 (m, 2H), 2.41 (s, 3H), 2.37 (s, 3H), 2.28 (s, 3H), 2.18-2.14 (m, 2H).
MH+534 (−2HCl).

Example 175

N-(3-(4-(2,3-dichlorophenyl)piperazin-1-yl)propyl)-2,5-dimethyl-1-(2-(trifluoromethyl)phenyl)-1H-imidazole-4-carboxamide dihydrochloride $^1$H NMR (400 MHz, MeOH-d$_4$) δ 8.12 (d, J=6.3 Hz, 1H), 8.08-7.96 (m, 2H), 7.78 (d, J=7.3 Hz, 1H), 7.31-7.25 (m, 2H), 7.19-7.13 (m, 1H), 3.73-3.65 (m, 3H), 3.66 (s, 3H), 3.62-3.54 (m, 3H), 3.41-3.26 (m, 4H), 3.17-3.09 (m, 2H), 2.41 (s, 3H), 2.28 (s, 3H), 2.18-2.14 (m, 2H).
MH+534 (−2HCl).

Example 176

N-(3-(4-(3-chloro-2-methylphenyl)piperazin-1-yl)-2-hydroxypropyl)-2,5-dimethyl-1-(2-(trifluoromethyl)phenyl)-1H-imidazole-4-carboxamide dihydrochloride $^1$H NMR (400 MHz, MeOH-d$_4$) δ 8.11 (d, J=6.4 Hz, 1H), 8.07-7.95 (m, 2H), 7.77 (d, J=7.2 Hz, 1H), 7.31-7.26 (m, 2H), 7.19-7.10 (m, 1H), 4.37-4.32 (m, 1H), 3.74-3.67 (m, 3H), 3.65 (s, 3H), 3.61-3.54 (m, 3H), 3.40-3.26 (m, 4H), 3.17-3.09 (m, 2H), 2.42 (s, 3H), 2.30 (s, 3H).
MH+550 (−2HCl).

Example 177

N-(3-(4-(2,3-dichlorophenyl)piperazin-1-yl)-2-hydroxypropyl)-2,5-dimethyl-1-(2-(trifluoromethyl)phenyl)-1H-imidazole-4-carboxamide dihydrochloride $^1$H NMR (400 MHz, MeOH-d$_4$) δ 8.12 (d, J=7.2 Hz, 1H), 8.08-7.95 (m, 2H), 7.79-7.77 (m, 1H), 7.16 (d, J=4.0 Hz, 1H), 7.10-7.01 (m, 1H), 4.35-4.32 (m, 1H), 3.74-3.67 (m, 3H), 3.65 (s, 3H), 3.61-3.54 (m, 3H), 3.40-3.26 (m, 4H), 3.17-3.09 (m, 2H), 2.43 (s, 3H).
MH+570 (−2HCl).

Example 178

N-(3-(4-(3-chloro-2-methylphenyl)piperazin-1-yl)-2-hydroxypropyl)-1-(4-methoxyphenyl)-5-methyl-2-propyl-1H-imidazole-4-carboxamide dihydrochloride $^1$H NMR (400 MHz, DMSO-d$_6$) δ 10.35 (br s, 1H), 8.81 (br s, 1H), 7.45 (d, J=8.4 Hz, 2H), 7.20-7.14 (m, 4H), 7.01 (dd, J=6.8, 2.4 Hz, 1H), 4.23-4.21 (m, 1H), 3.82 (s, 3H), 3.63-3.52 (m, 2H), 3.41-3.28 (m, 6H), 3.19-3.06 (m, 4H), 2.58 (t, J=7.6 Hz, 2H), 2.26 (s, 3H), 2.23 (s, 3H), 1.60-1.53 (m, 2H), 0.75 (t, J=7.2 Hz, 3H).
MH+540.

Example 179

N-(3-(4-(3-chloro-2-methylphenyl)piperazin-1-yl)-2-hydroxypropyl)-1-(2-methoxyphenyl)-2,5-dimethyl-1H-imidazole-4-carboxamide dihydrochloride $^1$H NMR (400 MHz, DMSO-d$_6$) δ 10.34 (br s, 1H), 8.62 (br s, 1H), 7.61 (t, J=8.0 Hz, 1H), 7.60 (d, J=7.6 Hz, 1H), 7.34 (d, J=8.8 Hz, 1H), 7.20-7.15 (m, 3H), 7.02 (dd, J=8.0, 2.4 Hz, 1H), 4.22-4.20 (m, 1H), 3.78 (s, 3H), 3.63-3.52 (m, 2H), 3.41-3.28 (m, 5H), 3.19-3.06 (m, 5H), 2.26 (s, 3H), 2.25 (s, 3H), 2.18 (s, 3H), 1.54-1.48 (m, 2H), 0.75 (t, J=7.6 Hz, 3H).
MH+512.

Example 180

N-(3-(4-(3-chloro-2-methylphenyl)piperazin-1-yl)-2-hydroxypropyl)-1-(4-chlorophenyl)-2-propyl-1H-imidazole-4-carboxamide dihydrochloride $^1$H NMR (400 MHz, DMSO-d$_6$) δ 10.38 (br s, 1H), 8.31 (br s, 1H), 7.71 (d, J=6.8 Hz, 2H), 7.63 (d, J=6.8 Hz, 2H), 7.22-7.18 (m, 2H), 7.04 (d, J=5.6 Hz, 1H), 4.26-4.24 (m, 1H), 3.65-3.62 (m, 1H), 3.56-3.53 (m, 1H), 3.39-3.71 (m, 2H), 3.32-3.27 (m, 2H), 3.20-3.09 (m, 6H), 2.71 (t, J=6.0 Hz, 2H), 2.29 (s, 3H), 1.61-1.53 (m, 2H), 0.80 (t, J=6.0 Hz, 3H).
MH+530.

Example 181

N-(3-(4-(3-chloro-2-methylphenyl)piperazin-1-yl)propyl)-1-(4-chlorophenyl)-2-propyl-1H-imidazole-4-carboxamide dihydrochloride $^1$H NMR (400 MHz, DMSO-d$_6$) δ 10.98 (br s, 1H), 8.29 (br s, 1H), 7.71 (d, J=6.8 Hz, 2H), 7.64 (d, J=7.2 Hz, 2H), 7.20-7.19 (m, 2H), 7.04 (d, J=5.6 Hz, 1H), 3.54-3.51 (m, 2H), 3.42-3.38 (m, 2H), 3.28-3.15 (m, 8H), 2.75-2.73 (m, 2H), 2.30 (s, 3H), 2.05-2.01 (m, 2H), 1.59-1.53 (m, 2H), 0.80 (t, J=5.6 Hz, 3H).
MH+514.

Example 182

N-(3-(4-(3-chloro-2-methylphenyl)piperazin-1-yl)-2-hydroxypropyl)-1-(2,3-dihydrobenzo[b][1,4]dioxin-6-yl)-2,5-dimethyl-1H-imidazole-4-carboxamide dihydrochloride $^1$H NMR (400 MHz, DMSO-d$_6$) δ 10.61 (br s, 1H), 8.76 (br s, 1H), 7.20-7.13 (m, 3H), 7.09 (d, J=8.4 Hz, 1H), 7.03-6.97 (m, 2H), 4.30 (s, 4H), 4.26-4.22 (m, 1H), 3.65-3.62 (m, 1H), 3.54-3.51 (m, 1H), 3.42-3.27 (m, 6H), 3.20-3.09 (m, 4H), 2.34 (s, 3H), 2.27 (s, 3H), 2.26 (s, 3H).
MH+540.

Example 183

N-(3-(4-(3-chloro-2-methylphenyl)piperazin-1-yl)propyl)-1-(2,3-dihydrobenzo[b][1,4]dioxin-6-yl)-2,5-dimethyl-1H-imidazole-4-carboxamide dihydrochloride $^1$H NMR (400 MHz, DMSO-d$_6$) δ 11.26 (br s, 1H), 8.92 (br s, 1H), 7.20-7.14 (m, 3H), 7.09 (d, J=8.8 Hz, 1H), 7.03-6.98 (m, 2H), 4.30 (s, 4H), 3.51-3.48 (m, 2H), 3.39-3.34 (m, 2H), 3.26-3.20 (m, 4H), 3.18-3.12 (m, 4H), 2.33 (s, 3H), 2.27 (s, 3H), 2.26 (s, 3H), 2.06-1.99 (m, 2H).
MH+524.

Example 184

1-(2,3-dihydrobenzo[b][1,4]dioxin-6-yl)-N-(3-(4-(2,3-dimethylphenyl)piperazin-1-yl)propyl)-5-methyl-2-propyl-1H-imidazole-4-carboxamide dihydrochloride $^1$H NMR (400 MHz, DMSO-d$_6$) δ 11.19 (br s, 1H), 9.23 (br s, 1H), 7.20 (d, J=2.4 Hz, 1H), 7.09 (d, J=8.4 Hz, 1H), 7.06-7.01 (m, 2H), 6.90-6.85 (m, 2H), 4.30 (s, 4H), 3.50-3.47 (m, 2H), 3.39-3.35 (m, 2H), 3.27-3.17 (m, 4H), 3.14-3.05 (m, 4H), 2.66-2.62 (m, 2H), 2.25 (s, 3H), 2.18 (s, 3H), 2.13 (s, 3H), 2.07-2.04 (m, 2H), 1.68-1.58 (m, 2H), 0.79 (t, J=7.2 Hz, 3H).
MH+532.

Example 185

N-(3-(4-(2,3-dichlorophenyl)piperazin-1-yl)propyl)-1-(2,3-dihydrobenzo[b][1,4]dioxin-6-yl)-5-methyl-2-propyl-1H-imidazole-4-carboxamide dihydrochloride $^1$H NMR (400 MHz, DMSO-$d_6$) δ 11.21 (br s, 1H), 9.04 (br s, 1H), 7.36-7.30 (m, 2H), 7.18 (d, J=2.4 Hz, 1H), 7.17-7.07 (m, 1H), 7.00 (d, J=2.4 Hz, 1H), 6.98 (d, J=2.4 Hz, 1H), 4.30 (s, 4H), 3.55-3.53 (m, 2H), 3.41-3.33 (m, 4H), 3.24-3.12 (m, 6H), 2.61 (t, J=7.2 Hz, 2H), 2.24 (s, 3H), 2.05-1.98 (m, 2H), 1.66-1.56 (m, 2H), 0.79 (t, J=7.2 Hz, 3H).
MH+572.

Example 186

N-(3-(4-(3-chloro-2-methylphenyl)piperazin-1-yl)propyl)-5-methyl-1-phenyl-2-propyl-1H-imidazole-4-carboxamide dihydrochloride $^1$H NMR (400 MHz, DMSO-$d_6$) δ 11.08 (br s, 1H), 9.01 (br s, 1H), 7.66-7.62 (m, 3H), 7.56-7.53 (m, 2H), 7.20-7.15 (m, 2H), 7.03-7.01 (m, 1H), 3.52-3.49 (m, 2H), 3.40-3.34 (m, 2H), 3.24-3.22 (m, 4H), 3.19-3.12 (m, 4H), 2.59 (t, J=7.2 Hz, 2H), 2.27 (s, 3H), 2.24 (s, 3H), 2.06-1.99 (m, 2H), 1.62-1.53 (m, 2H), 0.77 (t, J=7.6 Hz, 3H).
MH+494.

Example 187

N-(3-(4-(3-chloro-2-methylphenyl)piperazin-1-yl)-2-hydroxypropyl)-5-methyl-1-phenyl-2-propyl-1H-imidazole-4-carboxamide dihydrochloride $^1$H NMR (400 MHz, DMSO-$d_6$) δ 10.47 (br s, 1H), 8.82 (br s, 1H), 7.65-7.62 (m, 3H), 7.55-7.52 (m, 2H), 7.20-7.14 (m, 2H), 7.03-7.01 (m, 1H), 4.25-4.23 (m, 1H), 3.65-3.61 (m, 1H), 3.55-3.52 (m, 1H), 3.42-3.27 (m, 6H), 3.19-3.08 (m, 4H), 2.59 (t, J=7.2 Hz, 2H), 2.27 (s, 3H), 2.24 (s, 3H), 1.62-1.52 (m, 2H), 0.77 (t, J=7.2 Hz, 3H).
MH+510.

Example 188

N-(3-(4-(3-chloro-2-methylphenyl)piperazin-1-yl)propyl)-1-(2,3-dihydrobenzo[b][1,4]dioxin-6-yl)-5-methyl-2-propyl-1H-imidazole-4-carboxamide dihydrochloride $^1$H NMR (400 MHz, DMSO-$d_6$) δ 11.10 (br s, 1H), 9.08 (br s, 1H), 7.20-7.14 (m, 3H), 7.08 (d, J=8.8 Hz, 1H), 7.03-6.98 (m, 2H), 4.30 (s, 4H), 3.52-3.48 (m, 2H), 3.39-3.34 (m, 2H), 3.23-3.18 (m, 4H), 3.15-3.12 (m, 4H), 2.62 (t, J=6.4 Hz, 2H), 2.27 (s, 3H), 2.24 (s, 3H), 2.06-1.99 (m, 2H), 1.66-1.57 (m, 2H), 0.79 (t, J=7.2 Hz, 3H).
MH+552.

Example 189

N-(3-(4-(3-chloro-2-methylphenyl)piperazin-1-yl)-2-hydroxypropyl)-1-(2,3-dihydrobenzo[b][1,4]dioxin-6-yl)-5-methyl-2-propyl-1H-imidazole-4-carboxamide dihydrochloride $^1$H NMR (400 MHz, DMSO-$d_6$) δ 10.48 (br s, 1H), 8.87 (br s, 1H), 7.20-7.15 (m, 3H), 7.08 (d, J=8.4 Hz, 1H), 7.03-6.97 (m, 2H), 4.30 (s, 4H), 4.26-4.23 (m, 1H), 3.64-3.61 (m, 1H), 3.54-3.51 (m, 1H), 3.42-3.26 (m, 6H), 3.19-3.08 (m, 4H), 2.61 (t, J=7.2 Hz, 2H), 2.26 (s, 3H), 2.24 (s, 3H), 1.65-1.56 (m, 2H), 0.79 (t, J=7.2 Hz, 3H).
MH+568.

Example 190

1-(2,3-dihydrobenzo[b][1,4]dioxin-6-yl)-N-(3-(4-(2,3-dimethylphenyl)piperazin-1-yl)-2-hydroxypropyl)-5-methyl-2-propyl-1H-imidazole-4-carboxamide dihydrochloride $^1$H NMR (400 MHz, DMSO-$d_6$) δ 10.47 (br s, 1H), 8.99 (br s, 1H), 7.18 (d, J=2.4 Hz, 1H), 7.09 (d, J=8.4 Hz, 1H), 7.06-6.99 (m, 2H), 6.90-6.85 (m, 2H), 4.30 (s, 4H), 4.30-4.21 (m, 1H), 3.64-3.61 (m, 1H), 3.54-2.51 (m, 1H), 3.45-3.26 (m, 4H), 3.20-3.08 (m, 6H), 2.64 (t, J=6.4 Hz, 2H), 2.25 (s, 3H), 2.18 (s, 3H), 2.12 (s, 3H), 1.67-1.57 (m, 2H), 0.79 (t, J=7.2 Hz, 3H).
MH+548.

Example 191

N-(3-(4-(2,3-dichlorophenyl)piperazin-1-yl)-2-hydroxypropyl)-1-(2,3-dihydrobenzo[b][1,4]dioxin-6-yl)-5-methyl-2-propyl-1H-imidazole-4-carboxamide dihydrochloride $^1$H NMR (400 MHz, DMSO-$d_6$) δ 10.58 (br s, 1H), 8.84 (br s, 1H), 7.36-7.29 (m, 2H), 7.20-7.14 (m, 2H), 7.08 (d, J=8.4 Hz, 1H), 6.98 (dd, J=8.4, 2.4 Hz, 1H), 4.30 (s, 4H), 4.24-4.22 (m, 1H), 3.67-3.65 (m, 1H), 3.58-3.55 (m, 1H), 3.42-3.32 (m, 4H), 3.22-3.12 (m, 6H), 2.60 (t, J=7.2 Hz, 2H), 2.24 (s, 3H), 1.65-1.55 (m, 2H), 0.79 (t, J=7.2 Hz, 3H).
MH+588.

Example 192

N-(3-(4-(2,3-dimethylphenyl)piperazin-1-yl)propyl)-1-(4-fluorophenyl)-5-methyl-2-propyl-1H-imidazole-4-carboxamide dihydrochloride $^1$H NMR (400 MHz, DMSO-$d_6$) δ 11.25 (s, 1H), 9.05 (s, 1H), 7.95-7.81 (m, 2H), 7.77-7.61 (m, 2H), 7.39-7.27 (m, 2H), 7.25-7.13 (m, 1H), 3.76-3.66 (m, 2H), 3.65-3.51 (m, 2H), 3.49-3.31 (m, 4H), 2.91-2.63 (m, 6H), 2.43 (s, 3H), 2.31 (quartet, J=3.2 Hz, 2H), 2.22 (s, 3H), 1.58 (sextet, J=2.0 Hz, 2H), 0.85 (t, J=2.0 Hz, 3H).
MH+492.

Example 193

N-(3-(4-(2,3-dichlorophenyl)piperazin-1-yl)propyl)-1-(4-fluorophenyl)-5-methyl-2-propyl-1H-imidazole-4-carboxamide dihydrochloride $^1$H NMR (400 MHz, DMSO-$d_6$) δ 11.21 (s, 1H), 9.01 (s, 1H), 7.95-7.81 (m, 2H), 7.77-7.61 (m, 2H), 7.39-7.27 (m, 2H), 7.25-7.13 (m, 1H), 3.80-3.69 (m, 2H), 3.55-3.41 (m, 4H), 2.96-2.65 (m, 8H), 2.62 (quartet, J=8.0 Hz, 2H), 2.32 (s, 3H), 1.55 (sextet, J=8.0 Hz, 2H), 0.80 (t, J=7.6 Hz, 3H).
MH+532.

Example 194

N-(3-(4-(2,3-dimethylphenyl)piperazin-1-yl)-2-hydroxypropyl)-1-(4-fluorophenyl)-5-methyl-2-propyl-1H-imidazole-4-carboxamide dihydrochloride $^1$H NMR (400 MHz, DMSO-$d_6$) δ 10.48 (s, 1H), 8.84 (s, 1H), 7.72-7.61 (m, 2H), 7.59-7.48 (m, 2H), 7.07 (t, J=8.0 Hz, 1H), 6.92 (t, J=9.2 Hz, 2H), 4.34-4.23 (m, 1H), 3.69-3.62 (m, 1H), 3.60-3.52 (m, 1H), 3.48-3.25 (m, 6H), 3.23-3.05 (m, 6H), 2.62 (t, J=7.6 Hz, 2H), 2.27 (s, 3H), 2.22 (s, 3H), 2.17 (s, 3H), 1.62 (sextet, J=7.6 Hz, 2H), 0.81 (t, J=7.2 Hz, 3H). MH+508.

Example 195

N-(3-(4-(2,3-dichlorophenyl)piperazin-1-yl)-2-hydroxypropyl)-1-(4-fluorophenyl)-5-methyl-2-propyl-1H-imidazole-4-carboxamide dihydrochloride $^1$H NMR (400 MHz, DMSO-$d_6$) δ 10.50 (s, 1H), 8.87 (s, 1H), 7.74-7.60 (m, 2H), 7.55-7.45 (m, 2H), 7.15-6.99 (m, 1H), 6.91-6.81 (m, 2H), 4.30-4.21 (m, 1H), 3.75-3.62 (m, 1H), 3.60-3.55 (m, 1H), 3.50-3.27 (m, 6H), 3.25-3.10 (m, 6H), 2.55 (t, J=7.6 Hz, 2H), 2.31 (s, 3H), 1.62 (sextet, J=7.6 Hz, 2H), 0.91 (t, J=7.2 Hz, 3H). MH+548.

Example 196

N-(3-(4-(3-chloro-2-methylphenyl)piperazin-1-yl)propyl)-1-(4-fluorophenyl)-2,5-dimethyl-1H-imidazole-4-carboxamide dihydrochloride $^1$H NMR (400 MHz, DMSO-$d_6$) δ 11.32 (s, 1H), 9.01 (s, 1H), 7.87-7.78 (m, 2H), 7.75-7.65 (m, 2H), 7.41-7.32 (m, 2H), 7.25-7.17 (m, 1H), 3.76-3.66 (m, 2H), 3.62-3.52 (m, 2H), 3.47-3.29 (m, 6H), 2.66 (quartet, J=2.0 Hz, 4H), 2.47 (s, 3H), 2.43 (s, 3H), 2.27-2.16 (m, 2H). MH+484.

Example 197

N-(3-(4-(3-chloro-2-methylphenyl)piperazin-1-yl)propyl)-1-(4-fluorophenyl)-5-methyl-2-propyl-1H-imidazole-4-carboxamide dihydrochloride $^1$H NMR (400 MHz, DMSO-$d_6$) δ 10.50 (s, 1H), 8.85 (s, 1H), 7.91-7.81 (m, 2H), 7.77-7.60 (m, 2H), 7.41-7.27 (m, 2H), 7.25-7.11 (m, 1H), 3.77-3.61 (m, 2H), 3.58-3.47 (m, 2H), 3.45-3.31 (m, 4H), 2.90-2.67 (m, 6H), 2.36 (s, 3H), 2.31 (s, 3H). MH+512.

Example 198

N-(3-(4-(2,3-dichlorophenyl)piperazin-1-yl)-2-hydroxypropyl)-1-(2-fluorophenyl)-2,5-dimethyl-1H-imidazole-4-carboxamide dihydrochloride $^1$H NMR (400 MHz, DMSO-$d_6$) δ 10.34 (s, 1H), 8.31 (s, 1H), 7.70-7.55 (m, 3H), 7.45 (t, J=7.6 Hz, 1H), 7.36-7.30 (m, 2H), 7.17 (dd, J=7.2, 2.4 Hz, 1H), 4.21-4.19 (m, 1H), 3.35-3.55 (m, 2H), 3.42-3.10 (m, 10H), 2.23 (s, 3H), 2.20 (s, 3H). MH+520.

Example 199

1-(2-chlorophenyl)-N-(3-(4-(2,3-dimethylphenyl)piperazin-1-yl)-2-hydroxypropyl)-5-methyl-2-propyl-1H-imidazole-4-carboxamide dihydrochloride $^1$H NMR (400 MHz, DMSO-$d_6$) δ 10.23 (s, 1H), 8.43 (s, 1H), 7.82-7.80 (m, 1H), 7.68-7.59 (m, 3H), 7.04 (t, J=7.6 Hz, 1H), 6.91-6.86 (m, 2H), 4.23-4.21 (m, 1H), 3.62-3.52 (m, 2H), 3.36-3.25 (m, 6H), 3.17-3.04 (m, 4H), 2.44-2.41 (m, 2H), 2.18 (s, 6H), 2.13 (s, 3H), 1.57-1.51 (m, 2H), 0.79 (t, J=7.2 Hz, 3H). MH+524.

Example 200

1-(2-chlorophenyl)-N-(3-(4-(2,3-dimethylphenyl)piperazin-1-yl)propyl)-5-methyl-2-propyl-1H-imidazole-4-carboxamide dihydrochloride $^1$H NMR (400 MHz, DMSO-$d_6$) δ 11.04 (s, 1H), 8.85 (s, 1H), 7.83 (dd, J=8.0, 1.2 Hz, 1H), 7.75-7.62 (m, 3H), 7.04 (t, J=7.6 Hz, 1H), 6.91-6.86 (m, 2H), 3.52-3.49 (m, 2H), 3.36 (q, J=6.4 Hz, 2H), 3.23-3.13 (m, 4H), 3.10-3.08 (m, 4H), 2.53-2.50 (m, 2H), 2.19 (s, 3H), 2.18 (s, 3H), 2.13 (s, 3H), 2.06-2.01 (m, 2H), 1.61-1.55 (m, 2H), 0.79 (t, J=7.2 Hz, 3H). MH+508.

Example 201

(R)—N-(3-(4-(3-chloro-2-methylphenyl)piperazin-1-yl)-2-hydroxypropyl)-1-(4-fluorophenyl)-5-methyl-2-phenyl-1H-imidazole-4-carboxamide dihydrochloride $^1$H NMR (400 MHz, DMSO-$d_6$) δ 10.43 (s, 1H), 8.39 (s, 1H), 7.48-7.45 (m, 2H), 7.40-7.27 (m, 7H), 7.20-7.14 (m, 2H), 7.01 (dd, J=7.2, 2.4 Hz, 1H), 4.25-4.23 (m, 1H), 3.63-3.52 (m, 2H), 3.40-3.37 (m, 2H), 3.33-3.13 (m, 5H), 3.10-3.08 (m, 5H), 2.31 (s, 3H), 2.26 (s, 3H). MH+562.

Example 202

(R)-1-(4-chlorophenyl)-N-(3-(4-(2,3-dichlorophenyl)piperazin-1-yl)-2-hydroxypropyl)-2-propyl-1H-imidazole-4-carboxamide dihydrochloride $^1$H NMR (400 MHz, DMSO-$d_6$) δ 10.52 (s, 1H), 8.94 (s, 1H), 8.35 (s, 1H), 7.69 (d, J=6.8 Hz, 2H), 7.62 (d, J=8.4 Hz, 2H), 7.36-7.30 (m, 2H), 7.16 (dd, J=6.8, 2.8 Hz, 1H), 4.24-4.22 (m, 1H), 3.66-3.54 (m, 2H), 3.42-3.34 (m, 5H), 3.29-3.11 (m, 5H), 2.70 (t, J=7.6 Hz, 2H), 1.59-1.49 (m, 2H), 0.77 (t, J=7.6 Hz, 3H). MH+550.

Example 203

N-(3-(4-(3-chloro-2-methylphenyl)piperazin-1-yl)propyl)-1-(2-chlorophenyl)-2,5-dimethyl-1H-imidazole-4-carboxamide dihydrochloride $^1$H NMR (400 MHz, DMSO-$d_6$) δ 10.95 (s, 1H), 8.57 (s, 1H), 7.81 (d, J=7.6 Hz, 1H), 7.69-7.60 (m, 3H), 7.20-7.12 (m, 2H), 7.01 (dd, J=6.8, 2.4 Hz, 1H), 3.52-3.50 (m, 2H), 3.36-3.32 (m, 2H), 3.21-3.02 (m, 8H), 2.27 (s, 3H), 2.19 (s, 3H), 2.18 (s, 3H), 2.04-1.96 (m, 2H). MH+500.

Example 204

N-(3-(4-(3-chloro-2-methylphenyl)piperazin-1-yl)-2-hydroxypropyl)-1-(2-fluorophenyl)-2,5-dimethyl-1H-imidazole-4-carboxamide dihydrochloride $^1$H NMR (400 MHz, DMSO-d$_6$) δ 10.38 (s, 1H), 8.44 (s, 1H), 7.81-7.76 (m, 1H), 7.73-7.59 (m, 2H), 7.54-7.48 (m, 1H), 7.23-7.18 (m, 2H), 7.04 (d, J=6.0 Hz, 1H), 4.25-4.24 (m, 1H), 3.66-3.51 (m, 2H), 3.43-3.31 (m, 5H), 3.24-3.01 (m, 5H), 2.29 (s, 3H), 2.27 (s, 6H).
MH+500.

Example 205

N-(3-(4-(3-chloro-2-methylphenyl)piperazin-1-yl)-2-hydroxypropyl)-1-(4-methoxyphenyl)-2,5-dimethyl-1H-imidazole-4-carboxamide dihydrochloride $^1$H NMR (400 MHz, DMSO-d$_6$) δ 10.05 (br s, 1H), 8.40 (br s, 1H), 7.41 (d, J=8.8 Hz, 2H), 7.24-7.15 (m, 3H), 7.05 (dd, J=2.8, 2.0 Hz, 1H), 4.22-4.20 (m, 1H), 3.85 (s, 3H), 3.61-3.55 (m, 2H), 3.40-3.30 (m, 4H), 3.19-3.08 (m, 6H), 2.30 (s, 3H), 2.26 (s, 3H), 2.24 (s, 3H).
MH+512.

Example 206

N-(3-(4-(2,3-dimethylphenyl)piperazin-1-yl)propyl)-1-(4-methoxyphenyl)-5-methyl-2-phenyl-1H-imidazole-4-carboxamide dihydrochloride $^1$H NMR (400 MHz, DMSO-d$_6$) δ 10.98 (br s, 1H), 8.76 (br s, 1H), 7.39-7.29 (m, 7H), 7.05-7.01 (m, 3H), 6.90-6.82 (m, 2H), 3.77 (s, 3H), 3.51-3.48 (m, 2H), 3.37-3.36 (m, 2H), 3.18-3.07 (m, 8H), 2.29 (s, 3H), 2.17 (s, 3H), 2.12 (s, 3H), 1.96-1.86 (m, 2H).
MH+512.

Example 207

N-(3-(4-(3-chloro-2-methylphenyl)piperazin-1-yl)propyl)-1-(4-methoxyphenyl)-5-methyl-2-phenyl-1H-imidazole-4-carboxamide dihydrochloride $^1$H NMR (400 MHz, DMSO-d$_6$) δ 10.85 (br s, 1H), 8.58 (br s, 1H), 7.37-7.27 (m, 7H), 7.18-7.11 (m, 2H), 7.06-7.00 (m, 3H), 3.77 (s, 3H), 3.52-3.20 (m, 2H), 3.38-3.37 (m, 2H), 3.18-3.07 (m, 8H), 2.29 (s, 3H), 2.26 (s, 3H), 2.02-1.98 (m, 2H).
MH+558.

Example 208

N-(3-(4-(2,3-dichlorophenyl)piperazin-1-yl)propyl)-1-(4-methoxyphenyl)-5-methyl-2-phenyl-1H-imidazole-4-carboxamide dihydrochloride $^1$H NMR (400 MHz, DMSO-d$_6$) δ 11.19 (br s, 1H), 8.65 (br s, 1H), 7.38-7.27 (m, 9H), 7.18-7.15 (m, 1H), 7.06-7.02 (m, 2H), 3.77 (s, 3H), 3.59-3.54 (m, 2H), 3.40-3.34 (m, 4H), 3.24-3.12 (m, 6H), 2.29 (s, 3H), 2.04-1.97 (m, 2H).
MH+578.

Example 209

N-(3-(4-(2,3-dimethylphenyl)piperazin-1-yl)-2-hydroxypropyl)-1-(4-methoxyphenyl)-5-methyl-2-phenyl-1H-imidazole-4-carboxamide dihydrochloride $^1$H NMR (400 MHz, DMSO-d$_6$) δ 10.40 (br s, 1H), 8.60 (br s, 1H), 7.45-7.29 (m, 7H), 7.09-7.01 (m, 3H), 6.90-6.85 (m, 2H), 4.26-4.24 (m, 1H), 3.77 (s, 3H), 3.62-3.51 (m, 2H), 3.40-3.27 (m, 5H), 3.17-3.02 (m, 5H), 2.30 (s, 3H), 2.17 (s, 3H), 2.12 (s, 3H).
MH+554.

Example 210

N-(3-(4-(3-chloro-2-methylphenyl)piperazin-1-yl)-2-hydroxypropyl)-1-(4-methoxyphenyl)-5-methyl-2-phenyl-1H-imidazole-4-carboxamide dihydrochloride $^1$H NMR (400 MHz, DMSO-d$_6$) δ 10.37 (br s, 1H), 8.45 (br s, 1H), 7.37-7.27 (m, 7H), 7.19-7.10 (m, 2H), 7.05-6.98 (m, 3H), 4.24-4.23 (m, 1H), 3.77 (s, 3H), 3.63-3.52 (m, 2H), 3.39-3.27 (m, 5H), 3.14-3.07 (m, 5H), 2.29 (s, 3H), 2.26 (s, 3H).
MH+574.

Example 211

N-(3-(4-(2,3-dichlorophenyl)piperazin-1-yl)-2-hydroxypropyl)-1-(4-methoxyphenyl)-5-methyl-2-phenyl-1H-imidazole-4-carboxamide dihydrochloride $^1$H NMR (400 MHz, DMSO-d$_6$) δ 10.51 (br s, 1H), 8.46 (br s, 1H), 7.37-7.27 (m, 9H), 7.19-7.15 (m, 1H), 7.05-7.03 (m, 2H), 4.25-4.23 (m, 1H), 3.77 (s, 3H), 3.66-3.55 (m, 2H), 3.41-3.31 (m, 5H), 3.28-3.10 (m, 5H), 2.32 (s, 3H).
MH+594.

Example 212

1-(2,3-dihydrobenzo[b][1,4]dioxin-6-yl)-N-(3-(4-(2,3-dimethylphenyl)piperazin-1-yl)propyl)-5-methyl-2-phenyl-1H-imidazole-4-carboxamide dihydrochloride $^1$H NMR (400 MHz, DMSO-d$_6$) δ 11.02 (br s, 1H), 8.81 (br s, 1H), 7.44-7.41 (m, 2H), 7.40-7.31 (m, 3H), 7.05-7.01 (m, 2H), 6.97 (d, J=8.8 Hz, 1H), 6.90-6.85 (m, 3H), 4.27-4.24 (m, 4H), 3.51-3.48 (m, 2H), 3.39-3.35 (m, 2H), 3.19-3.13 (m, 4H), 3.10-3.05 (m, 4H), 2.31 (s, 3H), 2.17 (s, 3H), 2.13 (s, 3H), 2.04-2.00 (m, 2H).
MH+566.

Example 213

N-(3-(4-(3-chloro-2-methylphenyl)piperazin-1-yl)propyl)-1-(2,3-dihydrobenzo[b][1,4]dioxin-6-yl)-5-methyl-2-phenyl-1H-imidazole-4-carboxamide dihydrochloride $^1$H NMR (400 MHz, DMSO-d$_6$) δ 11.09 (br s, 1H), 8.74 (br s, 1H), 7.43-7.38 (m, 2H), 7.37-7.31 (m, 3H), 7.20-7.14 (m, 2H), 7.02-6.96 (m, 3H), 6.87-6.84 (m, 1H), 4.27-4.24 (m, 4H), 3.52-3.49 (m, 2H), 3.39-3.34 (m, 2H), 3.21-3.17 (m, 4H), 3.15-3.12 (m, 4H), 2.30 (s, 3H), 2.26 (s, 3H), 2.05-1.98 (m, 2H).
MH+586.

Example 214

N-(3-(4-(2,3-dichlorophenyl)piperazin-1-yl)propyl)-1-(2,3-dihydrobenzo[b][1,4]dioxin-6-yl)-5-methyl-2-phenyl-1H-imidazole-4-carboxamide dihydrochloride $^1$H NMR (400 MHz, DMSO-d$_6$) δ 11.10 (br s, 1H), 8.65 (br s, 1H), 7.4 (d, J=7.2 Hz, 2H), 7.38-7.29 (m, 5H), 7.17 (dd, J=7.2, 2.4 Hz, 1H), 7.00-6.99 (m, 1H), 6.97 (d, J=8.4 Hz, 1H), 6.83 (dd, J=8.4, 2.4 Hz, 1H), 4.27-4.24 (m, 4H), 3.56-3.53 (m, 2H), 3.40-3.33 (m, 4H), 3.24-3.12 (m, 6H), 2.30 (s, 3H), 2.02-1.99 (m, 2H).
MH+606.

Example 215

1-(2,3-dihydrobenzo[b][1,4]dioxin-6-yl)-N-(3-(4-(2,3-dimethylphenyl)piperazin-1-yl)-2-hydroxypropyl)-5-methyl-2-phenyl-1H-imidazole-4-carboxamide dihydrochloride $^1$H NMR (400 MHz, DMSO-d$_6$) δ 10.44 (br s, 1H), 8.65 (br s, 1H), 7.44-7.41 (m, 2H), 7.40-7.32 (m, 3H), 7.05-7.01 (m, 2H), 6.98 (d, J=8.8 Hz, 1H), 6.90-6.85 (m, 3H), 4.27-4.24 (m, 5H), 3.63-3.60 (m, 1H), 3.54-3.51 (m, 1H), 3.40-3.17 (m, 2H), 3.34-3.27 (m, 2H), 3.17-3.03 (m, 6H), 2.31 (s, 3H), 2.17 (s, 3H), 2.12 (s, 3H).
MH+582.

Example 216

N-(3-(4-(3-chloro-2-methylphenyl)piperazin-1-yl)-2-hydroxypropyl)-1-(2,3-dihydrobenzo[b][1,4]dioxin-6-yl)-5-methyl-2-phenyl-1H-imidazole-4-carboxamide dihydrochloride $^1$H NMR (400 MHz, DMSO-d$_6$) δ 10.42 (br s, 1H), 8.48 (br s, 1H), 7.41-7.39 (m, 2H), 7.38-7.30 (m, 3H), 7.20-7.13 (m, 2H), 7.04-6.06 (m, 3H), 6.83 (dd, J=8.4, 2.4 Hz, 1H), 4.28-4.24 (m, 5H), 3.63-3.60 (m, 1H), 3.55-3.52 (m, 1H), 3.39-3.36 (m, 2H), 3.32-3.25 (m, 2H), 3.13-3.07 (m, 6H), 2.31 (s, 3H), 2.26 (s, 3H).
MH+602.

Example 217

N-(3-(4-(2,3-dichlorophenyl)piperazin-1-yl)-2-hydroxypropyl)-1-(2,3-dihydrobenzo[b][1,4]dioxin-6-yl)-5-methyl-2-phenyl-1H-imidazole-4-carboxamide dihydrochloride $^1$H NMR (400 MHz, DMSO-d$_6$) δ 10.57 (br s, 1H), 8.51 (br s, 1H), 7.42-7.38 (m, 2H), 7.34-7.29 (m, 5H), 7.17 (dd, J=7.2, 2.4 Hz, 1H), 7.00 (d, J=2.4 Hz, 1H), 6.97 (d, J=8.4 Hz, 1H), 6.84 (dd, J=8.4, 2.4 Hz, 1H), 4.26-4.24 (m, 5H), 3.67-3.64 (m, 1H), 3.58-3.55 (m, 1H), 3.41-3.36 (m, 2H), 3.34-3.25 (m, 2H), 3.23-3.11 (m, 6H), 2.30 (s, 3H).
MH+622.

Example 218

1-(benzo[d][1,3]dioxol-5-yl)-N-(3-(4-(3-chloro-2-methylphenyl)piperazin-1-yl)propyl)-2,5-dimethyl-1H-imidazole-4-carboxamide dihydrochloride $^1$H NMR (400 MHz, DMSO-d$_6$) δ 11.24 (br s, 1H), 8.92 (br s, 1H), 7.25-7.13 (m, 4H), 7.08-7.00 (m, 2H), 6.17 (s, 2H), 3.51-3.48 (m, 2H), 3.39-3.35 (m, 2H), 3.24-3.18 (m, 4H), 3.16-3.12 (m, 4H), 2.35 (s, 3H), 2.27 (s, 6H), 2.06-1.99 (m, 2H).
MH+510.

Example 219

1-(benzo[d][1,3]dioxol-5-yl)-N-(3-(4-(3-chloro-2-methylphenyl)piperazin-1-yl)propyl)-5-methyl-2-propyl-1H-imidazole-4-carboxamide dihydrochloride $^1$H NMR (400 MHz, DMSO-d$_6$) δ 11.24 (br s, 1H), 9.19 (br s, 1H), 7.23 (d, J=2.0 Hz, 1H), 7.20-7.13 (m, 3H), 7.06 (dd, J=8.0, 2.0 Hz, 1H), 7.02 (dd, J=6.8, 2.0 Hz, 1H), 6.17 (s, 2H), 3.51-3.48 (m, 2H), 3.40-3.35 (m, 2H), 3.27-3.22 (m, 4H), 3.22-3.12 (m, 4H), 2.65 (t, J=7.6 Hz, 2H), 2.27 (s, 3H), 2.26 (s, 3H), 2.07-2.00 (m, 2H), 1.68-1.58 (m, 2H), 0.79 (t, J=7.2 Hz, 3H).
MH+538.

Example 220

N-(3-(4-(2,3-dimethylphenyl)piperazin-1-yl)propyl)-2,5-dimethyl-1-o-tolyl-1H-imidazole-4-carboxamide dihydrochloride $^1$H NMR (400 MHz, MeOH-d$_4$) δ 7.62-7.59 (m, 2H), 7.51 (t, J=7.2 Hz, 1H), 7.40 (d, J=3.2 Hz, 1H), 7.06 (t, J=3.6 Hz, 1H), 6.95 (t, J=7.6 Hz, 2H), 4.15-4.14 (m, 1H), 3.72-3.71 (m, 2H), 3.64-3.32 (m, 6H), 3.24-3.18 (m, 4H), 2.41 (s, 3H), 2.28 (s, 3H), 2.25 (s, 3H), 2.24 (s, 3H), 2.10 (s, 3H).
MH+460 (−2HCl).

Example 221

N-(3-(4-(3-chloro-2-methylphenyl)piperazin-1-yl)propyl)-2,5-dimethyl-1-o-tolyl-1H-imidazole-4-carboxamide dihydrochloride $^1$H NMR (400 MHz, MeOH-d$_4$) δ 7.63-7.58 (m, 2H), 7.52 (t, J=7.1 Hz, 1H), 7.40 (d, J=3.3 Hz, 1H), 7.11 (t, J=3.8 Hz, 1H), 6.97 (t, J=7.6 Hz, 2H), 4.17-4.13 (m, 1H), 3.73-3.70 (m, 2H), 3.65-3.32 (m, 6H), 3.23-3.18 (m, 4H), 2.41 (s, 3H), 2.27 (s, 3H), 2.20 (s, 3H), 2.04 (s, 3H).
MH+480 (−2HCl).

Example 222

N-(3-(4-(2,3-dichlorophenyl)piperazin-1-yl)propyl)-2,5-dimethyl-1-o-tolyl-1H-imidazole-4-carboxamide dihydrochloride $^1$H NMR (400 MHz, MeOH-d$_4$) δ 7.61-7.57 (m, 2H), 7.50 (t, J=7.2 Hz, 1H), 7.41 (d, J=3.4 Hz, 1H), 7.10 (t, J=3.7 Hz, 1H), 6.98 (t, J=7.6 Hz, 2H), 4.18-4.13 (m, 1H), 3.75-3.71 (m, 2H), 3.66-3.42 (m, 5H), 3.33-3.18 (m, 5H), 2.43 (s, 3H), 2.19 (s, 3H), 2.11 (s, 3H).
MH+500 (−2HCl).

Example 223

N-(3-(4-(2,3-dimethylphenyl)piperazin-1-yl)-2-hydroxypropyl)-2,5-dimethyl-1-o-tolyl-1H-imidazole-4-carboxamide dihydrochloride $^1$H NMR (400 MHz, MeOH-d$_4$) δ 7.64-7.57 (m, 2H), 7.51 (t, J=7.2 Hz, 1H), 7.41 (d, J=8.0 Hz, 1H), 7.06 (t, J=7.2 Hz, 1H), 6.95 (t, J=7.6 Hz, 2H), 4.15-4.13 (m, 1H), 3.71 (d, J=10.4 Hz, 2H), 3.57-3.54 (m, 2H), 3.46-3.32 (m, 4H), 3.30-3.18 (m, 5H), 2.41 (s, 3H), 2.28 (s, 3H), 2.25 (s, 3H), 2.24 (s, 3H), 2.10 (s, 3H).
MH+476 (−2HCl).

Example 224

N-(3-(4-(3-chloro-2-methylphenyl)piperazin-1-yl)-2-hydroxypropyl)-2,5-dimethyl-1-o-tolyl-1H-imidazole-4-carboxamide dihydrochloride $^1$H NMR (400 MHz, MeOH-d$_4$) δ 7.64-7.57 (m, 2H), 7.51 (t, J=7.2 Hz, 1H), 7.44-7.42 (m, 1H), 7.16 (d, J=4.0 Hz, 2H), 7.08 (t, J=4.4 Hz, 1H), 4.37-4.35 (m, 1H), 3.75-3.73 (m, 2H), 3.67-3.49 (m, 4H), 3.48-3.32 (m, 4H), 3.30-3.11 (m, 4H), 2.42 (s, 3H), 2.37 (s, 3H), 2.29 (s, 3H), 2.10 (s, 3H).
MH+496 (−2HCl).

Example 225

N-(3-(4-(2,3-dichlorophenyl)piperazin-1-yl)-2-hydroxypropyl)-2,5-dimethyl-1-o-tolyl-1H-imidazole-4-carboxamide dihydrochloride $^1$H NMR (400 MHz, MeOH-d$_4$) δ 7.64-7.57 (m, 2H), 7.51 (t, J=7.2 Hz, 1H), 7.40 (d, J=7.2 Hz, 1H), 7.31-7.26 (m, 2H), 7.16 (dd, J=6.8, 3.2 Hz, 1H), 4.38-4.31 (m, 1H), 3.76 (d, J=11.2 Hz, 2H), 3.57-3.33 (m, 6H), 3.24-3.18 (m, 4H), 2.41 (s, 3H), 2.28 (s, 3H), 2.10 (s, 3H).
MH+516 (−2HCl).

Example 226

N-(3-(4-(3-chloro-2-methylphenyl)piperazin-1-yl)propyl)-1-(4-chlorophenyl)-2,5-dimethyl-1H-imidazole-4-carboxamide dihydrochloride $^1$H NMR (400 MHz, MeOH-d$_4$) δ 7.72-7.70 (m, 2H), 7.59-7.57 (m 2H), 7.15-7.14 (m, 2H), 7.08-7.07 (m, 1H), 4.92 (brs, 6H), 3.72-3.70 (m, 2H), 3.59-3.57 (m, 3H), 3.41-3.25 (m, 6H), 2.49 (s, 3H), 2.36 (s, 6H).
MH+500 (−2HCl).

Example 227

1-(4-chlorophenyl)-N-(3-(4-(2,3-dimethylphenyl)piperazin-1-yl)-2-hydroxypropyl)-2,5-dimethyl-1H-imidazole-4-carboxamide dihydrochloride $^1$H NMR (400 MHz, MeOH-d$_4$) δ 7.72 (s, 2H), 7.56 (brs, 2H), 7.06 (t, J=7.6 Hz, 1H), 6.95 (t, J=7.6 Hz, 2H), 4.36 (s, 1H), 3.74-3.63 (m, 2H), 3.60-3.54 (m, 4H), 3.42-3.36 (m, 3H), 3.24-3.15 (m, 3H), 2.48 (s, 3H), 2.36 (s, 3H), 2.25 (s, 6H).
MH+496 (−2HCl).

Example 228

N-(3-(4-(3-chloro-2-methylphenyl)piperazin-1-yl)-2-hydroxypropyl)-1-(4-chlorophenyl)-2,5-dimethyl-1H-imidazole-4-carboxamide dihydrochloride $^1$H NMR (400 MHz, MeOH-d$_4$) δ 7.71 (s, 2H), 7.57 (s, 1H), 7.14-7.13 (m, 2H), 7.08-7.07 (m, 2H), 4.41-4.33 (m, 1H), 3.74-3.70 (m, 2H), 3.67-3.55 (m, 3H), 3.43-3.36 (m, 3H), 3.29 (s, 3H), 3.28-3.15 (m, 5H), 2.48 (brs, 1H), 2.35 (s, 6H).
MH+516 (−2HCl).

Example 229

1-(4-chlorophenyl)-N-(3-(4-(2,3-dichlorophenyl)piperazin-1-yl)-2-hydroxypropyl)-2,5-dimethyl-1H-imidazole-4-carboxamide dihydrochloride $^1$H NMR (400 MHz, MeOH-d$_4$) δ 7.72 (d, J=6.8 Hz, 2H), 7.55 (d, J=6.0 Hz, 2H), 7.30-7.26 (m, 2H), 7.17-7.15 (m, 1H), 4.42-4.33 (m, 1H), 3.77-3.71 (m, 2H), 3.67-3.59 (m, 4H), 3.57-3.37 (m, 4H), 3.43-3.36 (m, 3H), 3.24-3.15 (m, 2H), 2.47 (s, 3H), 2.35 (s, 3H).
MH+536 (−2HCl).

Example 230

1-(4-chlorophenyl)-N-(3-(4-(2,3-dimethylphenyl)piperazin-1-yl)propyl)-5-methyl-2-propyl-1H-imidazole-4-carboxamide dihydrochloride $^1$H NMR (400 MHz, MeOH-d$_4$) δ 7.72 (d, J=5.2 Hz, 2H), 7.56 (m, 2H), 7.06 (t, J=7.6 Hz, 1H), 6.95 (t, J=7.2 Hz, 2H), 3.67-3.65 (m, 2H), 3.59-3.56 (m, 3H), 3.42-3.21 (m, 6H), 3.13-3.10 (m, 2H), 2.75-2.73 (m, 2H), 2.33 (s, 3H), 2.25 (s, 3H), 2.24 (s, 3H), 2.22-2.16 (m, 1H), 0.91 (t, J=6.8 Hz, 3H).
MH+508 (−2HCl).

Example 231

N-(3-(4-(3-chloro-2-methylphenyl)piperazin-1-yl)propyl)-1-(4-chlorophenyl)-5-methyl-2-propyl-1H-imidazole-4-carboxamide dihydrochloride $^1$H NMR (400 MHz, MeOH-d$_4$) δ 7.73 (d, J=6.4 Hz, 2H), 7.56 (d, J=6.8 Hz, 2H), 7.16-7.15 (m, 2H), 7.10-7.06 (m, 1H), 3.75-3.63 (m, 3H), 3.62-3.51 (m, 4H), 3.46-3.36 (m, 5H), 3.30-3.26 (m, 2H), 3.18-3.12 (m, 2H), 2.77 (t, J=6.8 Hz, 2H), 2.37 (s, 3H), 2.25 (s, 3H), 0.91 (t, J=6.8 Hz, 3H).
MH+528 (−2HCl).

Example 232

1-(4-chlorophenyl)-N-(3-(4-(2,3-dichlorophenyl)piperazin-1-yl)propyl)-5-methyl-2-propyl-1H-imidazole-4-carboxamide dihydrochloride $^1$H NMR (400 MHz, MeOH-d$_4$) δ 7.72-7.70 (m, 2H), 7.57 (brs, 2H), 7.30-7.29 (m, 2H), 7.17-7.16 (m, 1H), 3.74-3.73 (m, 3H), 3.62-3.51 (m, 4H), 3.46-3.36 (m, 5H), 3.30-3.28 (m, 2H), 3.18-3.12 (m, 2H), 2.77 (t, J=6.8 Hz, 2H), 2.38 (s, 3H), 0.91 (t, J=6.8 Hz, 3H).
MH+548 (−2HCl).

Example 233

1-(4-chlorophenyl)-N-(3-(4-(2,3-dimethylphenyl)piperazin-1-yl)-2-hydroxypropyl)-5-methyl-2-propyl-1H-imidazole-4-carboxamide dihydrochloride $^1$H NMR (400 MHz, MeOH-d$_4$) δ 7.72 (d, J=8.0 Hz, 2H), 7.56 (d, J=8.4 Hz, 2H), 7.06 (t, J=7.6 Hz, 1H), 6.95 (t, J=9.2 Hz, 2H), 4.36-4.33 (m, 1H), 3.74-3.71 (m, 2H), 3.67-3.64 (m, 1H), 3.61-3.57 (m, 3H), 3.56-3.50 (m, 2H), 3.47-3.37 (m, 3H), 3.25-3.09 (m, 5H), 2.78 (t, J=8.0 Hz, 2H), 2.34 (s, 3H), 2.25 (s, 6H), 1.70-1.65 (m, 2H), 0.91 (t, J=7.2 Hz, 3H).
MH+524 (−2HCl).

Example 234

N-(3-(4-(3-chloro-2-methylphenyl)piperazin-1-yl)-2-hydroxypropyl)-1-(4-chlorophenyl)-5-methyl-2-propyl-1H-imidazole-4-carboxamide dihydrochloride $^1$H NMR (400 MHz, MeOH-d$_4$) δ 7.73 (d, J=8.0 Hz, 2H), 7.57 (d, J=8.4 Hz, H), 7.11 (m, 2H), 6.98 (t, J=7.2 Hz, 1H), 4.38-4.34 (m, 1H), 3.75-3.71 (m, 2H), 3.68-3.60 (m, 1H), 3.64-3.57 (m, 3H), 3.56-3.50 (m, 2H), 3.47-3.37 (m, 3H), 3.24-3.11 (m, 5H), 2.79 (t, J=8.6 Hz, 2H), 2.34 (s, 3H), 2.24 (s, 3H), 1.70-1.65 (m, 2H), 0.92 (t, J=7.6 Hz, 3H).
MH+544 (−2HCl).

Example 235

1-(4-chlorophenyl)-N-(3-(4-(2,3-dichlorophenyl)piperazin-1-yl)-2-hydroxypropyl)-5-methyl-2-propyl-1H-imidazole-4-carboxamide dihydrochloride $^1$H NMR (400 MHz, MeOH-d$_4$) δ 7.72 (d, J=7.6 Hz, 2H), 7.56 (d, J=8.0 Hz, 2H), 7.31-7.26 (m, 2H), 7.19-7.15 (m, 1H), 4.36-4.34 (m, 1H), 3.76 (d, J=10.2 Hz, 2H), 3.66-3.65 (m, 1H), 3.61-3.50 (m, 4H), 3.49-3.37 (m, 6H), 3.25-3.12 (m, 3H), 2.77 (t, J=7.6 Hz, 2H), 2.34 (s, 3H), 1.68-1.65 (m, 2H), 0.91 (t, J=7.2 Hz, 3H).
MH+564 (−2HCl).

Example 236

1-(2-chlorophenyl)-N-(3-(4-(2,3-dichlorophenyl)piperazin-1-yl)-2-hydroxypropyl)-5-methyl-2-propyl-1H-imidazole-4-carboxamide dihydrochloride $^1$H NMR (400 MHz, DMSO-d$_6$) δ 10.29 (s, 1H), 8.25 (s, 1H), 7.66 (d, J=7.6 Hz, 1H), 7.67-7.58 (m, 3H), 7.36-7.32 (m, 2H), 7.18-7.16 (m, 1H), 4.19 (m, 1H), 3.65-3.56 (m, 2H), 3.42-3.28 (m, 4H), 3.24-3.11 (m, 6H), 2.43-2.36 (m, 2H), 2.16 (s, 3H), 1.55-1.47 (m, 2H), 0.79 (t, J=7.2 Hz, 3H).
MH+564.

Example 237

1-(2-chlorophenyl)-N-(3-(4-(2,3-dichlorophenyl)piperazin-1-yl)propyl)-2,5-dimethyl-1H-imidazole-4-carboxamide dihydrochloride $^1$H NMR (400 MHz, DMSO-d$_6$) δ 11.35 (s, 1H), 8.69 (s, 1H), 7.82 (dd, J=8.0, 1.6 Hz, 1H), 7.72-7.61 (m, 3H), 7.35-7.29 (m, 2H), 7.17 (dd, J=6.8, 2.8 Hz, 1H), 4.19 (m, 1H), 3.56-3.53 (m, 2H), 3.41-3.33 (m, 4H), 3.26-3.13 (m, 6H), 2.24 (s, 3H), 2.19 (s, 3H), 2.06-1.99 (m, 2H).
MH+520.

Example 238

1-(2-chlorophenyl)-N-(3-(4-(2,3-dichlorophenyl)piperazin-1-yl)-2-hydroxypropyl)-2,5-dimethyl-1H-imidazole-4-carboxamide dihydrochloride $^1$H NMR (400 MHz, DMSO-d$_6$) δ 10.52 (s, 1H), 8.39 (s, 1H), 7.80 (d, J=7.2 Hz, 1H), 7.68-7.59 (m, 3H), 7.35-7.30 (m, 2H), 7.17 (dd, J=6.8, 2.4 Hz, 1H), 4.23-4.21 (m, 1H), 3.67-3.56 (m, 2H), 3.42-3.12 (m, 10H), 2.18 (s, 6H), 2.06-1.99 (m, 2H).
MH+536.

Example 239

N-(3-(4-(3-chloro-2-methylphenyl)piperazin-1-yl)propyl)-1-(2-fluorophenyl)-5-methyl-2-propyl-1H-imidazole-4-carboxamide dihydrochloride $^1$H NMR (400 MHz, DMSO-d$_6$) δ 10.93 (s, 1H), 8.56 (s, 1H), 7.71-7.55 (m, 3H), 7.46 (t, J=7.26 Hz, 1H), 7.20-7.15 (m, 2H), 7.02 (dd, J=6.8, 1.6 Hz, 1H), 3.52-3.49 (m, 2H), 3.35-3.34 (m, 2H), 3.20-3.08 (m, 8H), 2.52-2.47 (m, 2H), 2.27 (s, 3H), 2.22 (s, 3H), 2.05-1.98 (m, 2H), 1.58-1.49 (m, 2H), 0.76 (t, J=7.2 Hz, 3H).
MH+512.

Example 240

N-(3-(4-(2,3-dimethylphenyl)piperazin-1-yl)propyl)-1-(2-methoxyphenyl)-5-methyl-2-phenyl-1H-imidazole-4-carboxamide dihydrochloride $^1$H NMR (400 MHz, DMSO-d$_6$) δ 11.05 (br s, 1H), 8.72 (br s, 1H), 7.54-7.50 (m, 2H), 7.37-7.23 (m, 6H), 7.06-7.03 (m, 2H), 6.90-6.85 (m, 2H), 3.66 (s, 3H), 3.51-3.48 (m, 2H), 3.38-3.37 (m, 2H), 3.28-3.26 (m, 3H), 3.20-3.02 (m, 5H), 2.23 (s, 3H), 2.17 (s, 3H), 2.13 (s, 3H), 2.05-1.99 (m, 2H).
MH+538.

Example 241

N-(3-(4-(3-chloro-2-methylphenyl)piperazin-1-yl)propyl)-1-(2-methoxyphenyl)-5-methyl-2-phenyl-1H-imidazole-4-carboxamide dihydrochloride $^1$H NMR (400 MHz, DMSO-d$_6$) δ 10.82 (br s, 1H), 8.45 (br s, 1H), 7.53-7.48 (m, 2H), 7.33-7.24 (m, 6H), 7.20-7.14 (m, 2H), 7.11-7.02 (m, 2H), 3.65 (s, 3H), 3.53-3.50 (m, 2H), 3.36-3.35 (m, 2H), 3.21-3.08 (m, 8H), 2.26 (s, 3H), 2.22 (s, 3H), 2.02-1.98 (m, 2H).
MH+558.

Example 242

N-(3-(4-(2,3-dichlorophenyl)piperazin-1-yl)propyl)-1-(2-methoxyphenyl)-5-methyl-2-phenyl-1H-imidazole-4-carboxamide dihydrochloride $^1$H NMR (400 MHz, DMSO-d$_6$) δ 11.00 (br s, 1H), 8.47 (br s, 1H), 7.53-7.48 (m, 1H), 7.38-7.22 (m, 8H), 7.19-7.10 (m, 1H), 7.06-7.02 (m, 2H), 3.65 (s, 3H), 3.57-3.54 (m, 2H), 3.40-3.35 (m, 4H), 3.20-3.12 (m, 6H), 2.22 (s, 3H), 2.04-1.99 (m, 2H).
MH+578.

Example 243

N-(3-(4-(2,3-dimethylphenyl)piperazin-1-yl)propyl)-1-(2-fluorophenyl)-5-methyl-2-propyl-1H-imidazole-4-carboxamide dihydrochloride $^1$H NMR (400 MHz, DMSO-d$_6$) δ 11.07 (s, 1H), 8.86 (s, 1H), 7.85-7.74 (m, 2H), 7.67-7.62 (m, 1H), 7.54-7.50 (m, 1H), 7.08 (t, J=8.0 Hz, 1H), 6.94-6.87 (m, 2H), 3.55-3.52 (m, 2H), 3.41-3.39 (m, 2H), 3.24-3.06 (m, 10H), 2.62 (t, J=7.2 Hz, 2H), 2.28 (s, 3H), 2.17 (s, 3H), 2.11-2.04 (m, 2H), 1.66-1.57 (m, 2H), 0.81 (t, J=7.2 Hz, 3H).
MH+492.

Example 244

N-(3-(4-(2,3-dimethylphenyl)piperazin-1-yl)-2-hydroxypropyl)-1-(2-fluorophenyl)-5-methyl-2-propyl-1H-imidazole-4-carboxamide dihydrochloride $^1$H NMR (400 MHz, DMSO-$d_6$) δ 10.42 (s, 1H), 8.60 (s, 1H), 7.79-7.70 (m, 2H), 7.65 (t, J=9.2 Hz, 1H), 7.53 (t, J=7.6 Hz, 1H), 7.09 (t, J=7.6 Hz, 1H), 6.96-6.89 (m, 2H), 4.30-4.28 (m, 1H), 3.68-3.57 (m, 2H), 3.42-3.27 (m, 5H), 3.19-3.13 (m, 5H), 2.61-2.57 (m, 1H), 2.29 (s, 3H), 2.24 (s, 3H), 2.19 (s, 3H), 1.65-1.56 (m, 2H), 0.83 (t, J=7.2 Hz, 3H).
MH+508.

Example 245

N-(3-(4-(2,3-dichlorophenyl)piperazin-1-yl)-2-hydroxypropyl)-1-(2-fluorophenyl)-5-methyl-2-propyl-1H-imidazole-4-carboxamide dihydrochloride $^1$H NMR (400 MHz, DMSO-$d_6$) δ 10.51 (s, 1H), 8.42 (s, 1H), 7.75-7.60 (m, 3H), 7.50 (t, J=7.6 Hz, 1H), 7.40-7.34 (m, 2H), 7.21 (dd, J=6.8, 2.4 Hz, 1H), 4.27-4.26 (m, 1H), 3.71-3.60 (m, 2H), 3.46-3.15 (m, 10H), 2.55-2.51 (m, 2H), 2.27 (s, 3H), 1.62-1.53 (m, 2H), 0.81 (t, J=7.6 Hz, 3H).
MH+548.

Example 246

N-(3-(4-(2,3-dimethylphenyl)piperazin-1-yl)propyl)-5-methyl-2-propyl-1-o-tolyl-1H-imidazole-4-carboxamide dihydrochloride $^1$H NMR (400 MHz, MeOH-$d_4$) δ 7.65-7.57 (m, 2H), 7.51 (t, J=7.6 Hz, 1H), 7.44 (d, J=8.0 Hz, 1H), 7.06 (t, J=8.0 Hz, 1H), 6.95 (t, J=8.8 Hz, 2H), 3.67-3.64 (m, 3H), 3.61-3.58 (m, 3H), 3.42-3.36 (m, 2H), 3.30-3.11 (m, 6H), 2.77-2.75 (m, 1H), 2.66-2.63 (m, 1H), 2.27 (s, 3H), 2.24 (s, 6H), 2.09 (s, 3H), 1.71-1.65 (m, 2H), 0.91 (t, J=7.6 Hz, 3H).
MH+488 (−2HCl).

Example 247

N-(3-(4-(3-chloro-2-methylphenyl)piperazin-1-yl)propyl)-5-methyl-2-propyl-1-o-tolyl-1H-imidazole-4-carboxamide dihydrochloride $^1$H NMR (400 MHz, MeOH-$d_4$) δ 7.64-7.57 (m, 2H), 7.51 (t, J=7.6 Hz, 1H), 7.41 (d, J=7.6 Hz, 1H), 7.19-7.16 (m, 2H), 7.10-7.07 (m, 1H), 3.71-3.65 (m, 2H), 3.61-3.55 (m, 3H), 3.40-3.33 (m, 3H), 3.30-3.28 (m, 4H), 3.16 (d, J=12.0 Hz, 2H), 2.75-2.73 (m, 1H), 2.64-2.62 (m, 1H), 2.37 (s, 3H), 2.27 (s, 3H), 2.16-2.14 (m, 2H), 2.09 (s, 3H), 1.70-1.64 (m, 2H), 0.91 (t, J=7.6 Hz, 3H).
MH+508 (−2HCl).

Example 248

N-(3-(4-(2,3-dichlorophenyl)piperazin-1-yl)propyl)-5-methyl-2-propyl-1-o-tolyl-1H-imidazole-4-carboxamide dihydrochloride $^1$H NMR (400 MHz, MeOH-$d_4$) δ 7.65-7.57 (m, 2H), 7.51 (t, J=7.2 Hz, 1H), 7.43 (d, J=7.6 Hz, 1H), 7.31-7.27 (m, 2H), 7.20-7.16 (m, 1H), 3.75-3.72 (m, 2H), 3.68-3.65 (m, 1H), 3.62-3.56 (m, 8H), 3.41-3.36 (m, 4H), 3.33-3.28 (m, 2H), 3.26-3.22 (m, 3H), 2.89-2.88 (m, 2H), 2.75-2.73 (m, 1H), 2.64-2.62 (m, 1H), 2.28 (s, 3H), 2.20-2.18 (m, 2H), 2.09 (s, 3H), 1.69-1.67 (m, 2H), 0.91 (t, J=7.6 Hz, 3H).
MH+528 (−2HCl).

Example 249

1-(4-chlorophenyl)-N-(3-(4-(2,3-dimethylphenyl)piperazin-1-yl)propyl)-5-methyl-2-phenyl-1H-imidazole-4-carboxamide dihydrochloride $^1$H NMR (400 MHz, MeOH-$d_4$) δ 7.62 (d, J=8.0 Hz, 2H), 7.57 (t, J=7.2 Hz, 1H), 7.52-7.45 (m, 5H), 7.08 (t, J=8.0 Hz, 1H), 6.97 (t, J=7.2 Hz, 2H), 3.72-3.65 (m, 2H), 3.62-3.59 (m, 3H), 3.44-3.37 (m, 4H), 3.31-3.14 (m, 4H), 2.45 (s, 3H), 2.27 (s, 3H), 2.26 (s, 3H), 2.21-2.19 (m, 2H).
MH+542 (−2HCl).

Example 250

N-(3-(4-(3-chloro-2-methylphenyl)piperazin-1-yl)propyl)-1-(4-chlorophenyl)-5-methyl-2-phenyl-1H-imidazole-4-carboxamide dihydrochloride $^1$H NMR (400 MHz, MeOH-$d_4$) δ 7.62 (d, J=6.4 Hz, 2H), 7.58-7.55 (m, 1H), 7.50-7.45 (m, 5H), 7.19-7.16 (m, 2H), 7.11-7.09 (m, 1H), 3.73-3.69 (m, 2H), 3.63-3.60 (m, 3H), 3.45-3.35 (m, 3H), 3.21-3.18 (m, 2H), 2.46 (s, 3H), 2.39 (s, 3H), 2.22-2.21 (m, 2H).
MH+562 (−2HCl).

Example 251

1-(4-chlorophenyl)-N-(3-(4-(2,3-dichlorophenyl)piperazin-1-yl)propyl)-5-methyl-2-phenyl-1H-imidazole-4-carboxamide dihydrochloride $^1$H NMR (400 MHz, MeOH-$d_4$) δ 7.62 (d, J=8.0 Hz, 2H), 7.59-7.53 (m, 1H), 7.51-7.45 (m, 5H), 7.32-7.28 (m, 2H), 7.19-7.17 (m, 1H), 3.76 (d, J=10.2 Hz, 2H), 3.69-3.65 (m, 1H), 3.62-3.54 (m, 5H), 3.44-3.37 (m, 3H), 3.26-3.17 (m, 3H), 2.45 (s, 3H), 2.22-2.19 (m, 2H).
MH+582 (−2HCl).

Example 252

1-(4-chlorophenyl)-N-(3-(4-(2,3-dimethylphenyl)piperazin-1-yl)-2-hydroxypropyl)-5-methyl-2-phenyl-1H-imidazole-4-carboxamide dihydrochloride $^1$H NMR (400 MHz, MeOH-$d_4$) δ 7.63-7.49 (m, 10H), 7.08 (t, J=7.6 Hz, 1H), 7.01-6.96 (m, 2H), 4.44-4.43 (m, 1H), 3.76-3.73 (m, 2H), 3.69-3.66 (m, 1H), 3.63-3.57 (m, 3H), 3.50-3.44 (m, 2H), 3.23 (brs, 4H), 2.48 (s, 3H), 2.27 (s, 6H).
MH+558 (−2HCl).

Example 253

N-(3-(4-(3-chloro-2-methylphenyl)piperazin-1-yl)-2-hydroxypropyl)-1-(4-chlorophenyl)-5-methyl-2-phenyl-1H-imidazole-4-carboxamide dihydrochloride $^1$H NMR (400 MHz, MeOH-$d_4$) δ 7.60 (d, J=7.2 Hz, 2H), 7.55-7.42 (m, 6H), 7.17 (d, J=4.4 Hz, 2H), 7.09-7.07 (m, 1H), 4.17-4.13 (m, 1H), 3.72-3.70 (m, 2H), 3.67-3.65 (m, 1H), 3.63-3.57 (m, 3H), 3.50-3.44 (m, 2H), 3.21-3.10 (brs, 4H), 2.45 (s, 3H), 2.38 (s, 3H).
MH+578 (−2HCl).

Example 254

1-(4-chlorophenyl)-N-(3-(4-(2,3-dichlorophenyl)piperazin-1-yl)-2-hydroxypropyl)-5-methyl-2-phenyl-1H-imidazole-4-carboxamide dihydrochloride $^1$H NMR (400 MHz, MeOH-d$_4$) δ 7.62 (d, J=8.0 Hz, 2H), 7.56-7.43 (m, 6H), 7.32-7.28 (m, 2H), 7.19-7.17 (m, 1H), 4.38-4.36 (m, 1H), 3.76-3.70 (m, 2H), 3.69-3.65 (m, 1H), 3.63-3.57 (m, 3H), 3.50-3.44 (m, 2H), 3.21-3.15 (m, 4H), 2.45 (s, 3H).
MH+598 (−2HCl).

Example 255

1-(benzo[d][1,3]dioxol-5-yl)-N-(3-(4-(2,3-dichlorophenyl)piperazin-1-yl)propyl)-2,5-dimethyl-1H-imidazole-4-carboxamide dihydrochloride $^1$H NMR (400 MHz, DMSO-d$_6$) δ 11.33 (br s, 1H), 8.87 (br s, 1H), 7.40-7.33 (m, 2H), 7.24-7.19 (m, 2H), 7.17 (d, J=8.4 Hz, 1H), 7.05 (dd, J=8.0, 2.0 Hz, 1H), 6.20 (s, 2H), 3.59-3.56 (m, 2H), 3.45-3.37 (m, 2H), 3.29-3.23 (m, 4H), 3.21-3.15 (m, 4H), 2.36 (s, 3H), 2.30 (s, 3H), 2.09-2.02 (m, 2H).
MH+530.

Example 256

1-(benzo[d][1,3]dioxol-5-yl)-N-(3-(4-(2,3-dichlorophenyl)piperazin-1-yl)-2-hydroxypropyl)-2,5-dimethyl-1H-imidazole-4-carboxamide dihydrochloride $^1$H NMR (400 MHz, DMSO-d$_6$) δ 10.70 (br s, 1H), 8.68 (br s, 1H), 7.40-7.34 (m, 2H), 7.24-7.20 (m, 2H), 7.17 (d, J=8.4 Hz, 1H), 7.03 (dd, J=8.4, 2.0 Hz, 1H), 6.20 (s, 2H), 4.29-4.26 (m, 1H), 3.72-3.70 (m, 1H), 3.62-3.59 (m, 1H), 3.46-3.36 (m, 6H), 3.29-3.17 (m, 4H), 2.36 (s, 3H), 2.31 (s, 3H).
MH+546.

Example 257

1-(benzo[d][1,3]dioxol-5-yl)-N-(3-(4-(2,3-dimethylphenyl)piperazin-1-yl)propyl)-5-methyl-2-propyl-1H-imidazole-4-carboxamide dihydrochloride $^1$H NMR (400 MHz, DMSO-d$_6$) δ 11.23 (br s, 1H), 9.24 (br s, 1H), 7.27 (d, J=2.0 Hz, 1H), 7.18 (d, J=8.0 Hz, 1H), 7.11-7.06 (m, 2H), 6.95-6.90 (m, 2H), 6.21 (s, 2H), 3.55-3.52 (m, 2H), 3.44-3.39 (m, 2H), 3.31-3.21 (m, 4H), 3.19-3.09 (m, 4H), 2.70 (t, J=7.6 Hz, 2H), 2.30 (s, 3H), 2.23 (s, 3H), 2.18 (s, 3H), 2.12-2.04 (m, 2H), 1.73-1.63 (m, 2H), 0.84 (t, J=7.2 Hz, 3H).
MH+518.

Example 258

1-(benzo[d][1,3]dioxol-5-yl)-N-(3-(4-(2,3-dichlorophenyl)piperazin-1-yl)propyl)-5-methyl-2-propyl-1H-imidazole-4-carboxamide dihydrochloride $^1$H NMR (400 MHz, DMSO-d$_6$) δ 11.31 (br s, 1H), 9.05 (br s, 1H), 7.41-7.35 (m, 2H), 7.25-7.21 (m, 2H), 7.18 (d, J=8.4 Hz, 1H), 7.07 (dd, J=8.4, 2.0 Hz, 1H), 6.22 (s, 2H), 3.61-3.58 (m, 2H), 2.46-3.39 (m, 4H), 3.30-3.17 (m, 6H), 2.68 (t, J=7.6 Hz, 2H), 2.30 (s, 3H), 2.11-2.04 (m, 2H), 1.71-1.62 (m, 2H), 0.85 (t, J=7.6 Hz, 3H).
MH+558.

Example 259

1-(benzo[d][1,3]dioxol-5-yl)-N-(3-(4-(2,3-dimethylphenyl)piperazin-1-yl)-2-hydroxypropyl)-5-methyl-2-propyl-1H-imidazole-4-carboxamide dihydrochloride $^1$H NMR (400 MHz, DMSO-d$_6$) δ 10.63 (br s, 1H), 9.07 (br s, 1H), 7.29 (s, 1H), 7.21 (d, J=8.4 Hz, 1H), 7.12-7.08 (m, 2H), 6.97-6.92 (m, 2H), 6.24 (s, 2H), 4.33-4.31 (m, 1H), 3.71-3.68 (m, 1H), 3.61-3.57 (m, 1H), 3.51-3.48 (m, 2H), 3.46-3.43 (m, 2H), 3.42-3.33 (m, 2H), 3.27-3.11 (m, 4H), 2.72 (d. J=7.2 Hz, 2H), 2.33 (s, 3H), 2.25 (s, 3H), 2.20 (s, 3H), 1.72-1.66 (m, 2H), 0.87 (t, J=7.2 Hz, 3H).
MH+534.

Example 260

1-(benzo[d][1,3]dioxol-5-yl)-N-(3-(4-(2,3-dichlorophenyl)piperazin-1-yl)-2-hydroxypropyl)-5-methyl-2-propyl-1H-imidazole-4-carboxamide dihydrochloride $^1$H NMR (400 MHz, DMSO-d$_6$) δ 10.64 (br s, 1H), 8.83 (br s, 1H), 7.40-7.34 (m, 2H), 7.23-7.20 (m, 2H), 7.17 (d, J=8.4 Hz, 1H), 7.05 (dd, J=8.4, 1.6 Hz, 1H), 6.21 (s, 2H), 4.29-4.27 (m, 1H), 3.72-3.69 (m, 1H), 3.63-3.60 (m, 1H), 3.47-3.41 (m, 6H), 3.30-3.17 (m, 6H), 2.66 (t, J=7.6 Hz, 2H), 2.30 (s, 3H), 1.69-1.60 (m, 2H), 0.84 (t, J=7.2 Hz, 3H).
MH+574.

Example 261

N-(3-(4-(3-chloro-2-methylphenyl)piperazin-1-yl)propyl)-2,5-dimethyl-1-p-tolyl-1H-imidazole-4-carboxamide dihydrochloride $^1$H NMR (400 MHz, DMSO-d$_6$) δ 11.31 (br s, 1H), 8.95 (br s, 1H), 7.50-7.45 (m, 4H), 7.25-7.19 (m, 2H), 7.07 (dd, J=6.8, 2.0 Hz, 1H), 3.56-3.53 (m, 2H), 3.45-3.40 (m, 2H), 3.31-3.25 (m, 4H), 3.21-3.17 (m, 4H), 2.44 (s, 3H), 2.37 (s, 3H), 2.32 (s, 3H), 2.29 (s, 3H), 2.13-2.04 (s, 2H).
MH+480.

Example 262

N-(3-(4-(2,3-dimethylphenyl)piperazin-1-yl)propyl)-5-methyl-2-propyl-1-p-tolyl-1H-imidazole-4-carboxamide dihydrochloride $^1$H NMR (400 MHz, DMSO-d$_6$) δ 11.26 (br s, 1H), 9.27 (br s, 1H), 7.52-7.47 (m, 4H), 7.11-7.06 (m, 1H), 6.95-6.91 (m, 2H), 3.55-3.52 (m, 2H), 3.45-3.40 (m, 2H), 3.31-3.19 (m, 4H), 3.17-3.10 (m, 4H), 2.68 (t, J=7.6 Hz, 2H), 2.44 (s, 3H), 2.29 (s, 3H), 2.23 (s, 3H), 2.18 (s, 3H), 2.13-2.06 (m, 2H), 1.71-1.61 (m, 2H), 0.82 (t, J=6.8 Hz, 3H).
MH+488.

Example 263

N-(3-(4-(3-chloro-2-methylphenyl)piperazin-1-yl)propyl)-5-methyl-2-propyl-1-p-tolyl-1H-imidazole-4-carboxamide dihydrochloride $^1$H NMR (400 MHz, DMSO-d$_6$) δ 11.37 (br s, 1H), 9.23 (br s, 1H), 7.53-7.48 (m, 4H), 7.21-7.17 (m, 2H), 7.05 (dd, J=6.8, 2.0 Hz, 1H), 3.55-3.52 (m, 2H), 3.44-3.39 (m, 2H), 3.31-3.24 (m, 4H), 3.23-3.12 (m, 4H), 2.66 (t, J=8.0 Hz, 2H), 2.43 (s, 3H), 2.30 (s, 3H), 2.27 (s, 3H), 2.12-2.04 (m, 2H), 1.69-1.59 (m, 2H), 0.81 (t, J=7.2 Hz, 3H).
MH+508.

Example 264

N-(3-(4-(2,3-dimethylphenyl)piperazin-1-yl)-2-hydroxypropyl)-1-(2-methoxyphenyl)-5-methyl-2-phenyl-1H-imidazole-4-carboxamide dihydrochloride $^1$H NMR (400 MHz, DMSO-d$_6$) δ 10.55 (br s, 1H), 8.66 (br s, 1H), 7.59-7.55 (m, 1H), 7.42-7.33 (m, 6H), 7.30-7.28 (m, 1H), 7.12-7.05 (m, 2H), 6.94-6.89 (m, 2H), 4.32-4.30 (m, 1H), 3.70 (d, J=3.6 Hz, 3H), 3.68-3.65 (m, 1H), 3.59-3.56 (m, 1H), 3.49-3.32 (m, 5H), 3.29-3.08 (m, 5H), 2.28 (s, 3H), 2.21 (s, 3H), 2.14 (s, 3H). MH+554.

Example 265

N-(3-(4-(3-chloro-2-methylphenyl)piperazin-1-yl)-2-hydroxypropyl)-1-(2-methoxyphenyl)-5-methyl-2-phenyl-1H-imidazole-4-carboxamide dihydrochloride $^1$H NMR (400 MHz, DMSO-d$_6$) δ 10.56 (br s, 1H), 8.42 (br s, 1H), 7.59-7.55 (m, 1H), 7.39-7.28 (m, 7H), 7.25-7.19 (m, 2H), 7.13-7.08 (m, 2H), 4.31-4.29 (m, 1H), 3.71 (d, J=4.0 Hz, 3H), 3.65-3.62 (m, 2H), 3.46-3.38 (m, 5H), 3.34-3.15 (m, 5H), 2.31 (s, 3H), 2.28 (s, 3H).
MH+574.

Example 266

N-(3-(4-(2,3-dichlorophenyl)piperazin-1-yl)-2-hydroxypropyl)-1-(2-methoxyphenyl)-5-methyl-2-phenyl-1H-imidazole-4-carboxamide dihydrochloride $^1$H NMR (400 MHz, DMSO-d$_6$) δ 10.54 (br s, 1H), 8.42 (br s, 1H), 7.57-7.53 (m, 1H), 7.37-7.29 (m, 7H), 7.27-7.18 (m, 2H), 7.11-7.04 (m, 2H), 4.29-4.28 (m, 1H), 3.69 (d, J=4.0 Hz, 3H), 3.64-3.57 (m, 2H), 3.48-3.30 (m, 6H), 3.27-3.12 (m, 4H), 2.30 (s, 3H).
MH+594.

Example 267

1-(benzo[d][1,3]dioxol-5-yl)-N-(3-(4-(2,3-dimethylphenyl)piperazin-1-yl)propyl)-5-methyl-2-phenyl-1H-imidazole-4-carboxamide dihydrochloride $^1$H NMR (400 MHz, DMSO-d$_6$) δ 11.23 (br s, 1H), 9.00 (br s, 1H), 7.53-7.40 (m, 5H), 7.18 (s, 1H), 7.11-7.07 (m, 2H), 6.98-6.91 (m, 3H), 6.18 (s, 2H), 3.56-3.53 (m, 2H), 3.46-3.41 (m, 2H), 3.27-3.10 (m, 8H), 2.39 (s, 3H), 2.23 (s, 3H), 2.18 (s, 3H), 2.13-2.07 (m, 2H).
MH+552.

Example 268

1-(benzo[d][1,3]dioxol-5-yl)-N-(3-(4-(3-chloro-2-methylphenyl)piperazin-1-yl)propyl)-5-methyl-2-phenyl-1H-imidazole-4-carboxamide dihydrochloride $^1$H NMR (400 MHz, DMSO-d$_6$) δ 11.17 (br s, 1H), 8.80 (br s, 1H), 7.50-7.47 (m, 2H), 7.44-78.36 (m, 3H), 7.24-7.19 (m, 2H), 7.15 (d, J=2.0 Hz, 1H), 7.08-7.04 (m, 2H), 6.92 (dd, J=8.4, 2.4 Hz, 1H), 6.17 (s, 2H), 3.56-3.53 (m, 2H), 3.44-3.39 (m, 2H), 3.27-3.24 (m, 4H), 3.22-3.20 (m, 4H), 2.37 (s, 3H), 2.31 (s, 3H), 2.10-2.03 (m, 2H).
MH+572.

Example 269

1-(benzo[d][1,3]dioxol-5-yl)-N-(3-(4-(2,3-dichlorophenyl)piperazin-1-yl)propyl)-5-methyl-2-phenyl-1H-imidazole-4-carboxamide dihydrochloride $^1$H NMR (400 MHz, DMSO-d$_6$) δ 11.34 (br s, 1H), 8.82 (br s, 1H), 7.50-7.48 (m, 2H), 7.46-7.34 (m, 5H), 7.21 (dd, J=2.8, 2.4 Hz, 1H), 7.15 (d, J=2.0 Hz, 1H), 7.07 (d, J=8.4 Hz, 1H), 6.93 (dd, J=2.0, 1.6 Hz, 1H), 6.17 (s, 2H), 3.61-3.58 (m, 2H), 3.45-3.40 (m, 4H), 3.31-3.17 (m, 6H), 2.38 (s, 3H), 2.11-2.04 (m, 2H).
MH+592.

Example 270

1-(benzo[d][1,3]dioxol-5-yl)-N-(3-(4-(2,3-dimethylphenyl)piperazin-1-yl)-2-hydroxypropyl)-5-methyl-2-phenyl-1H-imidazole-4-carboxamide dihydrochloride $^1$H NMR (400 MHz, DMSO-d$_6$) δ 10.60 (br s, 1H), 8.74 (br s, 1H), 7.50-7.37 (m, 5H), 7.15 (d, J=1.6 Hz, 1H), 7.09-7.05 (m, 2H), 6.94-6.89 (m, 3H), 6.16 (s, 2H), 4.31-4.30 (m, 1H), 3.67-3.64 (m, 1H), 3.58-3.55 (m, 1H), 3.44-3.31 (m, 5H), 3.21-3.06 (m, 5H), 2.37 (s, 3H), 2.21 (s, 3H), 2.16 (s, 3H).
MH+568.

Example 271

1-(benzo[d][1,3]dioxol-5-yl)-N-(3-(4-(3-chloro-2-methylphenyl)piperazin-1-yl)-2-hydroxypropyl)-5-methyl-2-phenyl-1H-imidazole-4-carboxamide dihydrochloride $^1$H NMR (400 MHz, DMSO-d$_6$) δ 10.48 (br s, 1H), 8.49 (br s, 1H), 7.48-7.36 (m, 5H), 7.26-7.08 (m, 5H), 6.89 (dd, J=1.6, 1.6 Hz, 1H), 6.18 (s, 2H), 4.31-4.29 (m, 1H), 3.69-3.66 (m, 1H), 3.61-3.58 (m, 1H), 3.46-3.32 (m, 5H), 3.24-3.14 (m, 5H), 2.38 (s, 3H), 2.16 (s, 3H).
MH+588.

Example 272

1-(benzo[d][1,3]dioxol-5-yl)-N-(3-(4-(2,3-dichlorophenyl)piperazin-1-yl)-2-hydroxypropyl)-5-methyl-2-phenyl-1H-imidazole-4-carboxamide dihydrochloride $^1$H NMR (400 MHz, DMSO-d$_6$) δ 10.60 (br s, 1H), 8.47 (br s, 1H), 7.46-7.44 (m, 2H), 7.38-7.33 (m, 5H), 7.20 (dd, J=2.0, 2.4 Hz, 1H), 7.15 (d, J=1.6 Hz, 1H), 7.05 (d, J=8.0 Hz, 1H), 6.87 (dd, J=2.0, 2.0 Hz, 1H), 6.16 (s, 2H), 4.29-4.27 (m, 1H), 3.71-3.68 (m, 1H), 3.63-3.60 (m, 1H), 3.45-3.36 (m, 5H), 3.22-3.17 (m, 5H), 2.36 (s, 3H).
MH+608.

Example 273

N-(3-(4-(2,3-dimethylphenyl)piperazin-1-yl)propyl)-1-(2-fluorophenyl)-5-methyl-2-phenyl-1H-imidazole-4-carboxamide dihydrochloride $^1$H NMR (400 MHz, DMSO-d$_6$) δ 11.17 (s, 1H), 8.52-8.49 (m, 1H), 7.66-7.62 (m, 2H), 7.51-7.46 (m, 1H), 7.44-7.40 (m, 1H), 7.40-7.31 (m, 5H), 7.07 (t, J=7.6 Hz, 1H), 6.94-6.89 (m, 2H), 3.56-3.53 (m, 2H), 3.43-3.38 (m, 2H), 3.26-3.06 (m, 8H), 2.34 (s, 3H), 2.22 (s, 3H), 2.17 (s, 3H), 2.12-2.03 (m, 2H).
MH+526.

Example 274

N-(3-(4-(3-chloro-2-methylphenyl)piperazin-1-yl)propyl)-1-(2-fluorophenyl)-5-methyl-2-phenyl-1H-imidazole-4-carboxamide dihydrochloride $^1$H NMR (400 MHz, DMSO-d$_6$) δ 11.06 (s, 1H), 8.45 (s, 1H), 7.69-7.65 (m, 2H), 7.55-7.50 (m, 1H), 7.47-7.44 (m, 1H), 7.39-7.38 (m, 5H), 7.24 (m, 2H), 7.10-7.09 (m, 1H), 3.61-3.44 (m, 4H), 3.23 (m, 8H), 2.37 (s, 3H), 2.35 (s, 3H), 2.09 (m, 2H). MH+546.

Example 275

N-(3-(4-(2,3-dichlorophenyl)piperazin-1-yl)propyl)-1-(2-fluorophenyl)-5-methyl-2-phenyl-1H-imidazole-4-carboxamide dihydrochloride $^1$H NMR (400 MHz, DMSO-d$_6$) δ 11.13 (s, 1H), 8.43-8.40 (m, 1H), 7.65-7.61 (m, 2H), 7.51-7.47 (m, 1H), 7.44-7.40 (m, 1H), 7.38-7.31 (m, 7H), 7.21 (dd, J=7.2, 2.4 Hz 1H), 3.62-3.59 (m, 2H), 3.45-3.39 (m, 4H), 3.30-3.18 (m, 6H), 2.34 (s, 3H), 2.07-2.03 (m, 2H).
MH+566.

Example 276

N-(3-(4-(2,3-dimethylphenyl)piperazin-1-yl)-2-hydroxypropyl)-1-(2-fluorophenyl)-5-methyl-2-phenyl-1H-imidazole-4-carboxamide dihydrochloride $^1$H NMR (400 MHz, DMSO-d$_6$) δ 10.30 (s, 1H), 8.31-8.27 (m, 1H), 7.69-7.62 (m, 2H), 7.53-7.49 (m, 1H), 7.46-7.42 (m, 1H), 7.41-7.32 (m, 4H), 7.10 (t, J=8.0 Hz 1H), 6.97-6.92 (m, 2H), 4.31-4.29 (m, 1H), 3.68-3.59 (m, 2H), 3.49-3.35 (m, 5H), 3.20-3.09 (m, 5H), 2.36 (s, 3H), 2.24 (s, 3H), 2.24 (s, 3H).
MH+542.

Example 277

N-(3-(4-(3-chloro-2-methylphenyl)piperazin-1-yl)-2-hydroxypropyl)-1-(2-fluorophenyl)-5-methyl-2-phenyl-1H-imidazole-4-carboxamide dihydrochloride $^1$H NMR (400 MHz, DMSO-d$_6$) δ 10.29 (s, 1H), 8.27-8.26 (m, 1H), 7.68-7.61 (m, 2H), 7.52-7.48 (m, 1H), 7.45-7.42 (m, 1H), 7.36-7.32 (m, 4H), 7.25-7.20 (m, 2H), 7.08-7.06 (m, 2H), 4.28 (m, 1H), 3.68-3.58 (m, 2H), 3.48-3.35 (m, 5H), 3.23-3.12 (m, 5H), 2.35 (s, 3H), 2.32 (s, 3H).
MH+562.

Example 278

N-(3-(4-(2,3-dichlorophenyl)piperazin-1-yl)-2-hydroxypropyl)-1-(2-fluorophenyl)-5-methyl-2-phenyl-1H-imidazole-4-carboxamide dihydrochloride $^1$H NMR (400 MHz, DMSO-d$_6$) δ 10.42 (s, 1H), 8.29-8.26 (m, 1H), 7.69-7.62 (m, 2H), 7.51-7.46 (m, 1H), 7.44-7.42 (m, 1H), 7.42-7.32 (m, 7H), 7.23 (dd, J=7.2, 2.4 Hz, 1H), 4.30-4.28 (m, 1H), 3.72-3.63 (m, 2H), 3.48-3.16 (m, 10H), 2.36 (s, 3H).
MH+582.

Example 279

N-(3-(4-(2,3-dichlorophenyl)piperazin-1-yl)propyl)-5-methyl-2-propyl-1-p-tolyl-1H-imidazole-4-carboxamide dihydrochloride $^1$H NMR (400 MHz, DMSO-d$_6$) δ 11.42 (br s, 1H), 9.21 (br s, 1H), 7.55-7.50 (m, 4H), 7.41-7.35 (m, 2H), 7.30 (dd, J=7.2, 2.8 Hz, 1H), 3.62-3.58 (m, 2H), 3.47-3.41 (m, 4H), 3.34-3.18 (m, 6H), 2.68 (t, J=7.2 Hz, 2H), 2.45 (s, 3H), 2.92 (s, 3H), 2.31-2.06 (m, 2H), 1.71-1.61 (m, 2H), 0.83 (t, J=7.2 Hz, 3H).
MH+528.

Example 280

1-(benzo[d][1,3]dioxol-5-yl)-N-(3-(4-(3-chloro-2-methylphenyl)piperazin-1-yl)-2-hydroxypropyl)-2,5-dimethyl-1H-imidazole-4-carboxamide dihydrochloride $^1$H NMR (400 MHz, CD$_3$OD) δ 7.17-7.15 (m, 2H), 7.10-7.04 (m, 3H), 6.99 (dd, J=8.0, 2.0 Hz, 1H), 6.15 (s, 2H), 4.38-4.35 (m, 1H), 3.76-3.72 (m, 2H), 3.60-3.50 (m, 2H), 3.48-3.37 (m, 4H), 3.31-3.12 (m, 4H), 2.48 (s, 3H), 2.37 (s, 3H), 2.36 (s, 3H).
MH+526.

Example 281

1-(benzo[d][1,3]dioxol-5-yl)-N-(3-(4-(3-chloro-2-methylphenyl)piperazin-1-yl)-2-hydroxypropyl)-5-methyl-2-propyl-1H-imidazole-4-carboxamide dihydrochloride $^1$H NMR (400 MHz, CD$_3$OD) δ 7.17-7.15 (m, 2H), 7.10-7.05 (m, 3H), 7.00 (dd, J=8.4, 2.4 Hz, 1H), 6.16 (s, 2H), 4.38-4.34 (m, 1H), 3.76-3.72 (m, 2H), 3.60-3.50 (m, 2H), 3.48-3.34 (m, 4H), 3.31-3.12 (m, 4H), 2.37 (s, 3H), 2.35 (s, 3H), 1.73-1.67 (m, 2H), 0.93 (t, J=7.6 Hz, 3H).
MH+554.

Example 282

N-(3-(4-(3-chloro-2-methylphenyl)piperazin-1-yl)-2-hydroxypropyl)-2,5-dimethyl-1-p-tolyl-1H-imidazole-4-carboxamide dihydrochloride $^1$H NMR (400 MHz, CD$_3$OD) δ 7.50 (d, J=8.4 Hz, 2H), 7.39 (d, J=8.4 Hz, 2H), 7.17-7.15 (m, 2H), 7.10-7.07 (m, 1H), 4.38-4.34 (m, 1H), 3.76-3.72 (m, 2H), 3.60-3.50 (m, 2H), 3.48-3.37 (m, 4H), 3.30-3.12 (m, 4H), 2.48 (s, 3H), 2.46 (s, 3H), 2.37 (s, 3H), 2.34 (s, 3H).
MH+496.

Example 283

N-(3-(4-(2,3-dimethylphenyl)piperazin-1-yl)-2-hydroxypropyl)-5-methyl-2-propyl-1-p-tolyl-1H-imidazole-4-carboxamide dihydrochloride $^1$H NMR (400 MHz, CD$_3$OD) δ 7.51 (d, J=8.4 Hz, 2H), 7.41 (d, J=8.4 Hz, 2H), 7.10-7.06 (m, 1H), 7.02-6.99 (m, 2H), 4.41-4.36 (m, 1H), 3.76-3.74 (m, 2H), 3.61-3.53 (m, 2H), 3.51-3.47 (m, 4H), 3.56-3.24 (m, 4H), 2.78 (t, J=7.6 Hz, 2H), 2.49 (s, 3H), 2.33 (s, 3H), 2.65 (s, 3H), 1.70-1.63 (m, 2H), 0.90 (t, J=7.6 Hz, 3H).
MH+504.

Example 284

N-(3-(4-(3-chloro-2-methylphenyl)piperazin-1-yl)-2-hydroxypropyl)-5-methyl-2-propyl-1-p-tolyl-1H-imidazole-4-carboxamide dihydrochloride $^1$H NMR (400 MHz, CD$_3$OD) δ 7.51 (d, J=8.0 Hz, 2H), 7.40 (d, J=8.4 Hz, 2H), 7.17-7.15 (m, 2H), 7.11-7.07 (m, 1H), 4.40-4.35 (m, 1H), 3.76-3.73 (m, 2H), 3.61-3.51 (m, 2H), 3.49-3.31 (m, 4H), 3.30-3.12 (m, 4H), 2.77 (t, J=8.0 Hz, 2H), 2.49 (s, 3H), 2.37 (s, 3H), 2.33 (s, 3H), 1.70-1.62 (m, 2H), 0.90 (t, J=7.6 Hz, 3H).
MH+524.

Example 285

N-(3-(4-(2,3-dichlorophenyl)piperazin-1-yl)-2-hydroxypropyl)-5-methyl-2-propyl-1-p-tolyl-1H-imidazole-4-carboxamide dihydrochloride $^1$H NMR (400 MHz, CD$_3$OD) δ 7.51 (d, J=8.0 Hz, 2H), 7.39 (d, J=8.4 Hz, 2H), 7.31-7.26 (m, 2H), 7.19-7.16 (m, 1H), 4.39-4.35 (m, 1H), 3.79-3.75 (m, 2H), 3.61-3.59 (m, 2H), 3.57-3.38 (m, 4H), 3.34-3.30 (m, 4H), 2.77 (t, J=7.6 Hz, 2H), 2.48 (s, 3H), 2.33 (s, 3H), 1.69-1.62 (m, 2H), 0.90 (t, J=8.0 Hz, 3H).
MH+544.

Example 286

N-(3-(4-(2,3-dimethylphenyl)piperazin-1-yl)propyl)-5-methyl-2-phenyl-1-p-tolyl-1H-imidazole-4-carboxamide dihydrochloride $^1$H NMR (400 MHz, CD$_3$OD) δ 7.58-7.50 (m, 3H), 7.46-7.39 (m, 4H), 7.36-7.34 (m, 2H), 7.09-7.05 (m, 1H), 6.99-6.94 (m, 2H), 3.72-3.69 (m, 2H), 3.62-3.58 (m, 2H), 3.42-3.33 (m, 4H), 3.26-3.14 (m, 4H), 2.42 (s, 3H), 2.25 (s, 3H), 2.23-2.17 (m, 2H).
MH+522.

Example 287

N-(3-(4-(3-chloro-2-methylphenyl)piperazin-1-yl)-2-hydroxypropyl)-5-methyl-2-phenyl-1-p-tolyl-1H-imidazole-4-carboxamide dihydrochloride $^1$H NMR (400 MHz, CD$_3$OD) δ 7.57-7.49 (m, 3H), 7.45-7.39 (m, 4H), 7.35-7.33 (m, 2H), 7.17-7.16 (m, 2H), 7.09-7.07 (m, 1H), 4.41-4.38 (m, 1H), 3.77-3.73 (m, 2H), 3.61-3.57 (m, 2H), 3.51-3.32 (m, 4H), 3.29-3.14 (m, 4H), 2.43 (s, 3H), 2.42 (s, 3H), 2.37 (s, 3H).
MH+558.

Example 288

N-(3-(4-(2,3-dichlorophenyl)piperazin-1-yl)propyl)-5-methyl-2-phenyl-1-p-tolyl-1H-imidazole-4-carboxamide dihydrochloride $^1$H NMR (400 MHz, CD$_3$OD) δ 7.57-7.49 (m, 3H), 7.45-7.39 (m, 4H), 7.35-7.33 (m, 2H), 7.31-7.26 (m, 2H), 7.19-7.16 (m, 1H), 3.76-3.72 (m, 2H), 3.63-3.58 (m, 2H), 3.56-3.52 (m, 2H), 3.42-3.35 (m, 4H), 3.30-3.19 (m, 2H), 2.42 (s, 6H), 2.26-2.17 (m, 2H).
MH+562.

Example 289

N-(3-(4-(2,3-dimethylphenyl)piperazin-1-yl)-2-hydroxypropyl)-5-methyl-2-phenyl-1-p-tolyl-1H-imidazole-4-carboxamide dihydrochloride $^1$H NMR (400 MHz, CD$_3$OD) δ 7.58-7.50 (m, 3H), 7.46-7.39 (m, 4H), 7.37-7.34 (m, 2H), 7.09-7.05 (m, 1H), 7.00-6.94 (m, 2H), 4.42-4.38 (m, 1H), 3.77-3.74 (m, 2H), 3.61-3.58 (m, 2H), 3.52-5.48 (m, 2H), 3.37-3.30 (m, 2H), 3.28-3.23 (m, 4H), 2.44 (s, 3H), 2.42 (s, 3H), 2.25 (s, 6H).
MH+538.

Example 290

N-(3-(4-(2,3-dichlorophenyl)piperazin-1-yl)-2-hydroxypropyl)-5-methyl-2-phenyl-1-p-tolyl-1H-imidazole-4-carboxamide dihydrochloride $^1$H NMR (400 MHz, CD$_3$OD) δ 7.57-7.49 (m, 3H), 7.45-7.35 (m, 4H), 7.33-7.31 (m, 2H), 7.30-7.26 (m, 2H), 7.19-7.16 (m, 1H), 4.42-4.37 (m, 1H), 3.79-3.76 (m, 2H), 3.64-3.55 (m, 2H), 3.54-3.38 (m, 4H), 3.30-3.18 (m, 4H), 2.43 (s, 3H), 2.42 (s, 3H).
MH+578.

Example 291

N-(3-(4-(3-chloro-2-methylphenyl)piperazin-1-yl)-2-hydroxypropyl)-1-(2-chlorophenyl)-2,5-dimethyl-1H-imidazole-4-carboxamide dihydrochloride $^1$H NMR (400 MHz, DMSO-d$_6$) δ 7.85-7.83 (m, 1H), 7.78-7.72 (m, 1H), 7.71-7.66 (m, 2H), 7.18-7.15 (m, 2H), 7.11-7.08 (m, 1H), 4.39-4.35 (m, 1H), 3.76-3.73 (m, 2H), 3.59-3.54 (m, 4H), 3.48-3.37 (m, 2H), 3.28-3.14 (m, 4H), 2.46 (s, 3H), 2.38 (s, 3H), 2.33 (s, 3H).
MH+516.

Example 292

1-(2-chlorophenyl)-N-(3-(4-(2,3-dimethylphenyl)piperazin-1-yl)propyl)-5-methyl-2-phenyl-1H-imidazole-4-carboxamide dihydrochloride $^1$H NMR (400 MHz, DMSO-d$_6$) δ 11.14 (s, 1H), 8.54-8.51 (m, 1H), 7.79-7.72 (m, 2H), 7.68-7.59 (m, 2H), 7.42-7.33 (m, 5H), 7.10 (t, J=7.6 Hz, 1H), 6.98-6.93 (m, 2H), 3.59-3.57 (m, 2H), 3.46-3.41 (m, 2H), 3.30-3.12 (m, 8H), 2.31 (s, 3H), 2.25 (s, 3H), 2.20 (s, 3H), 2.15-2.06 (m, 2H).
MH+542.

Example 293

N-(3-(4-(3-chloro-2-methylphenyl)piperazin-1-yl)propyl)-1-(2-chlorophenyl)-5-methyl-2-phenyl-1H-imidazole-4-carboxamide dihydrochloride $^1$H NMR (400 MHz, DMSO-d$_6$) δ 10.97 (s, 1H), 8.44-8.41 (m, 1H), 7.75-7.67 (m, 2H), 7.64-7.55 (m, 2H), 7.38-7.29 (m, 5H), 7.24-7.15 (m, 2H), 7.06-7.05 (m, 1H), 3.58-3.55 (m, 2H), 3.42-3.38 (m, 2H), 3.23-3.17 (m, 8H), 2.31 (s, 3H), 2.28 (s, 3H), 2.09-2.02 (m, 2H).
MH+562.

Example 294

1-(2-chlorophenyl)-N-(3-(4-(2,3-dichlorophenyl)piperazin-1-yl)propyl)-5-methyl-2-phenyl-1H-imidazole-4-carboxamide dihydrochloride $^1$H NMR (400 MHz, DMSO-d$_6$) δ 11.11 (s, 1H), 8.45-8.42 (m, 1H), 7.77-7.69 (m, 2H), 7.66-7.57 (m, 2H), 7.44-7.30 (m, 7H), 7.24-7.22 (m, 1H), 3.63-3.61 (m, 2H), 3.47-3.39 (m, 4H), 3.31-3.12 (m, 6H), 2.29 (s, 3H), 2.13-2.03 (m, 2H).
MH+582.

Example 295

1-(2-chlorophenyl)-N-(3-(4-(2,3-dimethylphenyl)piperazin-1-yl)-2-hydroxypropyl)-5-methyl-2-phenyl-1H-imidazole-4-carboxamide dihydrochloride $^1$H NMR (400 MHz, DMSO-d$_6$) δ 10.41 (s, 1H), 8.33-8.30 (m, 1H), 7.78-7.66 (m, 2H), 7.65-7.58 (m, 2H), 7.39-7.32 (m, 5H), 7.12 (m, 1H), 6.96-6.92 (m, 2H), 4.32-4.30 (m, 1H), 3.69-3.59 (m, 2H), 3.44-3.35 (m, 5H), 3.21-3.09 (m, 5H), 2.30 (s, 3H), 2.24 (s, 3H), 2.19 (s, 3H).
MH+558.

Example 296

N-(3-(4-(3-chloro-2-methylphenyl)piperazin-1-yl)-2-hydroxypropyl)-1-(2-chlorophenyl)-5-methyl-2-phenyl-1H-imidazole-4-carboxamide dihydrochloride $^1$H NMR (400 MHz, DMSO-d$_6$) δ 10.34 (s, 1H), 8.29-8.26 (m, 1H), 7.76-7.57 (m, 4H), 7.38-7.30 (m, 5H), 7.25-7.19 (m, 2H), 7.09-7.05 (m, 1H), 4.29-4.28 (m, 1H), 3.68-3.58 (m, 2H), 3.43-3.31 (m, 5H), 3.23-3.12 (m, 5H), 2.31 (s, 3H), 2.29 (s, 3H).
MH+578.

Example 297

1-(2-chlorophenyl)-N-(3-(4-(2,3-dichlorophenyl)piperazin-1-yl)-2-hydroxypropyl)-5-methyl-2-phenyl-1H-imidazole-4-carboxamide dihydrochloride $^1$H NMR (400 MHz, DMSO-d$_6$) δ 10.51 (s, 1H), 8.30-8.27 (m, 1H), 7.78-7.58 (m, 4H), 7.42-7.31 (m, 6H), 7.26-7.22 (m, 1H), 4.31-4.29 (m, 1H), 3.73-3.59 (m, 2H), 3.48-3.17 (m, 10H), 2.30 (s, 3H).
MH+598.

Example 298

N-(3-(4-(2,3-dimethylphenyl)piperazin-1-yl)propyl)-5-methyl-2-phenyl-1-o-tolyl-1H-imidazole-4-carboxamide dihydrochloride $^1$H NMR (400 MHz, MeOH-d$_4$) δ 7.58-7.51 (m, 5H), 7.47-7.43 (m, 4H), 7.08 (t, J=7.6 Hz, 1H), 6.97 (t, J=8.4 Hz, 2H), 3.72-3.67 (m, 2H), 3.62-3.59 (m, 2H), 3.44-3.38 (m, 4H), 3.26-3.15 (m, 4H), 2.38 (s, 3H), 2.27 (s, 6H), 2.24-2.19 (m, 2H), 1.99 (s, 3H).
MH+522 (−2HCl).

Example 299

N-(3-(4-(3-chloro-2-methylphenyl)piperazin-1-yl)propyl)-5-methyl-2-phenyl-1-o-tolyl-1H-imidazole-4-carboxamide dihydrochloride $^1$H NMR (400 MHz, MeOH-d$_4$) δ 7.63 (d, J=6.4 Hz, 2H), 7.59-7.55 (m, 1H), 7.50-7.47 (m, 5H), 7.20-7.15 (m, 2H), 7.13-7.09 (m, 1H), 3.72-3.67 (m, 2H), 3.62-3.59 (m, 2H), 3.44-3.38 (m, 4H), 3.26-3.15 (m, 4H), 2.39 (s, 3H), 2.25 (s, 3H), 2.24-2.19 (m, 2H), 2.01 (s, 3H).
MH+542 (−2HCl).

Example 300

N-(3-(4-(2,3-dichlorophenyl)piperazin-1-yl)propyl)-5-methyl-2-phenyl-1-o-tolyl-1H-imidazole-4-carboxamide dihydrochloride $^1$H NMR (400 MHz, MeOH-d$_4$) δ 7.57-7.39 (m, 8H), 7.32-7.27 (m, 2H), 7.19-7.17 (m, 1H), 3.76-3.73 (m, 2H), 3.68-3.65 (m, 5H), 3.46-3.34 (m, 4H), 3.25-3.19 (m, 3H), 2.41 (s, 3H), 2.29-2.22 (m, 2H), 2.00 (s, 3H).
MH+562 (−2HCl).

Example 301

N-(3-(4-(2,3-dimethylphenyl)piperazin-1-yl)-2-hydroxypropyl)-5-methyl-2-phenyl-1-o-tolyl-1H-imidazole-4-carboxamide dihydrochloride $^1$H NMR (400 MHz, MeOH-d$_4$) δ 7.57-7.51 (m, 5H), 7.48-7.43 (m, 4H), 7.07 (t, J=7.6 Hz, 1H), 6.98 (t, J=8.0 Hz, 2H), 4.14-4.12 (m, 1H), 3.72-3.67 (m, 2H), 3.62-3.59 (m, 3H), 3.44-3.38 (m, 4H), 3.26-3.15 (m, 4H), 2.37 (s, 3H), 2.28 (s, 6H), 1.98 (s, 3H).
MH+538 (−2HCl).

Example 302

N-(3-(4-(3-chloro-2-methylphenyl)piperazin-1-yl)-2-hydroxypropyl)-5-methyl-2-phenyl-1-o-tolyl-1H-imidazole-4-carboxamide dihydrochloride $^1$H NMR (400 MHz, MeOH-d$_4$) δ 7.57-7.40 (m, 7H), 7.16 (d, 4.4 Hz, 2H), 7.10-7.07 (m, 1H), 4.38-4.37 (m, 1H), 3.76-3.73 (m, 2H), 3.68-3.65 (m, 1H), 3.62-3.58 (m, 3H), 3.56-3.36 (m, 3H), 3.29-3.15 (m, 3H), 2.37 (s, 3H), 2.17 (s, 3H), 1.97 (s, 3H).
MH+558 (−2HCl).

Example 303

N-(3-(4-(2,3-dichlorophenyl)piperazin-1-yl)-2-hydroxypropyl)-5-methyl-2-phenyl-1-o-tolyl-1H-imidazole-4-carboxamide dihydrochloride $^1$H NMR (400 MHz, MeOH-d$_4$) δ 7.57-7.41 (m, 6H), 7.17-7.15 (m, 2H), 7.10-7.07 (m, 1H), 4.37-4.37 (m, 1H), 3.75-3.71 (m, 2H), 3.69-3.62 (m, 3H), 3.62-3.58 (m, 3H), 3.56-3.37 (m, 3H), 3.27-3.15 (m, 4H), 2.36 (s, 3H), 1.99 (s, 3H). MH+578 (−2HCl).

Example 304

N-(3-(4-(3-chloro-2-methylphenyl)piperazin-1-yl)-2-hydroxypropyl)-2,5-dimethyl-1-(4-(trifluoromethyl)phenyl)-1H-imidazole-4-carboxamide dihydrochloride $^1$H NMR (400 MHz, CD$_3$OD) δ 8.03 (d, J=8.0 Hz, 2H), 7.78 (d, J=8.4 Hz, 2H), 7.17-7.15 (m, 2H), 7.10-7.06 (m, 1H), 4.38-4.34 (m, 1H), 3.75-3.72 (m, 2H), 3.60-3.49 (m, 2H), 3.47-3.36 (m, 4H), 3.29-3.10 (m, 4H), 2.48 (s, 3H), 2.37 (s, 3H), 2.36 (s, 3H). MH+550.

Example 305

N-(3-(4-(3-chloro-2-methylphenyl)piperazin-1-yl)propyl)-2,5-dimethyl-1-(4-(trifluoromethyl)phenyl)-1H-imidazole-4-carboxamide dihydrochloride $^1$H NMR (400 MHz, DMSO-d$_6$) δ 11.24 (br s, 1H), 8.82 (br s, 1H), 8.07 (d, J=8.4 Hz, 2H), 7.84 (d, J=8.4 Hz, 2H), 7.24-7.18 (m, 2H), 7.06 (dd, J=7.6, 2.4 Hz, 1H), 3.56-3.53 (m, 2H), 3.43-3.38 (m, 2H), 3.28-3.24 (m, 4H), 3.23-3.20 (m, 4H), 2.35 (s, 3H), 2.31 (s, 6H), 2.10-2.03 (m, 2H). MH+534.

Example 306

N-(3-(4-(3-chloro-2-methylphenyl)piperazin-1-yl)propyl)-5-methyl-2-phenyl-1-p-tolyl-1H-imidazole-4-carboxamide dihydrochloride $^1$H NMR (400 MHz, DMSO-d$_6$) δ 11.21 (br s, 1H), 8.83 (br s, 1H), 7.43-7.41 (m, 3H), 7.40-7.20 (m, 6H), 7.18-7.12 (m, 2H), 7.07-7.02 (m, 1H), 3.55-3.53 (m, 2H), 3.44-3.39 (m, 2H), 3.26-3.22 (m, 4H), 3.20-3.16 (m, 4H), 2.38 (s, 3H), 2.34 (s, 3H), 2.30 (s, 3H), 2.10-2.03 (m, 2H). MH+542.

Example 307

N-(3-(4-(3-chloro-2-methylphenyl)piperazin-1-yl)propyl)N,5-dimethyl-1,2-diphenyl-1H-imidazole-4-carboxamide dihydrochloride $^1$H NMR (400 MHz, MeOH-d$_4$) δ 7.61-7.41 (m, 8H), 7.16 (d, J=4.0 Hz, 2H), 7.08-7.07 (m, 1H), 3.74-3.72 (m, 4H), 3.67-3.28 (m, 4H), 3.27-3.09 (m, 4H), 2.86 (s, 3H), 2.37 (s, 3H). MH+542 (−2HCl).

Example 308

N-(3-(4-(2,3-dichlorophenyl)piperazin-1-yl)propyl)-N,5-dimethyl-1,2-diphenyl-1H-imidazole-4-carboxamide dihydrochloride $^1$H NMR (400 MHz, MeOH-d$_4$) δ 7.64-7.41 (m, 10H), 7.31-7.26 (m, 2H), 7.17-7.15 (m, 1H), 3.76-3.72 (m, 4H), 3.58-3.51 (m, 2H), 3.49-3.29 (m, 6H), 3.28-3.20 (m, 3H), 2.55 (s, 3H). MH+562 (−2HCl).

Example 309

N-(3-(4-(2,3-dimethylphenyl)piperazin-1-yl)propyl)-N,5-dimethyl-1,2-diphenyl-1H-imidazole-4-carboxamide dihydrochloride $^1$H NMR (400 MHz, MeOH-d$_4$) δ 7.64-7.40 (m, 10H), 7.32-7.27 (m, 2H), 7.19-7.15 (m, 1H), 3.77-3.72 (m, 4H), 3.57-3.53 (m, 2H), 3.50-3.29 (m, 6H), 3.28-3.20 (m, 3H), 2.84 (s, 3H), 2.55 (s, 3H), 2.10 (s, 3H), 2.04 (s, 3H). MH+522 (−2HCl).

Example 310

N-(3-(4-(3-chloro-2-methylphenyl)piperazin-1-yl)propyl)-1-cyclopentyl-N,2,5-trimethyl-1H-imidazole-4-carboxamide dihydrochloride $^1$H NMR (400 MHz, MeOH-d$_4$) δ 7.16 (d, J=4.8 Hz, 2H), 7.10-7.06 (m, 1H), 4.88-4.83 (m, 1H), 3.67-3.64 (m, 4H), 3.35-3.30 (m, 4H), 3.29-3.12 (m, 5H), 2.72 (s, 3H), 2.44 (s, 3H), 2.36 (s, 3H), 2.29-2.20 (m, 4H), 2.04-1.98 (m, 4H), 1.77-1.76 (m, 2H). MH+472 (−2HCl).

Example 311

1-cyclopentyl-N-(3-(4-(2,3-dichlorophenyl)piperazin-1-yl)propyl)-N,2,5-trimethyl-1H-imidazole-4-carboxamide dihydrochloride $^1$H NMR (400 MHz, MeOH-d$_4$) δ 7.31-7.26 (m, 2H), 7.17-7.15 (m, 1H), 4.86-4.81 (m, 1H), 3.69-3.65 (m, 4H), 3.37-3.31 (m, 4H), 3.29-3.14 (m, 6H), 2.46 (s, 3H), 2.31 (s, 3H), 2.28-2.21 (m, 4H), 2.01-1.96 (m, 4H), 1.75-1.71 (m, 2H). MH+492 (−2HCl).

Example 312

1-cyclopentyl-N-(3-(4-(2,3-dimethylphenyl)piperazin-1-yl)propyl)-N,2,5-trimethyl-1H-imidazole-4-carboxamide dihydrochloride $^1$H NMR (400 MHz, MeOH-d$_4$) δ 7.32-7.27 (m, 2H), 7.19-7.15 (m, 1H), 4.94-4.90 (m, 1H), 3.72-3.68 (m, 4H), 3.34-3.28 (m, 4H), 3.27-3.14 (m, 6H), 2.72 (s, 3H), 2.42 (s, 3H), 2.29 (s, 3H), 2.22-2.19 (m, 4H), 2.13 (s, 3H), 2.06 (s, 3H), 2.01-1.96 (m, 4H), 1.75-1.70 (m, 2H). MH+452 (−2HCl).

Example 313

N-(3-(4-(2,3-dimethylphenyl)piperazin-1-yl)propyl)-1-(4-methoxyphenyl)-N,5-dimethyl-2-phenyl-1H-imidazole-4-carboxamide dihydrochloride $^1$H NMR (400 MHz, DMSO-d$_6$) δ 11.10 (br s, 1H), 7.44-7.41 (m, 5H), 7.37 (d, J=10.4 Hz, 2H), 7.10-7.05 (m, 3H), 6.93 (d, J=7.6 Hz, 2H), 3.81 (s, 3H), 3.59-3.52 (m, 4H), 3.32-3.25 (m, 5H), 3.16-2.95 (m, 6H), 2.21 (s, 3H), 2.16-2.15 (m, 2H), 2.14 (s, 6H).
MH+552.

Example 314

1-(3-chlorophenyl)-N-(3-(4-(2,3-dimethylphenyl)piperazin-1-yl)propyl)-N,2,5-trimethyl-1H-imidazole-4-carboxamide dihydrochloride $^1$H NMR (400 MHz, DMSO-d$_6$) δ 11.22 (br s, 1H), 7.90 (br s, 1H), 7.78-7.70 (m, 3H), 7.07 (t, J=7.6 Hz, 1H), 6.93 (d, J=7.2 Hz, 1H), 6.89 (d, J=8.0 Hz, 1H), 3.61-3.56 (m, 4H), 3.27-3.24 (m, 5H), 3.19-3.12 (m, 6H), 2.42 (s, 3H), 2.22 (s, 3H), 2.17 (s, 3H), 2.16-2.14 (m, 2H), 2.08 (s, 3H).
MH+494.

Example 315

N-(3-(4-(3-chloro-2-methylphenyl)piperazin-1-yl)propyl)-1-(4-methoxyphenyl)-N,5-dimethyl-2-phenyl-1H-imidazole-4-carboxamide dihydrochloride $^1$H NMR (400 MHz, DMSO-d$_6$) δ 11.16 (br s, 1H), 7.49-7.40 (m, 7H), 7.22-7.18 (m, 2H), 7.11-7.09 (m, 3H), 3.81 (s, 3H), 3.59-3.52 (m, 4H), 3.34-3.30 (m, 5H), 3.19-3.16 (m, 6H), 2.30 (s, 3H), 2.17-2.16 (m, 2H), 2.14 (s, 3H).
MH+572.

Example 316

N-(3-(4-(3-chloro-2-methylphenyl)piperazin-1-yl)propyl)-1-(3-chlorophenyl)-N,2,5-trimethyl-1H-imidazole-4-carboxamide dihydrochloride $^1$H NMR (400 MHz, DMSO-d$_6$) δ 11.33 (br s, 1H), 7.91 (br s, 1H), 7.79-7.70 (m, 3H), 7.24-7.18 (m, 2H), 7.05 (d, J=6.4 Hz, 1H), 3.61-3.57 (m, 4H), 3.28-3.24 (m, 5H), 3.19-3.16 (m, 6H), 2.43 (s, 3H), 2.30 (s, 3H), 2.16-2.14 (m, 2H), 2.08 (s, 3H).
MH+514.

Example 317

1-(2-chlorophenyl)-N-(3-(4-(2,3-dimethylphenyl)piperazin-1-yl)propyl)-N,2,5-trimethyl-1H-imidazole-4-carboxamide dihydrochloride $^1$H NMR (400 MHz, DMSO-d$_6$) δ 7.03-7.01 (m, 1H), 6.96-6.92 (m, 2H), 6.88-6.85 (m, 1H), 6.28-6.24 (m, 1H), 6.18-6.13 (m, 2H), 2.89 (m, 4H), 2.57-2.53 (m, 2H), 2.52 (s, 3H), 2.42-2.35 (m, 6H), 1.66 (s, 3H), 1.44 (s, 6H), 1.44-1.40 (m, 2H), 1.33 (s, 3H).
MH+494.

Example 318

N-(3-(4-(3-chloro-2-methylphenyl)piperazin-1-yl)propyl)-1-(2-chlorophenyl)-N,2,5-trimethyl-1H-imidazole-4-carboxamide dihydrochloride $^1$H NMR (400 MHz, DMSO-d$_6$) δ 7.03-7.01 (m, 1H), 6.96-6.92 (m, 2H), 6.89-6.85 (m, 1H), 6.35 (d, J=4.4 Hz, 2H), 6.29-6.26 (m, 1H), 2.91-2.89 (m, 4H), 2.58-2.53 (m, 2H), 2.52 (s, 3H), 2.44-2.29 (m, 6H), 1.66 (s, 3H), 1.56 (s, 3H), 1.44-1.43 (m, 2H), 1.33 (s, 3H).
MH+514.

Example 319

1-(2-chlorophenyl)-N-(3-(4-(2,3-dichlorophenyl)piperazin-1-yl)propyl)-N,2,5-trimethyl-1H-imidazole-4-carboxamide dihydrochloride $^1$H NMR (400 MHz, DMSO-d$_6$) δ 7.03-7.01 (m, 1H), 6.96-6.92 (m, 2H), 6.89-6.85 (m, 1H), 6.50-6.47 (m, 2H), 6.38-6.35 (m, 1H), 2.94-2.89 (m, 4H), 2.74-2.70 (m, 2H), 2.55-2.52 (m, 2H), 2.52 (s, 3H), 2.46-2.40 (m, 4H), 1.66 (s, 3H), 1.44 (s, 2H), 1.33 (s, 3H).
MH+534.

Example 320

N-(3-(4-(2,3-dimethylphenyl)piperazin-1-yl)propyl)-N,2,5-trimethyl-1-phenyl-1H-imidazole-4-carboxamide dihydrochloride $^1$H NMR (400 MHz, DMSO-d$_6$) δ 11.41 (br s, 1H), 7.75-7.70 (m, 5H), 7.10-7.06 (m, 1H), 6.95-6.89 (m, 2H), 3.64-3.56 (m, 4H), 3.29-3.20 (m, 4H), 3.18-3.06 (m, 7H), 2.43 (s, 3H), 2.22 (s, 3H), 2.17 (s, 3H), 2.15-2.10 (m, 2H), 2.07 (s, 3H).
MH+460.

Example 321

N-(3-(4-(3-chloro-2-methylphenyl)piperazin-1-yl)propyl)-N,2,5-trimethyl-1-phenyl-1H-imidazole-4-carboxamide dihydrochloride $^1$H NMR (400 MHz, DMSO-d$_6$) δ 11.85 (br s, 1H), 7.70-7.65 (m, 5H), 7.24-7.18 (m, 2H), 7.07-7.04 (m, 1H), 3.62-3.57 (m, 4H), 3.29-3.26 (m, 4H), 3.20-3.16 (m, 7H), 2.42 (s, 3H), 2.31 (s, 3H), 2.17-2.13 (m, 2H), 2.07 (s, 3H).
MH+480.

Example 322

N-(3-(4-(2,3-dichlorophenyl)piperazin-1-yl)propyl)-N,2,5-trimethyl-1-phenyl-1H-imidazole-4-carboxamide dihydrochloride $^1$H NMR (400 MHz, DMSO-d$_6$) δ 11.51 (br s, 1H), 7.69-7.66 (m, 5H), 7.39-7.35 (m, 2H), 7.22-7.19 (m, 1H), 3.63-3.61 (m, 4H), 3.45-3.37 (m, 2H), 3.28-3.25 (m, 4H), 3.17-3.06 (m, 5H), 2.42 (s, 3H), 2.16-2.13 (m, 2H), 2.07 (s, 3H).
MH+500.

Example 323

N-(3-(4-(2,3-dimethylphenyl)piperazin-1-yl)propyl)-1-(4-fluorophenyl)-N,5-dimethyl-2-phenyl-1H-imidazole-4-carboxamide dihydrochloride $^1$H NMR (400 MHz, DMSO-d$_6$) δ 11.40 (br s, 1H), 7.68-7.66 (m, 2H), 7.51-7.31 (m, 7H), 7.09-7.05 (m, 1H), 6.94-6.83 (m, 2H), 3.88-0.82 (m, 1H), 3.63-3.52 (m, 5H), 3.32-2.95 (m, 9H), 2.22 (s, 3H), 2.17-2.16 (m, 2H), 2.15 (s, 3H).
MH+540.

Example 324

N-(3-(4-(3-chloro-2-methylphenyl)piperazin-1-yl)propyl)-1-(4-fluorophenyl)-N,5-dimethyl-2-phenyl-1H-imidazole-4-carboxamide dihydrochloride $^1$H NMR (400 MHz, DMSO-d$_6$) δ 11.40 (br s, 1H), 7.64-6.62 (m, 2H), 7.42-7.37 (m, 7H), 7.23-7.18 (m, 2H), 7.06-6.96 (m, 1H), 3.84-3.82 (m, 1H), 3.60-3.51 (m, 3H), 3.33-3.32 (m, 3H), 3.28-3.16 (m, 6H), 3.06-3.03 (m, 2H), 2.30-2.20 (m, 2H), 2.16 (s, 6H).
MH+560.

Example 325

N-(3-(4-(2,3-dichlorophenyl)piperazin-1-yl)propyl)-1-(4-fluorophenyl)-N,5-dimethyl-2-phenyl-1H-imidazole-4-carboxamide dihydrochloride $^1$H NMR (400 MHz, DMSO-d$_6$) δ 11.60 (br s, 1H), 7.66-7.64 (m, 2H), 7.44-7.42 (m, 7H), 7.38-7.35 (m, 2H), 7.21-7.11 (m, 1H), 3.83-3.82 (m, 1H), 3.63-3.61 (m, 3H), 3.44-3.42 (m, 2H), 3.33-3.12 (m, 7H), 3.06-3.03 (m, 2H), 2.22-2.20 (m, 2H), 2.16 (s, 3H).
MH+580.

Example 326

1-(2,3-dihydrobenzo[b][1,4]dioxin-6-yl)-N-(3-(4-(2,3-dimethylphenyl)piperazin-1-yl)propyl)-N,5-dimethyl-2-phenyl-1H-imidazole-4-carboxamide dihydrochloride $^1$H NMR (400 MHz, DMSO-d$_6$) δ 11.20 (br s, 1H), 7.48-7.39 (m, 5H), 7.15 (s, H), 7.09-6.82 (m, 5H), 4.31-4.28 (m, 4H), 3.82-3.81 (m, 1H), 3.59-3.51 (m, 3H), 3.31-3.26 (m, 4H), 3.17-3.12 (m, 5H), 3.03-2.96 (m, 2H), 2.22 (s, 3H), 2.18-2.16 (m, 3H), 2.15 (s, 6H).
MH+580.

Example 327

N-(3-(4-(3-chloro-2-methylphenyl)piperazin-1-yl)propyl)-1-(2,3-dihydrobenzo[b][1,4]dioxin-6-yl)-N,5-dimethyl-2-phenyl-1H-imidazole-4-carboxamide dihydrochloride $^1$H NMR (400 MHz, DMSO-d$_6$) δ 11.40 (br s, 1H), 7.49-7.41 (m, 5H), 7.24-7.18 (m, 3H), 7.04-6.97 (m, 3H), 4.31-4.28 (m, 4H), 3.82-3.80 (m, 1H), 3.60-3.51 (m, 3H), 3.30-3.29 (m, 3H), 3.19-3.16 (m, 6H), 3.06-3.03 (m, 2H), 2.30-2.17 (m, 2H), 2.15 (s, 6H).
MH+600.

Example 328

N-(3-(4-(2,3-dichlorophenyl)piperazin-1-yl)propyl)-1-(2,3-dihydrobenzo[b][1,4]dioxin-6-yl)-N,5-dimethyl-2-phenyl-1H-imidazole-4-carboxamide dihydrochloride

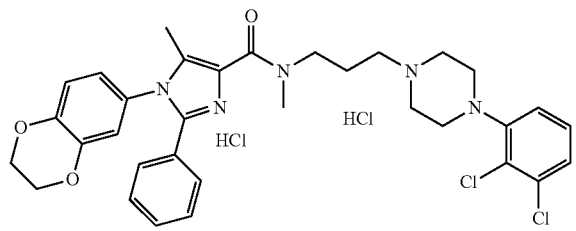 [SMILES: Cc1c(C(=O)N(C)CCCN2CCN(c3cccc(Cl)c3Cl)CC2)nc(-c2ccccc2)n1-c1ccc2c(c1)OCCO2 ; Cl ; Cl]

$^1$H NMR (400 MHz, DMSO-d$_6$) δ 11.45 (br s, 1H), 7.47-7.33 (m, 7H), 7.21-7.15 (m, 2H), 7.03-6.91 (m, 2H), 4.30-4.24 (m, 4H), 3.82-3.78 (m, 1H), 3.62-3.58 (m, 2H), 3.45-3.43 (m, 1H), 3.30-3.16 (m, 8H), 2.18-2.16 (m, 2H), 2.18 (s, 3H), 2.15 (s, 3H).
MH+620.

Example 329

(R)-1-(2,3-dihydrobenzo[b][1,4]dioxin-6-yl)-N-(3-(4-(2,3-dimethylphenyl)piperazin-1-yl)-2-hydroxypropyl)-2,5-dimethyl-1H-imidazole-4-carboxamide dihydrochloride

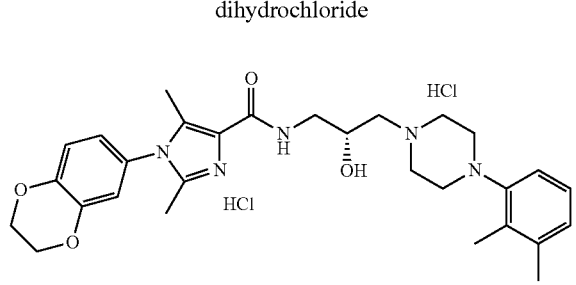

$^1$H NMR (400 MHz, DMSO-d$_6$) δ 10.36 (br s, 1H), 8.68 (br s, 1H), 7.16-7.06 (m, 3H), 7.00 (dd, J=8.8, 2.8 Hz, 1H), 6.94-6.89 (m, 2H), 4.34-4.33 (m, 4H), 4.28-4.24 (m, 1H), 3.65 (d, J=12.0 Hz, 1H), 3.56 (d, J=10.4 Hz, 1H), 3.44-3.30 (m, 6H), 3.22-3.12 (m, 4H), 2.35 (s, 3H), 2.29 (s, 3H), 2.22 (s, 3H), 2.17 (s, 3H).
MH+520.

Example 330

(R)—N-(3-(4-(3-chloro-2-methylphenyl)piperazin-1-yl)-2-hydroxypropyl)-1-(2,3-dihydrobenzo[b][1,4]dioxin-6-yl)-2,5-dimethyl-1H-imidazole-4-carboxamide dihydrochloride

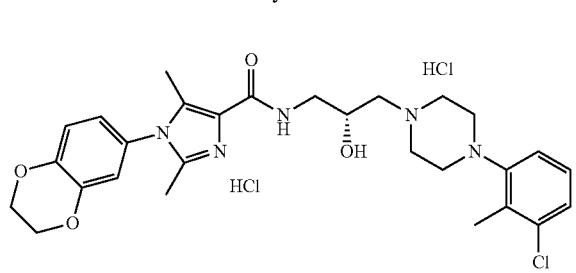

$^1$H NMR (400 MHz, DMSO-d$_6$) δ 10.56 (br s, 1H), 8.71 (br s, 1H), 7.24-7.16 (m, 3H), 7.13-7.10 (m, 1H), 7.08-6.99 (m,

2H), 4.34-4.33 (m, 4H), 4.29-4.26 (m, 1H), 3.67 (d, J=12.0 Hz, 1H), 3.57 (d, J=11.6 Hz, 1H), 3.46-3.39 (m, 2H), 3.38-3.32 (m, 2H), 3.22-3.12 (m, 6H), 2.35 (s, 3H), 2.30 (s, 3H), 2.29 (s, 3H).
MH+540.

Example 331

(R)—N-(3-(4-(2,3-dichlorophenyl)piperazin-1-yl)-2-hydroxypropyl)-1-(2,3-dihydrobenzo[b][1,4]dioxin-6-yl)-2,5-dimethyl-1H-imidazole-4-carboxamide dihydrochloride

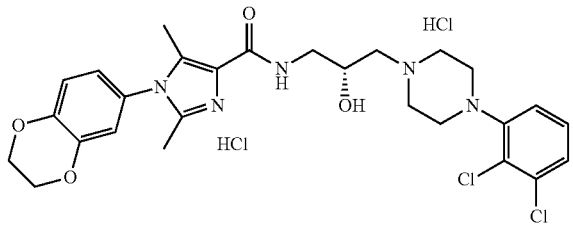 [SMILES: Cc1nc(C(=O)NC[C@@H](O)CN2CCN(c3cccc(Cl)c3Cl)CC2)c(C)n1-c1ccc2c(c1)OCCO2 ; Cl ; Cl]

$^1$H NMR (400 MHz, DMSO-d$_6$) δ 10.68 (br s, 1H), 8.69 (br s 1H), 7.39-7.34 (m, 2H), 7.21 (dd, J=7.2, 2.8 Hz, 1H), 7.16 (d, J=2.4 Hz, 1H), 7.11 (d, J=8.0 Hz, 1H), 7.00 (dd, J=8.4, 2.4 Hz, 1H), 4.34-4.33 (m, 4H), 4.30-4.25 (m, 1H), 3.70 (d, J=8.0 Hz, 1H), 3.60 (d, J=10.8 Hz, 1H), 3.46-3.38 (m, 4H), 3.36-3.18 (m, 6H), 2.35 (s, 3H), 2.29 (s, 3H).
MH+560.

Experimental Examples

Experimental Example 1

Measurement of Binding Affinity for Serotonin 5-HT$_{2A}$ and 5-HT$_{2C}$ Receptors Receptor binding affinities of the compounds for serotonin receptors were measured by the method described in the literature [Park W K et al., *Pharmacol Biochem Behav.* 2005, 82(2), 361-372].

For serotonin 5-HT$_{2A}$ binding, an aliquot of human recombinant serotonin 5-HT$_{2A}$ receptor (PerkinElmer Life and Analytical Sciences, USA) expressed in CHO-K1 cells (5 ug/well) and 1 nM [$^3$H]Ketanserin (PerkinElmer) were used in the presence of mianserin (20 uM) as a nonspecific. The reaction mixture was incubated for 60 min at 27° C. using 50 mM Tris-HCl (pH 7.4) buffer containing 4 mM CaCl$_2$ and 0.1% ascorbic acid, and harvested through filtermate A glass fiber filter (Wallac, Finland) presoaked in 0.5% polyethyleneimine (PEI) by microbeta filtermate-96 harvester (PerkinElmer) to terminate the reaction, and then washed with ice cold 50 mM Tris-HCl buffer solution (pH 7.4). The filter was then covered with MeltiLex, sealed in a sample bag, dried in an oven. The radioactivity retained in the filter was finally counted using MicroBeta Plus (Wallac).

The binding affinity (IC$_{50}$) of a compound for the receptor was calculated by computerized nonlinear regression analysis (GraphPad Prism Program, San Diego, USA) using 7-8 varied concentrations of the compound run in duplicate tubes.

For serotonin 5-HT$_{2C}$ binding, frozen membranes from stable CHO-K1 cell line expressing the human recombinant 5-HT$_{2C}$ receptor (PerkinElmer, 4 ug/well), [$^3$H]Mesulergine (Amersham, 1.3 nM) and test compounds were added into 50 mM Tris-HCl (pH 7.4) buffer containing 0.1% ascorbic acid and 4 mM CaCl$_2$. Nonspecific binding was determined using 100 uM mianserin. The incubations were performed for 60 min at 27° C., and these were terminated by rapid filtration through filtermate A glass fiber filter presoaked in 0.5% PEI. The results are shown in Table 1.

Experimental Example 2

Measurement of Binding Affinity for Serotonin Transporter

For serotonin transporter binding assays, a reaction mixture with a final volume of 0.25 ml was prepared by mixing a test compound, human serotonin transporter membrane expressed in HEK-293 cells (PerkinElmer, 5 ug/well), [$^3$H]Imipramine (PerkinElmer, 2 nM) and 50 mM Tris-HCl (pH 7.4) buffer containing 120 mM NaCl and 5 mM KCl. The reaction mixture was incubated for 30 min at 27° C., and harvested through filtermate A glass fiber filter presoaked in 0.5% PEI with ice cold 50 mM Tris-HCl buffer (pH 7.4) containing 0.9% NaCl. The results are shown in Table 1.

TABLE 1

Binding affinity to serotonin receptor 5-HT$_{2A}$, 5-HT$_{2C}$ and serotonin transporter (SERT): IC$_{50}$ (nM)

| Compound | 5-HT$_{2A}$ | 5-HT$_{2C}$ | SERT |
|---|---|---|---|
| Example 2 | 70.9 | 34.6 | 715 |
| Example 3 | 32.4 | 37.9 | 67.2 |
| Example 4 | 69 | 136 | 1093 |
| Example 6 | 18.6 | 12.1 | 10.2 |
| Example 7 | 21 | 189 | 13 |
| Example 8 | 31 | 66 | 129 |
| Example 9 | 39 | 109 | 82 |
| Example 10 | 20 | 88 | |
| Example 11 | 30 | 127 | |
| Example 12 | 48 | 140 | |
| Example 13 | 27 | 62 | |
| Example 88 | 1262 | 321 | |
| Example 89 | 2320 | 319 | |
| Example 90 | 127 | 146 | 298 |
| Example 92 | 217 | 10140 | 436 |
| Example 93 | 45.5 | 2221 | 447 |
| Example 94 | 1011 | 595 | 1262 |
| Example 96 | 840 | >10000 | 10.4 |
| Example 98 | 480 | 815 | 12.1 |
| Example 99 | 144 | 146 | 9 |
| Example 100 | 389 | 207 | 12 |
| Example 101 | 80 | 200 | 17 |
| Example 103 | 12 | 39 | 30 |
| Example 104 | 105 | 290 | 16 |
| Example 105 | 32 | 159 | 10 |
| Example 106 | 731 | 438 | 15 |
| Example 109 | 469 | 542 | 9 |
| Example 111 | 147 | 661 | 347 |
| Example 112 | 97 | 63 | 164 |
| Example 113 | 16 | 59 | 76 |
| Example 114 | 23 | 46 | |
| Example 115 | 29 | 27 | |
| Example 117 | 133 | 103 | |
| Example 121 | 504 | 635 | |
| Example 122 | 70.8 | 130 | |
| Example 132 | 297 | 388 | 12 |
| Example 133 | 137 | 463 | 323 |
| Example 134 | 19 | 101 | 42.6 |
| Example 135 | 15.2 | 204 | 10.2 |
| Example 136 | 63.1 | 544 | 51.8 |
| Example 137 | 126 | 425 | 6 |
| Example 138 | 23.1 | 93.6 | 12.4 |
| Example 139 | 646 | 1779 | 5.08 |
| Example 140 | 244 | 1031 | 10.3 |
| Example 141 | 264 | 737 | 786 |
| Example 142 | 20.1 | 534 | 232 |

TABLE 1-continued

Binding affinity to serotonin receptor 5-HT$_{2A}$, 5-HT$_{2C}$ and serotonin transporter (SERT): IC$_{50}$ (nM)

| Compound | 5-HT$_{2A}$ | 5-HT$_{2C}$ | SERT |
|---|---|---|---|
| Example 143 | 5.17 | 146 | 84 |
| Example 144 | 12.8 | 37.4 | 16.8 |
| Example 145 | 10.3 | 25.5 | 15.8 |
| Example 146 | 52.1 | 76.6 | 12.2 |
| Example 147 | 33 | 78.1 | 5.95 |
| Example 148 | 68.2 | 705 | 3.89 |
| Example 149 | 9.86 | 94.3 | 12 |
| Example 150 | 8.63 | 14.6 | 9.17 |
| Example 151 | 72.5 | 227 | 0.64 |
| Example 152 | 270 | 193 | 0.75 |
| Example 153 | 40 | 71 | 6.17 |
| Example 154 | 16.8 | 50.8 | 13 |
| Example 155 | 58.6 | 525 | 19.1 |
| Example 156 | 24 | 551 | 71.1 |
| Nefazodone[a] | 710 | 160 | 4 |

HU aNefazodone: Owens, M. J., et al., *J. Pharm. & Exp. Thera.*, 1997 (283) 1305

Experimental Example 3

Measurement of Anti-Depressants Activity in Forced Swimming Test

To evaluate the anti-depressants activity of the compounds, the inhibitory effects on immobility in forced swimming test in mice were measured according to the methods described by Porsolt et al. [Porsolt R D et al., *Eur J Pharmacol* 1978, 51, 291-294].

Each mouse was placed in a 25 cm glass cylinder (10 cm diameter) containing 15 cm of water maintained at 22±1° C., and was forced to swim for 10 min. 24 hours later, the mouse was replaced into the cylinder and the total duration of immobility was recorded during the last 5 min of the 6 min testing period. Mice are judged immobile when they float in an upright position and make only small movements to keep their head above water. Test drugs were suspended in 3% Tween 80 solution, and administered orally (po) 60 min before the testing. The results are shown in Table 2.

TABLE 2

Antidepressants activity-Immobility in forced swimming test on mice (unit: %)

| Compound | 100 mg/kg | 50 mg/kg | 25 mg/kg | 10 mg/kg |
|---|---|---|---|---|
| Example 2 | 20.0 ± 6.4 | | | |
| Example 3 | 78.1 ± 4.6 | | | |
| Example 4 | | 57.5 ± 7.2 | | |
| Example 6 | | 41.0 ± 4.1 | 45.7 ± 3.7 | 87.2 ± 3.7 |
| Example 7 | | 31.8 ± 3.3 | | |
| Example 8 | | 23.0 ± 7.1 | 57.8 ± 6.0 | 91.4 ± 4.4 |
| Example 9 | | 58.0 ± 7.8 | | |
| Example 10 | | 29.33 | | |
| Example 11 | | 26.70 | | |
| Example 12 | | 30.62 | | |
| Example 13 | | 19.78 | | |
| Example 14 | | 62.07 | | |
| Example 15 | | | 64.76 ± 14.1 | |
| Example 88 | 99.6 ± 4.6 | | | |
| Example 89 | 37.8 ± 7.7 | | | |
| Example 90 | 48.2 | | | |
| Example 92 | | 55.5 ± 11.9 | | |
| Example 93 | | 61.7 ± 9.6 | | |
| Example 94 | | | 89.3 ± 7.5 | |
| Example 95 | | 76.6 ± 8.2 | 79.4 ± 5.0 | |
| Example 96 | | | 89.5 ± 7.0 | |
| Example 97 | | 94.1 ± 6.8 | 72.8 ± 8.2 | |

TABLE 2-continued

Antidepressants activity-Immobility in forced swimming test on mice (unit: %)

| Compound | 100 mg/kg | 50 mg/kg | 25 mg/kg | 10 mg/kg |
|---|---|---|---|---|
| Example 98 | | | 88.1 ± 4.6 | |
| Example 99 | | 68.5 ± 10.6 | 69.7 ± 11.1 | |
| Example 100 | | | 84.6 ± 5.4 | |
| Example 101 | | | 85.5 ± 7.2 | |
| Example 102 | | 73.8 ± 9.7 | 57.0 ± 12.8 | |
| Example 103 | | | 85.1 ± 10.4 | |
| Example 104 | | | 91.4 ± 8.7 | |
| Example 105 | | | 93.3 ± 6.7 | |
| Example 106 | | 79.8 ± 5.9 | 71.5 ± 8.2 | |
| Example 107 | | | 103.5 ± 4.2 | |
| Example 108 | | 71.2 ± 12.1 | 75.9 ± 9.8 | |
| Example 109 | | 73.6 ± 5.6 | 78.9 ± 12.4 | |
| Example 110 | | 63.3 ± 7.6 | 76.5 ± 13.4 | |
| Example 111 | | | 89.9 ± 14.2 | |
| Example 112 | | | 81.1 ± 12.6 | |
| Example 113 | | 73.8 ± 6.3 | 76.0 ± 10.2 | |
| Example 114 | | | 83.6 ± 11.3 | |
| Example 115 | | | 95.2 ± 4.7 | |
| Example 116 | | | 84.3 ± 7.1 | |
| Example 117 | | 75.7 ± 6.9 | 72.3 ± 9.3 | |
| Example 121 | | 75.1 ± 10.3 | 77.8 ± 13.6 | |
| Example 123 | | | 71.9 ± 10.6 | |
| Example 124 | | | 80.8 ± 9.1 | |
| Example 125 | | | 40.9 ± 12.6 | |
| Example 126 | | | 49.5 ± 8.8 | |
| Example 127 | | | 62.1 ± 8.4 | |
| Example 128 | | | 89.7 ± 4.8 | |
| Example 129 | | | 81.8 ± 5.3 | |
| Example 131 | | | 93.9 ± 5.0 | |
| Fluoxetine[b] | 59.5 | 70.4 | | |

[b]Immobility in forced swimming test on mice of Fluoxetine was measured via in-house assay As shown in Tables 1 and 2, the inventive compounds of formula (I) exhibited good in vitro binding affinities to serotonin receptor 5-HT$_{2A}$, 5-HT$_{2C}$ and/or inhibitory activity against serotonin transporter (SERT), and in vivo anti-depressant activity on FST (forced swimming test) animal model as well. Thus, the current inventive compounds are useful in preventing or treating depressive disorders.

While the invention has been described with respect to the above specific embodiments, it should be recognized that various modifications and changes may be made to the invention by those skilled in the art which also fall within the scope of the invention as defined by the appended claims.

What is claimed is:

1. A compound or a pharmaceutically acceptable salt thereof selected from the group consisting of:
   1-(4-chlorophenyl)-N-(3-(4-(2,3-dichlorophenyl)piperazin-1-yl)-2-hydroxypropyl)-2-propyl-1H-imidazole-4-carboxamide;
   1-(4-chlorophenyl)-N-(3-(4-(2,3-dichlorophenyl)piperazin-1-yl)propyl)-2-propyl-1H-imidazole-4-carboxamide dihydrochloride;
   1-(4-chlorophenyl)-N-(3-(4-(2,3-dimethylphenyl)piperazin-1-yl)propyl)-2-propyl-1H-imidazole-4-carboxamide;
   1-(4-chlorophenyl)-N-(2-(4-(2,3-dichlorophenyl)piperazin-1-yl)ethyl)-2-propyl-1H-imidazole-4-carboxamide;
   N-(3-(4-(2,3-dichlorophenyl)piperazin-1-yl)-2-hydroxypropyl)-2,5-dimethyl-1-phenyl-1H-imidazole-4-carboxamide;
   N-(3-(4-(2,3-dichlorophenyl)piperazin-1-yl)propyl)-2,5-dimethyl-1-phenyl-1H-imidazole-4-carboxamide;

N-(3-(4-(2,3-dichlorophenyl)piperazin-1-yl)propyl)-5-methyl-1-phenyl-2-propyl-1H-imidazole-4-carboxamide dihydrochloride;
N-(2-(4-(2,3-dichlorophenyl)piperazin-1-yl)ethyl)-2,5-dimethyl-1-phenyl-1H-imidazole-4-carboxamide;
N-(2-(4-(2,3-dichlorophenyl)piperazin-1-yl)ethyl)-5-methyl-1-phenyl-2-propyl-1H-imidazole-4-carboxamide;
N-(3-(4-(2,3-dichlorophenyl)piperazin-1-yl)propyl)-1-(4-methoxyphenyl)-2,5-dimethyl-1H-imidazole-4-carboxamide;
1-(4-chlorophenyl)-N-(3-(4-(2,3-dichlorophenyl)piperazin-1-yl)propyl)-2,5-dimethyl-1H-imidazole-4-carboxamide;
N-(3-(4-(2,3-dichlorophenyl)piperazin-1-yl)propyl)-2-ethyl-5-methyl-1-phenyl-1H-imidazole-4-carboxamide;
N-(2-(4-(2,3-dichlorophenyl)piperazin-1-yl)ethyl)-2-ethyl-5-methyl-1-phenyl-1H-imidazole-4-carboxamide;
N-(2-(4-(2,3-dimethylphenyl)piperazin-1-yl)ethyl)-2,5-dimethyl-1-phenyl-1H-imidazole-4-carboxamide;
N-(3-(4-(2,3-dimethylphenyl)piperazin-1-yl)propyl)-2,5-dimethyl-1-phenyl-1H-imidazole-4-carboxamide;
N-(3-(4-(2,3-dimethylphenyl)piperazin-1-yl)propyl)-2-ethyl-5-methyl-1-phenyl-1H-imidazole-4-carboxamide;
N-(3-(4-(2,3-dimethylphenyl)piperazin-1-yl)propyl)-5-methyl-1-phenyl-2-propyl-1H-imidazole-4-carboxamide dihydrochloride;
N-(2-(4-(2,3-dimethylphenyl)piperazin-1-yl)ethyl)-2-ethyl-5-methyl-1-phenyl-1H-imidazole-4-carboxamide;
N-(2-(4-(2,3-dimethylphenyl)piperazin-1-yl)ethyl)-5-methyl-1-phenyl-2-propyl-1H-imidazole-4-carboxamide dihydrochloride;
N-(3-(4-(2,3-dichlorophenyl)piperazin-1-yl)propyl)-1-(4-fluorophenyl)-2,5-dimethyl-1H-imidazole-4-carboxamide;
N-(2-(4-(2,3-dichlorophenyl)piperazin-1-yl)ethyl)-1-(4-fluorophenyl)-2,5-dimethyl-1H-imidazole-4-carboxamide;
1-(4-chlorophenyl)-N-(3-(4-(2,3-dimethylphenyl)piperazin-1-yl)propyl)-2,5-dimethyl-1H-imidazole-4-carboxamide;
N-(3-(4-(2,3-dichlorophenyl)piperazin-1-yl)-2-hydroxypropyl)-2-ethyl-5-methyl-1-phenyl-1H-imidazole-4-carboxamide;
N-(3-(4-(2,3-dichlorophenyl)piperazin-1-yl)-2-hydroxypropyl)-5-methyl-1-phenyl-2-propyl-1H-imidazole-4-carboxamide;
1-(4-chlorophenyl)-N-(3-(4-(2,3-dichlorophenyl)piperazin-1-yl)propyl)-2-ethyl-5-methyl-1H-imidazole-4-carboxamide;
N-(3-(4-(2,3-dichlorophenyl)piperazin-1-yl)-2-hydroxypropyl)-1-(4-fluorophenyl)-2,5-dimethyl-1H-imidazole-4-carboxamide;
1-(4-chlorophenyl)-N-(2-(4-(2,3-dichlorophenyl)piperazin-1-yl)ethyl)-2,5-dimethyl-1H-imidazole-4-carboxamide;
1-(4-chlorophenyl)-N-(2-(4-(2,3-dichlorophenyl)piperazin-1-yl)ethyl)-2-ethyl-5-methyl-1H-imidazole-4-carboxamide;
N-(3-(4-(2,3-dichlorophenyl)piperazin-1-yl)propyl)-2,5-dimethyl-1-p-tolyl-1H-imidazole-4-carboxamide;
N-(2-(4-(2,3-dichlorophenyl)piperazin-1-yl)ethyl)-2,5-dimethyl-1-p-tolyl-1H-imidazole-4-carboxamide;
N-(3-(4-(2,3-dichlorophenyl)piperazin-1-yl)-2-hydroxypropyl)-2,5-dimethyl-1-p-tolyl-1H-imidazole-4-carboxamide;
1-(4-chlorophenyl)-N-(3-(4-(2,3-dichlorophenyl)piperazin-1-yl)-2-hydroxypropyl)-2,5-dimethyl-1H-imidazole-4-carboxamide;
1-(4-chlorophenyl)-N-(3-(4-(2,3-dichlorophenyl)piperazin-1-yl)-2-hydroxypropyl)-2-ethyl-5-methyl-1H-imidazole-4-carboxamide;
N-(3-(4-(2,3-dimethylphenyl)piperazin-1-yl)propyl)-1-(4-fluorophenyl)-2,5-dimethyl-1H-imidazole-4-carboxamide;
N-(3-(4-(2,3-dimethylphenyl)piperazin-1-yl)-2-hydroxypropyl)-1-(4-fluorophenyl)-2,5-dimethyl-1H-imidazole-4-carboxamide;
N-(3-(4-(2,3-dimethylphenyl)piperazin-1-yl)-2-hydroxypropyl)-2,5-dimethyl-1-phenyl-1H-imidazole-4-carboxamide;
N-(3-(4-(2,3-dimethylphenyl)piperazin-1-yl)propyl)-2,5-dimethyl-1-(4-(trifluoromethyl)phenyl)-1H-imidazole-4-carboxamide;
1-(benzo [d][1,3]dioxol-5-yl)-N-(3-(4-(2,3-dimethylphenyl)piperazin-1-yl)propyl)-2,5-dimethyl-1H-imidazole-4-carboxamide;
1-(benzo [d][1,3]dioxol-5-yl)-N-(3-(4-(2,3-dimethylphenyl)piperazin-1-yl)-2-hydroxypropyl)-2,5-dimethyl-1H-imidazole-4-carboxamide;
1-(2,3-dihydrobenz o [b][1,4]dioxin-6-yl)-N-(3-(4-(2,3-dimethylphenyl) piperazin-1-yl)prop yl)-2,5-dimethyl-1H-imidazole-4-carboxamide;
1-(2,3-dihydrobenz o [b][1,4]dioxin-6-yl)-N-(3-(4-(2,3-dimethylphenyl) piperazin-1-yl)-2-hydroxypropyl)-2,5-dimethyl-1H-imidazole-4-carboxamide;
N-(2-(4-(2,3-dichlorophenyl)piperazin-1-yl)ethyl)-1-(4-methoxyphenyl)-2,5-dimethyl-1H-imidazole-4-carboxamide;
N-(3-(4-(2,3-dichlorophenyl)piperazin-1- yl)-2hydroxypropyl)-1-(4-methoxyphenyl)-2,5-dimethyl-1H-imidazole-4-carboxamide;
N-(3-(4-(2,3-dichlorophenyl)piperazin-1-yl)prop yl)-2-ethyl-1-(4-methoxyphenyl)-5-methyl-1H-imidazole-4-carboxamide;
N-(3-(4-(2,3-dichlorophenyl)piperazin-1-yl)-2-hydroxypropyl)-2-ethyl-1-(4-methoxyphenyl)-5-methyl-1H-imidazole-4-carboxamide;
N-(2-(4-(2,3-dimethylphenyl)piperazin-1-yl)ethyl)-1-(4-methoxyphenyl)-2,5-dimethyl-1H-imidazole-4-carboxamide;
N-(3-(4-(2,3-dimethylphenyl)piperazin-1-yl)propyl)-1-(4-methoxyphenyl)-2,5-dimethyl-1H-imidazole-4-carboxamide;
1-(3-chlorophenyl)-N-(3-(4-(2,3-dimethylphenyl)piperazin-1-yl)propyl)-2,5-dimethyl-1H-imidazole-4-carboxamide;
1-(3-chlorophenyl)-N-(3-(4-(2,3-dimethylphenyl)piperazin-1-yl)-2-hydroxypropyl)-2,5-dimethyl-1H-imidazole-4-carboxamide;
N-(3-(4-(3-chloro-2-methylphenyl)piperazin-1-yl)propyl)-1-(3-chlorophenyl)-2,5-dimethyl-1H-imidazole-4-carboxamide;
N-(3-(4-(3-chloro-2-methylphenyl)piperazin-1-yl)-2-hydroxypropyl)-1-(3-chlorophenyl)-2,5-dimethyl-1H-imidazole-4-carboxamide;
N-(3-(4-(2,3-dimethylphenyl)piperazin-1-yl)propyl)-1-(3-fluorophenyl)-2,5-dimethyl-1H-imidazole-4-carboxamide;

N-(3-(4-(2,3-dimethylphenyl)piperazin-1-yl)-2-hydroxypropyl)-1-(3-fluorophenyl)-2,5-dimethyl-1H-imidazole-4-carboxamide;

1-(3,4-dimethoxyphenyl)-N-(3-(4-(2,3-dimethylphenyl)piperazin-1-yl)propyl)-2,5-dimethyl-1H-imidazole-4-carboxamide;

1-(3,4-dimethoxyphenyl)-N-(3-(4-(2,3-dimethylphenyl)piperazin-1-yl)-2-hydroxypropyl)-2,5-dimethyl-1H-imidazole-4-carboxamide;

N-(3-(4-(2,3-dimethylphenyl)piperazin-1-yl)-2-hydroxypropyl)-1-(4-methoxyphenyl)-2,5-dimethyl-1H-imidazole-4-carboxamide;

N-(3-(4-(2,3-dimethylphenyl)piperazin-1-yl)propyl)-2,5-dimethyl-1-(4-(methylthio)phenyl)-1H-imidazole-4-carboxamide;

N-(3-(4-(2,3-dimethylphenyl)piperazin-1-yl)-2-hydroxypropyl)-2,5-dimethyl-1-(4-(methylthio)phenyl)-1H-imidazole-4-carboxamide;

N-(3-(4-(2,3-dimethylphenyl)piperazin-1-yl)propyl)-1-(3-methoxyphenyl)-2,5-dimethyl-1H-imidazole-4-carboxamide;

N-(3-(4-(2,3-dimethylphenyl)piperazin-1-yl)-2-hydroxypropyl)-1-(3-methoxyphenyl)-2,5-dimethyl-1H-imidazole-4-carboxamide;

1-(2,4-dimethoxyphenyl)-N-(3-(4-(2,3-dimethylphenyl)piperazin-1-yl)propyl)-2,5-dimethyl-1H-imidazole-4-carboxamide;

1-(2,4-dimethoxyphenyl)-N-(3-(4-(2,3-dimethylphenyl)piperazin-1-yl)-2-hydroxypropyl)-2,5-dimethyl-1H-imidazole-4-carboxamide;

(S)-N-(3-(4-(2,3-dichlorophenyl)piperazin-1-yl)-2-hydroxypropyl)-2,5-dimethyl-1-phenyl-1H-imidazole-4-carboxamide;

(S)-N-(3-(4-(2,3-dichlorophenyl)piperazin-1-yl)-2-hydroxypropyl)-5-methyl-1-phenyl-2-propyl-1H-imidazole-4-carboxamide;

N-(3-(4-(2,3-dichlorophenyl)piperazin-1-yl)-2,2-difluoropropyl)-2,5-dimethyl-1-phenyl-1H-imidazole-4-carboxamide;

N-(3-(4-(2,3-dichlorophenyl)piperazin-1-yl)-2,2-difluoropropyl)-5-methyl-1-phenyl-2-propyl-1H-imidazole-4-carboxamide;

N-(3-(4-(2,3-dimethylphenyl)piperazin-1-yl)propyl)-1-(2-fluorophenyl)-2,5-dimethyl-1H-imidazole-4-carboxamide;

N-(3-(4-(2,3-dimethylphenyl)piperazin-1-yl)-2-hydroxypropyl)-1-(2-fluorophenyl)-2,5-dimethyl-1H-imidazole-4-carboxamide;

N-(2-(4-(3-chloro-2-fluorophenyl)piperazin-1-yl)ethyl)-2,5-dimethyl-1-phenyl-1H-imidazole-4-carboxamide;

N-(3-(4-(3-chloro-2-fluorophenyl)piperazin-1-yl)propyl)-2,5-dimethyl-1-phenyl-1H-imidazole-4-carboxamide;

N-(2-(4-(3-chloro-2-methylphenyl)piperazin-1-yl)ethyl)-2,5-dimethyl-1-phenyl-1H-imidazole-4-carboxamide;

N-(3-(4-(3-chloro-2-methylphenyl)piperazin-1-yl)propyl)-2,5-dimethyl-1-phenyl-1H-imidazole-4-carboxamide;

2,5-dimethyl-N-(2-(4-(2-methylquinolin-8-yl)piperazin-1-yl)ethyl)-1-phenyl-1H-imidazole-4-carboxamide;

2,5-dimethyl-1-phenyl-N-(2-(4-(quinolin-8-yl)piperazin-1-yl)ethyl)-1H-imidazole-4-carboxamide;

N-(3-(4-(3-chloro-2-methylphenyl)piperazin-1-yl)-2-hydroxypropyl)-2,5-dimethyl-1-phenyl-1H-imidazole-4-carboxamide;

1-cyclopentyl-N-(3-(4-(2,3-dimethylphenyl)piperazin-1-yl)propyl)-2,5-dimethyl-1H-imidazole-4-carboxamide;

1-cyclopentyl-N-(3-(4-(2,3-dimethylphenyl)piperazin-1-yl)-2-hydroxypropyl)-2,5-dimethyl-1H-imidazole-4-carboxamide;

N-(3-(4-(3-chloro-2-methylphenyl)piperazin-1-yl)propyl)-1-cyclopentyl-2,5-dimethyl-1H-imidazole-4-carboxamide;

N-(3-(4-(3-chloro-2-methylphenyl)piperazin-1-yl)-2-hydroxypropyl)-1-cyclopentyl-2,5-dimethyl-1H-imidazole-4-carboxamide;

1-cyclopentyl-N-(4-(4-(2,3-dimethylphenyl)piperazin-1-yl)butyl)-2,5-dimethyl-1H-imidazole-4-carboxamide;

1-cyclopentyl-N-(2-(4-(2,3-dichlorophenyl)piperazin-1-yl)ethyl)-2,5-dimethyl-1H-imidazole-4-carboxamide;

N-(3-(4-(2,3-dimethylphenyl)piperazin-1-yl)-2-hydroxypropyl)-1-(4-fluorophenyl)-5-methyl-2-phenyl-1H-imidazole-4-carboxamide;

N-(3-(4-(2,3-dimethylphenyl)piperazin-1-yl)propyl)-1-(4-fluorophenyl)-5-methyl-2-phenyl-1H-imidazole-4-carboxamide;

N-(3-(4-(3-chloro-2-methylphenyl)piperazin-1-yl)-2-hydroxypropyl)-1-(4-fluorophenyl)-5-methyl-2-phenyl-1H-imidazole-4-carboxamide;

N-(3-(4-(3-chloro-2-methylphenyl)piperazin-1-yl)propyl)-1-(4-fluorophenyl)-5-methyl-2-phenyl-1H-imidazole-4-carboxamide;

N-(3-(4-(2,3-dimethylphenyl)piperazin-1-yl)propyl)-5-methyl-1,2-diphenyl-1H-imidazole-4-carboxamide;

N-(3-(4-(3-chloro-2-methylphenyl)piperazin-1-yl)propyl)-5-methyl-1,2-diphenyl-1H-imidazole-4-carboxamide;

1-(4-bromophenyl)-N-(3-(4-(3-chlorophenyl)piperazin-1-yl)propyl)-2-(2,4-dichlorophenyl)-5-ethyl-1H-imidazole-4-carboxamide;

1-(4-bromophenyl)-2-(2,4-dichlorophenyl)-N-(3-(4-(2,3-dichlorophenyl)piperazin-1-yl)propyl)-5-ethyl-1H-imidazole-4-carboxamide;

1-(4-bromophenyl)-2-(2,4-dichlorophenyl)-N-(3-(4-(2,3-dimethylphenyl)piperazin-1-yl)propyl)-5-ethyl-1H-imidazole-4-carboxamide;

5-((1H-1,2,4-triazol-1-yl)methyl)-N-(3-(4-(3-chloro-2-methylphenyl)piperazin-1-yl)propyl)-1,2-diphenyl-1H-imidazole-4-carboxamide;

N-(3-(4-(2,3-dimethylphenyl)piperazin-1-yl)propyl)-1-isobutyl-2,5-dimethyl-1H-imidazole-4-carboxamide;

N-(3-(4-(3-chloro-2-methylphenyl)piperazin-1-yl)propyl)-1-isobutyl-2,5-dimethyl-1H-imidazole-4-carboxamide N-(3-(4-(2,3-dimethylphenyl)piperazin-1-yl)-2-hydroxypropyl)-1-isobutyl-2,5-dimethyl-1H-imidazole-4-carboxamide N-(3-(4-(2,3-dimethylphenyl)piperazin-1-yl)propyl)-2,5-dimethyl-1-propyl-1H-imidazole-4-carboxamide;

N-(3-(4-(2,3-dimethylphenyl)piperazin-1-yl)-2-hydroxypropyl)-2,5-dimethyl-1-propyl-1H-imidazole-4-carboxamide;

N-(3-(4-(3-chloro-2-methylphenyl)piperazin-1-yl)propyl)-2,5-dimethyl-1-propyl-1H-imidazole-4-carboxamide;

N-(3-(4-(3-chloro-2-methylphenyl)piperazin-1-yl)-2-hydroxypropyl)-2,5-dimethyl-1-propyl-1H-imidazole-4-carboxamide;

N-(3-(4-(2,3-dimethylphenyl)piperazin-1-yl)propyl)-1-(2-methoxyphenyl)-2,5-dimethyl-1H-imidazole-4-carboxamide;

N-(3-(4-(2,3-dimethylphenyl)piperazin-1-yl)-2-hydroxypropyl)-1-(2-methoxyphenyl)-2,5-dimethyl-1H-imidazole-4-carboxamide;

1-(2-chlorophenyl)-N-(3-(4-(2,3-dimethylphenyl)piperazin-1-yl)propyl)-2,5-dimethyl-1H-imidazole-4-carboxamide;

1-(2-chlorophenyl)-N-(3-(4-(2,3-dimethylphenyl)piperazin-1-yl)-2-hydroxypropyl)-2,5-dimethyl-1H-imidazole-4-carboxamide;

1-(2-chlorophenyl)-N-(4-(4-(2,3-dimethylphenyl)piperazin-1-yl)butyl)-2,5-dimethyl-1H-imidazole-4-carboxamide;

N-(3-(4-(2,3-dimethylphenyl)piperazin-1-yl)propyl)-2-isopropyl-5-methyl-1-phenyl-1H-imidazole-4-carboxamide;

1-(3,5-dimethoxyphenyl)-N-(3-(4-(2,3-dimethylphenyl)piperazin-l-yl)propyl)-2,5-dimethyl-1H-imidazole-4-carboxamide;

N-(3-(4-(2,3-dimethylphenyl)piperazin-1-yl)-2-hydroxypropyl)-2-isopropyl-5-methyl-1-phenyl-1H-imidazole-4-carboxamide;

1-(3,5-dimethoxyphenyl)-N-(3-(4-(2,3-dimethylphenyl)piperazin-1-yl)-2-hydroxypropyl)-2,5-dimethyl-1H-imidazole-4-carboxamide;

N-(3-(4-(2,3-dimethylphenyl)piperazin-1-yl)-2-hydroxypropyl)-2,5-dimethyl-1-(4-(trifluoromethyl)phenyl)-1H-imidazole-4-carboxamide;

N-(3-(4-(2,3-dimethylphenyl)piperazin-1-yl)-2-hydroxypropyl)-2-ethyl-5-methyl-1-phenyl-1H-imidazole-4-carboxamide;

N-(3-(4-(2,3-dimethylphenyl)piperazin-1-yl)-2-hydroxypropyl)-5-methyl-1-phenyl-2-propyl-1H-imidazole-4-carboxamide;

1-(4-chlorophenyl)-N-(3-(4-(2,3-dimethylphenyl)piperazin-1-yl)-2-hydroxypropyl)-2-propyl-1H-imidazole-4-carboxamide;

1-(3,5-dimethoxyphenyl)-N-(2-(4-(2,3-dimethylphenyl)piperazin-1-yl)ethyl)-2,5-dimethyl-1H-imidazole-4-carboxamide;

N-(2-(4-(2,3-dimethylphenyl)piperazin-1-yl)ethyl)-2-isopropyl-5-methyl-1-phenyl-1H-imidazole-4-carboxamide;

N-(2-(4-(2,3-dimethylphenyl)piperazin-1-yl)ethyl)-1-(4-fluorophenyl)-2,5-dimethyl-1H-imidazole-4-carboxamide;

1-(benzo[d][1,3]dioxol-5-yl)-N-(2-(4-(2,3-dimethylphenyl)piperazin-1-yl)ethyl)-2,5-dimethyl-1H-imidazole-4-carboxamide;

1-(2,3-dihydrobenzo[b][1,4]dioxin-6-yl)-N-(2-(4-(2,3-dimethylphenyl)piperazin-1-yl)ethyl)-2,5-dimethyl-1H-imidazole-4-carboxamide;

N-(3-(4-(2,3-dimethylphenyl)piperazin-1-yl)propyl)-1-phenyl-2-propyl-1H-imidazole-4-carboxamide;

N-(3-(4-(2,3-dichlorophenyl)piperazin-1-yl)propyl)-1-phenyl-2-propyl-1H-imidazole-4-carboxamide;

N-(2-(4-(2,3-dichlorophenyl)piperazin-1-yl)ethyl)-1-phenyl-2-propyl-1H-imidazole-4-carboxamide;

N-(2-(4-(2,3-dimethylphenyl)piperazin-1-yl)ethyl)-1-phenyl-2-propyl-1H-imidazole-4-carboxamide;

N-(3-(4-(2,3-dimethylphenyl)piperazin-1-yl)-2-hydroxypropyl)-1-phenyl-2-propyl-lH-imidazole-4-carboxamide;

N-(3-(4-(2,3-dimethylphenyl)piperazin-1-yl)propyl)-1-(4-methoxyphenyl)-5-methyl-2-propyl-1H-imidazole-4-carboxamide;

N-(2-(4-(2,3-dimethylphenyl)piperazin-1-yl)ethyl)-1-(4-methoxyphenyl)-5-methyl-2-propyl-1H-imidazole-4-carboxamide;

N-(3-(4-(2,3-dimethylphenyl)piperazin-1-yl)propyl)-2,5-dimethyl-1-(quinolin-6-yl)-1H-imidazole-4-carboxamide;

N-(3-(4-(2,3-dichlorophenyl)piperazin-1-yl)-2-hydroxypropyl)-2,5-dimethyl-1-(quinolin-6-yl)-1H-imidazole-4-carboxamide;

N-(3-(4-(2,3-dichlorophenyl)piperazin-1-yl)-2-hydroxypropyl)-1-phenyl-2-propyl-1H-imidazole-4-carboxamide;

N-(3-(4-(2,3-dichlorophenyl)piperazin-1-yl)-2-hydroxypropyl)-1-(4-fluorophenyl)-2-propyl-1H-imidazole-4-carboxamide;

N-(3-(4-(2,3-dimethylphenyl)piperazin-1-yl)-2-hydroxypropyl)-1-(4-fluorophenyl)-2-propyl-1H-imidazole-4-carboxamide;

N-(3-(4-(2,3-dimethylphenyl)piperazin-1-yl)propyl)-1-(4-fluorophenyl)-2-propyl-1H-imidazole-4-carboxamide;

N-(3-(4-(2,3-dichlorophenyl)piperazin-1-yl)-2-hydroxypropyl)-1,2-diphenyl-lH-imidazole-4-carboxamide;

N-(3-(4-(2,3-dimethylphenyl)piperazin-1-yl)propyl)-1,2-diphenyl-1H-imidazole-4-carboxamide;

N-(3-(4-(2,3-dimethylphenyl)piperazin-1-yl)propyl)-2,5-dimethyl-1-(pyridin-2-yl)-1H-imidazole-4-carboxamide trihydrochloride;

N-(3-(4-(2,3-dichlorophenyl)piperazin-1-yl)-2-hydroxypropyl)-1-(4-methoxyphenyl)-2-phenyl-1H-imidazole-4-carboxamide;

N-(3-(4-(2,3-dimethylphenyl)piperazin-1-yl)propyl)-1-(4-methoxyphenyl)-2-phenyl-1H-imidazole-4-carboxamide ;

N-(3-(4-(3-chloro-2-methylphenyl)piperazin-1-yl)propyl)-1-(4-methoxyphenyl)-5-methyl-2-propyl-1H-imidazole-4-carboxamide;

N-(3-(4-(2,3-dichlorophenyl)piperazin-1-yl)-2-hydroxypropyl)-1-(4-methoxyphenyl)-5-methyl-2-propyl-1H-imidazole-4-carboxamide;

N-(3-(4-(2,3-dimethylphenyl)piperazin-1-yl)-2-hydroxypropyl)-1-(4-methoxyphenyl)-5-methyl-2-propyl-1H-imidazole-4-carboxamide;

N-(3-(4-(3-chloro-2-methylphenyl)piperazin-1-yl)propyl)-1-(4-methoxyphenyl)-2,5-dimethyl-1H-imidazole-4-carboxamide;

(S)-N-(3-(4-(2,3-dimethylphenyl)piperazin-1-yl)-2-hydroxypropyl)-2,5-dimethyl-1-phenyl-1H-imidazole-4-carboxamide;

N-((S)-3-(4-(2,3-dimethylphenyl)piperazin-1-yl)-2-hydroxypropyl)-1-(2-fluorophenyl)-2,5-dimethyl-1H-imidazole-4-carboxamide;

(S)-1-(4-chlorophenyl)-N-(3-(4-(2,3-dichlorophenyl)piperazin-1-yl)-2-hydroxypropyl)-2-propyl-1H-imidazole-4-carboxamide;

(S)-N-(3-(4-(3-chloro-2-methylphenyl)piperazin-1-yl)-2-hydroxypropyl)-1-(4-fluorophenyl)-5-methyl-2-phenyl-1H-imidazole-4-carboxamide;

N-(3-(4-(2,3-dichlorophenyl)piperazin-1-yl)propyl)-1-(4-methoxyphenyl)-5-methyl-2-propyl-1H-imidazole-4-carboxamide;

N-(3-(4-(3-chloro-2-methylphenyl)piperazin-1-yl)propyl)-1-(2-methoxyphenyl)-2,5-dimethyl-1H-imidazole-4-carboxamide;

N-(3-(4-(2,3-dichlorophenyl)piperazin-1-yl)propyl)-1-(2-methoxyphenyl)-2,5-dimethyl-1H-imidazole-4-carboxamide;

N-(3-(4-(2,3-dichlorophenyl)piperazin-1-yl)-2-hydroxypropyl)-1-(2-methoxyphenyl)-2,5-dimethyl-1H-imidazole-4-carboxamide;

N-(3-(4-(2,3-dimethylphenyl)piperazin-1-yl)propyl)-2,5-dimethyl-1-p-tolyl-1H-imidazole-4-carboxamide;

N-(3-(4-(2,3-dimethylphenyl)piperazin-1-yl)-2-hydroxypropyl)-2,5-dimethyl-1-p-tolyl-1H-imidazole-4-carboxamide;

N-(3-(4-(2,3-dichlorophenyl)piperazin-1-yl)-2-hydroxypropyl)-1-(2,3-dihydrobenzo[b][1,4]dioxin-6-yl)-2,5-dimethyl-1H-imidazole-4-carboxamide;

N-(3-(4-(2,3-dichlorophenyl)piperazin-1-yl)propyl)-1-(2,3-dihydrobenzo[b][1,4]dioxin-6-yl)-2,5-dimethyl-1H-imidazole-4-carboxamide;

(R)-N-(3-(4-(2,3-dimethylphenyl)piperazin-1-yl)-2-hydroxypropyl)-2,5-dimethyl-1-phenyl-1H-imidazole-4-carboxamide;

N-((R)-3-(4-(2,3-dimethylphenyl)piperazin-1-yl)-2-hydroxypropyl)-1-(2-fluorophenyl)-2,5-dimethyl-1H-imidazole-4-carboxamide;

N-(3-(4-(3-chloro-2-methylphenyl)piperazin-1-yl)propyl)-1-(2-fluorophenyl)-2,5-dimethyl-1H-imidazole-4-carboxamide;

N-(3-(4-(2,3-dichlorophenyl)piperazin-1-yl)propyl)-1-(2-fluorophenyl)-2,5-dimethyl-1H-imidazole-4-carboxamide;

N-(3-(4-(2,3-dimethylphenyl)piperazin-1-yl)-2-hydroxypropyl)-5-methyl-1,2-diphenyl-1H-imidazole-4-carboxamide;

N-(3-(4-(2,3-dichlorophenyl)piperazin-1-yl)-2-hydroxypropyl)-5-methyl-1,2-diphenyl-1H-imidazole-4-carboxamide;

N-(3-(4-(2,3-dichlorophenyl)piperazin-1-yl)-2-hydroxypropyl)-1-(4-fluorophenyl)-5-methyl-2-phenyl-1H-imidazole-4-carboxamide;

N-(3-(4-(2,3-dichlorophenyl)piperazin-1-yl)propyl)-5-methyl-1,2-diphenyl-1H-imidazole-4-carboxamide;

N-(3-(4-(2,3-dichlorophenyl)piperazin-1-yl)propyl)-1-(4-fluorophenyl)-5-methyl-2-phenyl-1H-imidazole-4-carboxamide;

N-(3-(4-(3-chloro-2-methylphenyl)piperazin-1-yl)-2-hydroxypropyl)-5-methyl-1,2-diphenyl-1H-imidazole-4-carboxamide;

N-(3-(4-(3-chloro-2-methylphenyl)piperazin-1-yl)-2-hydroxypropyl)-1-(4-fluorophenyl)-5-methyl-2-propyl-1H-imidazole-4-carboxamide;

N-(3-(4-(3-chloro-2-methylphenyl)piperazin-1-yl)-2-hydroxypropyl)-1-(4-fluorophenyl)-2,5-dimethyl-1H-imidazole-4-carboxamide;

1-cyclopentyl-N-(3-(4-(2,3-dichlorophenyl)piperazin-1-yl)propyl)-2,5-dimethyl-1H-imidazole-4-carboxamide;

1-cyclopentyl-N-(3-(4-(2,3-dichlorophenyl)piperazin-1-yl)-2-hydroxypropyl)-2,5-dimethyl-1H-imidazole-4-carboxamide;

N-(3-(4-(2,3-dichlorophenyl)piperazin-1-yl)propyl)-2,5-dimethyl-1-propyl-1H-imidazole-4-carboxamide;

N-(3-(4-(2,3-dichlorophenyl)piperazin-1-yl)-2-hydroxypropyl)-2,5-dimethyl-1-propyl-1H-imidazole-4-carboxamide;

N-(3-(4-(2,3-dimethylphenyl)piperazin-1-yl)propyl)-1-(2-methoxyphenyl)-5-methyl-2-propyl-1H-imidazole-4-carboxamide;

N-(3-(4-(3-chloro-2-methylphenyl)piperazin-1-yl)propyl)-1-(2-methoxyphenyl)-5-methyl-2-propyl-1H-imidazole-4-carboxamide;

N-(3-(4-(2,3-dichlorophenyl)piperazin-1-yl)propyl)-1-(2-methoxyphenyl)-5-methyl-2-propyl-1H-imidazole-4-carboxamide;

N-(3-(4-(2,3-dimethylphenyl)piperazin-1-yl)-2-hydroxypropyl)-1-(2-methoxyphenyl)-5-methyl-2-propyl-1H-imidazole-4-carboxamide;

N-(3-(4-(3-chloro-2-methylphenyl)piperazin-1-yl)-2-hydroxypropyl)-1-(2-methoxyphenyl)-5-methyl-2-propyl-1H-imidazole-4-carboxamide;

N-(3-(4-(2,3-dichlorophenyl)piperazin-1-yl)-2-hydroxypropyl)-1-(2-methoxyphenyl)-5-methyl-2-propyl-1H-imidazole-4-carboxamide;

N-(3-(4-(2,3-dimethylphenyl)piperazin-1-yl)propyl)-2,5-dimethyl-1-(2-(trifluoromethyl)phenyl)-1H-imidazole-4-carboxamide;

N-(3-(4-(3-chloro-2-methylphenyl)piperazin-1-yl)propyl)-2,5-dimethyl-1-(2-(trifluoromethyl)phenyl)-1H-imidazole-4-carboxamide;

N-(3-(4-(2,3-dichlorophenyl)piperazin-1-yl)propyl)-2,5-dimethyl-1-(2-(trifluoromethyl)phenyl)-1H-imidazole-4-carboxamide;

N-(3-(4-(3-chloro-2-methylphenyl)piperazin-1-yl)-2-hydroxypropyl)-2,5-dimethyl-1-(2-(trifluoromethyl)phenyl)-1H-imidazole-4-carboxamide;

N-(3-(4-(2,3-dichlorophenyl)piperazin-1-yl)-2-hydroxypropyl)-2,5-dimethyl-1-(2-(trifluoromethyl)phenyl)-1H-imidazole-4-carboxamide;

N-(3-(4-(3-chloro-2-methylphenyl)piperazin-1-yl)-2-hydroxypropyl)-1-(4-methoxyphenyl)-5-methyl-2-propyl-1H-imidazole-4-carboxamide;

N-(3-(4-(3-chloro-2-methylphenyl)piperazin-1-yl)-2-hydroxypropyl)-1-(2-methoxyphenyl)-2,5-dimethyl-1H-imidazole-4-carboxamide;

N-(3-(4-(3-chloro-2-methylphenyl)piperazin-1-yl)-2-hydroxypropyl)-1-(4-chlorophenyl)-2-propyl-1H-imidazole-4-carboxamide;

N-(3-(4-(3-chloro-2-methylphenyl)piperazin-1-yl)propyl)-1-(4-chlorophenyl)-2-propyl-1H-imidazole-4-carboxamide;

N-(3-(4-(3-chloro-2-methylphenyl)piperazin-1-yl)-2-hydroxypropyl)-1-(2,3-dihydrobenzo[b][1,4]dioxin-6-yl)-2,5-dimethyl-1H-imidazole-4-carboxamide;

N-(3-(4-(3-chloro-2-methylphenyl)piperazin-1-yl)propyl)-1-(2,3-dihydrobenzo[b][1,4]dioxin-6-yl)-2,5-dimethyl-1H-imidazole-4-carboxamide;

1-(2,3-dihydrobenzo[b][1,4]dioxin-6-yl)-N-(3-(4-(2,3-dimethylphenyl)piperazin-1-yl)propyl)-5-methyl-2-propyl-1H-imidazole-4-carboxamide;

N-(3-(4-(2,3-dichlorophenyl)piperazin-1-yl)propyl)-1-(2,3-dihydrobenzo[b][1,4]dioxin-6-yl)-5-methyl-2-propyl-1H-imidazole-4-carboxamide;

N-(3-(4-(3-chloro-2-methylphenyl)piperazin-1-yl)propyl)-5-methyl-1-phenyl-2-propyl-1H-imidazole-4-carboxamide;

N-(3-(4-(3-chloro-2-methylphenyl)piperazin-1-yl)-2-hydroxypropyl)-5-methyl-1-phenyl-2-propyl-1H-imidazole-4-carboxamide;

N-(3-(4-(3-chloro-2-methylphenyl)piperazin-1-yl)propyl)-1-(2,3-dihydrobenzo[b][1,4]dioxin-6-yl)-5-methyl-2-propyl-1H-imidazole-4-carboxamide;

N-(3-(4-(3-chloro-2-methylphenyl)piperazin-1-yl)-2-hydroxypropyl)-1-(2,3-dihydrobenzo[b][1,4]dioxin-6-yl)-5-methyl-2-propyl-1H-imidazole-4-carboxamide;

1-(2,3-dihydrobenzo[b][1,4]dioxin-6-yl)-N-(3-(4-(2,3-dimethylphenyl)piperazin-1-yl)-2-hydroxypropyl)-5-methyl-2-propyl-1H-imidazole-4-carboxamide;

N-(3-(4-(2,3-dichlorophenyl)piperazin-1-yl)-2-hydroxypropyl)-1-(2,3-dihydrobenzo[b][1,4]dioxin-6-yl)-5-methyl-2-propyl-1H-imidazole-4-carboxamide;

N-(3-(4-(2,3-dimethylphenyl)piperazin-1-yl)propyl)-1-(4-fluorophenyl)-5-methyl-2-propyl-1H-imidazole-4-carboxamide;

N-(3-(4-(2,3-dichlorophenyl)piperazin-1-yl)propyl)-1-(4-fluorophenyl)-5-methyl-2-propyl-1H-imidazole-4-carboxamide;

N-(3-(4-(2,3-dimethylphenyl)piperazin-1-yl)-2-hydroxypropyl)-1-(4-fluorophenyl)-5-methyl-2-propyl-1H-imidazole-4-carboxamide;

N-(3-(4-(2,3-dichlorophenyl)piperazin-1-yl)-2-hydroxypropyl)-1-(4-fluorophenyl)-5-methyl-2-propyl-1H-imidazole-4-carboxamide;

N-(3-(4-(3-chloro-2-methylphenyl)piperazin-1-yl)propyl)-1-(4-fluorophenyl)-2,5-dimethyl-1H-imidazole-4-carboxamide;

N-(3-(4-(3-chloro-2-methylphenyl)piperazin-1-yl)propyl)-1-(4-fluorophenyl)-5-methyl-2-propyl-1H-imidazole-4-carboxamide;

N-(3-(4-(2,3-dichlorophenyl)piperazin-1-yl)-2-hydroxypropyl)-1-(2-fluorophenyl)-2,5-dimethyl-1H-imidazole-4-carboxamide;

1-(2-chlorophenyl)-N-(3-(4-(2,3-dimethylphenyl)piperazin-1-yl)-2-hydroxypropyl)-5-methyl-2-propyl-1H-imidazole-4-carboxamide;

1-(2-chlorophenyl)-N-(3-(4-(2,3-dimethylphenyl)piperazin-1-yl)propyl)-5-methyl-2-propyl-1H-imidazole-4-carboxamide;

(R)-N-(3-(4-(3-chloro-2-methylphenyl)piperazin-1-yl)-2-hydroxypropyl)-1-(4-fluorophenyl)-5-methyl-2-phenyl-1H-imidazole-4-carboxamide;

(R)-1-(4-chlorophenyl)-N-(3-(4-(2,3-dichlorophenyl)piperazin-1-yl)-2-hydroxypropyl)-2-propyl-1H-imidazole-4-carboxamide;

N-(3-(4-(3-chloro-2-methylphenyl)piperazin-1-yl)propyl)-1-(2-chlorophenyl)-2,5-dimethyl-1H-imidazole-4-carboxamide;

N-(3-(4-(3-chloro-2-methylphenyl)piperazin-1-yl)-2-hydroxypropyl)-1-(2-fluorophenyl)-2,5-dimethyl-1H-imidazole-4-carboxamide;

N-(3-(4-(3-chloro-2-methylphenyl)piperazin-1-yl)-2-hydroxypropyl)-1-(4-methoxyphenyl)-2,5-dimethyl-1H-imidazole-4-carboxamide;

N-(3-(4-(2,3-dimethylphenyl)piperazin-1-yl)propyl)-1-(4-methoxyphenyl)-5-methyl-2-phenyl-1H-imidazole-4-carboxamide;

N-(3-(4-(3-chloro-2-methylphenyl)piperazin-1-yl)propyl)-1-(4-methoxyphenyl)-5-methyl-2-phenyl-1H-imidazole-4-carboxamide;

N-(3-(4-(2,3-dichlorophenyl)piperazin-1-yl)propyl)-1-(4-methoxyphenyl)-5-methyl-2-phenyl-1H-imidazole-4-carboxamide;

N-(3-(4-(2,3-dimethylphenyl)piperazin-1-yl)-2-hydroxypropyl)-1-(4-methoxyphenyl)-5-methyl-2-phenyl-1H-imidazole-4-carboxamide;

N-(3-(4-(3-chloro-2-methylphenyl)piperazin-1-yl)-2-hydroxypropyl)-1-(4-methoxyphenyl)-5-methyl-2-phenyl-1H-imidazole-4-carboxamide;

N-(3-(4-(2,3-dichlorophenyl)piperazin-1-yl)-2-hydroxypropyl)-1-(4-methoxyphenyl)-5-methyl-2-phenyl-1H-imidazole-4-carboxamide;

1-(2,3-dihydrobenzo [b][1,4]dioxin-6-yl)-N-(3-(4-(2,3-dimethylphenyl)piperazin-1-yl)propyl)-5-methyl-2-phenyl-1H-imidazole-4-carboxamide;

N-(3-(4-(3-chloro-2-methylphenyl)piperazin-1-yl)propyl)-1-(2,3-dihydrobenzo [b][1,4]dioxin-6-yl)-5-methyl-2-phenyl-1H-imidazole-4-carboxamide;

N-(3-(4-(2,3-dichlorophenyl)piperazin-1-yl)propyl)-1-(2,3-dihydrobenzo [b][1,4]dioxin-6-yl)-5-methyl-2-phenyl-1H-imidazole-4-carboxamide;

1-(2,3-dihydrobenzo [b][1,4]dioxin-6-yl)-N-(3-(4-(2,3-dimethylphenyl)piperazin-1-yl)-2-hydroxypropyl)-5-methyl-2-phenyl-1H-imidazole-4-carboxamide;

N-(3-(4-(3-chloro-2-methylphenyl)piperazin-1-yl)-2-hydroxypropyl)-1-(2,3-dihydrobenzo [b][1,4]dioxin-6-yl)-5-methyl-2-phenyl-1H-imidazole-4-carboxamide;

N-(3-(4-(2,3-dichlorophenyl)piperazin-1-yl)-2-hydroxypropyl)-1-(2,3-dihydrobenzo [b][1,4]dioxin-6-yl)-5-methyl-2-phenyl-1H-imidazole-4-carboxamide;

1-(benzo[d][1,3]dioxol-5-yl)-N-(3-(4-(3-chloro-2-methylphenyl)piperazin-1-yl)propyl)-2,5-dimethyl-1H-imidazole-4-carboxamide;

1-(benzo[d][1,3]dioxol-5-yl)-N-(3-(4-(3-chloro-2-methylphenyl)piperazin-1-yl)propyl)-5-methyl-2-propyl-1H-imidazole-4-carboxamide;

N-(3-(4-(2,3-dimethylphenyl)piperazin-1-yl)propyl)-2,5-dimethyl-1-o-tolyl-1H-imidazole-4-carboxamide;

N-(3-(4-(3-chloro-2-methylphenyl)piperazin-1-yl)propyl)-2,5-dimethyl-1-o-tolyl-1H-imidazole-4-carboxamide;

N-(3-(4-(2,3-dichlorophenyl)piperazin-1-yl)propyl)-2,5-dimethyl-1-o-tolyl-1H-imidazole-4-carboxamide;

N-(3-(4-(2,3-dimethylphenyl)piperazin-1-yl)-2-hydroxypropyl)-2,5-dimethyl-1-o-tolyl-1H-imidazole-4-carboxamide;

N-(3-(4-(3-chloro-2-methylphenyl)piperazin-1-yl)-2-hydroxypropyl)-2,5-dimethyl-1-o-tolyl-1H-imidazole-4-carboxamide;

N-(3-(4-(2,3-dichlorophenyl)piperazin-1-yl)-2-hydroxypropyl)-2,5-dimethyl-1-o-tolyl-1H-imidazole-4-carboxamide;

N-(3-(4-(3-chloro-2-methylphenyl)piperazin-1-yl)propyl)-1-(4-chlorophenyl)-2,5-dimethyl-1H-imidazole-4-carboxamide;

1-(4-chlorophenyl)-N-(3-(4-(2,3-dimethylphenyl)piperazin-1-yl)-2-hydroxypropyl)-2,5-dimethyl-1H-imidazole-4-carboxamide;

N-(3-(4-(3-chloro-2-methylphenyl)piperazin-1-yl)-2-hydroxypropyl)-1-(4-chlorophenyl)-2,5-dimethyl-1H-imidazole-4-carboxamide;

1-(4-chlorophenyl)-N-(3-(4-(2,3-dichlorophenyl)piperazin-1-yl)-2-hydroxypropyl)-2,5-dimethyl-1H-imidazole-4-carboxamide;

1-(4-chlorophenyl)-N-(3-(4-(2,3-dimethylphenyl)piperazin-1-yl)propyl)-5-methyl-2-propyl-1H-imidazole-4-carboxamide;

N-(3-(4-(3-chloro-2-methylphenyl)piperazin-1-yl)propyl)-1-(4-chlorophenyl)-5-methyl-2-propyl-1H-imidazole-4-carboxamide;

1-(4-chlorophenyl)-N-(3-(4-(2,3-dichlorophenyl)piperazin-1-yl)propyl)-5-methyl-2-propyl-1H-imidazole-4-carboxamide;

1-(4-chlorophenyl)-N-(3-(4-(2,3-dimethylphenyl)piperazin-1-yl)-2-hydroxypropyl)-5-methyl-2-propyl-1H-imidazole-4-carboxamide;

N-(3-(4-(3-chloro-2-methylphenyl)piperazin-1-yl)-2-hydroxypropyl)-1-(4-chlorophenyl)-5-methyl-2-propyl-1H-imidazole-4-carboxamide;

1-(4-chlorophenyl)-N-(3-(4-(2,3-dichlorophenyl)piperazin-1-yl)-2-hydroxypropyl)-5-methyl-2-propyl-1H-imidazole-4-carboxamide;

1-(2-chlorophenyl)-N-(3-(4-(2,3-dichlorophenyl)piperazin-1-yl)-2-hydroxypropyl)-5-methyl-2-propyl-1H-imidazole-4-carboxamide;

1-(2-chlorophenyl)-N-(3-(4-(2,3-dichlorophenyl)piperazin-1-yl)propyl)-2,5-dimethyl-1H-imidazole-4-carboxamide;

1-(2-chlorophenyl)-N-(3-(4-(2,3-dichlorophenyl)piperazin-1-yl)-2-hydroxypropyl)-2,5-dimethyl-1H-imidazole-4-carboxamide;

N-(3-(4-(3-chloro-2-methylphenyl)piperazin-1-yl)propyl)-1-(2-fluorophenyl)-5-methyl-2-propyl-1H-imidazole-4-carboxamide;

N-(3-(4-(2,3-dimethylphenyl)piperazin-1-yl)propyl)-1-(2-methoxyphenyl)-5-methyl-2-phenyl-1H-imidazole-4-carboxamide;

N-(3-(4-(3-chloro-2-methylphenyl)piperazin-1-yl)propyl)-1-(2-methoxyphenyl)-5-methyl-2-phenyl-1H-imidazole-4-carboxamide;

N-(3-(4-(2,3-dichlorophenyl)piperazin-1-yl)propyl)-1-(2-methoxyphenyl)-5-methyl-2-phenyl-1H-imidazole-4-carboxamide;

N-(3-(4-(2,3-dimethylphenyl)piperazin-1-yl)propyl)-1-(2-fluorophenyl)-5-methyl-2-propyl-1H-imidazole-4-carboxamide;

N-(3-(4-(2,3-dimethylphenyl)piperazin-1-yl)-2-hydroxypropyl)-1-(2-fluorophenyl)-5-methyl-2-propyl-1H-imidazole-4-carboxamide;

N-(3-(4-(2,3-dichlorophenyl)piperazin-1-yl)-2-hydroxypropyl)-1-(2-fluorophenyl)-5-methyl-2-propyl-1H-imidazole-4-carboxamide;

N-(3-(4-(2,3-dimethylphenyl)piperazin-1-yl)propyl)-5-methyl-2-propyl-1-o-tolyl-1H-imidazole-4-carboxamide;

N-(3-(4-(3-chloro-2-methylphenyl)piperazin-1-yl)propyl)-5-methyl-2-propyl-1-o-tolyl-1H-imidazole-4-carboxamide;

N-(3-(4-(2,3-dichlorophenyl)piperazin-1-yl)propyl)-5-methyl-2-propyl-1-o-tolyl-1H-imidazole-4-carboxamide;

1-(4-chlorophenyl)-N-(3-(4-(2,3-dimethylphenyl)piperazin-1-yl)propyl)-5-methyl-2-phenyl-1H-imidazole-4-carboxamide;

N-(3-(4-(3-chloro-2-methylphenyl)piperazin-1-yl)propyl)-1-(4-chlorophenyl)-5-methyl-2-phenyl-1H-imidazole-4-carboxamide;

1-(4-chlorophenyl)-N-(3-(4-(2,3-dichlorophenyl)piperazin-1-yl)propyl)-5-methyl-2-phenyl-1H-imidazole-4-carboxamide;

1-(4-chlorophenyl)-N-(3-(4-(2,3-dimethylphenyl)piperazin-1-yl)-2-hydroxypropyl)-5-methyl-2-phenyl-1H-imidazole-4-carboxamide;

N-(3-(4-(3-chloro-2-methylphenyl)piperazin-1-yl)-2-hydroxypropyl)-1-(4-chlorophenyl)-5-methyl-2-phenyl-1H-imidazole-4-carboxamide;

1-(4-chlorophenyl)-N-(3-(4-(2,3-dichlorophenyl)piperazin-1-yl)-2-hydroxypropyl)-5-methyl-2-phenyl-1H-imidazole-4-carboxamide;

1-(benzo [d][1,3]dioxol-5-yl)-N-(3-(442,3-dichlorophenyl)piperazin-1-yl)propyl)-2,5-dimethyl-1H-imidazole-4-carboxamide;

1-(benzo [d][1,3]dioxol-5-yl)-N-(3-(442,3-dichlorophenyl)piperazin-1-yl)-2-hydroxypropyl)-2,5-dimethyl-1H-imidazole-4-carboxamide;

1-(benzo [d][1,3]dioxol-5-yl)-N-(3-(442,3-dimethylphenyl)piperazin-1-yl)propyl)-5-methyl-2-propyl-1H-imidazole-4-carboxamide;

1-(benzo [d][1,3]dioxol-5-yl)-N-(3-(442,3-dichlorophenyl)piperazin-1-yl)propyl)-5-methyl-2-propyl-1H-imidazole-4-carboxamide;

1-(benzo [d][1,3]dioxol-5-yl)-N-(3-(442,3-dimethylphenyl)piperazin-1-yl)-2-hydroxypropyl)-5-methyl-2-propyl-1H-imidazole-4-carboxamide;

1-(benzo [d][1,3]dioxol-5-yl)-N-(3-(442,3-dichlorophenyl)piperazin-1-yl)-2-hydroxypropyl)-5-methyl-2-propyl-1H-imidazole-4-carboxamide;

N-(3-(4-(3-chloro-2-methylphenyl)piperazin-1-yl)propyl)-2,5-dimethyl-1-p-tolyl-1H-imidazole-4-carboxamide;

N-(3-(4-(2,3-dimethylphenyl)piperazin-1-yl)propyl)-5-methyl-2-propyl-1-p-tolyl-1H-imidazole-4-carboxamide;

N-(3-(4-(3-chloro-2-methylphenyl)piperazin-1-yl)propyl)-5-methyl-2-propyl-1-p-tolyl-1H-imidazole-4-carboxamide;

N-(3-(4-(2,3-dimethylphenyl)piperazin-1-yl)-2-hydroxypropyl)-1-(2-methoxyphenyl)-5-methyl-2-phenyl-1H-imidazole-4-carboxamide;

N-(3-(4-(3-chloro-2-methylphenyl)piperazin-1-yl)-2-hydroxypropyl)-1-(2-methoxyphenyl)-5-methyl-2-phenyl-1H-imidazole-4-carboxamide;

N-(3-(4-(2,3-dichlorophenyl)piperazin-1-yl)-2-hydroxypropyl)-1-(2-methoxyphenyl)-5-methyl-2-phenyl-1H-imidazole-4-carboxamide;

1-(benzo [d][1,3]dioxol-5-yl)-N-(3-(442,3-dimethylphenyl)piperazin-1-yl)propyl)-5-methyl-2-phenyl-1H-imidazole-4-carboxamide;

1-(benzo [d][1,3]dioxol-5-yl)-N-(3-(4-(3-chloro-2-methylphenyl)piperazin-1-yl)propyl)-5-methyl-2-phenyl-1H-imidazole-4-carboxamide;

1-(benzo [d][1,3]dioxol-5-yl)-N-(3-(442,3-dichlorophenyl)piperazin-1-yl)propyl)-5-methyl-2-phenyl-1H-imidazole-4-carboxamide;

1-(benzo [d][1,3]dioxol-5-yl)-N-(3-(442,3-dimethylphenyl)piperazin-1-yl)-2-hydroxypropyl)-5-methyl-2-phenyl-1H-imidazole-4-carboxamide;

1-(benzo [d][1,3]dioxol-5-yl)-N-(3-(4-(3-chloro-2-methylphenyl)piperazin-1-yl)-2-hydroxypropyl)-5-methyl-2-phenyl-1H-imidazole-4-carboxamide;

1-(benzo [d][1,3]dioxol-5-yl)-N-(3-(442,3-dichlorophenyl)piperazin-1-yl)-2-hydroxypropyl)-5-methyl-2-phenyl-1H-imidazole-4-carboxamide;

N-(3-(4-(2,3-dimethylphenyl)piperazin-1-yl)propyl)-1-(2-fluorophenyl)-5-methyl-2-phenyl-1H-imidazole-4-carboxamide;

N-(3-(4-(3-chloro-2-methylphenyl)piperazin-1-yl)propyl)-1-(2-fluorophenyl)-5-methyl-2-phenyl-1H-imidazole-4-carboxamide;

N-(3-(4-(2,3-dichlorophenyl)piperazin-1-yl)propyl)-1-(2-fluorophenyl)-5-methyl-2-phenyl-1H-imidazole-4-carboxamide;

N-(3-(4-(2,3-dimethylphenyl)piperazin-1-yl)-2-hydroxypropyl)-1-(2-fluorophenyl)-5-methyl-2-phenyl-1H-imidazole-4-carboxamide;

N-(3-(4-(3-chloro-2-methylphenyl)piperazin-1-yl)-2-hydroxypropyl)-1-(2-fluorophenyl)-5-methyl-2-phenyl-1H-imidazole-4-carboxamide;

N-(3-(4-(2,3-dichlorophenyl)piperazin-1-yl)-2-hydroxypropyl)-1-(2-fluorophenyl)-5-methyl-2-phenyl-1H-imidazole-4-carboxamide;

N-(3-(4-(2,3-dichlorophenyl)piperazin-1-yl)propyl)-5-methyl-2-propyl-1-p-tolyl-1H-imidazole-4-carboxamide;

1-(benzo [d][1,3]dioxol-5-yl)-N-(3-(4-(3-chloro-2-methylphenyl)piperazin-1-yl)-2-hydroxypropyl)-2,5-dimethyl-1H-imidazole-4-carboxamide;

1-(benzo [d][1,3]dioxol-5-yl)-N-(3-(4-(3-chloro-2-methylphenyl)piperazin-1-yl)-2-hydroxypropyl)-5-methyl-2-propyl-1H-imidazole-4-carboxamide;

N-(3-(4-(3-chloro-2-methylphenyl)piperazin-1-yl)-2-hydroxypropyl)-2,5-dimethyl-1-p-tolyl-1H-imidazole-4-carboxamide;

N-(3-(4-(2,3-dimethylphenyl)piperazin-1-yl)-2-hydroxypropyl)-5-methyl-2-propyl-1-p-tolyl-1H-imidazole-4-carboxamide;

N-(3-(4-(3-chloro-2-methylphenyl)piperazin-1-yl)-2-hydroxypropyl)-5-methyl-2-propyl-1-p-tolyl-1H-imidazole-4-carboxamide;

N-(3-(4-(2,3-dichlorophenyl)piperazin-1-yl)-2-hydroxypropyl)-5-methyl-2-propyl-1-p-tolyl-1H-imidazole-4-carboxamide;

N-(3-(4-(2,3-dimethylphenyl)piperazin-1-yl)propyl)-5-methyl-2-phenyl-1-p-tolyl-1H-imidazole-4-carboxamide;

N-(3-(4-(3-chloro-2-methylphenyl)piperazin-1-yl)-2-hydroxypropyl)-5-methyl-2-phenyl-1-p-tolyl-1H-imidazole-4-carboxamide;

N-(3-(4-(2,3-dichlorophenyl)piperazin-1-yl)propyl)-5-methyl-2-phenyl-1-p-tolyl-1H-imidazole-4-carboxamide;

N-(3-(4-(2,3-dimethylphenyl)piperazin-1-yl)-2-hydroxypropyl)-5-methyl-2-phenyl-1-p-tolyl-1H-imidazole-4-carboxamide;

N-(3-(4-(2,3-dichlorophenyl)piperazin-1-yl)-2-hydroxypropyl)-5-methyl-2-phenyl-1-p-tolyl-1H-imidazole-4-carboxamide;

N-(3-(4-(3-chloro-2-methylphenyl)piperazin-1-yl)-2-hydroxypropyl)-1-(2-chlorophenyl)-2,5-dimethyl-1H-imidazole-4-carboxamide;

1-(2-chlorophenyl)-N-(3-(4-(2,3-dimethylphenyl)piperazin-1-yl)propyl)-5-methyl-2-phenyl-1H-imidazole-4-carboxamide;

N-(3-(4-(3-chloro-2-methylphenyl)piperazin-1-yl)propyl)-1-(2-chlorophenyl)-5-methyl-2-phenyl-1H-imidazole-4-carboxamide;

1-(2-chlorophenyl)-N-(3-(4-(2,3-dichlorophenyl)piperazin-1-yl)propyl)-5-methyl-2-phenyl-1H-imidazole-4-carboxamide;

1-(2-chlorophenyl)-N-(3-(4-(2,3-dimethylphenyl)piperazin-1-yl)-2-hydroxypropyl)-5-methyl-2-phenyl-1H-imidazole-4-carboxamide;

N-(3-(4-(3-chloro-2-methylphenyl)piperazin-1-yl)-2-hydroxypropyl)-1-(2-chlorophenyl)-5-methyl-2-phenyl-1H-imidazole-4-carboxamide;

1-(2-chlorophenyl)-N-(3-(4-(2,3-dichlorophenyl)piperazin-1-yl)-2-hydroxypropyl)-5-methyl-2-phenyl-1H-imidazole-4-carboxamide;

N-(3-(4-(2,3-dimethylphenyl)piperazin-1-yl)propyl)-5-methyl-2-phenyl-1-o-tolyl-1H-imidazole-4-carboxamide;

N-(3-(4-(3-chloro-2-methylphenyl)piperazin-1-yl)propyl)-5-methyl-2-phenyl-1-o-tolyl-1H-imidazole-4-carboxamide;

N-(3-(4-(2,3-dichlorophenyl)piperazin-1-yl)propyl)-5-methyl-2-phenyl-1-o-tolyl-1H-imidazole-4-carboxamide;

N-(3-(4-(2,3-dimethylphenyl)piperazin-1-yl)-2-hydroxypropyl)-5-methyl-2-phenyl-1-o-tolyl-1H-imidazole-4-carboxamide;

N-(3-(4-(3-chloro-2-methylphenyl)piperazin-1-yl)-2-hydroxypropyl)-5-methyl-2-phenyl-1-o-tolyl-1H-imidazole-4-carboxamide;

N-(3-(4-(2,3-dichlorophenyl)piperazin-1-yl)-2-hydroxypropyl)-5-methyl-2-phenyl-1-o-tolyl-1H-imidazole-4-carboxamide;

N-(3-(4-(3-chloro-2-methylphenyl)piperazin-1-yl)-2-hydroxypropyl)-2,5-dimethyl-1-(4-(trifluoromethyl)phenyl)-1H-imidazole-4-carboxamide;

N-(3-(4-(3-chloro-2-methylphenyl)piperazin-1-yl)propyl)-2,5-dimethyl-1-(4-(trifluoromethyl)phenyl)-1H-imidazole-4-carboxamide;

N-(3-(4-(3-chloro-2-methylphenyl)piperazin-1-yl)propyl)-5-methyl-2-phenyl-1-p-tolyl-1H-imidazole-4-carboxamide;

N-(3-(4-(3-chloro-2-methylphenyl)piperazin-1-yl)propyl)-N,5-dimethyl-1,2-diphenyl-1H-imidazole-4-carboxamide;

N-(3-(4-(2,3-dichlorophenyl)piperazin-1-yl)propyl)-N,5-dimethyl-1,2-diphenyl-1H-imidazole-4-carboxamide;

N-(3-(4-(2,3-dimethylphenyl)piperazin-1-yl)propyl)-N,5-dimethyl-1,2-diphenyl-1H-imidazole-4-carboxamide;

N-(3-(4-(3-chloro-2-methylphenyl)piperazin-1-yl)propyl)-1-cyclopentyl-N,2,5-trimethyl-1H-imidazole-4-carboxamide;

1-cyclopentyl-N-(3-(4-(2,3-dichlorophenyl)piperazin-1-yl)propyl)-N,2,5-trimethyl-1H-imidazole-4-carboxamide;

1-cyclopentyl-N-(3-(4-(2,3-dimethylphenyl)piperazin-1-yl)propyl)-N,2,5-trimethyl-1H-imidazole-4-carboxamide;

N-(3-(4-(2,3-dimethylphenyl)piperazin-1-yl)propyl)-1-(4-methoxyphenyl)-N,5-dimethyl-2-phenyl-1H-imidazole-4-carboxamide;

1-(3-chlorophenyl)-N-(3-(4-(2,3-dimethylphenyl)piperazin-1-yl)propyl)-N,2,5-trimethyl-1H-imidazole-4-carboxamide;

N-(3-(4-(3-chloro-2-methylphenyl)piperazin-1-yl)propyl)-1-(4-methoxyphenyl)-N,5-dimethyl-2-phenyl-1H-imidazole-4-carboxamide;

N-(3-(4-(3-chloro-2-methylphenyl)piperazin-1-yl)propyl)-1-(3-chlorophenyl)-N,2,5-trimethyl-1H-imidazole-4-carboxamide;

1-(2-chlorophenyl)-N-(3-(4-(2,3-dimethylphenyl)piperazin-1-yl)propyl)-N,2,5-trimethyl-1H-imidazole-4-carboxamide;

N-(3-(4-(3-chloro-2-methylphenyl)piperazin-1-yl)propyl)-1-(2-chlorophenyl)-N,2,5-trimethyl-1H-imidazole-4-carboxamide;

1-(2-chlorophenyl)-N-(3-(4-(2,3-dichlorophenyl)piperazin-1-yl)propyl)-N,2,5-trimethyl-1H-imidazole-4-carboxamide;

N-(3-(4-(2,3-dimethylphenyl)piperazin-1-yl)propyl)-N,2,5-trimethyl-1-phenyl-1H-imidazole-4-carboxamide;

N-(3-(4-(3-chloro-2-methylphenyl)piperazin-1-yl)propyl)-N,2,5-trimethyl-1-phenyl-1H-imidazole-4-carboxamide;

N-(3-(4-(2,3-dichlorophenyl)piperazin-1-yl)propyl)-N,2,5-trimethyl-1-phenyl-1H-imidazole-4-carboxamide;

N-(3-(4-(2,3-dimethylphenyl)piperazin-1-yl)propyl)-1-(4-fluorophenyl)-N,5-dimethyl-2-phenyl-1H-imidazole-4-carboxamide;

N-(3-(4-(3-chloro-2-methylphenyl)piperazin-1-yl)propyl)-1-(4-fluorophenyl)-N,5-dimethyl-2-phenyl-1H-imidazole-4-carboxamide;

N-(3-(4-(2,3-dichlorophenyl)piperazin-1-yl)propyl)-1-(4-fluorophenyl)-N,5-dimethyl-2-phenyl-1H-imidazole-4-carboxamide;

1-(2,3-dihydrobenzo[b][1,4]dioxin-6-yl)-N-(3-(4-(2,3-dimethylphenyl)piperazin-1-yl)propyl)-N,5-dimethyl-2-phenyl-1H-imidazole-4-carboxamide;

N-(3-(4-(3-chloro-2-methylphenyl)piperazin-1-yl)propyl)-1-(2,3-dihydrobenzo [b][1,4]dioxin-6-yl)-N,5-dimethyl-2-phenyl-1H-imidazole-4-carboxamide N-(3-(4-(2,3-dichlorophenyl)piperazin-1-yl)propyl)-1-(2,3-dihydrobenzo [b][1,4]dioxin-6-yl)-N,5-dimethyl-2-phenyl-1H-imidazole-4-carboxamide;

(R)-1-(2,3-dihydrobenzo[b][1,4]dioxin-6-yl)-N-(3-(4-(2,3-dimethylphenyl)piperazin-1-yl)-2-hydroxypropyl)-2,5-dimethyl-1H-imidazole-4-carboxamide;

(R)-N-(3-(4-(3-chloro-2-methylphenyl)piperazin-1-yl)-2-hydroxypropyl)-1-(2,3-dihydrobenzo [b][1,4]dioxin-6-yl)-2,5-dimethyl-1H-imidazole-4-carboxamide; and (R)-N-(3-(4-(2,3-dichlorophenyl)piperazin-1-yl)-2-hydroxypropyl)-1-(2,3-dihydrobenzo [b][1,4]dioxin-6-yl)-2,5-dimethyl-1H-imidazole-4-carboxamide.

2. A pharmaceutical composition, which comprises the compound or a pharmaceutically acceptable salt thereof according to claim 1 or a pharmaceutically acceptable salt thereof, and a pharmaceutically acceptable carrier.

3. A method for treating a depressive disorder in a mammal, comprising administering the compound according to claim 1 or a pharmaceutically acceptable salt thereof to the mammal in need thereof.

* * * * *